United States Patent [19]
Hagiwara

[11] Patent Number: 5,680,207
[45] Date of Patent: Oct. 21, 1997

[54] DEFECT INSPECTING APPARATUS AND DEFECT INSPECTING METHOD

[75] Inventor: Tsuneyuki Hagiwara, Kawasaki, Japan

[73] Assignee: Nikon Corporation, Tokyo, Japan

[21] Appl. No.: 638,446

[22] Filed: Apr. 26, 1996

Related U.S. Application Data

[62] Division of Ser. No. 527,386, Sep. 13, 1995, abandoned, which is a continuation of Ser. No. 405,401, Mar. 15, 1995, abandoned, which is a continuation of Ser. No. 117,900, Sep. 8, 1993, abandoned, which is a continuation-in-part of Ser. No. 95,912, Jul. 23, 1993, abandoned, which is a continuation-in-part of Ser. No. 45,793, Apr. 14, 1993, abandoned, which is a continuation-in-part of Ser. No. 990,292, Dec. 14, 1992, abandoned.

[51] Int. Cl.$^6$ ............................................. G01N 21/47
[52] U.S. Cl. ........................................................ 356/237
[58] Field of Search ................................. 356/237, 343; 250/559.41

[56] References Cited

U.S. PATENT DOCUMENTS

| | | | |
|---|---|---|---|
| 4,556,903 | 12/1985 | Blitchington et al. | 356/237 |
| 4,610,541 | 9/1986 | Tanimoto et al. | 356/237 |
| 4,740,708 | 4/1988 | Batchelder | 356/237 |
| 4,999,510 | 3/1991 | Hayano et al. | 356/237 |
| 5,363,187 | 11/1994 | Hagiwara et al. | 356/237 |

*Primary Examiner*—Richard A. Rosenberger
*Attorney, Agent, or Firm*—Shapiro and Shapiro

[57] ABSTRACT

A defect inspecting apparatus and a defect inspecting method are provided to conduct discriminating detection of minute circuit patterns and foreign particles as well as to detect defectives on the surface of a substrate with a high precision. The beams from a laser light source are converged by a lens to be incident upon an inspecting point. The light emitted from the inspecting point by the incident beam is detected by a photoreceiver. On the light receiving surface of the photoreceiver, a plurality of light receiving areas are provided. Each of the light receiving areas has longitudinal direction and shorter direction on its positively projected view. The arrangement of the light receiving areas is selected in accordance with the arrangement information of the patterns formed on the substrate. The foreign particles and the patterns are distinguished by obtaining the logical product of the output signals from the selected light receiving area.

7 Claims, 59 Drawing Sheets

FIG. 31A
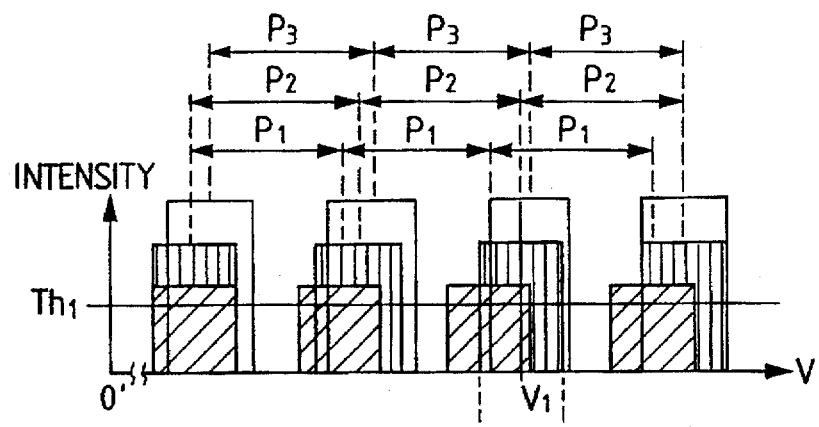
FIG. 31B
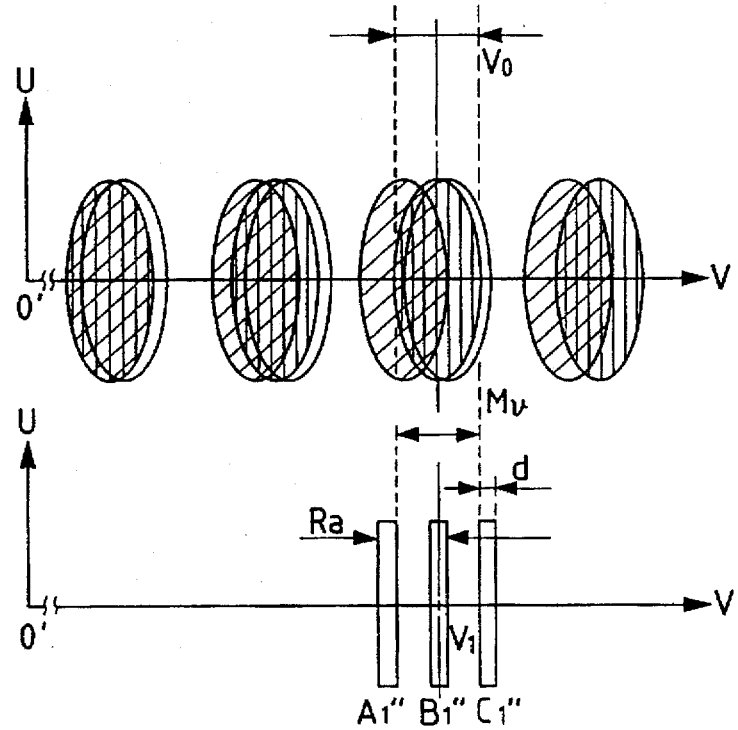
FIG. 31C
FIG. 31D
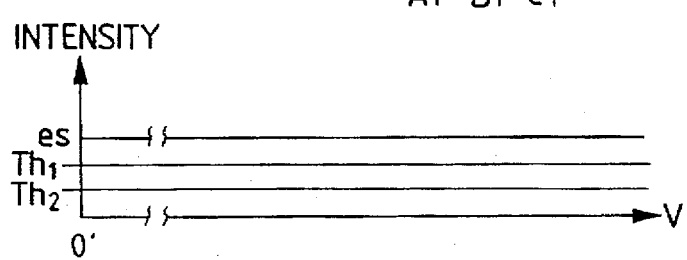

FIG. 56
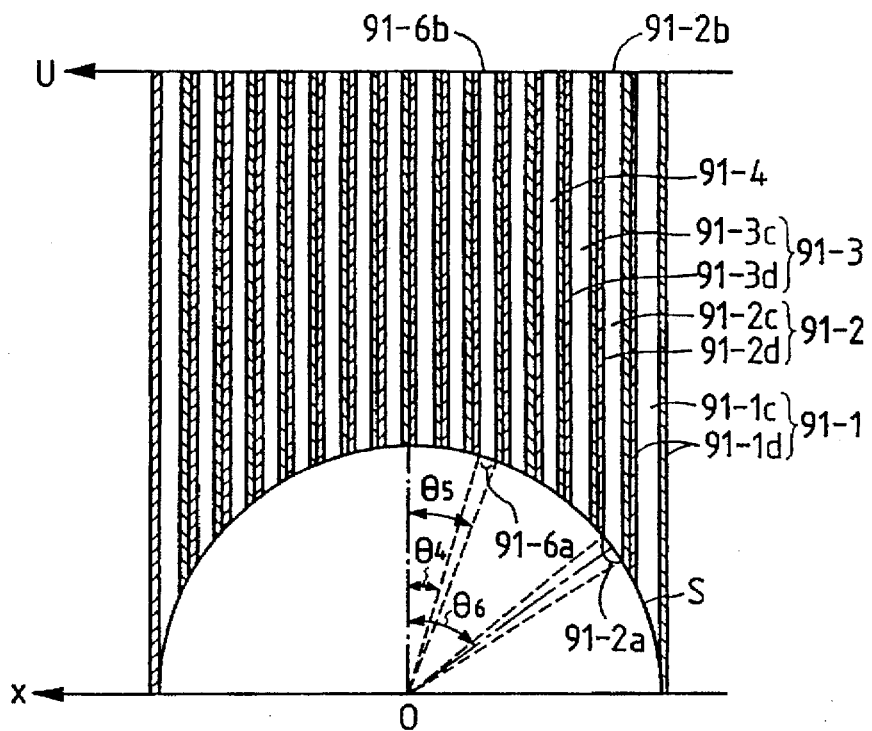
FIG. 57A
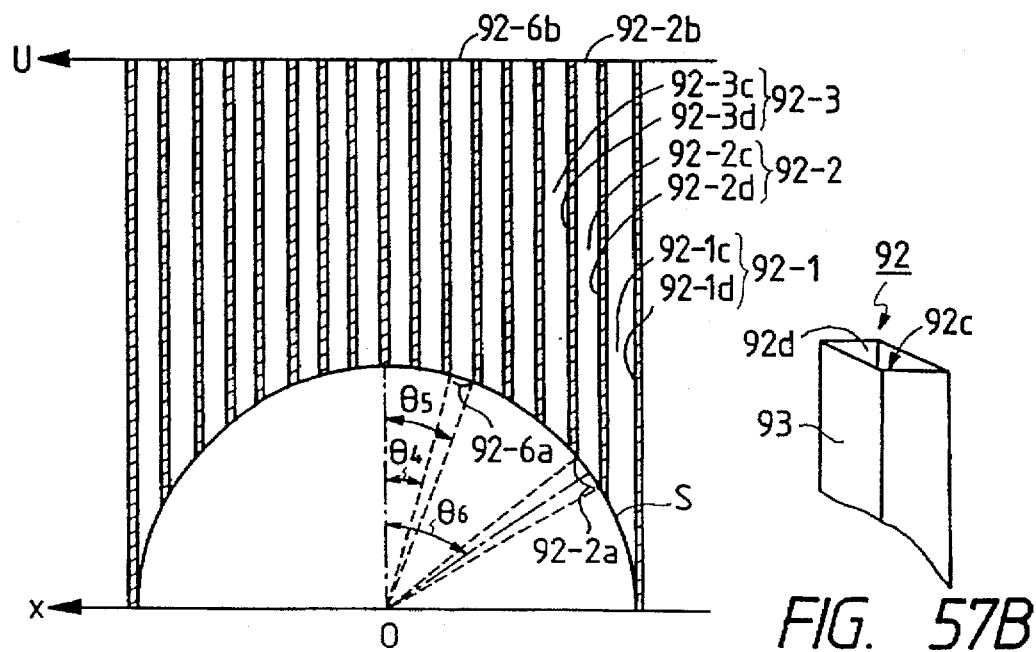
FIG. 57B

DISTRIBUTIONAL POSITIONS OF
THE DIFFRACTIVE LIGHT ON
THE PROJECTED VIEW

DISTRIBUTIONAL POSITIONS OF
THE DIFFRACTIVE LIGHT ON
THE PROJECTED VIEW

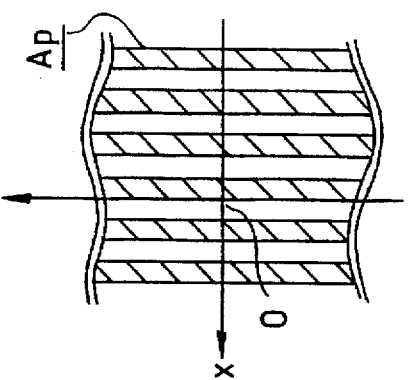
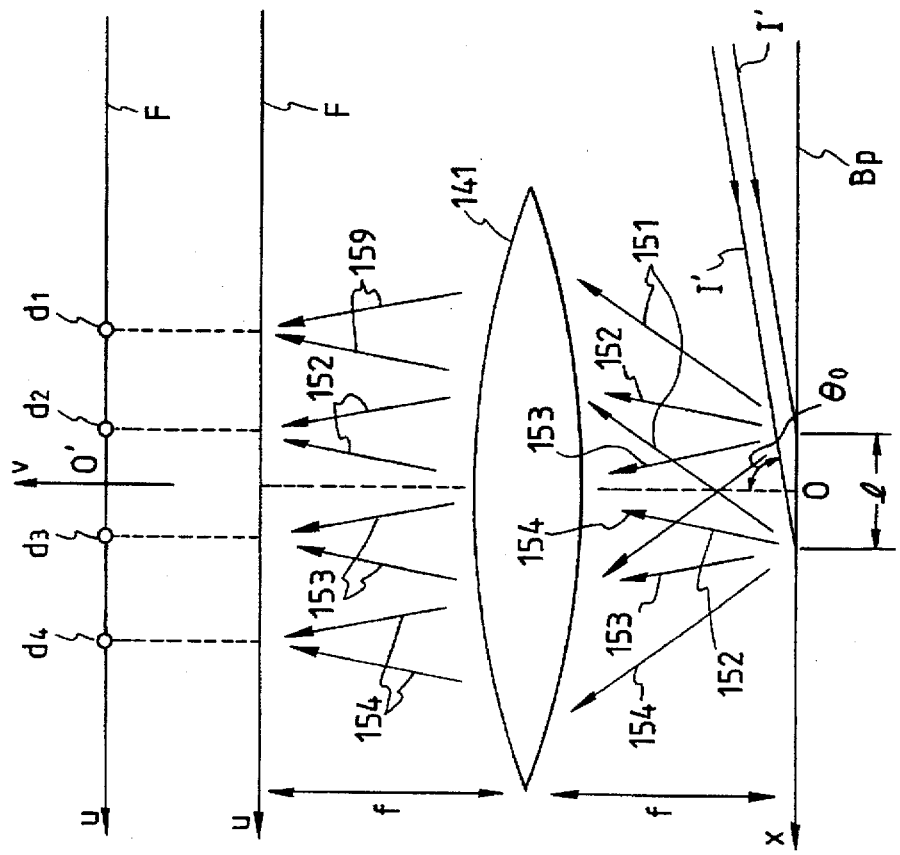

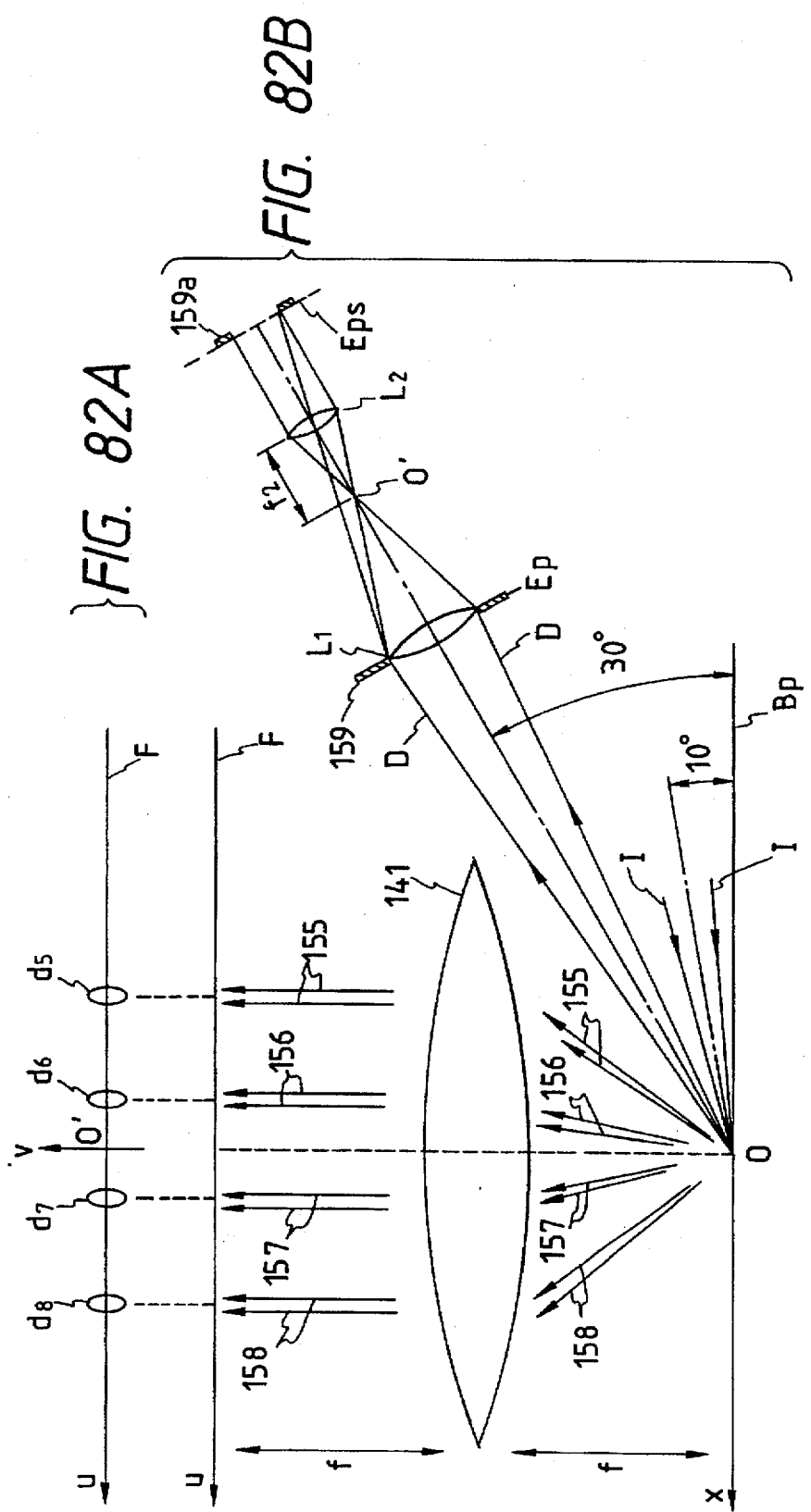

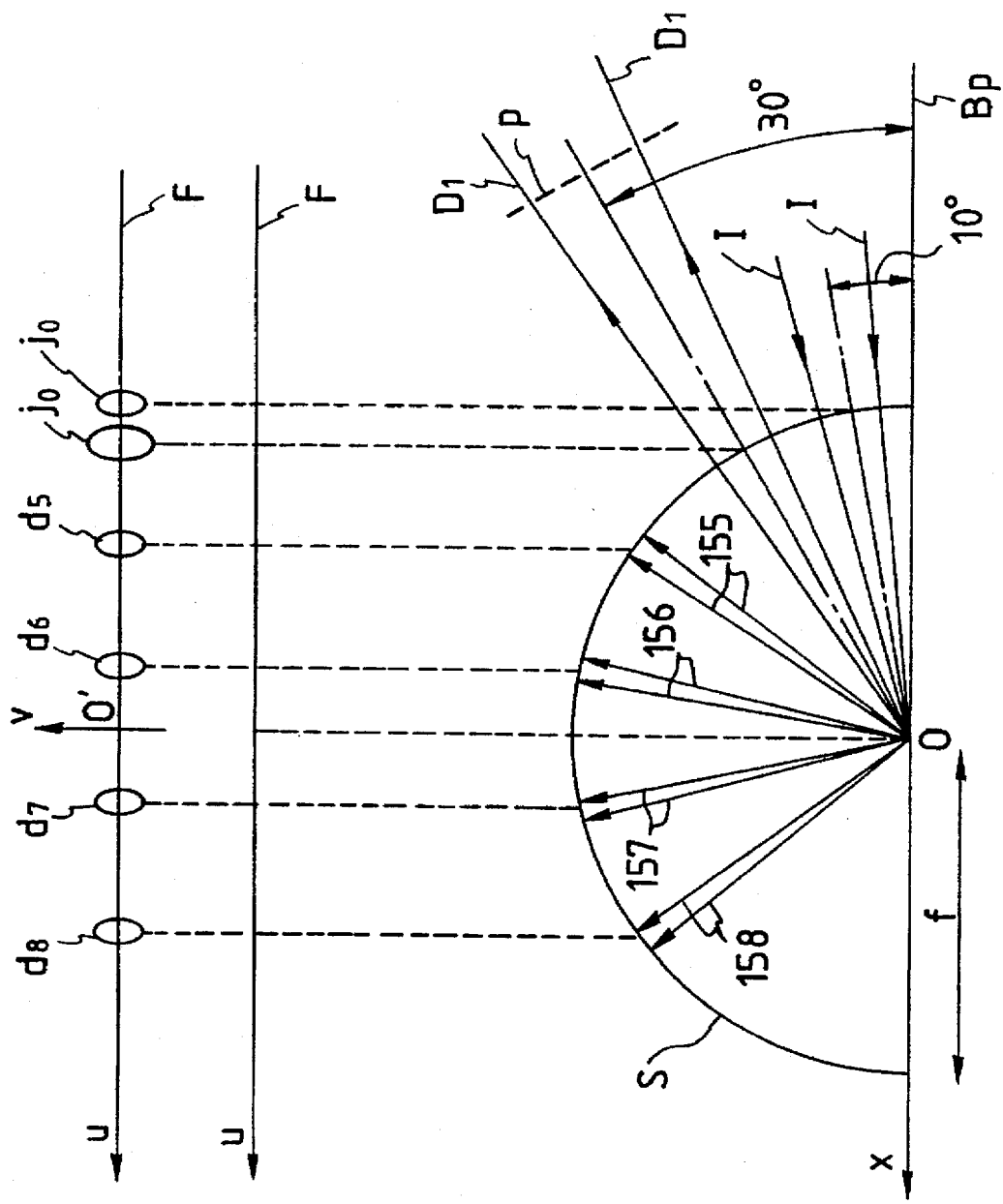

DEFECT INSPECTING APPARATUS AND DEFECT INSPECTING METHOD

This is a division of application Ser. No. 08/527,386 filed Sep. 13, 1995, abandoned, which is a continuation of application Ser. No. 08/405,401 filed Mar. 15, 1995 (abandoned), which is a continuation of application Ser. No. 08/117,900 filed Sep. 8, 1993 (abandoned), which is a continuation-in-part of application Ser. No. 08/095,912 filed Jul. 23, 1993 (abandoned), which is a continuation-in-part of application Ser. No. 08/045,793 filed Apr. 14, 1993 (abandoned), which is a continuation-in-part of application Ser. No. 07/990,292 filed Dec. 14, 1992 (abandoned).

BACKGROUND OF THE INVENTION

1. Field of the Invention

The present invention relates to a defect inspecting apparatus and a defect inspecting method. More particularly, the present invention relates to an apparatus and a method for inspecting defectives (foreign particles, defective circuit patterns, and others) on the surface of a reticle and other substrates.

2. Related Background Art

Generally, in fabricating integrated circuits, the circuit patterns for exposure formed on a reticle, photomask, or other boards are transferred by a semiconductor printing apparatus (such as a stepper or an aligner) onto the surface of a wafer on which resist is coated.

In this case, if foreign substances such as dust particles are present with the circuit patterns on the surface of a board, such foreign particles are also transferred together with the circuit patterns; thus causing the reduction of the IC fabrication yield. Therefore, in fabricating integrated circuits, it is imperative that the presence of any foreign particles on the board should be detected. In this respect, various inspecting methods have hitherto been proposed.

FIG. 64 illustrates an example of a foreign particle inspecting apparatus according to the prior art. In FIG. 64, a beam I emitted from a laser light source 161 enters the surface of a board 165 through a scanning mirror 163 and a scanning lens 164 after being expanded in parallel by a beam expander 162 and others. The scanning mirror 163 is arranged to be rotative or vibrative to scan the incident beam upon the board surface on the board 165. Then, a plurality of photoreceivers 166, 167, and 168 are arranged in the positions away from the optical paths of the positive refection rays of light and positive transmittable rays of light from the board 165. On the basis of output signals from these plural photoreceivers 166, 167, and 168, the presence of any foreign particles on the board 165 are detected. The detection of foreign particles is performed by obtaining a logical product of the output signals from the photoreceivers 166, 167, and 168, for example. In other words, the directivity of the diffractive light from the circuit pattern is intensive, the scattering rays of light from foreign particles have almost no directivity although the output values from the respective photoreceivers are different. The output signals from each of the photoreceiving means are substantially equal. As a result, with an appropriate threshold value, it becomes possible to distinguish the foreign particles from the circuit patterns by obtaining the logical product of the output values from the respective photoreceivers.

Also, the size of any defectives such as foreign particles is classified in accordance with the amount of light received only from the photoreceivers in one direction.

In recent years, however, along with the microminiaturization of the IC circuit patterns, the circuit patterns on a reticle, photomask, and other boards are also micromiaturized. Consequently, it becomes difficult for a conventional apparatus to distinguish the foreign particles from the circuit patterns. Here, with reference to FIG. 65 and FIG. 66, the description will be made specifically of a case where the foreign particles are distinguished from the patterns by receiving light from the photoreceivers within an area H.

FIG. 65 and FIG. 66 are views showing the examples where the photoreceivers are respectively arranged with optical axes at angles more than 90 degrees with respect to the direction of the positive reflection light from the incident beam I upon the board 165. In FIG. 65 and FIG. 66, it is assumed that the axes of ordinate axes represent the intensity of diffractive light while the axes of abscissa represent the distributional positions of the diffractive light on the positively projected view of the diffractive light upon the board. (The positively projected view will be described later in detail). Also, in FIG. 65 and FIG. 66, reference marks $O_1$ designates the position of the positive reflection light; $I_0$, the intensity of the positive reflection light; and $V_0$, the width of the diffractive light.

FIG. 65 shows a case of the pattern which is not very minute. In the area H, the intensity of diffractive light from the pattern is small as compared with the intensity N of scattering rays of light from a foreign particle indicated by a dotted line. In FIG. 65, it is now considered that the scattering rays of light from the foreign particle having its intensity N are received within the area H (assuming that no diffractive light is being emitted in the area H). In this case, the amount of light Sd which enters the photoreceiver is expressed as follows:

$$Sd = N \times H \tag{1}$$

Therefore, it becomes possible to detect the foreign particle by establishing a threshold value at less than the amount of light received Sd.

On the other hand, in a case where diffractive light is being emitted in the area H, the amount of the diffractive light of the pattern to be received becomes equal to the sum of integral values 12-1 and 12-2 of the diffractive light indicated by the slanted lines in FIG. 65. In a case represented by FIG. 65, the amount of the diffractive light from the pattern is smaller than the amount of light SD of the scattering rays from the foreign particle. It is thus possible to make the required discrimination by defining a threshold value.

However, when the minuteness of the pattern becomes finer, the degree of the spatial dispersion of diffractive light also becomes greater. The intensity distribution of the diffractive light which appears dispersively becomes isotropic simultaneously (see FIG. 66). When the photoreceivers are arranged as in FIG. 65, the amount of diffractive light from the pattern is the integral value of the portion 13-1 indicated by slanted lines in FIG. 55. Hence, the amount of diffractive light exceeds the amount of light Sd of the scattering rays of light from the foreign particle, making any discrimination by a threshold value impossible.

Also, in the prior art described above, there is a problem that when the contour of a foreign particle is great as compared with the wavelength of incident light, the scattering rays of light emitted therefrom inevitably has directivity; thus making its detection as a foreign particle impossible.

Also, of the scattering rays of light emitted from the board 165, the scattering rays received by the photoreceivers 167 (166) or only the scattering rays received by the photoreceiver 167 is extracted to determine the size of the foreign particle. It is thus inevitable that the accuracy with which to measure the size of a foreign particle is yet to be improved.

SUMMARY OF THE INVENTION

In consideration of the above-mentioned problems, the present invention is designed with a particular attention Given to the fact that the directivity of scattering rays of light from defectives depends on its size and contour. In other words, foreign particles and other defectives can be regarded as those which are sufficiently small with respect to a wavelength if its maximum contour dimension is less than several times the wavelength of an incident light, its scattering directivity becomes isotropic. On the other hand, if the maximum contour dimension of the defectives becomes more than several times the wavelength, its scattering directivity is biased. In the present invention, using two threshold values having different levels, the detection of defectives is performed by obtaining the logical product of the signals higher than the lower threshold value and the logical sum of the signals lower than the higher threshold value. It is thus aimed by the present invention at providing an apparatus capable of detecting defectives without any errors even when there is a directivity in the scattering rays of light emitted from them. Also, it is an object of the present invention to enhance the accuracy with which to measure the size of defectives.

Also, the present invention is designed with a particular attention to the fact that the finer the pattern minuteness becomes on the board 1, the greater becomes the spatial dispersion of the diffractive light and at the same time, the intensity distribution of the diffractive light becomes isotropic. The attention is also given to the fact that the Fourier spectrum component of the incident light becomes substantially equal. With the present invention thus designed, the substances foreign to the circuit patterns can be detected with a high ratio of separative detection when inspecting defectives of a board (to be examined) having minute circuit patterns. It is an object of the present invention to provide a defect inspecting apparatus and a defect inspecting method capable of inspecting with a high precision defectives on the surface of a board including foreign particles adhering to it.

In order to achieve this object, there are provided the following according to the present invention for a defect inspecting apparatus having irradiating means to irradiate a given beam onto an inspecting surface, and a plurality of light receiving means which receive scattering rays of light emitted from the inspecting surface and output photoelectric conversion signals in accordance with the intensity of light thus received; thus inspecting defectives on the inspecting surface on the basis of the signals from the light receiving means:

first comparison means to compare each size of plural photoelectric conversion signals with a first reference level which is predetermined and to output a first detection signal when all of the plural photoelectric conversion signals are higher than the first reference level;

second comparison means to compare each size of plural photoelectric conversion signals with a second reference level which is defined to be higher than the first reference level and to output a second detection signal when at least one of the plural photoelectric conversion signals is higher than the second reference level; and detecting means to output a signal to indicate the detection of the presence of the foregoing defectives in accordance with at least one of the first detection signal and the second detection signal.

Also, in order to achieve the above-mentioned object, there are provided the following according to the present invention for a defect inspecting apparatus having a light source to irradiate Given beams onto an inspecting object with given patterns being formed on the surface thereof, light converging means to converge the beams from the light source at an inspecting point on the inspecting object with a given aperture angle, shifting means to interrelatedly shift the incident beams from the light converging means and the inspecting object, and light receiving means to receive beams emitted from the inspecting point by the incident beams and to output signals in accordance with the intensity of the light received; thus inspecting the presence of defectives on the surface of the inspecting object on the basis of the signals from the light receiving means:

light receiving means having a plurality of light receiving areas where light to be received can be photoelectrically converted independently; and selecting means to select the arrangement of the plural light receiving areas in accordance with information regarding patterns.

Also, according to the present invention, there are provided the following for a defect inspecting apparatus having a light source to irradiate given beams onto an inspecting object with given patterns being formed on the surface thereof, light converging means to converge the beams from the light source at an inspecting point on the inspecting object with a given aperture angle, shifting means to interrelatedly shift the incident beams and the inspecting object, and light receiving means to receive beams emitted from the inspecting point by the converged beam and to output signals in accordance with the intensity of light thus received; thus detecting the presence of defectives on the surface of the inspecting object:

image processing means to process images on the basis of signals from light receiving means;

detecting means to detect the presence of the foregoing defectives on the basis of the signals of the processed images; and light receiving means having an aperture angle wider than the aperture angle of the converged beam, at the same time having a plurality of photoelectric conversion elements which are two dimensionally arranged substantially on the pupil plane of the light receiving means and are capable of outputting the image on the pupil plane as its two dimensional image information.

It is still another object of the present invention to optimize a relationship between the periodic direction of a circuit pattern and the incident direction of an incident beam to optimize the positional relationship between the intensity distribution of light diffracted from a circuit pattern on the light receiving surface of the optical receiver located at a position spaced apart from an inspecting point by a predetermined distance and the plurality of light receiving areas formed on the light receiving surface.

In order to achieve the above object, there is provided a defect inspecting apparatus including a light source for emitting a predetermined beam on an inspecting object having a predetermined pattern thereon, focusing means for focusing the beam from the light source on an inspecting point on the inspecting object at a predetermined angular aperture, moving means for relatively moving the incident beam radiated on the inspecting object and the inspecting object, and light receiving means, spaced apart from the inspecting point by a predetermined distance, for receiving a beam emerging from the inspecting point upon incidence of the incident beam and outputting a signal corresponding to an intensity of the received beam, so that the presence/absence of a defect on the surface of the inspecting object is inspected on the basis of an intensity distribution on the light receiving surface of the light receiving means, comprising: input means for inputting periodic information of a predetermined pattern; and driving means for adjusting a relative position between the incident beam and the predetermined pattern on the basis of the information from the input means.

It is still another object of the present invention to provide a defect inspecting apparatus capable of inspecting a foreign particle different from a circuit pattern at a high discriminating detection ratio regardless of the degree of micropatterning of the circuit pattern. In other words, this object of the present invention is to provide a defect inspecting apparatus capable of inspecting, at a high discriminating detection ratio, the foreign particle different from the circuit pattern which generates spatially continuous diffracted light in such a manner that light diffracted by a coarse pattern which generates the spatially continuous diffracted light is converted into a pseudo discrete diffracted light.

In order to achieve the above object of the present invention, there is provided a defect inspecting apparatus including a light source for emitting a predetermined beam on an inspecting object having a predetermined pattern thereon, focusing means for focusing the beam from the light source on an inspecting point on the inspecting object at a predetermined angular aperture, moving means for relatively moving the incident beam radiated on the inspecting object and the inspecting object, and light receiving means, spaced apart from the inspecting point by a predetermined distance, for receiving a beam emerging from the inspecting point upon incidence of the incident beam and outputting a signal corresponding to an intensity of the received beam, so that the presence/absence of a defect on the surface of the inspecting object is inspected on the basis of a light receiving signal from the light receiving means, comprising an adjusting member for forming a dark portion (non-spectral region) in which an intensity of the diffracted light incident on the light receiving means is partially almost zero, wherein the light receiving means has a plurality of light receiving areas for outputting independent light receiving signals, and the light receiving areas are so determined that a distance between two adjacent ones of the plurality of light receiving areas is smaller than a width of the dark portion.

It is still another object of the present invention to provide an optical element capable of focusing light on a plane in accordance with a predetermined conversion rule even at an exit angle is close to as large as, e.g., 90° when the light emerging from a predetermined area is focused on the plane in accordance with the predetermined conversion rule.

It is still another object of the present invention to provide an optical element capable of observing a Fourier spectrum of particularly a fine object in a wider frequency range than a conventional frequency range.

In order to achieve the above objects, a plurality of optical transmission elements having light incident ends arranged on different positions on a spherical surface and light exit ends two-dimensionally arranged in matrix form are bundled.

Also, according to the present invention, there are provided the following for a defect inspecting apparatus having:
irradiating means to irradiate a given beam onto an inspecting object with given patterns formed on its surface;
light receiving means to receive beams from said inspecting object and output signals in accordance with the intensity of said beams, said light receiving means having a plurality of light receiving areas capable of photoelectrically converting the light received independently;
measuring means to measure distribution condition of said beams from said inspecting object;
selecting means to select and the arrangement of said plural light receiving areas in accordance with said distribution condition; and
detecting means to detect defectives in accordance with signals from said light receiving means.

BRIEF DESCRIPTION OF THE DRAWINGS

FIGS. 31A to 31D are views for explaining the principle of discriminating a circuit pattern from a foreign particle.

FIG. 56 is a schematic sectional view of the first application example.

FIGS. 57A and 57B are a schematic sectional view and a perspective view, respectively, showing the second application example of the optical element according to the present invention.

FIGS. 81A, 81B, and 81C are views showing an optical path system for explaining Fourier transform, in which FIG. 81A a view showing the Fourier spectrum on the Fourier transform plane, FIG. 81B is a view showing diffracted light from a Fourier transform lens and a circuit pattern $A_p$, and FIG. 81C shows the circuit pattern $A_p$;

FIGS. 82A and 82B are views showing an optical path system obtained when a lens is used as a Fourier transform element, in which FIG. 82A is a view showing a Fourier spectrum on the Fourier transform plane and FIG. 82B is a view showing the Fourier transform lens, the optical system of the defect inspecting apparatus, and diffracted light; and FIG. 83A and 83B are views illustrating an optical path system obtained when a new optical element except for a lens is used as a Fourier transform element, in which FIG. 83A is a view showing a Fourier spectrum on a Fourier spectrum plane and FIG. 83B is a view showing light diffracted from an optical element using an optical filter.

DETAILED DESCRIPTION OF THE PREFERRED EMBODIMENTS

Figure 1:
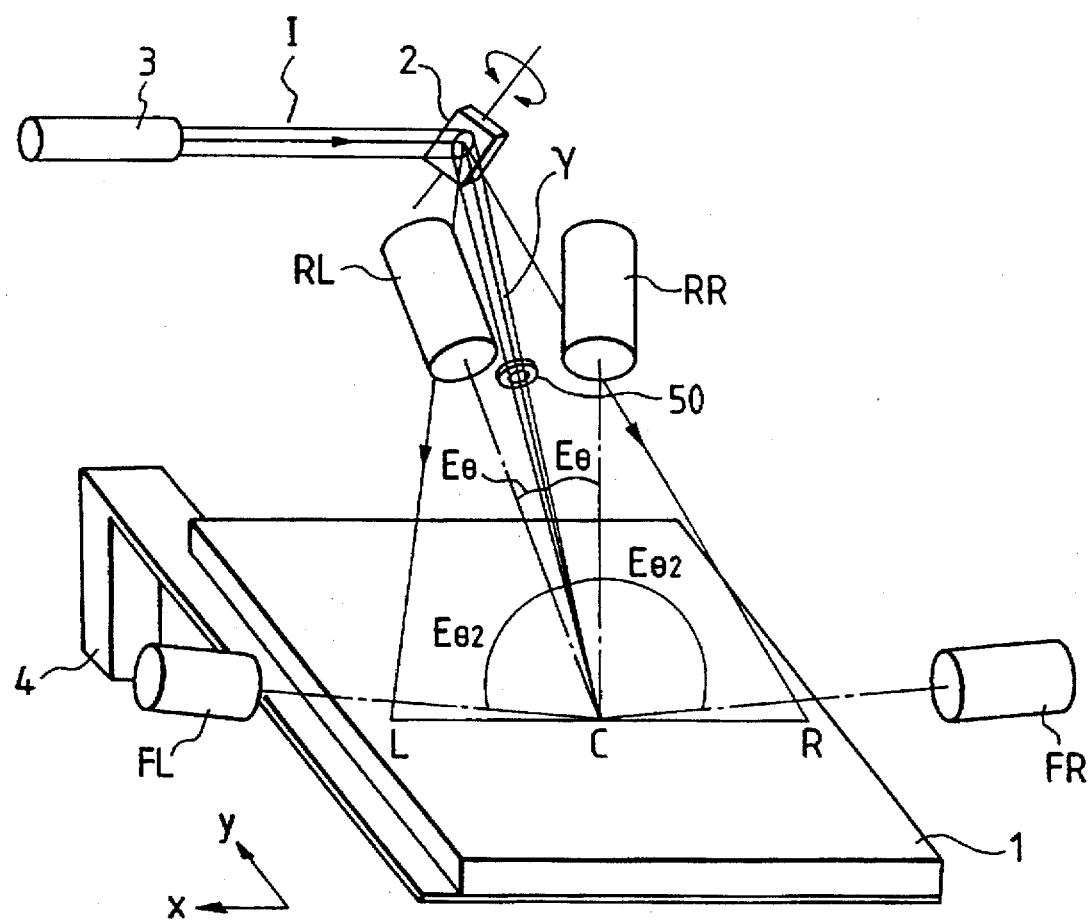
FIG. 1 is a view schematically illustrating a defect inspecting apparatus according to a first embodiment of the present invention.

FIG. 1 is a perspective view schematically illustrating a defect inspecting apparatus preferably applicable as a first embodiment according to the present invention. Light from a light source 3 is incident diagonally upon a substrate (reticle, wafer, or the like) 1 at a given incident angle through a vibrating mirror 2, and an f-θ lens 50. The incident light I is converged by the f-θ lens 50 onto the substrate 1 at a given aperture angle γ. The vibrating mirror 2 scans the incident light I on the substrate 1 in the direction X. The optical scanning is performed over a scanning area L - C - R. The substrate 1 is stacked on a carrier arm 4. The carrier arm 4 is movable by a motor or other driving means (not shown) in direction (direction Y) substantially perpendicular to the direction of the optical scan. Then, the carrier arm 4 is moved on the scanning area L - C - R in the direction Y so as to enable the optical scan to be performed over the entire surface of the substrate 1. Further, the scanning position in the direction X is obtainable by the driving signals from the driving system of the vibrating mirror 2, for example, while the scanning position in the direction Y is obtainable by the encoder which detects the position of the carrier arm 4, for example. The f-θ lens 50 is a lens capable of scanning the entire scanning area L - C - R.

Each of the optical axes of optical receivers RL and RR is arranged in the direction intersecting at angles $E_θ$ (an acute angle) or the direction parallel to each of the incident surfaces of the incident light I on the scanning area L - C - R. The two optical receivers are provided at angles substantially symmetrical to the incident surface.

Each of the axes of the optical receivers FL and FR are arranged in the directions intersecting at angles α2 of approximately 90°±20° to each of the incident surfaces of the incident light I on the scanning area L - C - R. The two optical receivers are arranged at angles substantially symmetrical to the incident surface.

Each of the axes of the optical receivers RL and RR and the optical receivers FL and FR is provided at an acute angle to the surface of the substrate 1.

Figure 2:
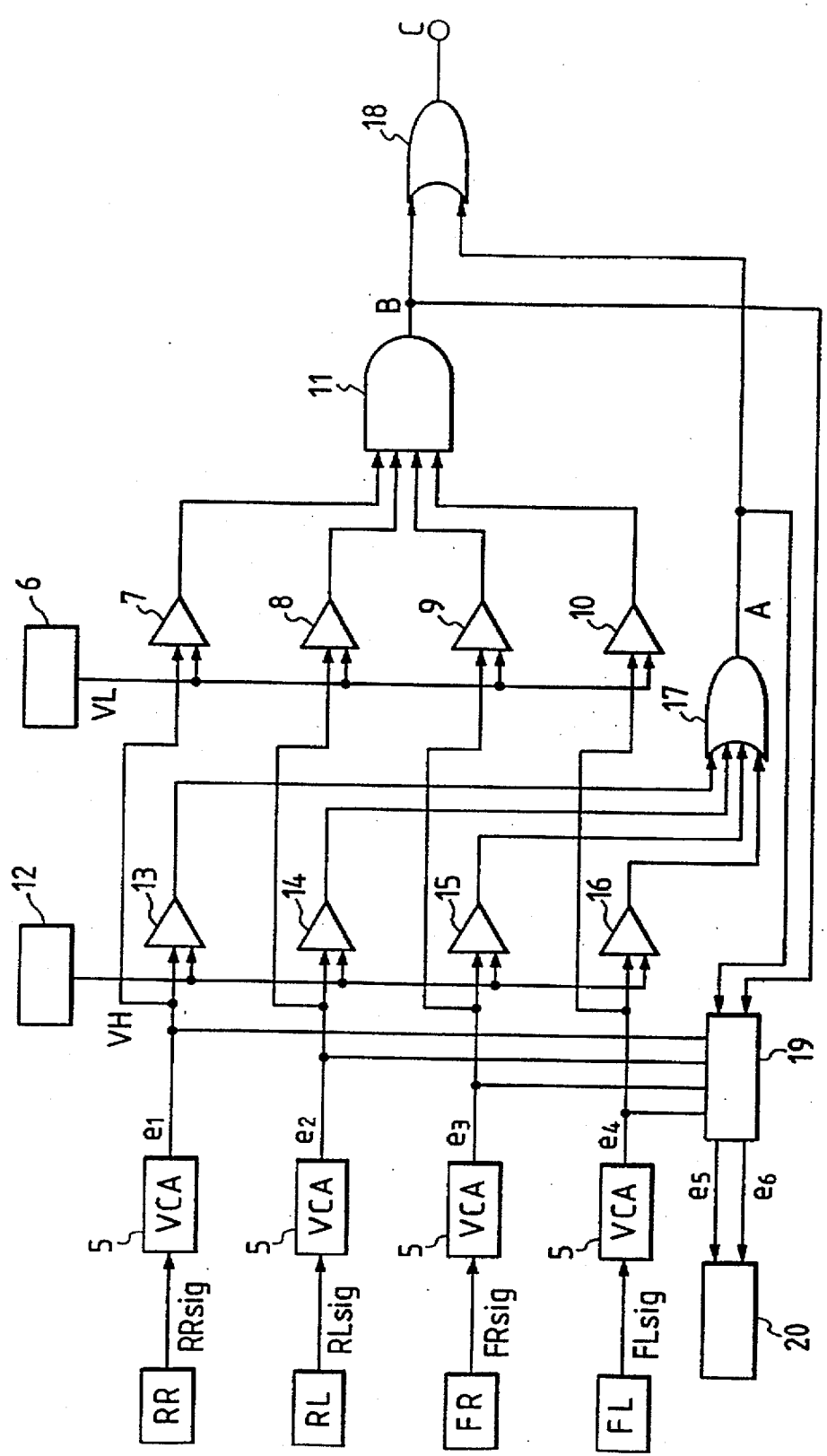
FIG. 2 is a diagram showing a signal processing system according to the first embodiment of the present invention.

FIG. 2 is a view showing the signal processing systems according to the first embodiment of the present invention. The scattering rays of light or diffractive light received by the optical receivers RR, RL, FR, and FL in FIG. 1 are photoelectrically converted to become signals RRsig, RLsig, FRsig, and FLsig shown in FIG. 2. Each signal is controlled by a variable gain amplifier (VCA) 5 so that its light receiving sensitivity is constant without depending on its inspecting position in the direction X. Each of the signals $e_1$, $e_2$, $e_3$, and $e_4$ amplified by each of the VCAs 5 is inputted into each of the comparators 7, 8, 9, and 10. Further, to the other input of each of the comparators 7, 8, 9, and 10, a slice voltage VL is applied from a slice level generator 6. Each of the comparators 7, 8, 9, and 10 outputs logical value 1 only when the signals $e_1$, $e_2$, $e_3$, and $e_4$ are greater than the slice voltage VL. Then, each output of the comparators 7, 8, 9, and 10 is applied to an AND circuit 11. The AND circuit 11 Generates the logical value 1 as an output B only when all the outputs from the comparators 7, 8, 9, and 10 are of the logical value 1.

Also, each of the signals $e_1$, $e_2$, $e_3$, and $e_4$ amplified by the VCA 5 is inputted into each of the comparators 13, 14, 15, and 16, respectively. Further, to the other inputs of the comparators 13, 14, 15, and 16, is applied a slice voltage VH from the slice level generator 12. The slice voltage VH is higher than the slice voltage VL applied to the comparators 7, 8, 9, and 10, and is set in such a manner that its value is higher than the maximum values of the output signals $e_1$, $e_2$, $e_3$, and $e_4$ (these being the maximum values of the output signals by the scattering rays of light and diffractive light from the circuit pattern) irrespective of the intensity of the scattering rays of light from the circuit pattern that may take place. Each of the comparators 13, 14, 15, and 16 outputs the logical value 1 only when the signals $e_1$, $e_2$, $e_3$, and $e_4$ are greater than the slice voltage VH. Then, each output from the comparators 13, 14, 15, and 16 is applied to The OR circuit 17. The OR circuit 17 generates the logical value 1 as its output A when at least one of the outputs of the comparators 13, 14, 15, and 16 is of the logical value 1.

The output A from the OR circuit 17 and the output B from the AND circuit 11 are applied to an OR circuit 18. The OR circuit 18 generates the logical value 1 as its output C when at least one of the output A and output B is of the logical value 1. This output C becomes a signal to detect the presence of a foreign particle. Also, each of the output signals $e_1$, $e_2$, $e_3$, and $e_4$ from the VCA 5 is inputted into a signal selector 19. The signal selector 19 has two comparators, an H comparator to select a signal $e_5$ which represents the greatest level of the output signals $e_1$, $e_2$, $e_3$, and $e_4$, and an L comparator to select $e_6$ which is the smallest level. These selected signals $e_5$ and $e_6$ are stored in a memory 20, respectively.

The foreign particle (comparatively small foreign particle) which has a contour less than several times the wavelength of the incident light I is detected by the logical product of the signals binary coded by the slice voltage VL. On the other hand, since there is directivity in the scattering rays of light emitted from the foreign particle (comparatively large foreign particle) which has a contour more than several times the wavelength of the incident light I, these rays may not be inputted into any one of the photoreceivers RL, RR, FR, and FL. A comparatively large foreign particle such as this is detected by the logical sum of the signals binary coded by the slice voltage VH. There is no foreign particle which remains undetected accordingly.

In other words, the output A is used for detecting any foreign particles which have its contour more than several times the wavelength of the incident light I (comparatively large foreign particle), for example, while the output B is used for detecting any foreign particles which have its contour less than several times the wavelength of the incident light I (comparatively small foreign particle), for example.

Then, the output from the OR circuit 18 can be output to a display or a printer (not shown) together with the positional information regarding directions X and Y as well as the sizes of the foreign particles, which is provided by the foregoing driving signals and encoder. (Such an information will be described later in detail.) These pieces of information will be stored in the memory 20.

Hereinafter, using these outputs A and B, the description will be made of the logic with which to obtain detection signals corresponding to the sizes of the foreign particles.

When the logical value of the output A is 1, the pattern noise can be regarded as small. Therefore, it is possible to make measurement with the greatest level signal $e_5$ as its detection signal. Also, when the logical value of the output B is 1, it is possible to make measurement with the smallest level signal $e_6$ as its detection signal taking pattern noise into account. In this way, the accuracy with which to measure the sizes of foreign particles can be improved. It is particularly possible to improve the measurement accuracy for the comparatively large foreign particles. Also, for the selection of the signal $e_5$ and signal $e_6$, it may be possible to select either one of the two comparators 19 for inputting the signals $e_1$ to $e_4$ in accordance with the output of the signal A or signal B.

In this respect, while the description has been made so as to set a high slice level and a low slice level with a level difference given to the two slice levels, it may be possible to give a level difference between the signals to be inputted into the two comparators with only one value for the slice level. For example, the slice levels applied to the comparator 13 and comparator 7 are made equal. Then, for the signal applied to the comparator 13, a signal produced by lowering a given amount of level from the signal $e_1$ of the photoreceiver RR, while for a signal to be inputted into the comparator 7, the signal $e_1$ from the photoreceiver RR is used as it is. In other words, it should be good enough only if two cases are established where the differences between the signal levels and slice levels to be compared differ interrelatedly.

Here, the slice voltage $VH_1$ is set higher than the maximum value of the output signals $e_{11}$, $e_{12}$, $e_{21}$, $e_{22}$, $e_{31}$, $e_{32}$, $e_{41}$, and $e_{42}$ by the scattering rays of light (diffractive light) from the circuit pattern irrespective of the intensity of the scattering rays of light (or diffractive light) by the circuit pattern on the substrate 1.

Also, for the apparatus shown in FIG. 1, a visual observation microscope and a television camera (not shown) are provided. These observation systems are arranged movably in accordance with the information of the adhering position of any foreign particles. For example, a foreign particle detection is displayed on a CRT in accordance with the information regarding the foreign particle detection and adhering position. Thus, by designating on the map a foreign particle to be observed, the observation systems are driven to the position where such a foreign particle adheres; hence making it possible to easily observe the target particle visually.

Further, depending on the contour of the foreign particles, directivity is generated in the scattering rays of light from them, which may conceivably make its measurement reproducibility inferior. Therefore, it may be possible for those presenting the logical value of the output A as 1 and the logical value of the output B as 0 to arrange a sequence which enables a visual observation thereof possible by driving the observation system to the coordinated position where such foreign particles adhere.

Figure 3:
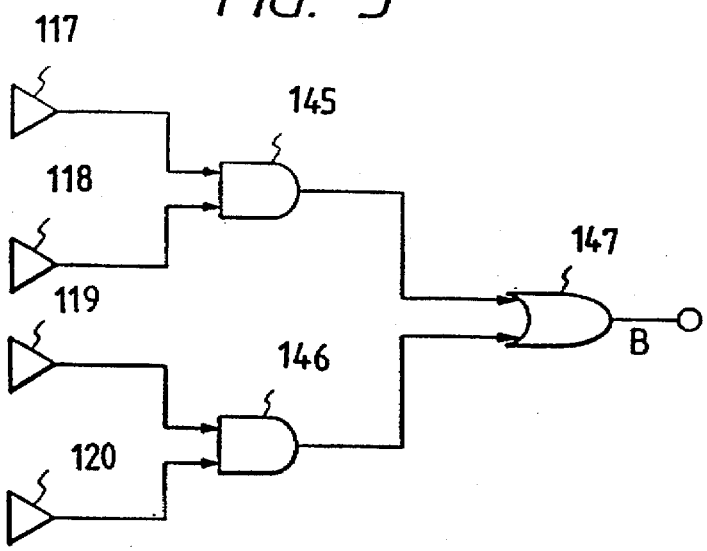
FIG. 3 is a diagram showing a variation of the signal processing system shown in FIG. 2.

FIG. 3 is a view illustrating a variation of the logic represented in FIG. 2. In FIG. 2, it is arranged that the AND circuit 11 outputs the output B as its foreign particle detection signal when all of the signals $e_1$, $e_2$, $e_3$, and $e_4$ are of the logical value 1. In FIG. 3, however, the outputs from a comparator 117 and comparator 118 are inputted into an AND circuit 145 while the outputs from a comparator 119 and comparator 120 are inputted into an AND circuit 146. The outputs from the AND circuit 145 and AND circuit 146 are inputted into an OR circuit 147. The logic of the OR circuit 147 is arranged so that it generates the logical value 1 as its output B when at least one of the AND circuit 145 and AND circuit 146 outputs the logical value 1. With the logic thus arranged, it is possible to improve the accuracy with which to detect any foreign particles having a given directivity in the scattering rays of light therefrom. Also, the outputs from the comparator 117 and comparator 119 may be inputted into the AND circuit 145 while the outputs from the comparator 118 and comparator 120 may be inputted into the AND circuit 146. Then, the outputs from the AND circuit 145 and AND circuit 146 are inputted into the OR circuit 147. The logic may be arranged in this way. Further, it may be possible to make the number of signals three to provide a logical product. It may also be possible to arrange so that the outputs from the comparators 117, 118, and 119 are inputted into the AND circuit 145 while the output from the AND circuit 145 and the output from the comparator 120 are inputted into the OR circuit 147.

Further, in order to obtain a foreign particle detection signal, the logic may be made to output the logical value 1 when all the $m_1$ numbers of signals among the signals $e_1$, $e_2$, $e_3$, and $e_4$ exceed the low slice level VL, and the logic is further arranged so that the logical value 1 is output when at least $m_2$ number of the signals $e_1$, $e_2$, $e_3$, and $e_4$ exceeds the high slice level VH; and at the same time, the relationship $m_1 > m_2$ is maintained.

Now, the description will be made of a second embodiment according to the present invention.

Figure 4:
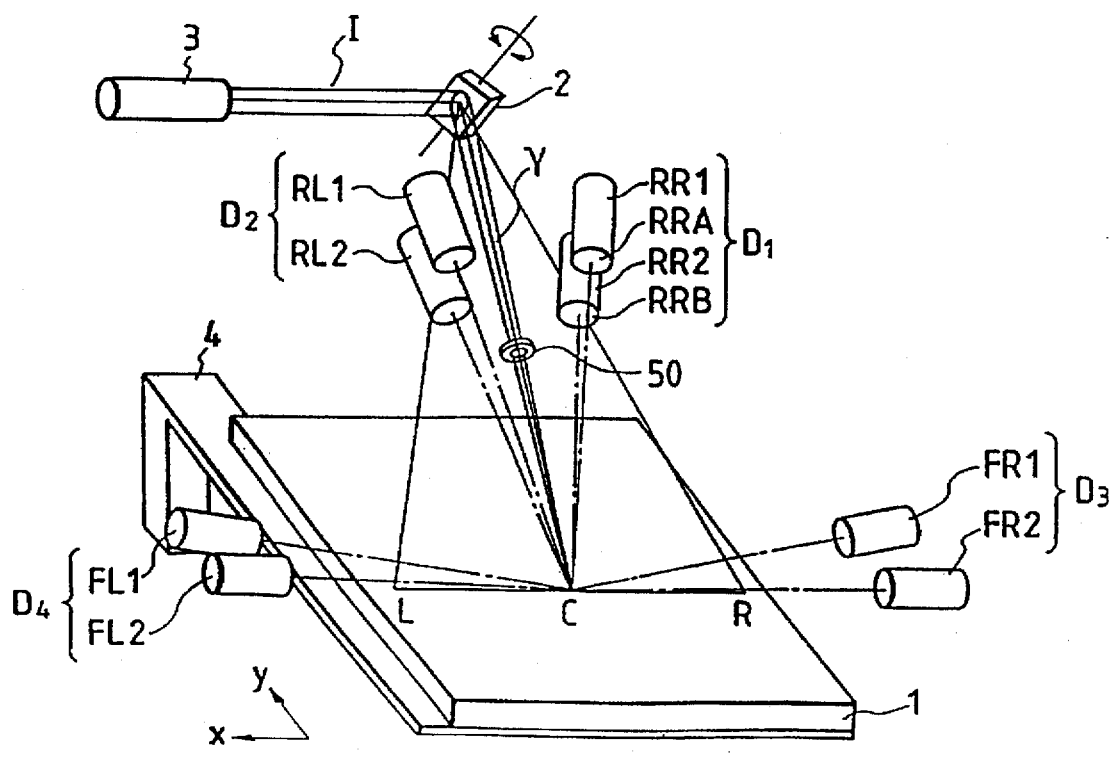
FIG. 4 is a view schematically illustrating a defect inspecting apparatus according to a second embodiment of the present invention.

FIG. 4 is a perspective view schematically showing a defect inspecting apparatus to which the second embodiment is preferably applicable according to the present invention. Compared to the apparatus shown in FIG. 1, the number of the optical receivers is double. This is needed to enhance the capability to distinguish foreign particles from patterns. Eight photoreceivers are classified into four sets of photoreceiver groups D1 (RR1 and RR2), D2 (RL1 and RL2), D3 (FR1 and FR2), and D4 (FL1 and FL2) each having a set of two photoreceivers.

The two photoreceivers (RR1 and RR2, and others) constituting the photoreceiver groups are the photoreceivers wherein the angles made by the optical axis of each photoreceiver and the center line of the incident light I are substantially equal.

Now, hereinafter, the description will be made of the present embodiment with the assumption that circuit patterns such DRAM are formed on the substrate 1. A circuit pattern such as this often includes periodic patterns (particularly, two dimensional periodic patterns). The two dimensional periodic patterns on the substrate 1 are assumed to be element separation patterns, capacitors, contact holes, and the like. These periodic patterns are formed by a comparatively minute high patterning. Most of them are such patterns as having cycles in the directions X and Y on the substrate 1 or linearly symmetrical cycles in the direction X or Y. Here, it is assumed that the directions X and Y of the substrate and the directions X and Y in FIG. 4 are matched, and hereinafter, these are referred to simply as direction X and/or direction Y.

Subsequently, the description will be made of the diffractive light emitted by the two dimensional periodic patterns.

Figure 5:
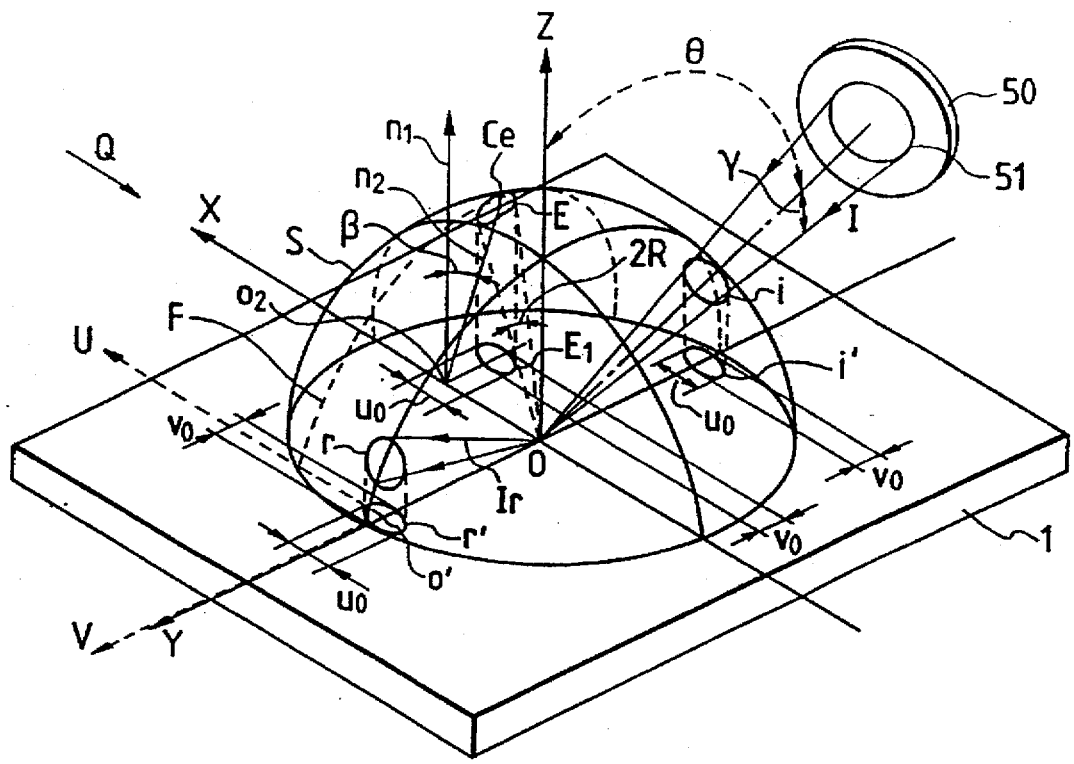
FIG. 5 is a view illustrating the distribution of diffractive light using an imaginary sphere.

FIG. 5 is a view schematically showing a part of FIG. 4 in order to illustrate a state where the diffractive light being emitted by the two dimensional periodic patterns. In FIG. 5, the incident light I is a conical beam having a given aperture angle (an angle being determined by the aperture number of the f-θ lens 50) γ with an inspecting point 0 as its center. It penetrates a part of the spherical plane of the sphere S. The sphere S is an imaginary sphere of an arbitrary radius with the surface of the substrate 1 is its equator. This penetrated portion (where the incident beam I and the spherical plane of the sphere S are superposed) is represented as a curved section i in FIG. 5. Also, the positive projection to the surface of the substrate 1 (X - Y plane) of the curved section i is designated by a reference mark i' in FIG. 5. Likewise, regarding the positively reflective beam $I_r$, the curved section which is superposed with the sphere S is designated a reference mark r while the positive projection to the X - Y plane of the curved section r, as r' in FIG. 5. Here, since the focus point of the incident beam I and the inspecting point O are matched, the positive projection i' and positive projection r' are congruent figures.

The figures of the positive projection i' and positive projection r' (hereinafter represented as positive projection i' (r')) are determined by the aperture angle γ of the incident beam I and the incident angle θ. Now, given the radius of the sphere S as 1/λ (λ=the wavelength of the incident light), the length $V_0$ of the positive projection i' (r') in the direction V and the length $U_0$ in the direction U are expressed in the following equations (2) and (3):

$$V_0 = (2/\lambda) \cdot \sin\gamma \cdot \cos\theta \qquad (2)$$

$$U_0 = (2/\lambda) \cdot \sin\gamma \qquad (3)$$

Figure 6:
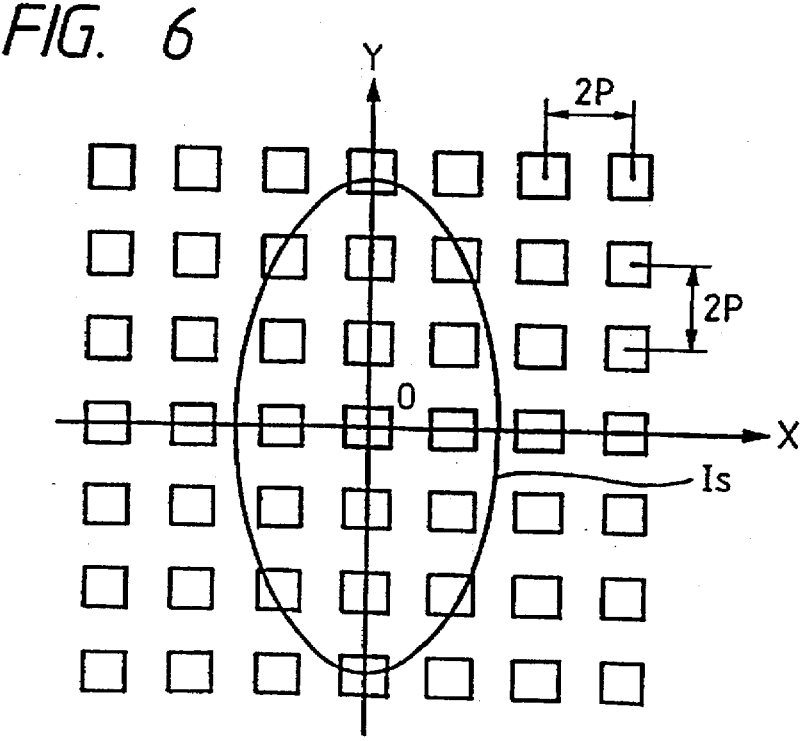
FIG. 6 is a view showing the irradiating area of an incident beam.

Here, if the irradiating area of the incident beam I is small as compared with the circuit patterns so that plural circuit patterns cannot enter the irradiating area, the emission of diffractive light is simple. Hence, it is possible even for a conventional apparatus to meet the requirements. However, with the patterns which are now more minute, a plurality of circuit patterns are present in the irradiating area and diffractive light is emitted shatteringly. Also, an isotropic distribution of diffractive light will result after all. Therefore, it is difficult to distinguish foreign particles from circuit patterns using the two photoreceivers as described above. FIG. 6 shows two dimensional patterns arranged both in directions X and Y with pitches 2P. In the present embodiment, the exit pupil 51 (see FIG. 5) of the f-θ lens 50 is circular, and since the incident beam I enters the circuit patterns at an incident angle θ, the irradiating area $I_s$ becomes elliptic. As a result, even with the diffractive light from the patterns which are arranged at the same pitches in the directions X and Y, the figure of the positive projection is such that it has its shorter direction in the direction Y and the interval between the diffractive light in the direction Y becomes wider than in the direction X.

Now, the description will be made of the distributional state of diffractive light with a particular attention given to the periodicity of minute two dimensional cycle patterns.

Figure 7A:
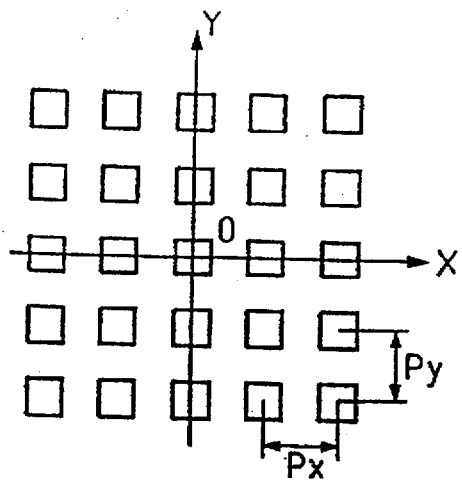
FIG. 7A shows an example of circuit patterns.
Figure 7B:
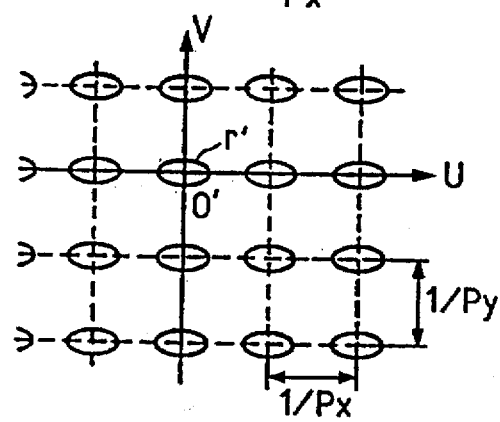
FIG. 7B illustrates the distribution of diffractive light on a positively projected view.
Figure 7C:
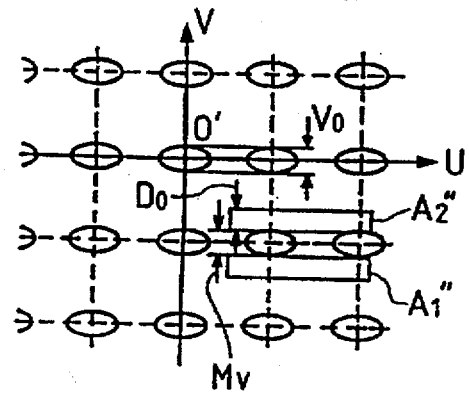
FIGS. 7C and 7D are views illustrating the distribution of diffractive light and the arrangement of light receiving areas.
Figure 7D:
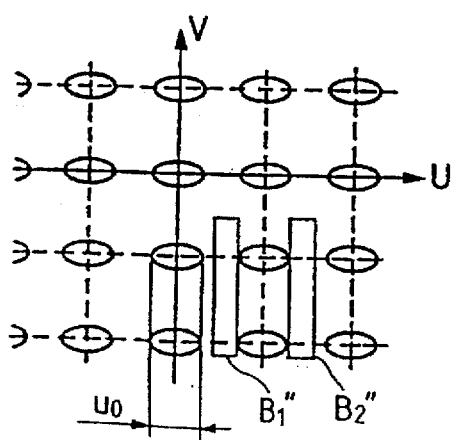

At first, the state of emission is considered as to the diffractive light from a two dimensional cycle pattern (its pitch in the direction X being $P_X$, and pitch in the direction Y, $P_Y$) along the orthogonal coordinates X and Y shown in FIG. 7A. A two dimensional cycle pattern along the orthogonal coordinates X and Y such as shown in FIG. 7A is often used for capacitors, contact holes, and the like for DRAM. FIG. 7B is a view showing the positive projection of the curved section, that is, a superposed area of the diffractive light from a circuit pattern and the sphere S, which is drawn in the same procedure as drawing the positive projection r' (i') in FIG. 5. The coordinate axes U and V in FIG. 7B are new coordinate axes with its origin O' as the center of the positively reflective light $I_r$ and positive projection r'. The X and Y coordinate axes represent its actual plane. Whereas its unit is length, the U and V coordinate axes are the Fourier plane representing the directional cosine of the diffractive light and its unit is spatial frequency. The diffractive light from a minute circuit pattern is spatially emitted at a degree of scattering. As shown in FIG. 7B, the positive projection of the diffractive light also scatters. At the same time, each of the positive projections of the scattering diffractive light shows a congruent figure to the positive projection r' of the positively reflective light. Further, the pitch of the positive projection of the diffractive light is inversely proportional to the pitch of an actual pattern. The pitch in the U axial direction becomes $1/P_X$ while the pitch in the axis direction becomes $1/P_Y$.

Figure 8A:
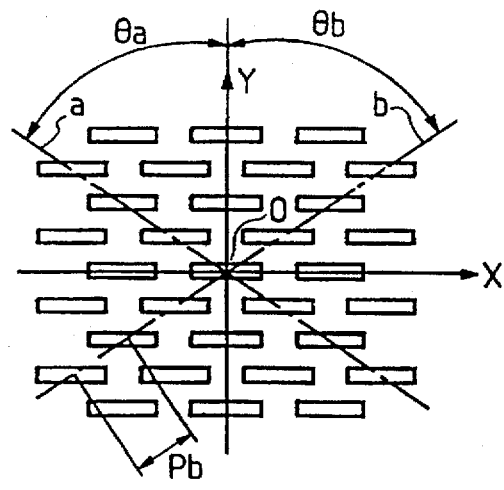
FIG. 8A shows an example of circuit patterns.
Figure 8B:
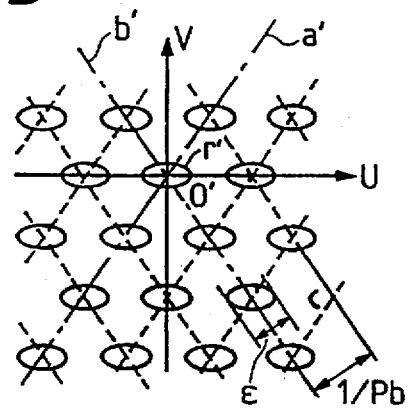
FIG. 8B illustrates the distribution of diffractive light on a positively projected view.

FIG. 8A shows a cycle pattern arranged at each pitch Pb in the axial directions a and b. The axis a and axis b and the axis X and axis Y are in a linearly symmetrical relations, and the axis a inclined to the axis Y by $\theta_a$ and the axis b is inclined b to the axis Y by $\theta_b$. The pattern shown in FIG. 8A is often used as an element separator. FIG. 8B shows the positive projection of the diffractive light from a circuit pattern. Its relation to FIG. 8A is the same as the relation between FIG. 7A and FIG. 7B. The periodic directions a' and b' of the diffractive light in FIG. 8B are perpendicular to the periodic directions a and b of the pattern, respectively. The pitch in the periodic direction a' or b' of the positive projection of the diffractive light becomes $1/P_b$, and is inversely proportional to the pitch $P_b$ of the pattern.

Figure 8C:
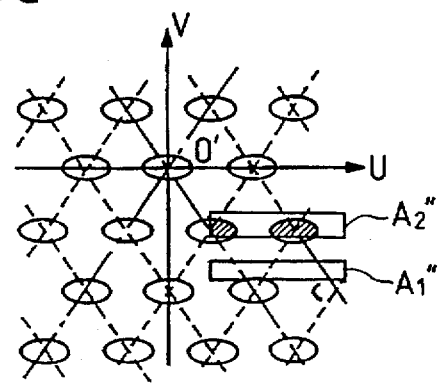
FIGS. 8C, 8D, and 8E are views illustrating the distribution of diffractive light and the arrangement of light receiving areas.
Figure 8D:
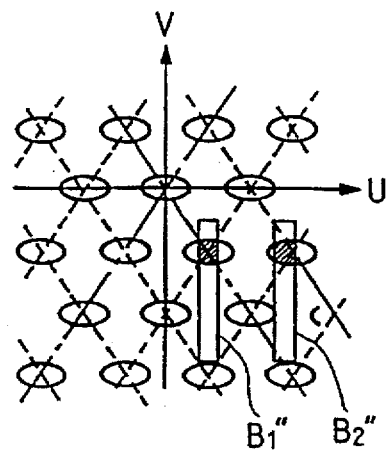
Figure 8E:
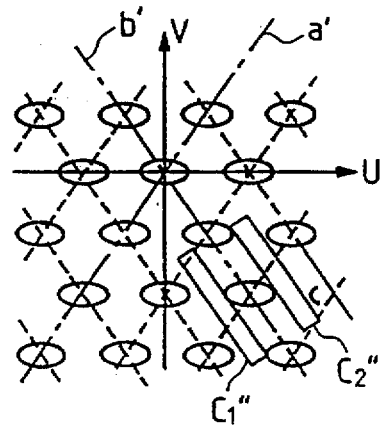
Figure 9A:
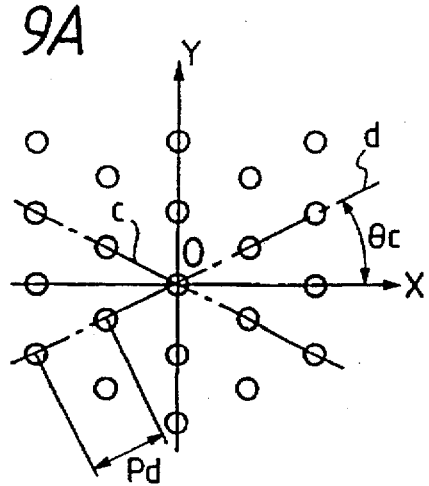
FIG. 9A shows an example of circuit patterns.
Figure 9B:
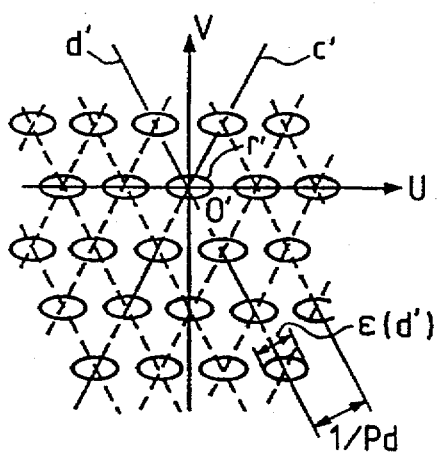
FIG. 9B illustrates the distribution of diffractive light on a positively projected view.
Figure 9C:
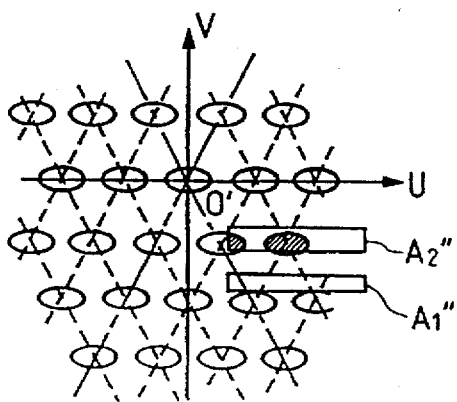
FIGS. 9C, 9D, and 9E are views illustrating the distribution of diffractive light and the arrangement of light receiving areas.
Figure 9D:
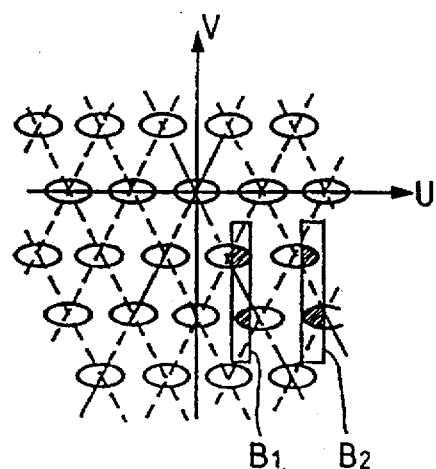
Figure 9E:
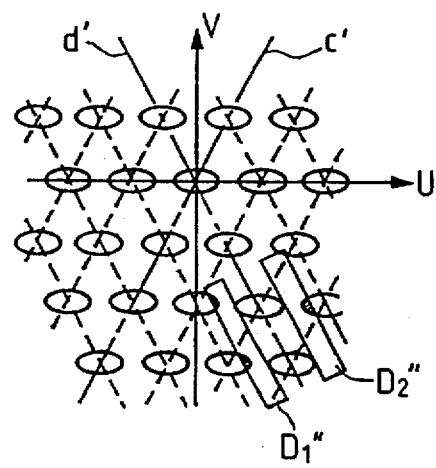

FIG. 9A is a view showing an example in which a general pattern having periodic directions in the c axis and d axis which are symmetrical to the axis X and axis Y is arranged in each of the periodic directions at a pitch $P_d$, respectively. The axis c and axis d are inclined to the axis X by $\theta_c$, respectively. The coordinate positions of the UV coordinates where the diffractive light is distributed are independent of each individual figure of the pattern. Therefore, only its existing locations are designated by circles. FIG. 9B shows the positive projection of the diffractive light from the circuit pattern shown in FIG. 9A. The relation with FIG. 9A is the same as the relation between FIG. 7A and FIG. 7B. The positive projection of the diffractive light in FIG. 9B is distributed over the axis c' and axis d'. As in the case in FIG. 8, the axis c and axis c', and the axis d and axis d' are orthogonal to each other, respectively, and the pitch $1/P_d$ in the periodic direction of the diffractive light is inversely proportional to the $p_d$ of the pattern.

As described above, if the geometrical figure of a circuit pattern is known, it is possible to predict the possible distribution of a diffractive light to be emitted. It is thus easy to obtain the pitch and periodic direction in the positively projected view of the scattering diffractive light from the two dimensional cycle pattern as described in conjunction with FIGS. 7A to 9E.

FIG. 5 shows a positive projection $E_1$ which is one of these diffractive rays of light, and its curved section E. Here, the intersecting point of the straight line parallel to the axis Y (axis V), which run through the center of the positive projection $E_1$, and the axis X is designated by a mark O'. The straight line parallel to the axis Z including the intersecting point O' is designated by a mark $n_1$. The straight line including the center Ce of curved section E and the intersecting point O' is designated by a mark $n_2$. The angle (a spatial angle formed by curved lines F on the sphere S parallel to the direction Y) formed by the straight lines $n_1$ and $n_2$ is given as $\beta$. Also, the spatial angle with respect to the direction Y with the incident point O of the curved section E as its center is given as 2R.

Hereinafter, using FIGS. 7C and 7D, FIGS. 8C, 8D and 8E, and FIGS. 9C, 9D, and 9E, the description will be made of the optimization of the light receiving area arrangement. The optical receivers RR1, RR2, RL1, RL2, FR1, FR2, FL1, and FL2 shown in FIG. 1 are so arranged that light receiving surfaces thereof are located on the imaginary sphere S (FIG. 2). In these figures, only the width $D_0$ of the positive projection $A_1$, $A_2$, $B_1$, $B_2$, $C_1$, $C_2$, $D_1$, and $D_2$ of each light receiving area, the interval between the light receiving areas and the angle are represented by modifying them on the positively projected view.

The two dimensional cycle patterns shown in FIG. 7A, FIG. 8A, and FIG. 9A are the patterns having two symmetrical periodic directions in the axis X (or axis Y). Therefore, the distribution of the emitted diffractive light has its periodic directions in the U and V axial directions besides in the directions (a', b', c', and d') perpendicular to the periodic directions of the circuit pattern (a, b, c, and d) as shown in FIG. 7B, FIG. 8B, and FIG. 9B.

Now, as an example, the circuit pattern in FIG. 8A is considered. In this case, the direction in which the light receiving area having its longitudinal direction is arranged is the direction parallel to the four directions of U axis, V axis, a' axis, and b' axis. FIG. 8C, FIG. 8D, and FIG. 8E represent the light receiving areas corresponding to them. As shown in these figures, since the emitted diffractive light becomes elliptical on the positively projected view (on the UV coordinates), the width of the ellipse in each of the directions (U axis direction, V axis direction, a' axis direction, and b' axis direction) is defined as $\epsilon$. As described earlier, the width in the U axis direction and V axis direction are $\epsilon$ (U)=$V_0$, $\epsilon$ (V)=$U_0$.

Now, the description will be made of the discrimination between patterns and foreign particles in the present embodiment. Here, the photoreceiver group D1 is taken as an example, and the description will be made of the discrimination between the circuit patterns and foreign particles performed by a set of photoreceivers according to the present embodiment.

Figure 10:
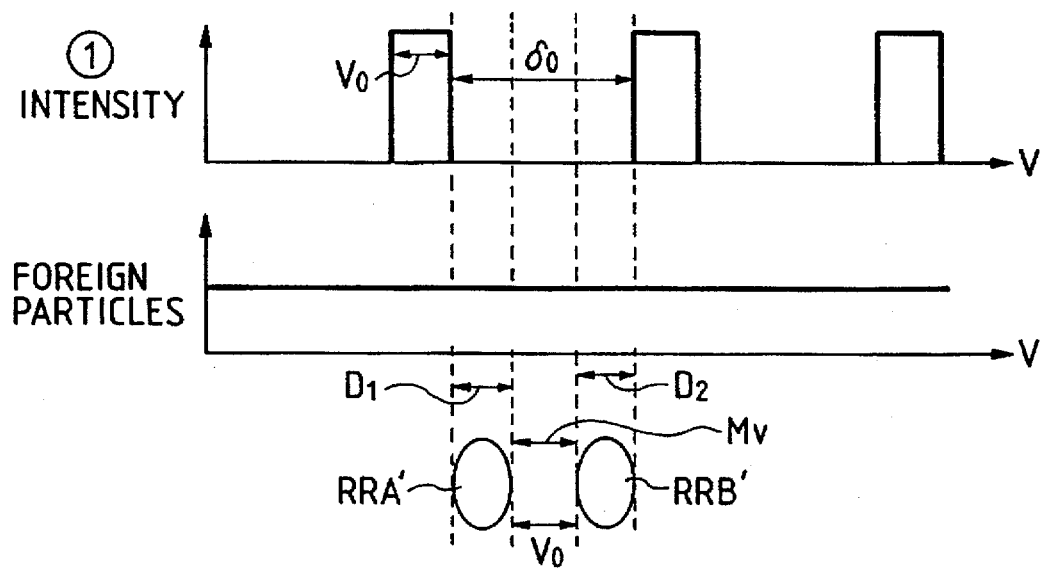
FIG. 10 is a view illustrating the principle of discrimination between foreign particles and circuit patterns according to the second embodiment of the present invention.

FIG. 10 is a view showing the principle of the discrimination where two light receiving surface exist. The axis of ordinate represents the intensity of diffractive light as well as the intensity of scattering rays of light from foreign particles while the axis of abscissa represents the positions of positive projection on the V axis. Here, as shown in FIG. 7A, a two dimensional cycle pattern is taken into account, and then there will be considered the intensity distribution of the diffractive light in one array, the positive projection of which is in the direction parallel to the V axis, among the distributions of diffractive light. As described earlier, the diffractive light from a minute pattern is scatteringly distributed. Also, as described earlier, the positive projection of each diffractive light and the positive projection r' of the positively reflective beam Ir are substantially congruent in its figures. Also, the positive projection r' of the positively reflective beam Ir and the positive projection i' of the incident beam I shown in FIG. 5 are substantially congruent in its figures. Therefore, the positive projection i' and the positive projection of each diffractive light are substantially congruent in its figures. The photoreceivers are arranged with a particular attention to this scattering degree as well as the figures of the positive projection of each diffractive light, and in describing the present embodiment with reference to FIG. 5 and FIG. 10, two photoreceivers are arranged to satisfy the following two conditions:

(1) The interval Mv between the positive projections RRA' and RRB' of the respective light receiving surfaces of the photoreceivers RR1 and RR2 is defined to be more than the width $v_0$ of the positive projection i of the incident beam I in the V direction.

(2) The sum of the width $D_1$ of the positive projection RRA' on the light receiving surface RRA in the V direction, the width $D_2$ of the positive projection RRB' on the light receiving surface RRB in the V direction, and the interval Mv between the two positive projections is defined to be less than the interval between the diffractive rays of light adjacent in the V direction.

By arranging the photoreceivers in this way, the spatially scattering rays of diffractive light from the minute circuit pattern are not allowed to enter any of the light receiving surfaces RRA and RRB. On the other hand, the scattering rays of light which are spatially continuous from foreign particles enter both of the two light receiving surfaces RRA and RRB. As a result, it becomes possible to distinguish foreign particles from circuit patterns by obtaining the logical product of signals from each of the light receiving surfaces as described earlier.

Hereinafter, this is referred to as discrimination by discreteness.

The resolution Res at this juncture is determined by the following equation (4):

$$Res = D_1 + Mv + D_2 \quad (4)$$

In FIG. 10, a mark 1 in circle designates the distribution of the positive projections in FIG. 7B.

In this case, the width of the positive projection of each diffractive light is given as $v_0$, and it is assumed that $Mv = v_0$. Then, the sizes (sizes of $D_1$ and $D_2$) of the light receiving surfaces RRA and RRB are determined so at to make $A_0 \geq D_1 + v_0 + D_2$.

From the equation (4) it is clear that the smaller the ($D_1$, $D_2$) and Mv, the more is the resolution enhanced. From the viewpoint of the resolution, it is advantageous to make the Mv and $v_0$ substantially equal.

The same is applicable to the U direction, it is good enough to arrange the photoreceivers in a condition $Mv \geq u_0$ and satisfy the foregoing conditions (1) and (2). The principle of discrimination by the above discreteness is described in a continuation of application Ser. No. 757,042 (filed on Sep. 9, 1991).

Figure 54:
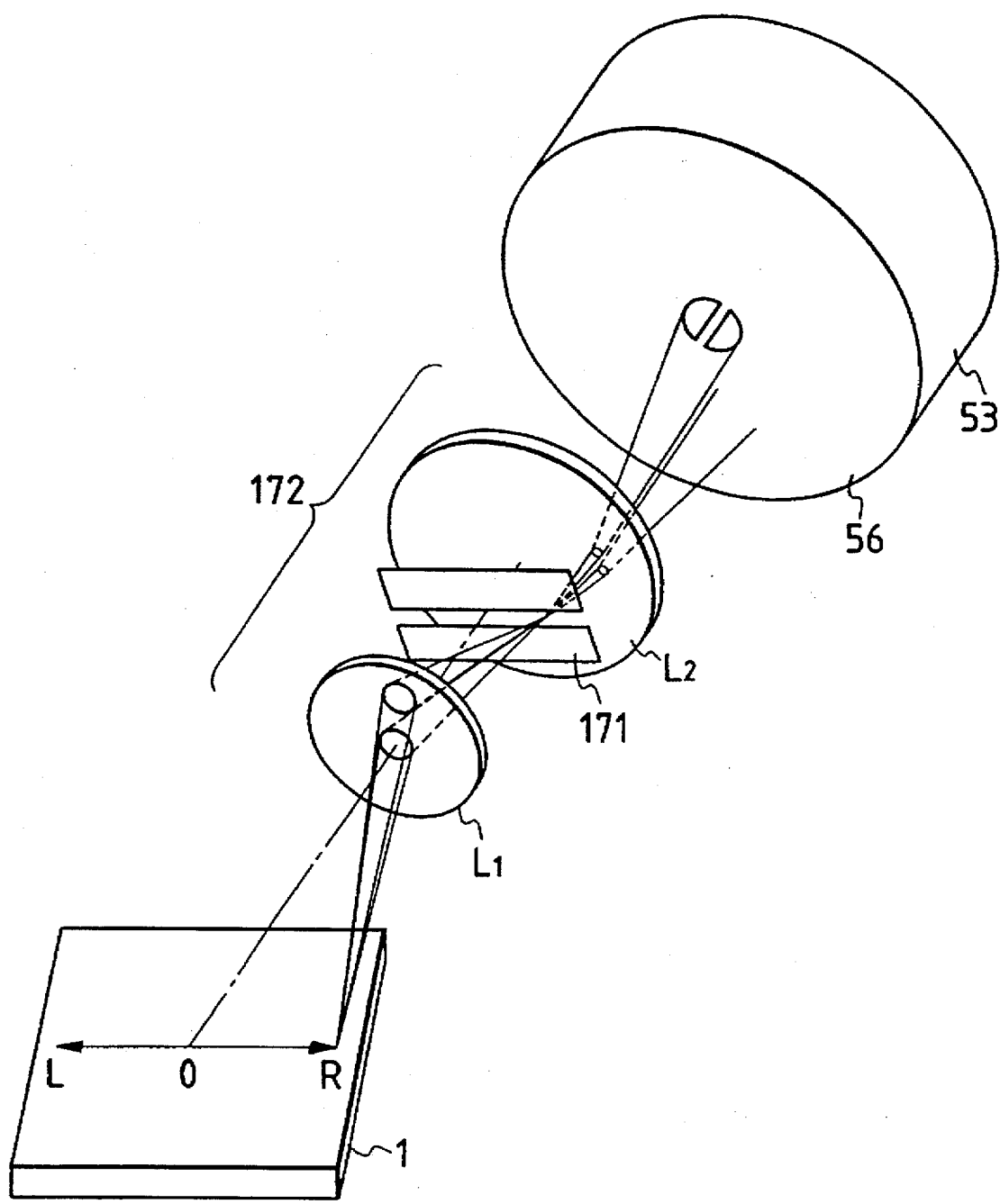
FIG. 54 is a view for explaining an arrangement in which a light receiving surface is formed on the pupil plane of a light receiving optical system.

Generally, in a defect inspecting apparatus of the kind, it is practiced to inspect the defectives from which photoelectric signals of more than a given slice level are obtainable. As described in conjunction with FIG. 54 and FIG. 55, the intensity of diffractive light from circuit patterns and the spatial angles formed by the diffractive light vary depending on the minuteness of the circuit patterns. When the minuteness of the pattern becomes smaller (the pattern becoming greater), the spatial angle of the diffractive light becomes smaller, and the intensity of the diffractive light also becomes smaller in a position away from the direction of the positive reflection (positive transmission) of the incident light I. Therefore, it becomes possible to distinguish the foreign particle from the diffractive light which is scatteringly emitted spatially at more than a given slice level in accordance with the foregoing conditions (1) and (2) by setting the slice level at an appropriate value on the basis of the size of the foreign particle to be detected as well as the minuteness of the circuit pattern.

Figure 11:
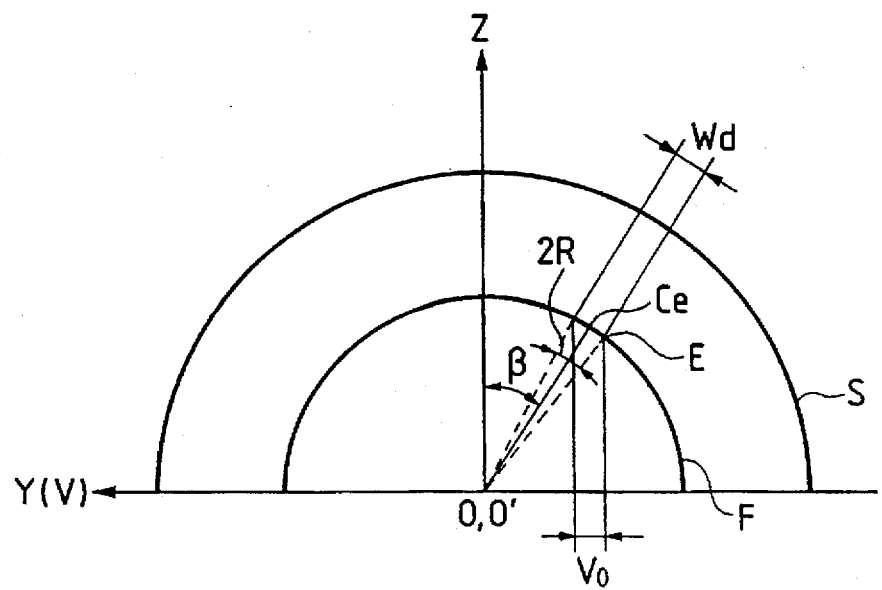
FIG. 11 is a view illustrating the relationship between the arrangement of light receiving surface on a positively projected view and the arrangement of the actual light receiving surface.

Now, with reference to FIG. 5 and FIG. 11, the description will be made of the relationship between the positive projection of diffractive light and the real image on the light receiving area. FIG. 11 is a plan view of the imaginary sphere in FIG. 5 observed in the direction Q. In FIG. 11, given the width tangential to the sphere S on the curved section j' as $W_d$, the $W_d$ can be expressed as follows:

$$W_d = V_0 / \cos\beta \quad (5)$$

Also, in consideration of the R of the spatial angle in FIG. 5, the relationship will be $2/\lambda \sin R = W_d$. Thus, $$\sin R = \lambda \cdot W_d / 2 \quad (6)$$

From the equations (2), (5), and (6), the relationship will be expressed as follows:

$$\sin R = \lambda \cdot V_0 / 2\cos\beta = \sin\gamma \cdot \cos\theta / \cos\beta \quad (7)$$

Therefore, if only the $\beta$ corresponding to the incident angle $\theta$, aperture angle $\gamma$, and the desired position for the arrangement of the light receiving areas is predetermined, the interval between the light receiving areas on the curved section is obtained from the equation (7). Then, it is good enough to define the interval between the light receiving area and the width to satisfy the foregoing conditions (1) and (2) on the positively projected view.

Figure 12:
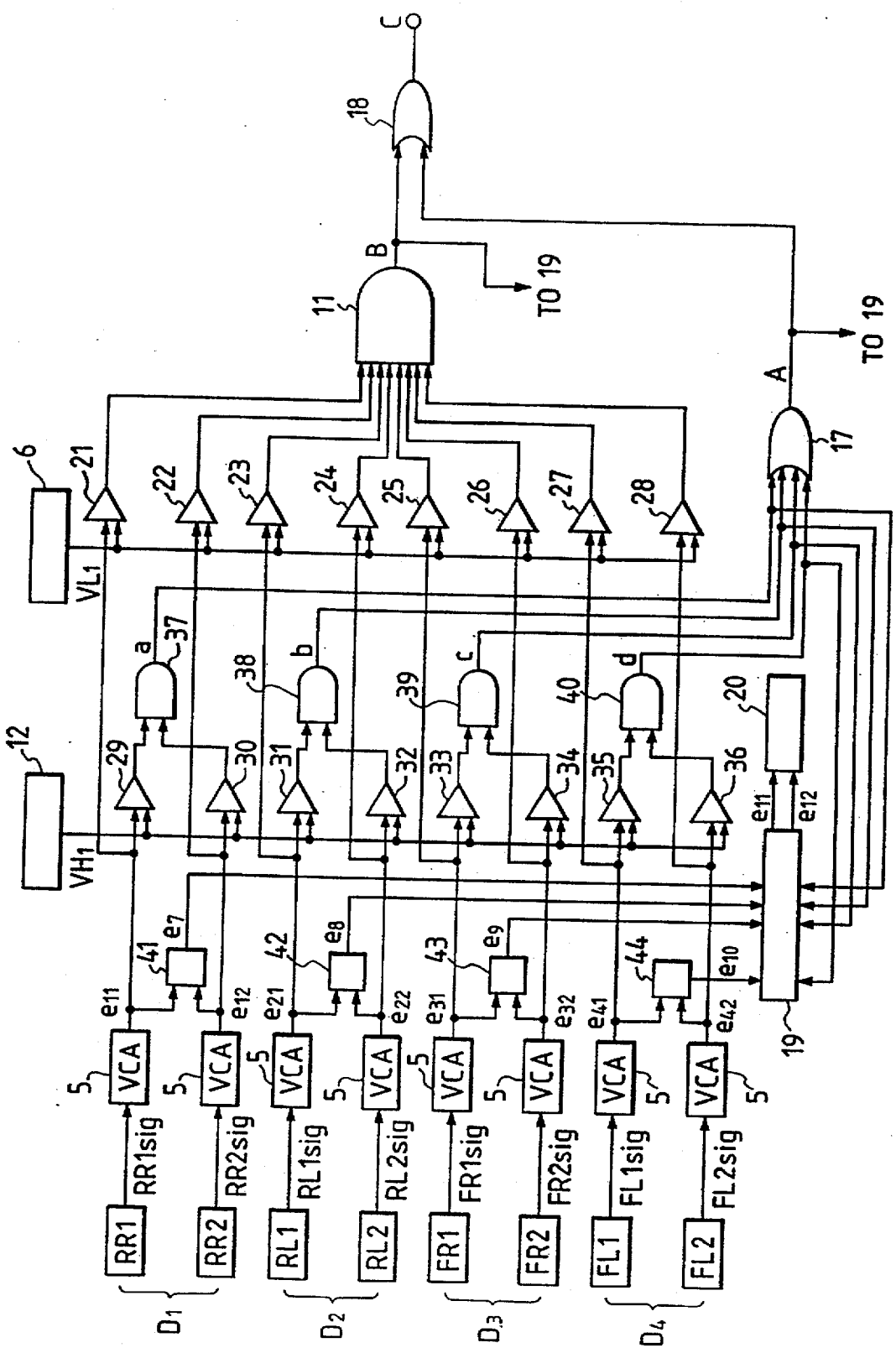
FIG. 12 is a view showing a signal processing systems according to the second embodiment of the present invention.

FIG. 12 is a view showing a signal processing circuit according to the second embodiment of the present invention. In order to prevent the rank of the foreign particle detection from being varied by the diffractive light from the patterns, the logic is made different from the first embodiment. Here, the same reference marks and numerals are given to the same members appearing in the first embodiment.

For the photoelectric signals RR1sig, RR2sig, RL1sig, RL2sig, FR1sig, FR2sig, FL1sig, and FL2sig form the eight photoreceivers shown in FIG. 4, the light receiving sensitivity is made constant by the variable gain amplifiers (VCA) 5 without depending on the inspecting positions (light beam positions) in the direction X. Also, using sensitivity fiducial grains, the control is made so as not to give any sensitivity difference among the photoreceivers. The signals $e_{11}$, $e_{12}$, $e_{21}$, $e_{22}$, $e_{31}$, $e_{32}$, $e_{41}$, and $e_{42}$ amplified by the VCAs are inputted into comparators 21, 22, 23, 24, 25, 26, 27, and 28, respectively. To each of the other inputs of the comparators 21, 22, 23, 24, 25, 26, 27, and 28, a slice voltage $VL_1$ is applied from a slice level generator 6. Each of the comparators 21, 22, 23, 24, 25, 26, 27, and 28 outputs the logical value 1 only when the signals $e_{11}$, $e_{12}$, $e_{21}$, $e_{22}$, $e_{31}$, $e_{32}$, $e_{41}$, and $e_{42}$ are greater than the slice voltage $VL_1$. Then, each output of the comparators 21, 22, 23, 24, 25, 26, 27, and 28 is applied to an AND circuit 11. The AND circuit 11 generates the logical value 1 as its output B when all of the outputs from the comparators 21, 22, 23, 24, 25, 26, 27, and 28 are of the logical value 1.

Also, the signals $e_{11}$, $e_{12}$, $e_{21}$, $e_{22}$, $e_{31}$, $e_{32}$, $e_{41}$, and $e_{42}$ amplified by the VCAs 5 are inputted into comparators 29, 30, 31, 32, 33, 34, 35, and 36, respectively. To each of the other inputs of the comparators 29, 30, 31, 32, 33, 43, 35, and 36, a slice voltage $VH_1$ is applied from a slice level generator 12. The slice voltage $VH_1$ is set higher than the slice voltage $VL_1$. In the first embodiment, the slice voltage $VH_1$ is set higher than the maximum value of the output signals $e_{11}$, $e_{12}$, $e_{21}$, $e_{22}$, $e_{31}$, $e_{32}$, $e_{41}$, and $e_{42}$ irrespective of the intensity of the scattering rays of light (or diffractive light) from the circuit patterns. In the present embodiment, however, a plurality of photoreceivers in one photoreceiver group are arranged to enable the foregoing discrimination by discreteness; thus making it possible to set the value of a slice voltage without depending on the intensity of the scattering (or diffraction) of light from the circuit patterns.

Now, each of the comparators 29, 30, 31, 32, 33, 34, 35, and 36 outputs the logical value 1 only when the signals $e_{11}$, $e_{12}$, $e_{21}$, $e_{22}$, $e_{31}$, $e_{32}$, $e_{41}$, and $e_{42}$ are greater than the slice voltage $VH_1$. The signals from the comparators 29 and 30 are inputted into an AND circuit 37, which generates the logical value 1 as its output a when both of the two comparators 29 and 30 output the logical value 1. Likewise, the signals from the comparators 31 and 32, signals from the comparators 33 and 34, and signals from the comparators 35 and 36 are inputted into AND circuits 38, 39, and 40, respectively. The AND circuit 38 generates the logical value 1 as its output b when both of the two comparators 31 and 32 output the logical value 1, the AND circuit 39 generates the logical value 1 as its output c when both of the two comparators 33 and 34 output the logical value 1, and the AND circuit 40 generates the logical value 1 as its output d when both of the two comparators 35 and 36 output the logical value 1. The outputs a, b, c, and d from the AND circuits 37, 38, 39, and 40 are applied to an OR circuit 17. The OR circuit 17 generates the logical value 1 as its output A when at least one of the output a, output b, output c, and output d is of the logical value 1.

Also, the output signals $e_{11}$ and $e_{12}$ from the VCAs 5 are inputted into a signal selector 41. The selector 41 selects a signal $e_7$ which indicates the smaller level of the output signals $e_{11}$ and $e_{12}$. Likewise, the output signals $e_{21}$ and $e_{22}$ from the VCAs 5 are inputted into a signal selector 42, the output signals $e_{31}$ and $e3_{22}$ from the VCAs 5 are inputted into a signal selector 43, and the output signals $e_{41}$ and $e_{42}$ from the VCAs 5 are inputted into a signal selector 44. Then, the selector 42 selects a signal $e_8$ which indicates the smaller level of the output signals $e_{21}$ and $e_{22}$, the selector 43 selects a signal $e_9$ which indicates the smaller level of the output signals $e_{31}$ and $e_{32}$, and the selector 44 selects a signal $e_{10}$ which indicates the smaller level of the output signals $e_{41}$ and $e_{42}$.

The output signals $e_7$, $e_8$, $e_9$, and $e_{10}$ from the selectors 41, 42, 43, and 44 are inputted into a selector 19, respectively. The selector 19 has two comparators to select a signal $e_{11}$ indicating the maximum level and a signal $e_{12}$ indicating the minimum level among the output signals $e_7$, $e_8$, $e_9$, and $e_{10}$. The selected signals $e_{11}$ and $e_{12}$ are stored in a memory 20, respectively.

The presence of any foreign particles is determined in the same manner as the first embodiment.

Hereinafter, using these outputs A and B, the description will be made of the logic with which to obtain the detection signals which correspond to the sizes of the foreign particles.

In the logic according to the present embodiment, the pattern noise is taken into account.

As described earlier, the signal $e_7$ from the photoreceiver group D1, the signal $e_8$ from the photoreceiver group D2, the signal $e_9$ from the photoreceiver group D3, and the signal $e_{10}$ from the photoreceiver group D4 are inputted into the selector 19. When the output A is of the logical value 1, the selector 19 selects as a detection signal, among the signals $e_7$, $e_8$, $e_9$, and $e_{10}$, a signal of the largest level from the photoreceiver group wherein the outputs a, b, c, and d from the AND circuit represent the logical value 1. More specifically, when the logical values of the output a from the AND circuit 37 and the output b from the AND circuit 38 are 1, the signals selected by the selector 19 become the signals $e_7$ and $e_8$ and either one of the two, which has a greater value, is output as a detection signal $e_{11}$. Also, when the logical value of the output A is 0, the signal of the smallest value is output as a detection signal $e_{12}$. As described above, according to the present invention, it is possible to detect large foreign particles reliably even when there is a mixture of sizes, large and small, of the foreign particles with respect to the wavelength of the incident beam.

Here, as shown in FIG. 4, both the pattern surface and glass surface of the reticle can be inspected using the photoreceiver group (photoreceiver group D1, for example) having a set of plural photoreceivers, but it may be possible to conduct the inspection in such a manner that while the photoreceiver group as shown in FIG. 4 is used for the pattern surface, the photoreceiver as shown in FIG. 1 is used for the glass surface.

Figure 13:
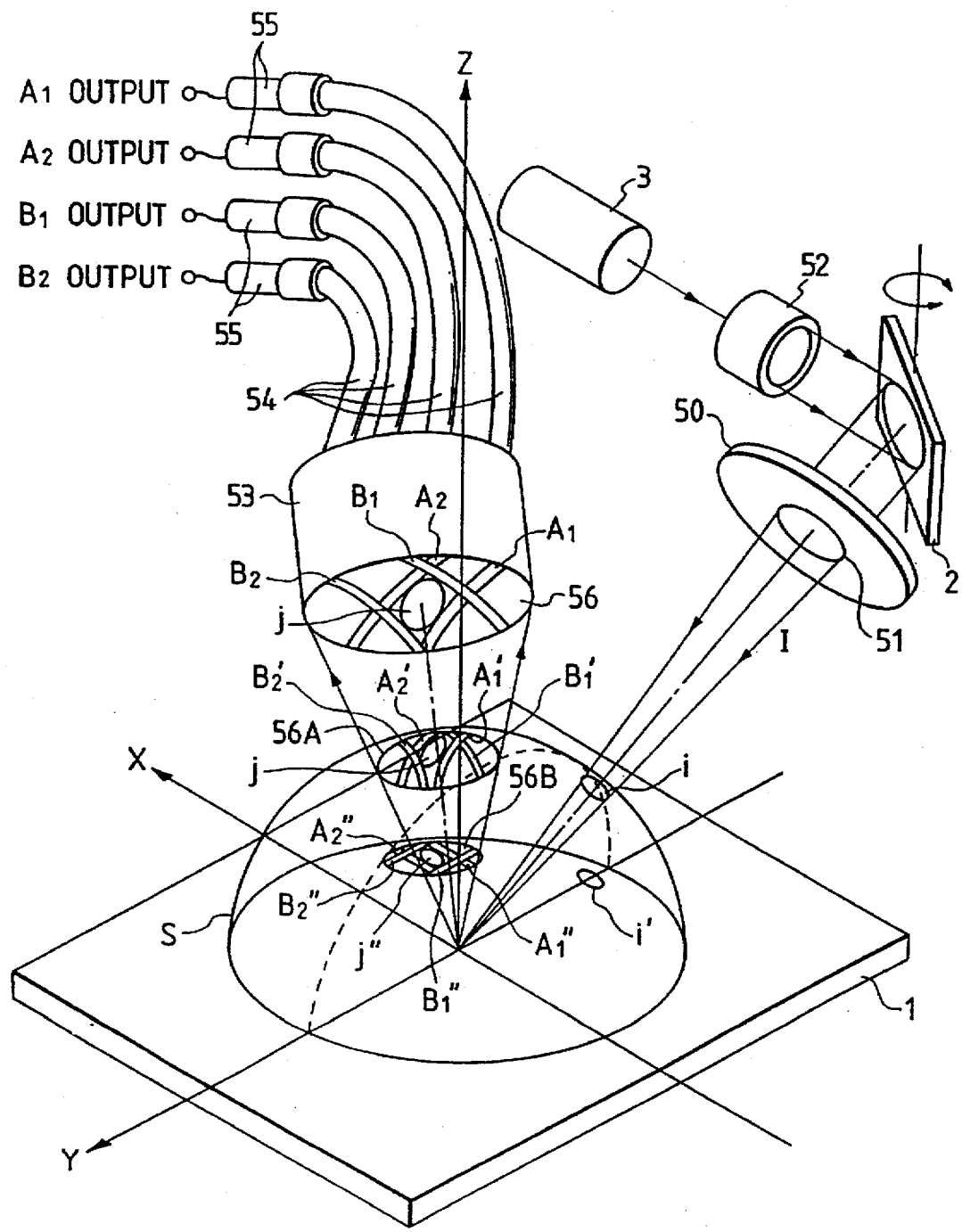
FIG. 13 is a perspective view illustrating the structure of the principal part of a defect inspecting apparatus according to a third embodiment of the present invention.

Subsequently, the description will be made of a third embodiment according to the present invention. FIG. 13 is a perspective view illustrating the structure of the third embodiment according to the present invention, in which the same reference marks are given to the same members appearing in FIG. 1.

In FIG. 13, the beam emitted from a laser light source 3 is converged onto a inspecting point O on the substrate where the circuit patterns are formed through a beam expander 52 and an f-θ lens 50 which constitutes a part of driving means to move the substrate 1 (reticle, wafer, and the like) and the beam interrelatedly. The converged incident beam I is caused by a vibrating mirror 2 to scan optically in the direction X on the substrate 1. The f-θ lens 50 is a lens system having a great focal length. The incident direction of the incident beam I upon the substrate 1 is substantially equal to the direction Y in FIG. 13. The substrate 1 is stacked on a stage (not shown) movable in the direction Y. By the vibrating mirror 2 and the stage, the entire surface of the substrate 1 can be inspected for foreign particles. A photoreceiver 53 has, on its light receiving surface 56, light receiving areas $A_1$, $A_2$, $B_1$, and $B_2$, each of which is photoelectrically converted individually. Each of the light receiving areas has longer and shorter directions. The arrangement of the light receiving areas $A_1$, $A_2$, $B_1$, and $B_2$ will be described later. The outputs from the light receiving areas $A_1$, $A_2$, $B_1$, and $B_2$ are inputted into photoelectric conversion elements 55 respectively through optical fibers 54 and are photoelectrically converted. From the photoelectric conversion elements 55, output signals $A_{out1}$, $A_{out2}$, $B_{out1}$, and $B_{out2}$ are output, respectively.

Here, a schematically drawn sphere S is considered with the inspecting point O (the converging point of the incident beam I) as its center. In FIG. 13, the curved section which is an area where the incident I and spherical plane of the sphere S are superposed is designated by a reference mark i. Also, the positive projection (projection in the vertical direction on the surface (XY plane) of the substrate 1 in the curved section 1 is represented by the positive projection i'. Also, the light receiving surface 56 corresponds to the curved section 56A on the spherical plane of the sphere S, and the positive projection of the curved section 56A onto the surface of the substrate 1 is designated by a reference numeral 56B.

In this embodiment, the radius Sr of the sphere is defined as Sr=1/λ (λ: the wavelength of the incident beam), and the size of the irradiated area on the substrate 1 upon incidence of the incident beam I is much smaller than the radius Sr.

Figure 16:
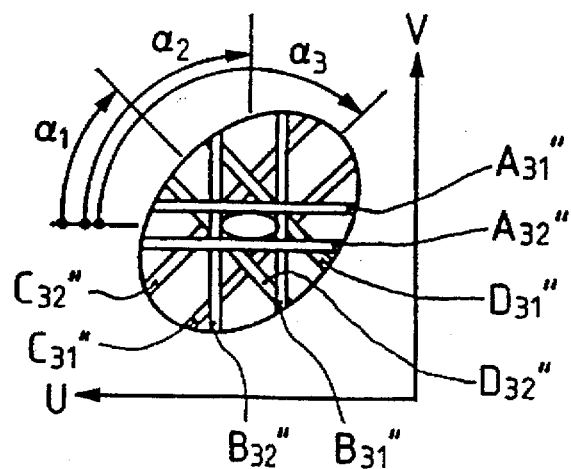
FIG. 16 is a view illustrating the arrangement of light receiving area for a defect inspecting apparatus according to a fourth embodiment of the present invention.

A figure j on the light receiving surface 56 represents the irradiating area (diffractive image) when the diffractive light which is scatteringly emitted enters the center of the light receiving surface 56. In FIG. 16, the curved section which is an area where this diffractive light and the spherical plane of the sphere S are superposed is designated by a reference mark j' while the positive projection of the curved section j" onto the surface of the substrate 1 is designated by a reference mark j". This positive projection j" is a figure congruent to the positive projection i' of the incident beam I. Also, the positive projection onto the substrate 1 of the curved sections $A_1'$, $A_2'$, $B_1'$, and $B_2'$ which are area where the sphere S and the beam reaching the light receiving areas $A_1$, $A_2$, $B_1$, and $B_2$ from the inspecting point O are superposed becomes a positive projection $A_2"$, a positive projection $B_1"$, and a positive projection $B_2"$. The longitudinal directions of the positive projections $A_1"$ and $A_2"$ are parallel to the axis Y while the interval between the shorter directions is equal to the width of the positive projection j" of the diffractive light in the direction X. Also, the longitudinal directions of the positive projections $B_1"$ and $B_2"$ are parallel to the axis X while the interval between the shorter directions is equal to the width of the positive projection j" of the diffractive light in the direction Y. In other words, the light receiving areas $A_1$, $A_2$, $B_1$, and $B_2$ in the present embodiment are arranged to be in contact with the positive projection of the diffractive light on the positively projected view. Also, in FIG. 13, when the exit pupil 51 of the f-θ lens 50 is circle, the figure j showing the scattering diffractive light incident upon the photoreceiver 53 is increasingly closer to a circle as the angle $E_θ$ formed by the optical axis of the light received and the axis of the incident light axial becomes smaller. It becomes a circle at $E_θ=0$. As a result, if the angle $E_θ$ is small, the intervals between the light receiving areas $A_1$ and $A_2$, and $B_1$ and $B_2$ shown in FIG. 13 can be set substantially the same. In the specification hereof, the exit pupil 51 of the f-θ lens 50 is circle, and since the incident beam I enters the circuit pattern at the incident angle θ, the irradiating area $I_s$ becomes elliptical. Therefore, even with the diffractive light from the patterns arranged at the same pitches in the directions X and Y, the figure of the positive projection has a shorter direction in the direction Y and the interval between the diffractive light in the direction Y is wider than in the direction X.

Here, the description will be made of an incident light upon the photoreceiver 53 in conjunction with FIG. 21 which corresponds to FIG. 13. In FIG. 13, if the length of the positive projection j" of the diffractive light in the direction X as $U_0$ and the length in the direction Y as $V_0$ and the linear components $U_1"$ and $U_2$ parallel to the axis Y which is in contact with the positive projection j" on the XY plane are considered, these components are the positive projection of the curve $U_1'$ and $U_2'$ on the sphere S. Also, of the vectors starting with the inspecting point O and terminating at the point on the light receiving surface 56, the concurrences of the terminating points of the vectors existing in the aperture angle of the photoreceiver 53 and penetrating the curves $U_1'$ and $U_2'$ become $U_1$ and $U_2$ on the light receiving surface. The same is applicable to the linear components $V_1"$ and $V_2"$ parallel to the axis X which is in contact with the positive projection j". The curved lines $V_1'$ and $V_2'$ on the sphere S correspond to the linear components $V_1$ and $V_2$ on the light receiving surface. Even when the positive projections $U_1"$, $U_2"$, $V_1"$, and $V_2"$ are straight lines, the $U_1$ will not be a straight line. However, when the $U_1$ is short, the photoreceiver 53 is sufficiently away from the inspecting point, or the light receiving area 56 is small, there will be no problem even if it approximates a straight line in the light receiving surface 56 of the photoreceiver 53.

Figure 14:
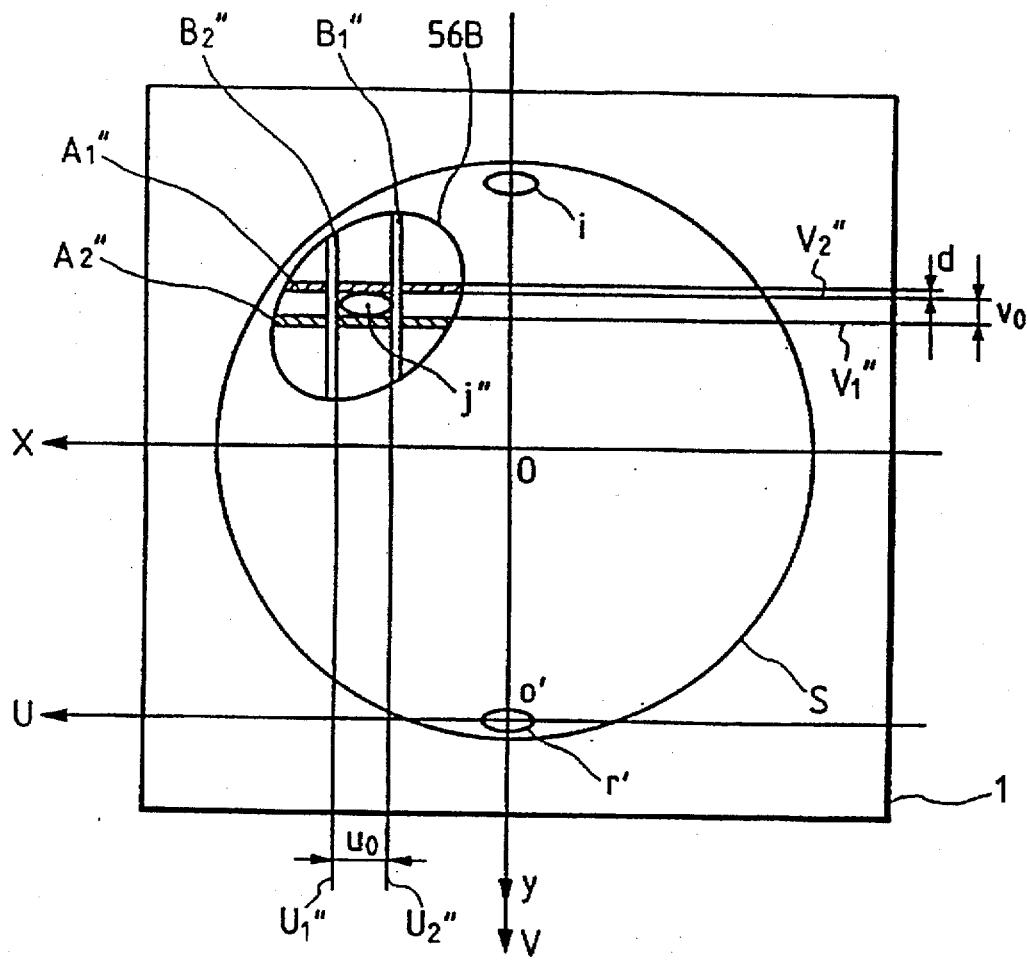
FIG. 14 is a conceptual view illustrating the distribution of diffractive light on a positively projected view.

Now, FIG. 14 is a schematic view illustrating the third embodiment shown in FIG. 13 observed in the direction Z, in which the positive projections $A_1"$, $A_2"$, $B_1"$, and $B_2"$ of the respective light receiving areas are shown. In FIG. 14, a reference mark r' designates the positive projection r' of the curved section r which is the area where the positive reflective light Ir (see FIG. 5) and the sphere S are superposed. The UV coordinate axes in FIG. 14 are new orthogonal coordinates with the central position of the positive projection r' as its original point O'. In FIG. 14, the positive projections $A_1"$ and $A_2"$ are as described earlier have its longitudinal directions in the direction parallel to the U axis (X axis) in FIG. 14 and are apart at an interval $V_0$. Also, the widths of its shorter directions are of a same width $D_0$ in order to make its light receiving sensitivity equal. In this respect, even if the widths $D_0$ are made equal, the light receiving areas $A_1$ and $A_2$ of the photoreceiver 53 in FIG. 13 cannot necessarily be equal. There may be some cases where an appropriate adjustment is needed. Also, the positive projections $B_2"$ and $B_1"$ have its longitudinal directions in the direction parallel to the V axis (Y axis) and are apart at an interval $U_0$. The widths of its shorter directions are of a width $D_0$ as in the positive projections $A_1"$ and $A_2"$. In consideration of the capability to distinguish foreign particles from circuit patterns, it is preferable to make the widths $D_0$ narrower. The reduction of the light receiving areas due to the narrower widths can be compensated by making the length of the longitudinal directions longer. Thus, it becomes possible to prevent the reduction of the electrical SN ratio.

Also, it is preferable to arrange the f-θ lens 50 and photoreceiver 53 sufficiently far as compared with the optical scanning distance. This is due to the fact that when the inspecting point O is shifted as a result of the optical scanning by the vibrating mirror 2, the relationship between the respective positive projections on the positively projected view is not to be varied from the foregoing relationship as far as possible. If the f-θ lens 50 and photoreceiver 53 can hardly be arranged far, it may be possible to provide the light receiving areas so that the intervals between the positive projections $A_1"$ and $A_2"$ and the positive projections $B_2"$ and $B_1"$ are matched with $V_0$ and $U_0$ when the inspecting point approaches the photoreceiver 53 most closely.

Now, in the present embodiment, too, there are formed on the substrate 1, the DRAM and other IC patterns by patterning of a comparatively high minuteness. The state of diffractive light emitted from the circuit patterns is the same as those described in conjunction with FIGS. 7A to 7D, FIGS. 8A to 8E, and FIGS. 9A to 9E. As described above, if the geometrical figures of the circuit patterns are known, it is possible to predict the distribution of the diffractive light to be emitted. Therefore, as described with FIG. 7 to FIG. 9, it is easy to obtain the pitches and periodic directions in the positively projected view of the scattering diffractive light from the two dimensional cycle patterns. Hereinafter, using FIG. 7C, FIG. 7D, FIG. 8C, FIG. 8D, FIG. 8E, FIG. 9C, FIG. 9D, and FIG. 9E, the description will be made of the optimization of the arrangement of light receiving areas according to the present embodiment. In these figures, it is assumed that the widths $D_0$ of the positive projections $A_1$, $A_2$, $B_1$, $B_2$, $C_1$, $C_2$, $D_1$, and $D_2$ of the respective light receiving areas are all the same. Only the interval between and angle of the light receiving areas are varied on the positively projected view and are represented accordingly.

The two dimensional cycle patterns shown by FIG. 7A, FIG. 8A, and FIG. 9A are the patterns having two periodic directions symmetrical to the axis X (or axis Y). Hence, the distributions of the diffractive light to be emitted have the periodic directions in U and V axes in addition to the directions (a', b', c', and d') perpendicular to the periodic direction (a, b, c, and d) of the circuit patterns shown in FIG. 7B, FIG. 8B, and FIG. 9B.

Now, as an example, the circuit pattern shown in FIG. 8A is considered. In this case, the direction in which the light receiving area having the longitudinal direction can be arranged is four directions parallel to the axis U, axis V, axis a' and axis b'. The arrangements of the light receiving areas corresponding to these directions are shown in FIG. 8C, FIG. 8D, and FIG. 8E. As shown in these figures, the diffractive light to be emitted becomes elliptical on the positively projected view (on UV coordinates). Here, the width of the ellipse in each of the directions (U axis direction, V axis direction, a' axis direction, and b' axis direction) is defined as $\epsilon$. As described earlier, the widths $\epsilon$ in the U axis direction and V axis direction are $\epsilon(U)=V_0$, $\epsilon(V)=U_0$, respectively.

Subsequently, the description will be made of a method to determine the optimal arrangement of the light receiving areas from the four directional arrangements (U axis direction, V axis direction, a' axis direction, and b' axis direction). Here, the interval between the diffractive light on the positively projected view in each of the directions is given as $\delta(U)$, $\delta(V)$, $\delta(a')$, and $\delta(b')$. These will be expresses in the following equations (8) to (11), respectively:

$$\delta(a') = (1/Pa) - \epsilon(a') \quad (8)$$
$$\delta(b') = (1/Pb) - \epsilon(b') \quad (9)$$

$$\delta(U) = (1/Pb) \cdot \{(\cos(90° - \theta_0)/\cos(2\theta_0 - 90°)\} - \epsilon(U) \quad (10)$$
$$= (1/Pb) \cdot (\sin\theta_0/\sin 2\theta_0) - \epsilon(U)$$

$$\delta(V) = (1/Pb) \cdot \{(\cos\theta_0/\cos(90° - 2\theta_0)\} - \epsilon(V) \quad (11)$$
$$= (1/Pb) \cdot (\sin\theta_0/\sin 2\theta_0) - \epsilon(V)$$

where $\theta_1=\theta_b=\theta_0$, $1/Pa=1/Pb$.

The direction in which the interval $\delta$ between diffractive light predictable from the above equations (8) to (11) becomes greatest is the direction in which the absence of the diffractive light is most prominent, and becomes the direction in which the capability of discrimination will be most enhanced when the light receiving area having the longitudinal direction is arranged. The $\delta(U)$ or $\delta(V)$ exists as a two dimensional cycle pattern of $1/Pa=1/Pb$ when $\theta_a=\theta_b=\theta_0$. In other cases, the $\delta(a')$ or $\delta(b')$ will become greatest. In the present embodiment, it is assumed that a substrate 1 having two dimensional cycle patterns ($\theta_a=\theta_b=\theta_0$, $1/Pa=1/Pb$) such as shown in FIGS. 7A to 9E are arranged as its inspecting object. With this, the light receiving areas $A_1$, $A_2$, $B_1$, and $B_2$ are arranged in parallel to the axis U and axis V on the positively projected view. In the present embodiment, the arrangement is made to switch over the light receiving areas in order to make the number of the photoelectric elements as small as possible, but if there is no particular limitation is required for the number of the photoelectric elements, it may be possible to obtain the logical product of the output signals from the photoelectric elements which will be arranged in each of the four directions in the above case. Also, it may be possible for a simpler arrangement to use only the information regarding the periodic direction of the pattern without depending on the equations (4) to (7) and thus to select the light receiving area in the direction perpendicular to this periodic direction on the UV plane.

Now, the description will be made of the discrimination of the patterns and foreign particles in the present embodiment.

As shown in FIG. 8C, the light receiving areas $A_1$ and $A_2$ are arranged so that the positive projections $A_1"$ and $A_2"$ are positioned in parallel to the axis U at the interval $V_0$, and when the positive diffractive light is between the positive projections $A_1"$ and $A_2"$, the diffractive light is not incident upon the light receiving areas $A_1$ and $A_2$. If any foreign particles are present in the irradiating area of the incident beam I in this state, isotropic scattering rays of light will enter the light receiving areas $A_1$ and $A_2$ to cause the foreign particles to be detected.

Also, in a case of FIG. 8C (or FIG. 7C), the diffractive light from the pattern enters the light receiving area $A_2$ (which is the portion where the positive projection $A_2"$ and the positive projection of the diffractive light are superposed), but no diffractive light is incident upon the light receiving area $A_1$ (where no positive projection $A_1"$ and the positive projection of the diffractive light are superposed). Therefore, the rays of light which are received in the light receiving area $A_2$ are determined as the scattering diffractive light. If, in this sate, any foreign particles are present in the irradiating area of the incident beam I, the scattering rays of light from the foreign particles also enter the light receiving area $A_1$. Hence, the foreign particles are detected.

In other words, it is necessary to satisfy the condition that at least one of the plural light receiving areas, no diffractive light from the patterns are allowed to enter in order to distinguish the patterns from the foreign particles. This condition can be expressed in the following equation (12):

$$\delta \geq 2D_0 + \{\epsilon - (n-2)d\}/(n-1) \quad M_v \geq \epsilon \quad (12)$$

Here, $\delta$ is the interval between the diffractive light from the pattern on the positive projection, $\epsilon$ is the width of the diffractive light on the positive projection, d is the width of the light receiving area on the positive projection, n is the number of light receiving areas to be used, and $M_v$ is the interval between the photoreceivers on the positive projection.

In other words, the interval between the diffractive light in each of the direction is obtained from the equations (8) to (11). Then, it is good enough to arrange the light receiving areas at a given interval by selecting the direction which satisfies the condition of by the equation (12). If there is a plurality of the directions which satisfy the condition of the equation (12), it may be possible to select a direction in which the interval between the diffractive light becomes the widest of all, or it may be possible to arrange the light receiving areas in those plural directions which satisfy the condition of the equation (12). If the number of the light receiving areas and photoelectric conversion elements is not necessarily confined, there is no problem in arranging the light receiving areas and photoelectric conversion elements in all the directions which may become the periodic direction of the circuit patterns. Also, it may be possible to use only information regarding the periodic direction.

Figure 15:
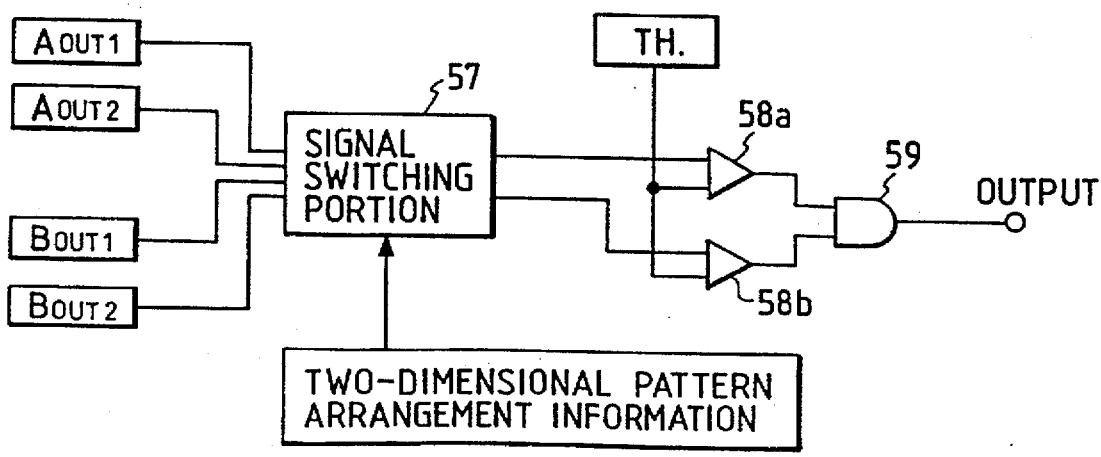
FIG. 15 is a block diagram showing the structure of the signal processing systems of a defect inspecting apparatus according to the third embodiment of the present invention.

Now, with reference to FIG. 15, the description will be made of a signal processing method in the present embodiment. In FIG. 15, each of the output signals $A_{out1}$, $A_{out2}$, $B_{out1}$, and $B_{out2}$ is inputted into a signal switching portion 57 which constitutes selection means according to the present invention. To this switching portion 57, the arrangement information of two dimensional patterns of a circuit pattern formed on the substrate 1 is also inputted. On the basis of these pieces of information, the signal which will be used for signal processing is selected from the output signals $A_{out1}$, $A_{out2}$, $B_{out1}$, and $B_{out2}$. The arrangement information of the two dimensional patterns includes the arrangement direction of patterns and pitches, for which the data obtainable at the time of circuit formation and the data on the actual measurements of the pattern arrangement can be used. On the basis of the information of this pattern arrangement, the signal switching portion 57 is caused to select the light receiving area which is arranged in the direction where the interval between the diffractive light becomes the greatest.

More specifically, in the examples shown in FIGS. 7A to 7D, the light receiving areas $A_1$ and $A_2$ (FIG. 8C) arranged in the direction where the interval between the diffractive light is larger are selected. Likewise, in the examples shown in FIGS. 8A to 8E and FIGS. 9A to 9D, the light receiving areas $A_1$ and $A_2$ are selected. At this juncture, whereas it is possible to distinguish foreign particles form circuit patterns (the equation (8) being satisfied) even when the light receiving areas $B_1$ and $B_2$ (FIG. 7D) are selected in the cases shown in FIGS. 7A to 7D, it is impossible to make any discrimination if the light receiving areas $B_1$ and $B_2$ (FIG. 8D and FIG. 9D) are selected in the cases shown in FIGS. 8A to 8E and FIGS. 9A to 9E because the diffractive light is incident upon both in the light receiving areas $B_1$ and $B_2$ (both of the positive projections $B_1"$ and $B_2"$ and the positive projection of the diffractive light being superposed), making it impossible to determine whether these are diffractive light or light from any foreign particles.

In FIG. 15, the selected light receiving areas ($A_{out1}$ and $A_{out2}$) or ($B_{out1}$ and $B_{out2}$) are output from the signal switching portion 57 to comparators 58a and 58b. In the comparators 58a and 58b, a threshold value TH and the output signals ($A_{out1}$ and $A_{out2}$) or ($B_{out1}$ and $B_{out2}$) are compared, respectively. If the output signals from the signal switching portion 57 exceed the threshold value, the signals are output to an AND circuit 59. In the AND circuit 59, the discrimination between foreign particles and circuit patterns are performed by obtaining the logical product of the signals from the comparators 58a and 58b. In other words, in the present embodiment, a set of the light receiving areas which satisfies the equation (8) (a set in which no diffractive light from the patterns is incident upon at least one of the light receiving areas) is being selected of the sets of the light receiving areas ($A_1$ and $A_2$) and ($B_1$ and $B_2$). Therefore, if there is no foreign particle on the surface of the substrate 1, the result of the calculation in the AND circuit will be zero. On the other hand, if any foreign particle is present, the scattering rays of light from the foreign particle is continuously emitted spatially. Hence, the output signals $A_{out1}$ and $A_{out2}$ (or $B_{out1}$ and $B_{out2}$) will both exceed the threshold value to make the result of the calculation in the AND circuit one; thus the foreign particle being detected.

Figure 17:
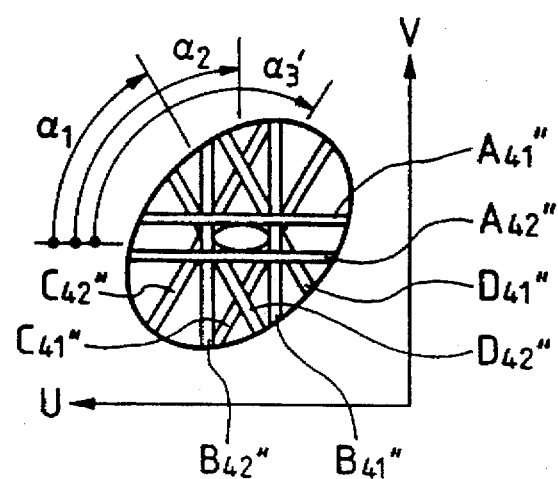
FIG. 17 is a view illustrating another arrangement of light receiving area for a defect inspecting apparatus according to the fourth embodiment of the present invention.

Now, FIG. 16 and FIG. 17 are views (positively projected views) illustrating the arrangement of the light receiving areas according to a fourth embodiment of the present invention. Although the fundamental structure of a defect inspecting apparatus of the fourth embodiment is the same as the third embodiment, it differs from the latter in that the number of the light receiving areas is increased. In the example shown in FIG. 16, there are provided as newly increased light receiving areas in addition to the light receiving area having the longitudinal directions of the positive projections $A_{31}"$ and $A_{32}"$ parallel to the axis U and the light receiving area having the longitudinal directions of the positive projections $B_{31}"$ and $B_{32}"$ parallel to the axis V ($\alpha_2=90°$), a light receiving area having the longitudinal directions of the positive projections $C_{31}"$ and $C_{32}"$ parallel to the axis U at an angle of $\alpha_1$ and a light receiving area having the longitudinal directions of the positive projections $D_{31}"$ and $D_{32}"0$ parallel to the axis U at an angle of $\alpha_3$. In the case of FIG. 17, the light receiving areas are newly increased likewise, but the angle formed by the longitudinal directions of the positive projections $C_{41}"$ and $C_{42}"$ and the axis U is $\alpha_3'$.

Thus, whereas the light receiving areas in the first embodiment are designed in consideration of its main inspecting object which is a circuit pattern linearly symmetrical to the axes X and Y as shown in FIG. 8A, it becomes possible to optimize the light receiving areas for performing the inspection of the circuit patterns which have its cycles in various directions by increasing the number of light receiving areas. It is possible to select the arrangement of the optimal light receiving areas even when the interval between the diffractive light in direction of the a' axis (or b' axis) in FIG. 8B is the widest, for example. For the two dimensional cycle pattern as shown in FIG. 8A, The angles $\theta_a$ and $\theta_b$ are often confined to a certain extent. Therefore, it is possible to implement an arrangement having an excellent capability of discrimination by defining the value of $\alpha_3$ ($\alpha_3'$) appropriately. At this juncture, if the pitches and the like in the a axis direction and b axis direction in FIG. 8A are the same, it may be possible to select the direction (a' axis, b' axis direction in FIG. 8B) perpendicular to either direction, or it may be possible to arrange light receiving areas in both directions.

Figure 18:
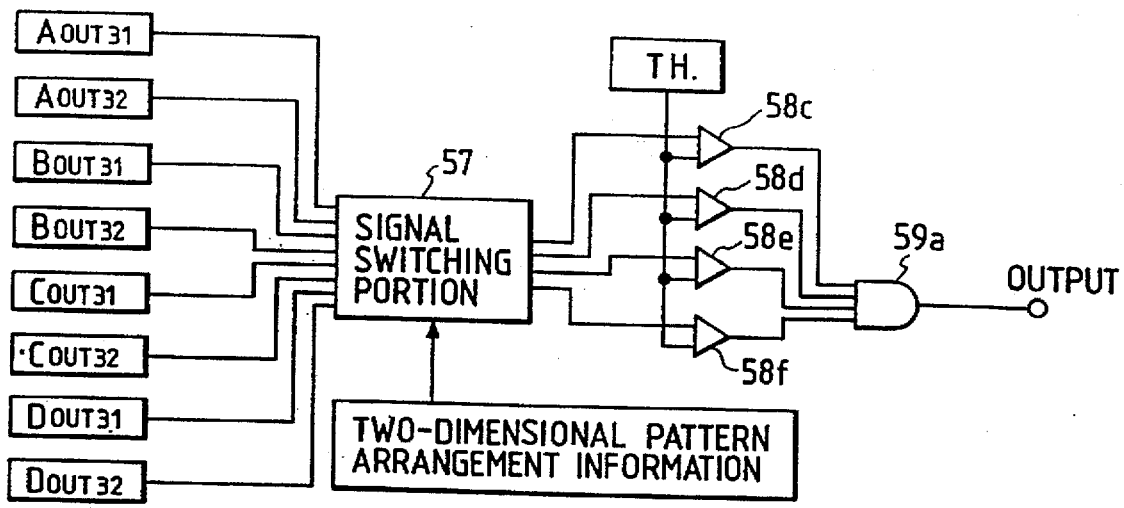
FIG. 18 is a block diagram showing the structure of the signal processing systems of a defect inspecting apparatus according to the fourth embodiment of the present invention.

FIG. 18 illustrates the structure of the signal processing system according to the present embodiment. The fundamental structure is the same as the embodiment represented by FIG. 16. In FIG. 18, the output signals $A_{out31}$, $A_{out32}$, $B_{out31}$, $B_{out32}$, $C_{out31}$, $C_{out32}$, $D_{out31}$ and $D_{out32}$ form the respective light receiving areas are inputted into the signal switching portion 57. To this signal switching portion 57, information regarding the arrangement of two dimensional patterns of a circuit pattern is also inputted. On the basis of this information, the signals to be used for the signal processing are selected from the output signals corresponding to the respective light receiving areas. From the signal switching portion 57, the selected signals ($A_{out31}$ and $A_{out32}$, and $B_{out31}$ and $B_{out32}$, for example) are output to the comparators 58c, 58d, 58e and 58f. In the comparators 58c, 58d, 58e, and 58f, the threshold value TH and each of the selected output signals are compared. When the output signals from the signal switching portion 57 exceed the threshold value TH, the signals are output to the AND circuit 59a. In the AND circuit 59a, the discrimination between foreign particles and circuit patterns are performed by obtaining the logical product of the signals from the comparators 58c, 58d, 58e, and 58f.

In this respect, according to the above-mentioned example, specific light receiving areas are selected by switching over the output signals from the light receiving areas by the signal switch portion, but as described earlier, there is no problem at all in performing the discrimination between foreign particles and circuit patterns by obtaining the required logical value by photoelectrically converting signals from all the light receiving areas with the provision of the light receiving areas in the directions corresponding to all possible periodic directions of the circuit. Also, it may be possible to use only the information regarding the periodic direction. Also, it may be possible to adopt a structure where any light receiving areas which are not used are masked by a shielding material. The masking may be arranged electrically by the use of a liquid crystal, electrochromic element or the like besides slit or others.

Figure 19:
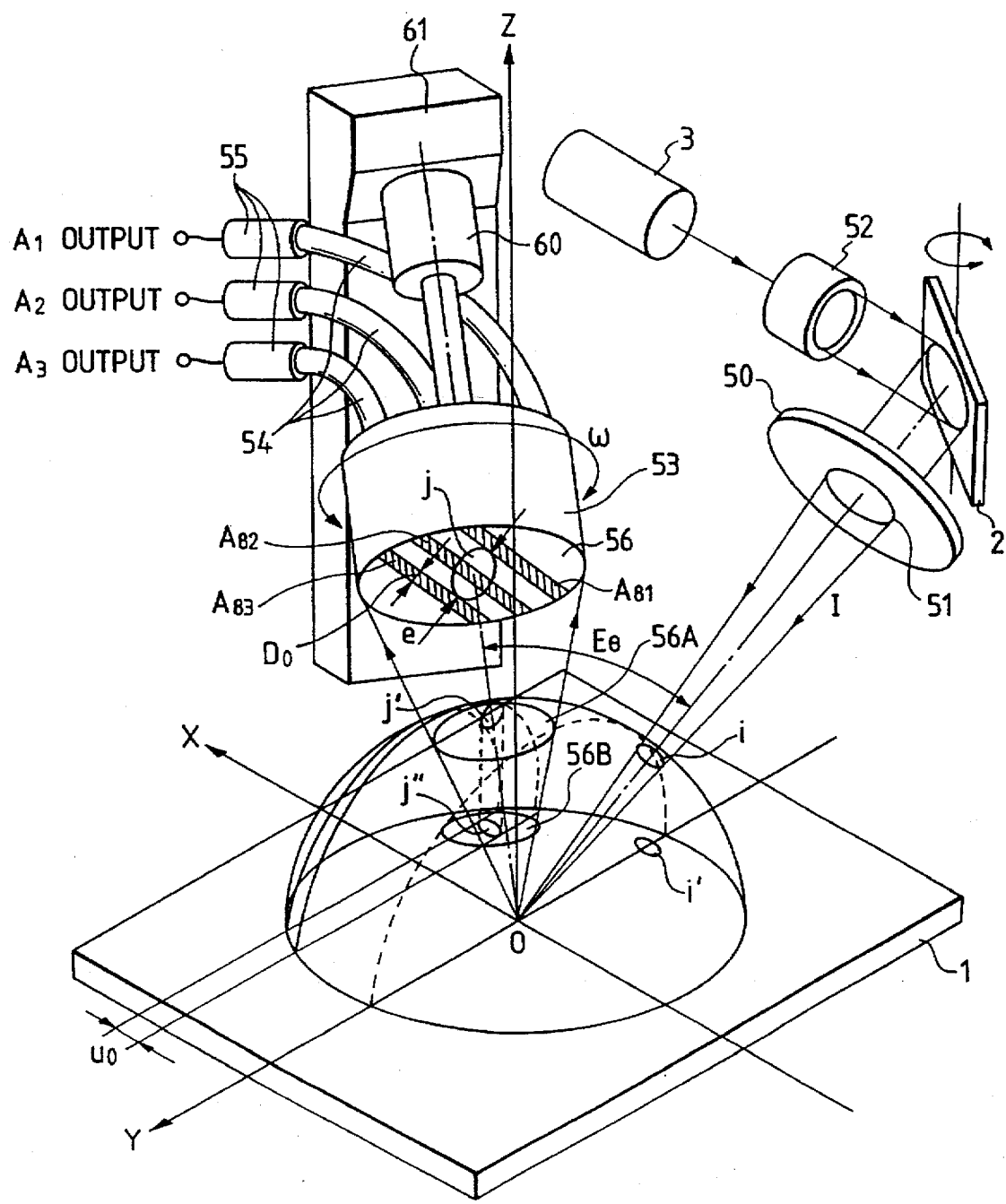
FIG. 19 is a perspective view showing the structure of the principal part of a defect inspecting apparatus according to a fifth embodiment of the present invention.

Now, FIG. 19 is a perspective view showing the structure of a fifth embodiment according to the present invention. The present embodiment is designed to perform defect inspections corresponding to the geometrical arrangements of patterns using a smaller number of photoelectric elements and light receiving areas. In the present embodiment, while light converging means is of the same structure as the third embodiment, the structures of the light receiving means and selecting means for the light receiving means are different from the third embodiment. In FIG. 19, a photoreceiver 53 has light receiving areas $A_{81}$, $A_{82}$, and $A_{83}$. The longitudinal direction of each of the light receiving areas $A_{81}$, $A_{82}$, and $A_{83}$ is of a straight line while the longitudinal directions themselves are in parallel. The interval between the light receiving areas $A_{81}$ and $A_{82}$ at the both ends on the positively reflected view is equal to the width $U_0$ of the diffractive light. Also, in order to make the light receiving area constant, the width $D_0$ of each of the shorter directions is equal to each other. The incident beam upon each of these light receiving areas is guided by optical fibers 54 to the photoelectric converter 55 where it is photoelectrically converted to the outputs $A_{out81}$, $A_{out82}$, and $A_{out83}$.

In this embodiment, the radius Sr of the sphere is defined as $Sr=1/\lambda$ ($\lambda$: the wavelength of the incident beam), and the size of the irradiated area on the substrate 1 upon incidence of the incident beam I is much smaller than the radius Sr.

Also, the photoreceiver 53 is arranged on supporting means 61 through a rotation driving unit 60, and is rotative around the optical axis. In other words, with the rotation driving unit 60, it is possible to set the light receiving areas $A_{81}$, $A_{82}$, and $A_{83}$ at an arbitrary angle in the present invention. According to the present embodiment, an angle $\alpha$ formed by the optical axis of the light to be received and the optical axis of the incident light is comparatively small so as to make the diameter e of the scattering diffractive incident light j substantially constant without depending on the rotational angle $\omega$ of the photoreceiver 53. With the provision of a smaller angle $E_0$, the figure j is made close to a circle; thus enabling the interval between the light receiving areas at both ends to be always substantially the same as the width of the diffractive light. Also, the exit pupil 51 of the f-θ lens 50 is circular in the present embodiment, but it may be possible to modify the figure of the exit pupil 51 so that the diffractive light incident j upon the photoreceiver 53 becomes circular.

Figure 20:
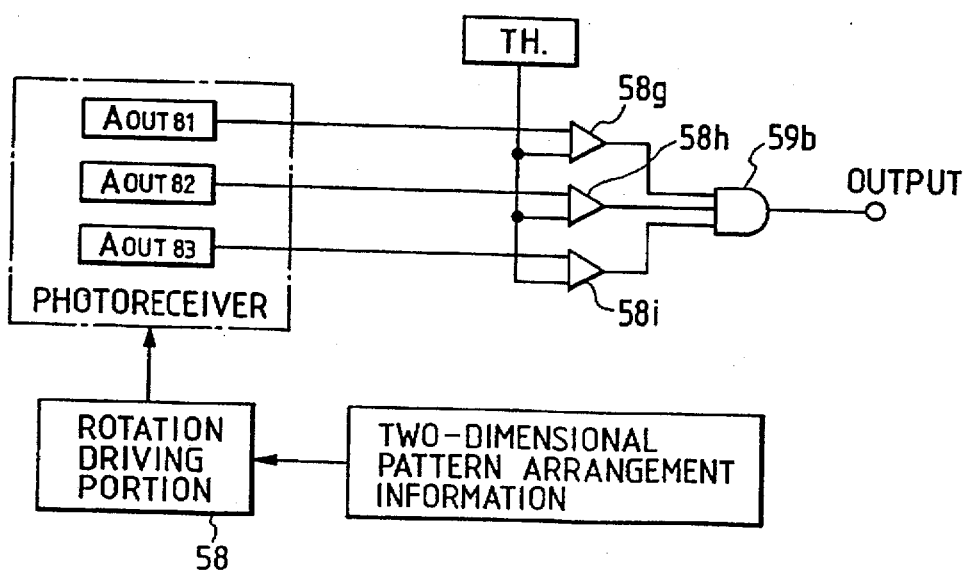
FIG. 20 is a block diagram showing the structure of the signal processing systems of a defect inspecting apparatus according to the fifth embodiment of the present invention.

FIG. 20 is a schematic view showing the structure of the signal processing system according to the present embodiment. In FIG. 20, information regarding two dimensional pattern arrangement of the circuit patterns is inputted into the rotation driving unit 60. The rotation driving unit determines the direction in which the interval between the diffractive light becomes greatest, and causes the photoreceiver to be rotated along the rotation of the optical axis so as to match this direction and the longitudinal direction of the light receiving areas. In this state, the surface of the substrate is scanned and light from the inspecting point O will be received. The output signals $A_{out81}$, $A_{out82}$, and $A_{out83}$ of the respective light receiving areas are inputted into comparators 58g, 58h, and 58i. In the comparators 58g, 58h, and 58i, a threshold value TH and each of the selected signals is compared. When the output signal $A_{out\,81}$, $A_{out82}$, and $A_{out83}$ exceed the threshold value TH, signals are output to an AND circuit 59b. In the AND circuit, the logical product of the signals from the comparators 58g, 58h, and 58i is obtained to distinguish foreign particles from circuit patterns.

Also, in the present embodiment, it is not necessarily required to obtain the optimal light receiving areas by conducting the calculation in accordance with the pattern arrangement information, but it may be possible to optimize the arrangement by trial and error method. In other words, using a normal substrate to which no foreign particles adhere, light from the inspecting point is being received while rotating the photoreceiver. In this case, the light to be received is only diffractive light from the patterns. As a result, at least one of the light receiving areas does not receive the diffractive light. Therefore, it is good enough to fix the photoreceiver at a position where the intensity of the diffractive light becomes the lowest. In this case, it may be possible to predict by the calculation of the pattern arrangement information to a certain extent the direction in which the interval between the light receiving areas becomes the greatest, and then to determine the optimal arrangement further by the above-mentioned trial and error method. In this way, the light receiving areas can be set in the most suitable direction more accurately and efficiently. In the foregoing the third and fourth embodiments, too, this method is applicable by receiving light from the inspecting point while switching over the light receiving areas. Also, as far as a trial and error method of the kind is concerned, it may also be an effective way to practice this method by lowering the scattering intensity of foreign particles by enlarging the beam spot of the incident light. Also, it may be possible to obtain the same effect by exercising the trial and error while rotating the substrate with respect to the incident surface of the incident light instead of switching over the light receiving areas. Also, it may be possible to measure the distributional state of the diffractive light from the actual patterns.

In this respect, the above description has been made of examples in which foreign particles are detected, but a defect inspecting apparatus according to the present invention can be used for other objectives than the foreign particle inspection. If, for example, a pattern itself has defectives such as an unwanted protrusion, the detection thereof can be conducted likewise with the apparatus as a matter of course.

Also, an apparatus according to the present invention is applicable not only to the reticles for which a light shielding pattern is formed with chrome and the like, but also to the defect inspection of phase shift reticles. In other words, by irradiating a converged beam, the scattering diffractive light can be emitted from a pattern formed with a phase material (dielectric film). Therefore, it is possible to conduct a separating detection of the phase shift patterns and foreign particles as well as a defect inspection of the phase shift patterns themselves.

Figure 21:
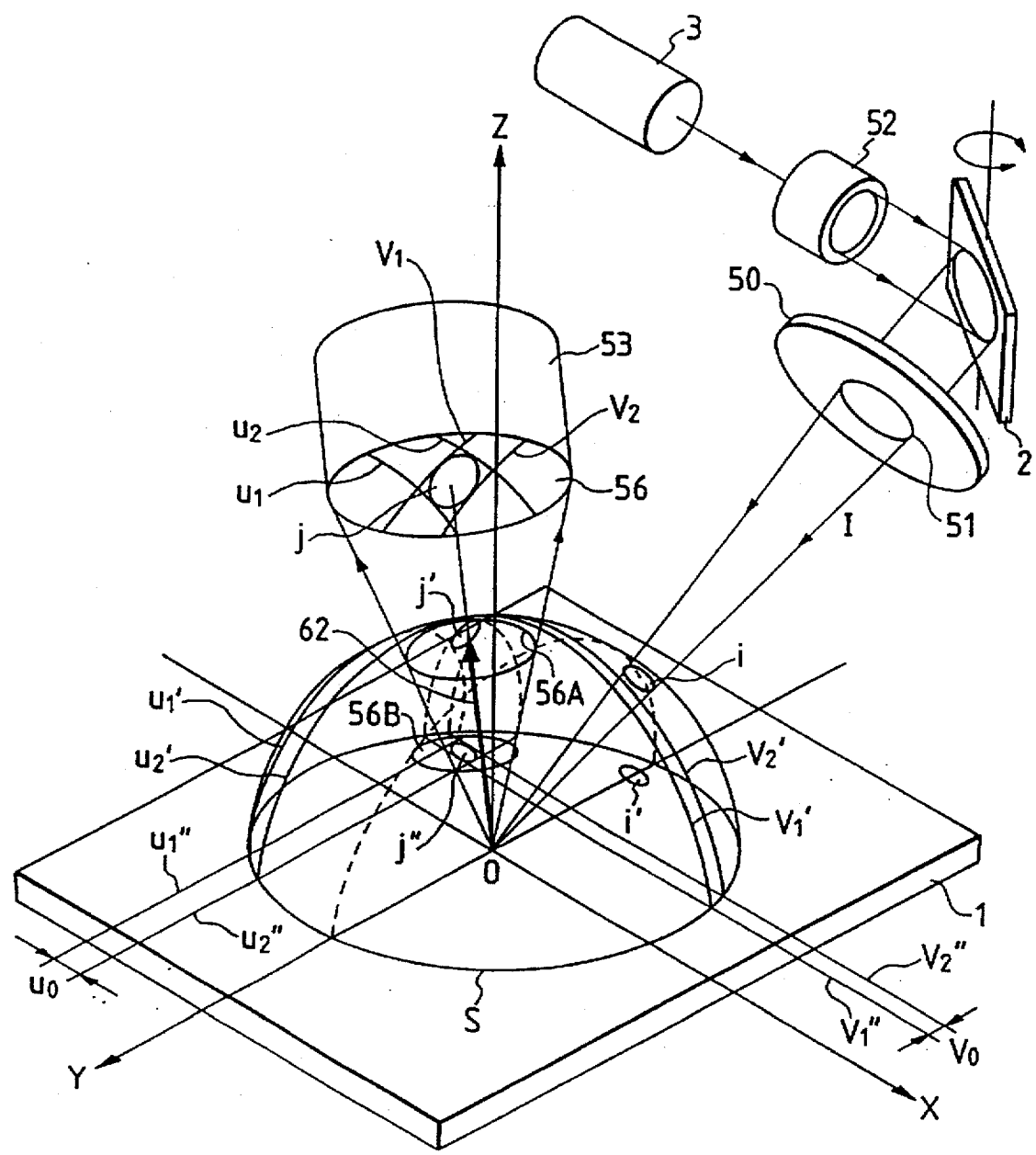
FIG. 21 is a perspective view showing the structure of the principal part of a defect inspecting apparatus according to a sixth embodiment of the present invention.

FIG. 21 is a perspective view schematically showing the structure of a preferable defect inspecting apparatus according to a sixth embodiment of the present invention. In FIG. 21, a beam emitted from a laser light source 3 is converged to an inspecting point O on a substrate having circuit patterns formed thereon through a beam expander 52 and an f-θ land 50 which constitutes a part of shifting means to shift the substrate 1 (reticle, wafer, or the like) and the beam interrelatedly. The converged incident beam I is caused by a vibrating mirror 2 to be optically scanned on the substrate 1 in the direction X. The f-θ lens 50 is a lens system having a large focal length. The incident direction of the incident beam I upon the substrate 1 is substantially equal to the direction Y in FIG. 21. The substrate 1 is stacked on a stage (not shown) movable in the direction Y. Thus, with the vibrating mirror 2 and the state, it is possible to conduct an foreign particle inspection over the entire surface of the substrate 1.

In this embodiment, the radius Sr of the sphere is defined as $Sr=1/\lambda$ ($\lambda$: the wavelength of the incident beam), and the size of the irradiated area on the substrate 1 upon incidence of the incident beam I is much smaller than the radius Sr.

On the substrate 1, minute circuit patterns are formed, and by the irradiation of the incident beam I, scattering diffractive light is emitted from the circuit patterns. A photoreceiver 53 has an aperture angle larger than the aperture angle of the incident beam I, at the same time photoelectric conversion elements being arranged two dimensionally on a light receiving surface 56 (pupil plane). Thus, the image on the light receiving surface 56 can be output as two dimensional image information. Also, although not shown in FIG. 21, there are provided for an apparatus according to the present embodiment, image processing means to process images in accordance with the two dimensional image information and detecting means to detect defectives on the surface of the substrate 1 in accordance with signals from the processed images. The image processing method will be described later.

Here, a sphere S schematically drawn with the inspecting point O (converged point of the incident beam I) as its center is considered. In FIG. 21, the curved section which is an area where the incident beam I and the spherical plane of the sphere S are superposed is designated by a reference mark i, and the positive projection (projection in the vertical direction) on the surface of substrate 1 (XY plane) of the curved section i is represented by a positive projection i'. This positive projection i' is, in other words, a positive projection on the substrate 1 of the terminating points of all the unit vectors 62 present in the incident beam I among the unit vectors 62 having the size with the inspecting point O as its starting point, which matches the radius of the sphere S.

Also, the light receiving surface 56 corresponds to the curved section 56A on the spherical plane of the sphere S, and the positive projection to the surface of the substrate 1 on curved section 56A is at 56B. Using the above-mentioned unit vector 62, the curved section 56A can be expressed as a concurrence of the terminating points of all the unit vectors 62 present in the aperture angle of the photoreceiver 53. The position (position of each pixel) of arbitrary point on the light receiving surface can be defined by the direction of the unit vector 62.

The figure j on the light receiving surface 56 represents the irradiating area (diffractive image) when the scatteringly emitted diffractive light is incident upon the central part of the light receiving area 56. In FIG. 21, the curved section which is an area where this diffractive light and the spherical plane of the sphere S are superposed is designated by a reference mark j' while the positive projection of the curved section j' to the surface of the substrate 1 is represented by a positive projection j". The curved section j' can also be expressed as a concurrence of the terminating points of all the unit vectors 62 present in the diffractive light, and the positive projection j" is of the congruent figure with the positive projection i'.

Also, Given the length of the positive projection j" in the direction X as $U_0$ and the length in the direction Y as $V_0$, and if the linear components $U_1$" and $U_2$" parallel to the axis Y which is tangential to the positive projection j" on XY are considered, these are the positive projections of the curved lines $U_1'$ and $U_2'$ on the sphere S. Also, of the vectors beginning with the inspecting point O and terminating at the point on the light receiving surface, the concurrences of the terminating points of the vectors which exist in the aperture angle of the photoreceiver 53 and penetrate the curved lines $U_1'$ and $U_2'$ become $U_1$ and $U_2$. The same is applicable to the linear components $V_1$" and $V_2$" parallel to the axis X which is tangential to j", and the curved lines $V_1'$ and $V_2'$ of the sphere and the linear components $V_1$ and $V_2$ on the light receiving surface correspond to each other.

As described earlier, there are formed comparatively minute patterns on the substrate 1, and the state of emission of diffractive light from these patterns is the same as those described in conjunction with FIGS. 7A to 7D, FIGS. 8A to 8E, and FIGS. 9A to 9E.

Now, the description will be made of the signal processing method according to the present embodiment.

In the present embodiment, the photoreceiver 53 has a plurality of photoelectric conversion elements arranged two dimensionally and outputs the images formed on the light receiving surface 56 as two dimensional pixel information. Then, the image processing is conducted on the basis of this pixel information.

Figure 22:
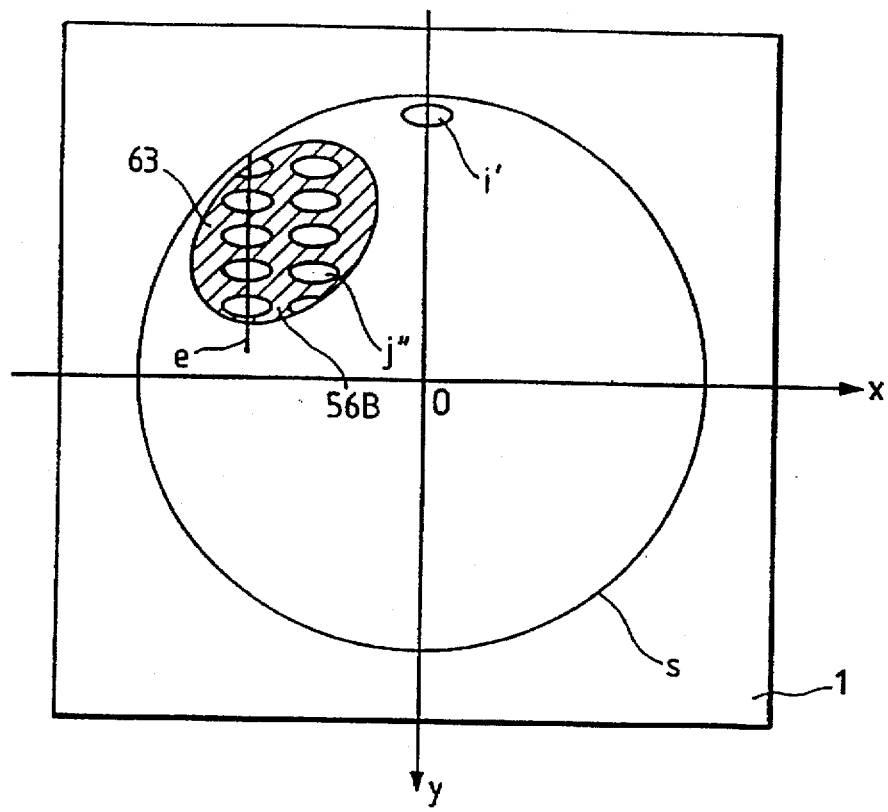
FIG. 22 is a conceptual view illustrating the distribution of diffractive light on a positively projected view.

Here, an arbitrary point on the light receiving surface 56 corresponds to one point of the positive projection 56B described earlier. For simplicity, the image processing method will be described using a positively projected view. FIG. 22 is a schematic view of the apparatus shown in FIG. 21 observed in the axial direction Z, in which is shown the state where a number of positive projection j" corresponding to the diffractive image on the light receiving surface 56 exist in the positive projection 56B.

Figure 23A:
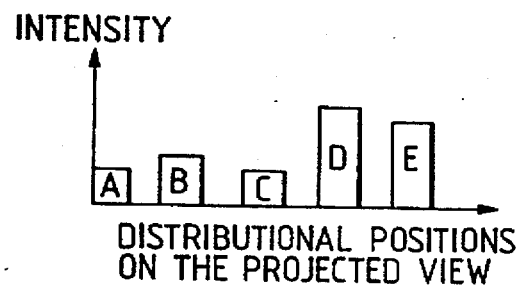
FIGS. 23A, 23B, 23C, and 23D are graphs showing the intensity distributions on a positively projected view.
Figure 23C:
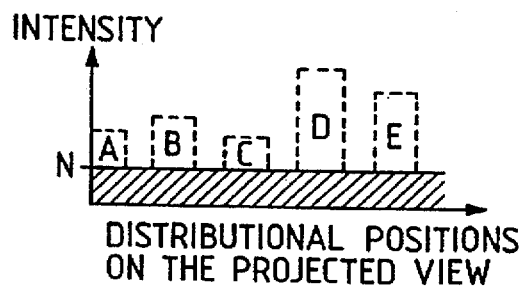
Figure 23B:
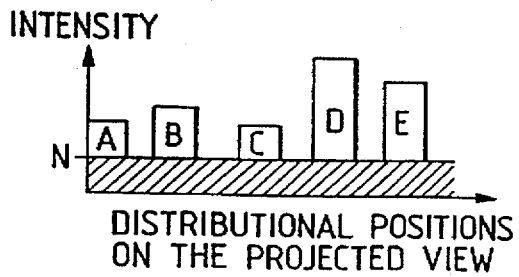

The one dimensional intensity distribution on the linear component e on the positive projection 56B is shown in FIGS. 23A, 23B, 23C, and 23D (the axis of ordinate represents light intensity while the axis of abscissa represents the distributional positions on the positively projected view). FIG. 23A shows only the intensity distribution of diffractive light from the pattern. FIG. 23B shows the intensity distributions when both the scattering rays of light from the foreign particle and the diffractive light from the pattern are received. The intensity distribution shown in FIG. 23B is such that the signals corresponding to the intensity of the scattering rays of light from the foreign particle are superposed as a d.c. component in contrast to the intensity distribution shown in FIG. 23A.

Figure 23D:
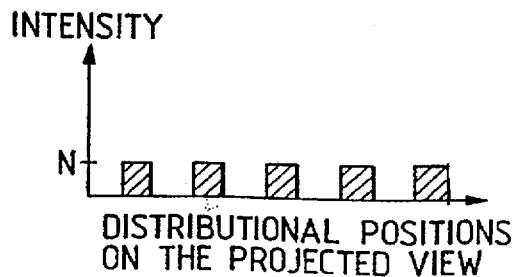

The optimal intensity distribution for the foreign particle detection is the intensity distribution where only the scattering rays of light from the foreign particle are represented as in FIG. 23C. In FIG. 23B, however, the intensities A, B, C, D, and E of the diffractive light will be added in the position where the positive projection j" of the diffractive light from the pattern is present. Since the ratio between the intensity of the scattering rays of light from the foreign particle and the intensity of the diffractive light from the pattern is unknown, it is impossible to take out only information regarding the scattering rays of light from the foreign particle in the position where the intensity of the diffractive light is added. Therefore, in the present embodiment, the foreign particle inspection is performed in a position where no positive projection j" of the diffractive light from the pattern is present, which is regarded as an effective light receiving area. The effective light receiving area is an area at 63 which is hatched with slanted lines in FIG. 22 where the positive projection j" of the diffractive light is removed from the positive projection 56B of the light receiving surface 56. FIG. 23D shows the intensity distribution of light to be received in the effective light receiving area, that is, only the distribution of the intensified portion of the scattering rays of light from the foreign particle.

Subsequently, the specific description will be made of an example of the image processing which extracts the positive projection j" from the positive projection 56B with reference to FIG. 24.

Figure 24:
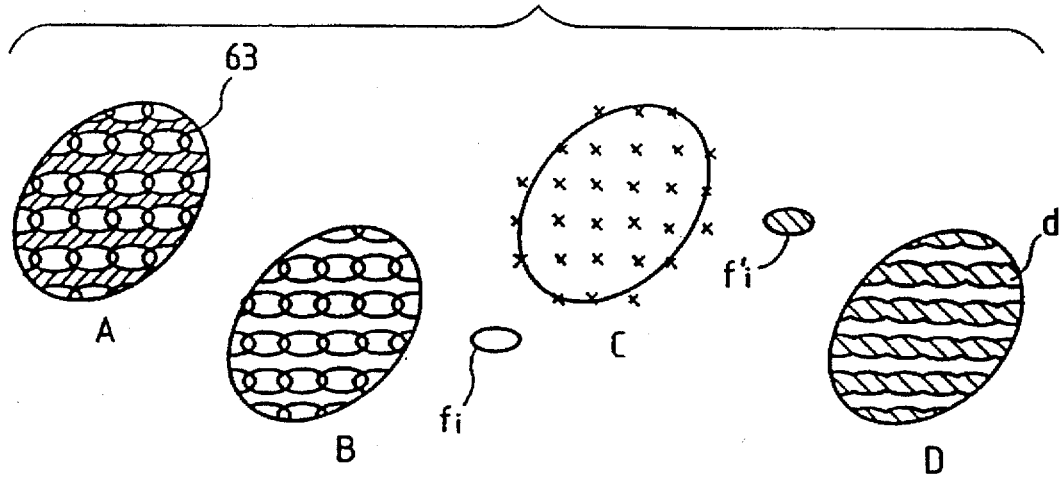
FIG. 24 (A, B, C, and D) illustrates an example of image processing, respectively.

A in FIG. 24 shows an in inputted image (output image from the photoreceiver 53) corresponding to the positive projections 56B in FIG. 21 and FIG. 22. In order to remove the portion corresponding to the positive projection of the diffractive light from this inputted image, the illuminance level of each pixel is at first diffranciated by its position, and then it is binary coded by an appropriate threshold value. In this way, the contour of the positive projection of the diffractive light is extracted. Thus, an image having only the contour of the positive projection of the diffractive light is obtained as shown B in FIG. 25. Subsequently, while correlating each one of contours $f_i$ of the positive projections of the diffractive light, each central coordinates of the positive projections of the diffractive light are extracted (C in FIG. 24). The contour $f_i$ is of a congruent figure with the positive projection of the incident beam I as described earlier. This can be obtained from the information regarding the incident angle θ of the incident beam I and the aperture angle γ. Further, if a senseless zone at $f_i'$ (the contour of which is the same as $f_i$, B in FIG. 24) in the central coordinates C in FIG. 24 is combined, a senseless zone D is formed as indicated by slanted lines D in FIG. 24. This senseless zone D is nothing but the location where the positive projection of the diffractive light is present, and the portion indicated by slanted lines A in FIG. 24 is the portion where this senseless zone D is removed, that is, the effective light receiving area 63 in which no positive projection of the diffractive light from the pattern exists.

Figure 25:
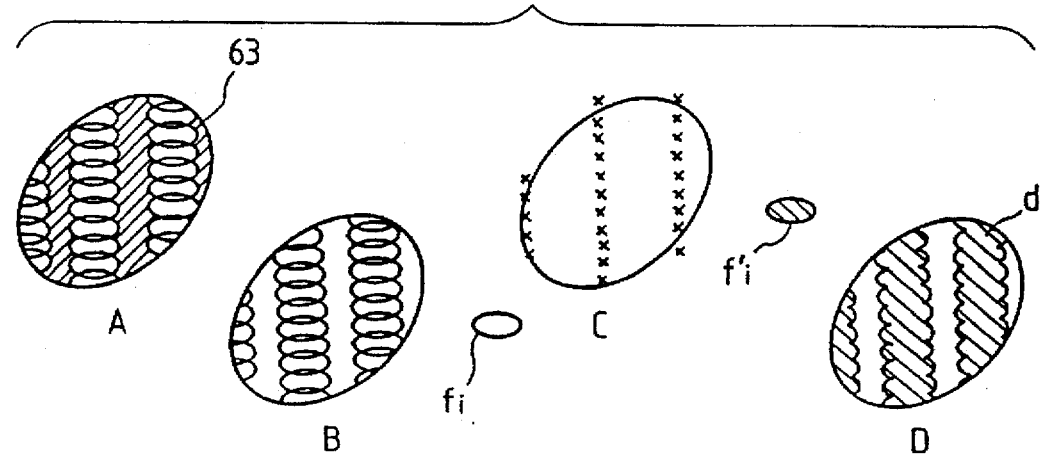
FIG. 25 (A, B, C, and D) illustrates an example of image processing, respectively.

FIG. 25 illustrates an image processing where the arrangement of pasterns is different from FIG. 24. In a case shown in FIG. 25, the effective light receiving area 63 in which no positive projection of the diffractive light exists can be obtained in exactly the same manner as in FIG. 24. In other words, an inputted image (A in FIG. 25) is binary coded to obtain the contour of the positive projection of the diffractive light (B in FIG. 25). Then, the central coordinates of each positive projection is obtained by taking the correlation with the contour $f_i$ of each individual positive projection (C in FIG. 25). Subsequently, the central coordinates are combined with the senseless zone $f_i'$ to obtain the image of the senseless zone d (D in FIG. 25). Thus, it is possible to obtain the effective light receiving area 63 where no positive projection of the diffractive light exists.

In this respect, it is needless to mention that the image can be processed in the same manner in any other cases of patterns such as shown in FIGS. 8A to 8E and FIGS. 9A to 9E than the cases where the positive projections of the diffractive light are arranged in parallel to the UV coordinates as shown in FIG. 24 and FIG. 25. Also, the image processing method is not confined to the examples shown in FIG. 24 and FIG. 25.

Now, using FIG. 26, a second example of the image processing will be described. In this example, a consideration is given to enable the extract of the positive projections of the diffractive light with a desirable precision when a plurality of positive projections of the diffractive light to be extracted are scatteringly present.

Figure 26:
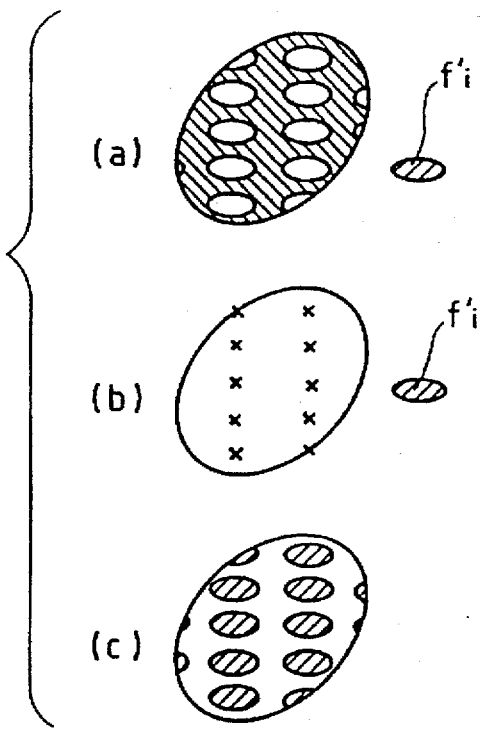
FIG. 26 illustrates another example of image processing, respectively.

(a) in FIG. 26 is an inputted image, which corresponds to the positive projections 56B in FIG. 21 and FIG. 22. In order to remove from this inputted image the portion corresponding to the positive projection of the diffractive light, the central coordinates of each of the positive projections of the diffractive light are extracted at first while taking correlating the senseless zone $f_i'$ shown (a) in FIG. 26 ((b) in FIG. 26). Then, the senseless zone indicated by slanted lines (c) in FIG. 26 is formed when these central coordinates and the senseless zone $f_i'$ are combined.

Now, using FIG. 27, a third example of the image processing will be described. In the present example, a consideration is given to extract the positive projection of the diffractive light with a desirable precision when the positive projection of the diffractive light to be extracted is arranged in parallel to the U and V coordinate axes.

Figure 27:
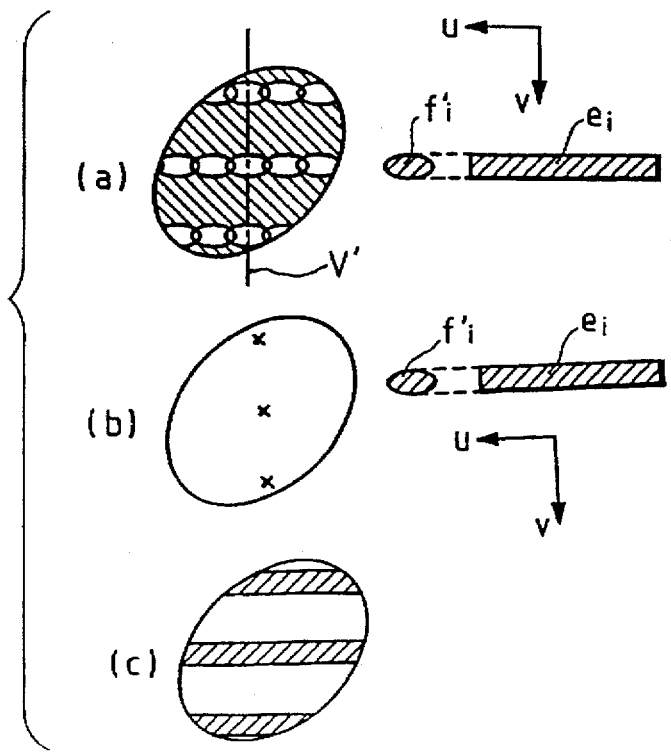
FIG. 27 illustrates still another example of image processing, respectively.

(a) in FIG. 27 is an inputted image. In order to remove from this inputted image the portion corresponding to the positive projection of the diffractive light, just only one dimensional processing in the direction parallel either to the U axis or the V axis is required. At first, a correlation is taken in the V axis direction V' using a senseless zone $e_i$ having the width in the direction V which is equal to the senseless zone $f_i'$ and the width in the U axis direction which is equal to the width of the inputted image as shown (a) in FIG. 27. In this way, each of the central coordinates of the diffractive light array is obtained. Then, when these central coordinates and the senseless zone $e_i$ are combined, the senseless zone indicated by slanted lines (c) in FIG. 26 is formed. In the present example, while a one dimensional processing is performed in the V axis direction, it may be possible to do likewise in the U axis direction. Also, it may be possible to conduct the processing in the two directions of V and U axes simultaneously.

Figure 28:
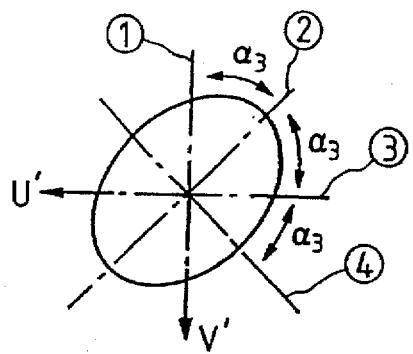
FIG. 28 is a view illustrating a method of image processing.
Figure 29:
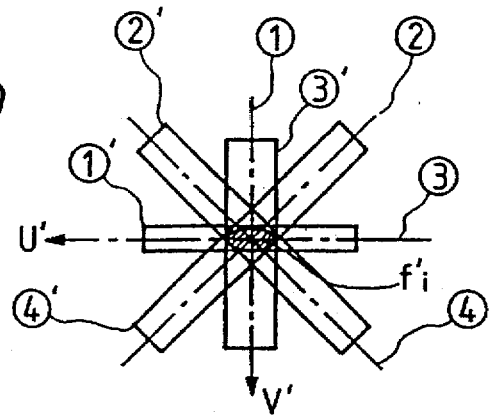
FIG. 29 is a view illustrating a method of image processing.

Also, as shown in FIG. 28, it may be possible to determine an axis (1), axis (2), axis (3) and axis (4) at an appropriate interval $\alpha_3$ with respect to the fiducial coordinate U' axis and V' axis of an inputted image, and then to conduct processing in these directions. At this juncture, the figure of the senseless zone to be used for obtaining the central coordinates of the diffractive light array can be determined by matching it with the width in each direction of the senseless zone $f_i'$ shown in FIG. 29 (the contour of f' being the same as f, B in FIG. 24) in such a manner that a senseless zone (1)' is arranged for the axis (1) and so on, for example.

In the above-mentioned first to third examples of the image processing, the central coordinates of the positive projection of the diffractive light are obtained by taking the correlation using the contour $f_i$ of the diffractive light, the senseless zone $f_i'$, or the senseless zone $e_i$ in the one dimensional direction, but it may be possible to arrange an inputted image to be binary coded by an appropriate threshold value and extract only the positive projection of the diffractive light as a simpler method. Further, while the contour of the positive projection of the diffractive light is obtained by binary coding the inputted image or taking the correlation, it may be possible to obtain the contour of the positive projection of the diffractive light by calculations using information regarding the pitches and periodic direction of the circuit patterns.

As described above, subsequent to the image processing, the incident light upon the effective light receiving area 63 is detected. Such an incident light upon this effective light receiving area 63 is nothing but the scattering rays of light from foreign particles (or defectives on the patterns). Therefore, just by providing an appropriate threshold value to distinguish them from any noises, it is possible to detect any foreign particles efficiently with a high discriminating detection ratio. At this juncture, in order to detect only the incident light upon the effective light receiving area 63, it may be possible to select the outputs from the photoelectric conversion elements positioned in the effective light receiving area 63 or to mask the senseless zones D other than the effective light receiving area 63 with a light shielding material. The masking can be performed by a liquid crystal or electrochromic element beside slit and others.

Here, in the above-mentioned descriptions, an example is shown in which the portion where no positive projection of the diffractive light from the patterns exists is obtained by image processing and then foreign particles are detected utilizing this portion as an effective light receiving area 63, but a defect inspecting apparatus according to the present invention is applicable to other uses than the above-mentioned foreign particle inspection. For example, by utilizing the scattering diffractive light from the patterns which is regularly distributed in response to the periodicity of the patterns, it is possible to detect the deviation of the pitches of the pattern arrangement or the like. In other words, if the pitches of the positive projection of the diffractive light in a positively projected view are locally varied, it is known that there is some abnormality in the pattern pitches in the corresponding part.

Also, by conducting a defect inspection after the effective light receiving area 63 is determined by the image processing as in the present embodiment, it is possible to enhance the inspection efficiency more significantly than the comparison between each of the outputs of the photoelectric conversion elements of the photoreceiver 53 with the data of the circuit patterns.

Furthermore, an apparatus according to the present invention is not confined to the application to a reticle on which are formed light shielding patterns of chrome and others, but it is also applicable to the defect inspection of phase shift reticles. In other words, by irradiating a converged beam, the scattering diffractive light is emitted from the patterns formed with a phase material (dielectric film). Therefore, it is possible to conduct the discriminating inspection of the phase patterns and foreign particles as well as any defectives on the phase shift patterns themselves as described in conjunction with FIG. 24 and FIG. 25. Also, the phase shift patterns are often arranged in the same periodic directions and same pitches as the chrome patterns. In such a case, the distribution of diffractive light is equal for both of them. It is also easy for both of them to conduct the required image processing.

Figure 30:
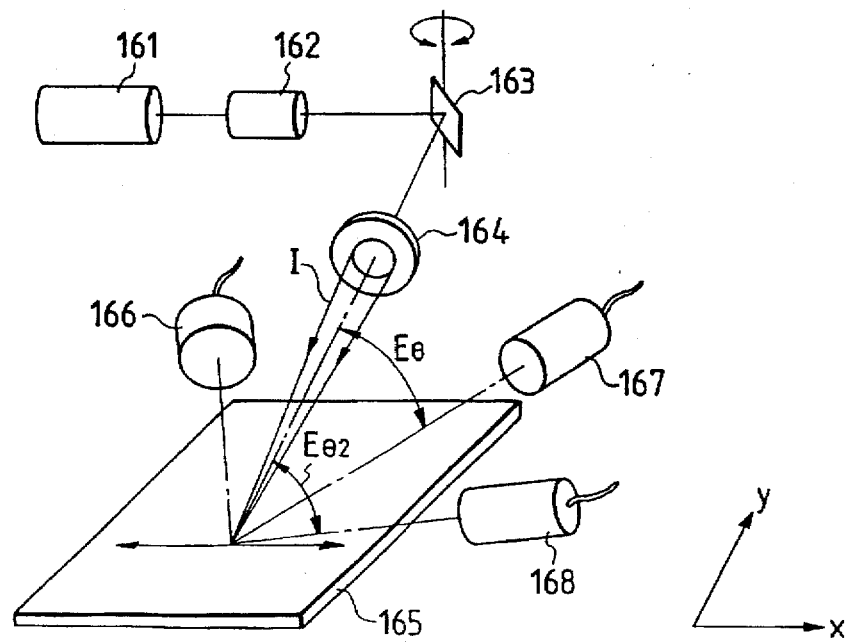
FIG. 30 is a perspective view schematically showing a defect inspecting apparatus according to the seventh embodiment of the present invention.

FIG. 30 is a perspective view showing the schematic arrangement of a defect inspecting apparatus according to the seventh embodiment of the present invention. The same reference numerals as in FIGS. 1 and 13 denote the same parts in FIG. 30. A detailed description of members having the same functions as in FIG. 1 and 13 will be omitted. In FIGS. 1 and 13, the beam expander 52 is fixed in the optical path of the incident optical system. A beam expander 52 in FIG. 30 is retractable from the optical path of the incident optical system by a driving means 69 such as an air cylinder. Although not shown in FIGS. 1 and 13, a substrate 1 is placed on a stage 70 movable in the Y direction, as shown in FIG. 30. A foreign particle can be inspected on the entire surface of the substrate 1 by a vibrating mirror 2 and the stage 70. The stage 70 is two-dimensionally movable in the X and Y directions by a stage driving means 71 and is rotatable within the X-Y plane.

The light receiving surface of the optical receiver 53 is constituted by a fiber bundle (light receiving segment D). The light receiving surface can detect the intensity distribution of the incident beam on the light receiving surface 56 by a two-dimensional photoelectric conversion element array 72 such as a two-dimensional CCD array through an image fiber 73 for guiding a beam incident on the light receiving surface.

The light receiving surface 56 has light receiving areas A, B, and C capable of performing independent photoelectric conversion. The beams incident on the light receiving areas A, B, and C are guided to photoelectric converters 55 through optical fibers 54 and are independently photoelectrically converted. Signals $A_1$, $B_2$, and $C_3$ from the photoelectric converters 55 are input to a controller 100. The controller 100 logically ANDs the signals to discriminate the foreign particle from the circuit pattern (this discrimination will be described in detail later). The controller 100 controls the overall operation of the apparatus.

A beam incident on the light receiving surface 56 corresponds to a curved section 56A on the spherical surface of the sphere S. The positive projection of the curved section 56A onto the surface of the substrate 1 is designated by reference numeral 56B. Light receiving areas A', B', and C' correspond to the curved sections on the spherical surface of the sphere S, and the positive projections of the curved sections A', B', and C' are designated by reference numerals A", B", and C".

The width of each of the positive projections A", B", and C" on the light receiving areas is defined as d. The width d is preferably minimized in consideration of a capability of discriminating a pattern from a foreign particle. The light receiving area reduced with a decrease in the width d can be compensated by increasing the length parallel to the U direction. In this case, the distance between the positive projection A" and the positive projection C" is equal to the width of positive projection j" (positive projection i") of the diffracted light. A figure j" is congruent to figures i' and r'.

In this embodiment, the Fourier spectral distribution of the diffracted light is actually measured to optimize a light receiving area. A relationship between each point on the sphere S and a corresponding point on the Fourier transform plane will be described below.

When the incident beam I is incident to be focused on the circuit pattern on the substrate 1, the incident beam becomes a plane wave on the substrate. The amplitude distribution of light determined by the presence/absence of the circuit pattern and a reflectance is formed in an irradiated area on the substrate. When a diffraction phenomenon occurring due to the amplitude distribution of the incident plane wave is observed at a point of infinity of the area irradiated with the incident beam, it can be dealt as Fraunhofer diffraction. The amplitude distribution of the incident plane wave determined by a two-dimensional circuit pattern on the substrate surface is defined as F(x,y). The amplitude distribution F(x,y) has the Fourier transform relationship with a diffracted image f(u,v) at the point of infinity. This relationship is defined as equation (13)

$$f(u,v) = Ca \int \int_{-\infty}^{\infty} F(x,y) \exp[-2\pi i(ux+vy)] dxdy \quad (13)$$

where f is a distance to the observation point, Ca is a constant, x and y on the substrate surface are coordinates representing a position, and u and v are coordinates of the diffracted image to represent a spatial frequency. The coordinates u and v are represented by equations (14) and (15) below:

$$(l-l_0)/\lambda = u \quad (14)$$

$$(m-m_0)/\lambda = v \quad (15)$$

where $\lambda$ is a wavelength of the incident beam, $l_0$ and $m_0$ represent the directional cosine in which the plane wave is incident on the substrate surface, and l and m represent the directional cosine of space vectors corresponding to the observation point at the point of infinity from the substrate.

If the irradiated area is defined as ±xe and ±ye, the point of infinity can be defined by satisfying the following condition:

$$f \gg \frac{2(xe^2 + ye^2)}{\lambda} \quad (16)$$

Assume a sphere S having a radius f and an irradiated area as its center. In this case, u and v are defined as equations (17) and (18) as follows:

$$f \cdot (l-l_0) = U = u \cdot \lambda \cdot f \quad (17)$$

$$f \cdot (m-m_0) = V = v \cdot \lambda \cdot f \quad (18)$$

If (directional cosine) x f is satisfied, i.e., if a point on the sphere S corresponding to the directional cosine is positively projected on the substrate, coordinates can be converted into U and V coordinates corresponding to the coordinates u and v on the Fourier transform plane. For the descriptive convenience, the U-V plane will be called a Fourier plane, and the origin is the position of the 0th-order diffracted light component.

In the following description, the radius of the imaginary sphere is defined as f=1/λ, which defines the condition (16). The circuit patterns formed on the substrate 1 in FIG. 30 include a large number of two-dimensional periodic patterns as in the third embodiment. Most of the patterns have periodic patterns in the X and Y directions of the substrate 1 and periodic patterns of line symmetry with respect to the X or Y direction. Diffracted light components described with reference to FIGS. 7, 8, and 9 are obtained from the two-dimensional periodic patterns. The shapes of the positive projection i' and the positive projection r' (to be referred to as the positive projection i' (r') hereinafter) are determined by the an angular aperture γ and an incident angle θ of the incident beam I. If the radius of the sphere S is defined as 1/λ, a length $v_0$ of the positive projection i' (r') in the V (Y) direction, and a length $u_0$ thereof in the U (X) direction are defined by equations (19) and (20):

$$v_0 = (f/2\lambda) \cdot \sin\gamma \cdot \cos\theta \quad (19)$$

$$u_0 = (2/\lambda) \cdot \sin\gamma \quad (20)$$

Discrimination of a circuit pattern on the substrate from a foreign particle by means of discreteness will be described again with reference to FIGS. 31A and 31B, and then a relationship between a threshold value and discrimination by discreteness will be described.

FIG. 31A shows a one-dimensional V-axis intensity distribution of diffracted light obtained by positively projecting the two-dimensional periodic patterns shown in FIGS. 7A to 9E. Referring to FIG. 31A, pitches (non-diffracted light components) $P_1$, $P_2$, and $P_3$ of discretely produced diffracted light components (positive projection) are determined in accordance with the periodic direction of the pattern and the degree of micropatterning thereof. FIG. 7B shows the distribution of the diffracted light of FIG. 7A in the U-V coordinate system. The hatched portions in FIG. 7A correspond to those of FIG. 7B. FIG. 7D shows the intensity distribution of scattering light from the foreign particle. The scattering light from the foreign particle is produced as continuous light while light diffracted by the pattern is discrete. FIG. 7C shows the positive projection of independent light receiving areas for receiving light from the inspecting point in the U-V coordinate system. In this case, three positive projections $A_1''$, $B_1''$, and $C_1''$ corresponding to the three light receiving areas in FIGS. 31A and 31B are illustrated.

To discriminate the discreteness of light diffracted by the pattern from continuity of light scattering from the foreign particle, the respective light receiving areas must be arranged on the positive projection view so as to satisfy the following condition. First of all, a distance Mv between the farthest light receiving areas of all the light receiving areas must be a width $v_0$ or more of the light diffracted by the pattern. If Mv=$v_0$, condition (21) must also be satisfied:

$$\delta = P_{UV} - v_0 \geq 2d + [v_0 - (n-2)d]/(n-1) = R_a(n) \quad (21)$$

where

δ: distance between light components diffracted by pattern $P_{UV}$: pitch of light components diffracted by pattern n: number of light receiving areas $v_0$: width of light receiving area Note that $R_a$ is an evaluation value representing the discrimination capability or resolution. The discrimination resolution increases when this evaluation value decreases.

When the above condition is satisfied, the positive projections (FIG. 31B) of the diffracted light components do not overlap on the three light receiving areas in FIG. 31C, and discrimination of discreteness can be properly performed. More specifically, signals from the respective light receiving areas are logically ANDed to obtain a signal for discriminating the pattern from the foreign particle.

To determine the number n of light receiving areas based on condition (21), a minimum distance between the light components diffracted by the patterns and subjected to discrimination must be known. The signals from the respective light receiving areas are binarized with reference to a given threshold value, and these digital signals are logically ANDed to discriminate the pattern from the foreign particle.

To detect a foreign particle having a scattering light intensity es in FIG. 31D, a threshold value $Th_1$ is set at an intensity level slightly lower than the scattering light intensity es. As can be apparent from FIG. 31D, the levels of all the signals from the light receiving areas $A_1''$, $B_1''$, and $C_1''$ are higher than the threshold value $Th_1$.

The diffracted light components having the pitches $P_1$, $P_1$, and $P_1$ and produced by the circuit pattern shown in FIG. 31A have higher levels than the threshold value $Th_1$. The width $v_0$ of the light component diffracted by the pattern and the pitches of the light components diffracted by the pattern satisfy condition (21). In this case, the diffracted light is not incident on at least one light receiving area.

When the binary signals of the signals from the respective light receiving areas are logically ANDed, the truth value becomes different from that obtained by logically ANDing the signals obtained upon detection of the foreign particle (FIG. 31D), so that the pattern can be easily discriminated from the foreign particle.

In practical design of an apparatus, a signal intensity corresponding to a detected minimum foreign particle is determined, the threshold value $Th_1$ is determined to allow detection of the minimum foreign particle, and discrimination by discreteness is performed for signal levels exceeding the threshold value $Th_1$. In other words, condition (21) is established only when the levels of the light components diffracted by the patterns exceed the threshold value $Th_1$.

The pitch of the light components diffracted by the periodic pattern is in inverse proportion to the pitch of the periodic pattern. As shown in FIG. 22A, when the pitches ($P_1$, $P_2$, $P_3$) are reduced, the intensity decreases accordingly because the light receiving areas are located at a position of the positively reflected light, i.e., at a position away from the origin O on the U-V plane. Therefore, the pitch of the light components diffracted by the patterns, which exceeds the threshold value $Th_1$ shown in FIG. 31A, will not be smaller than a given value $\delta_0$. The width d of the light receiving area determines the number n of light receiving areas so that condition (21) is established for the minimum value $\delta_0$ of the pitch P of the light components diffracted by the pattern and having levels exceeding the threshold value $Th_1$. Parameters for determining the minimum value $\delta_0$ are ① the angle of an incident beam ② the position of the light receiving area, and ③ the spot size of the incident light beam.

The parameters ① to ③ are experimentally optimized, and the minimum value $\delta_0$ is maximized. Discrimination by discreteness is performed using a minimum number n of light receiving areas.

Figure 32:
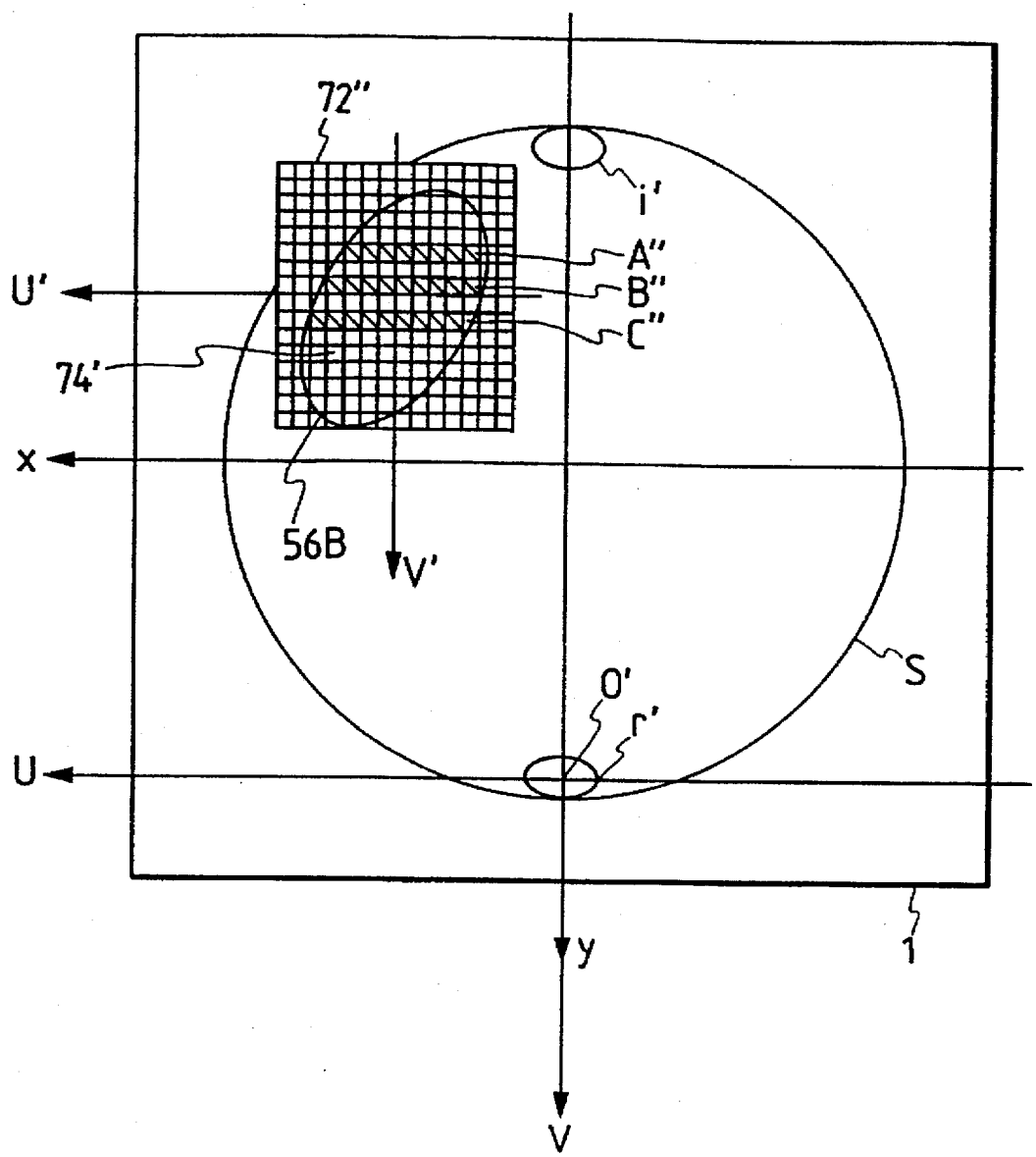
FIG. 32 is a view showing the surface of a substrate in FIG. 30 in correspondence with a two-dimensional photoelectric conversion element array when viewed from the Z direction.

A relationship between a beam incident on the light receiving segment D of the optical receiver 53 in FIG. 30 and the two-dimensional photoelectric conversion element array 72 will be described with reference to FIG. 32. FIG. 32 shows the two-dimensional photoelectric conversion element array 72 on the Fourier plane as in FIG. 14.

The light receiving segment D and the image fiber 73 constitute a Fourier transform optical element. More specifically, light incident from the image fiber 73 on each element of the two-dimensional photoelectric conversion element array 72 corresponds to each point of the positive projection of the curved section of the sphere S on the substrate 1, as shown in FIG. 32. That is, a light beam corresponding to a point 74 in FIG. 32 corresponds to a point 74' on the U'-V' plane in FIG. 32. The U'-V' coordinate system is a new coordinate system having as its origin the center of the photoelectric conversion element array 72 on the Fourier plane.

The light receiving areas A, B, and C of the optical receiver 53 in FIG. 30 are prepared for detecting foreign particles. A fourier spectrum from the circuit pattern on the substrate 1 is measured using the two-dimensional photoelectric conversion element array 72. Referring to FIG. 32, the positive projection 56B represents the Fourier spectral range of the light included in the light receiving surface, and a positive projection 72" represents a spectrum measured by the array.

Figure 33:
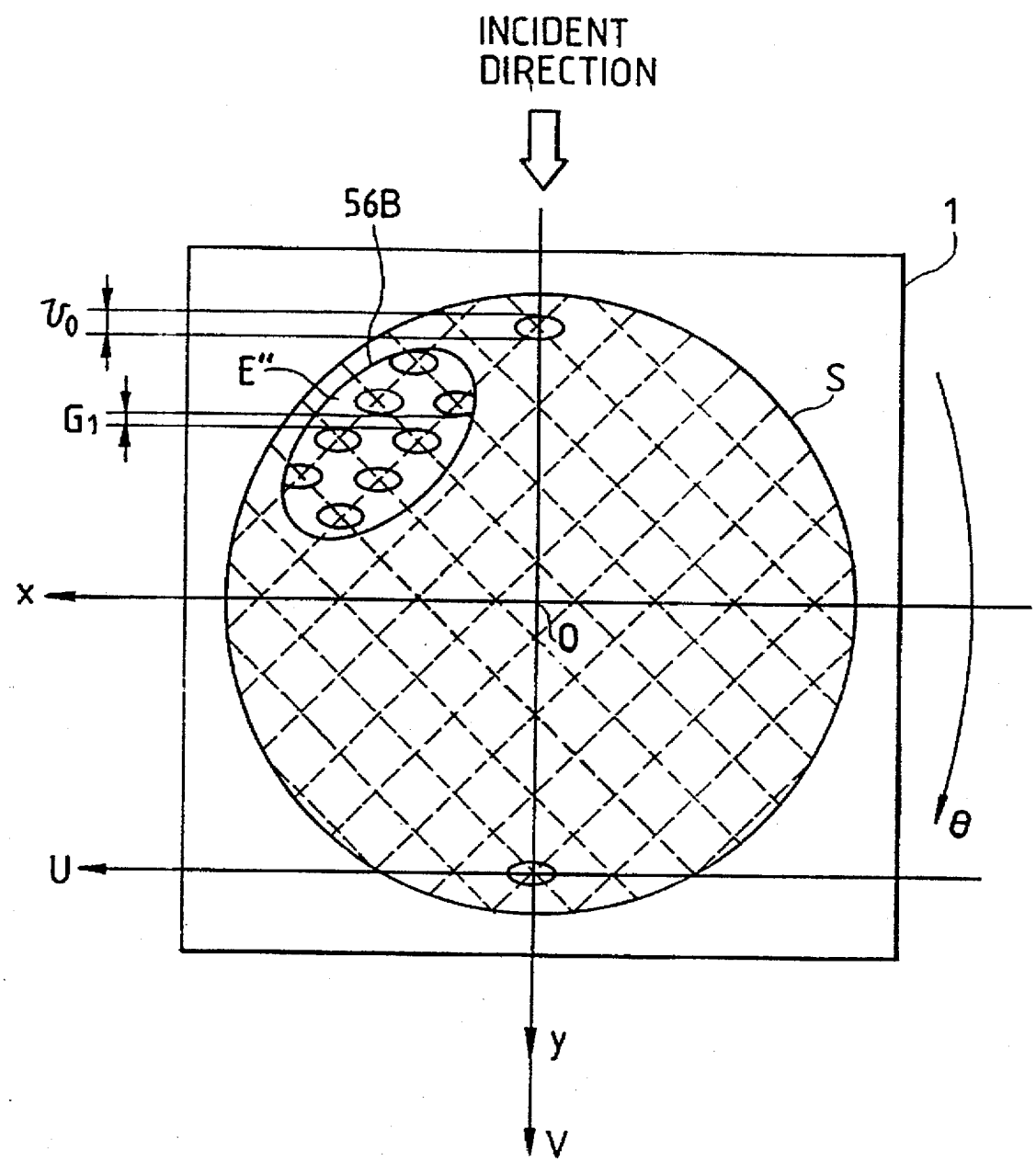
FIGS. 33 and 34 are views each showing a relationship between the direction of a periodic pattern and an incident direction.

A Fourier spectrum obtained upon rotating the substrate i on the X-Y plane will be described below. FIG. 33 shows a Fourier spectrum of pattern elements having a periodic direction symmetrical about the X or Y direction, as shown in FIG. 8A. FIG. 33 shows the Fourier spectrum when the Z-Y plane of the substrate 1 serves as an incident plane. A total Fourier spectrum of the light beams incident on the light receiving surfaces is assumed as E" on the Fourier plane.

Figure 34:
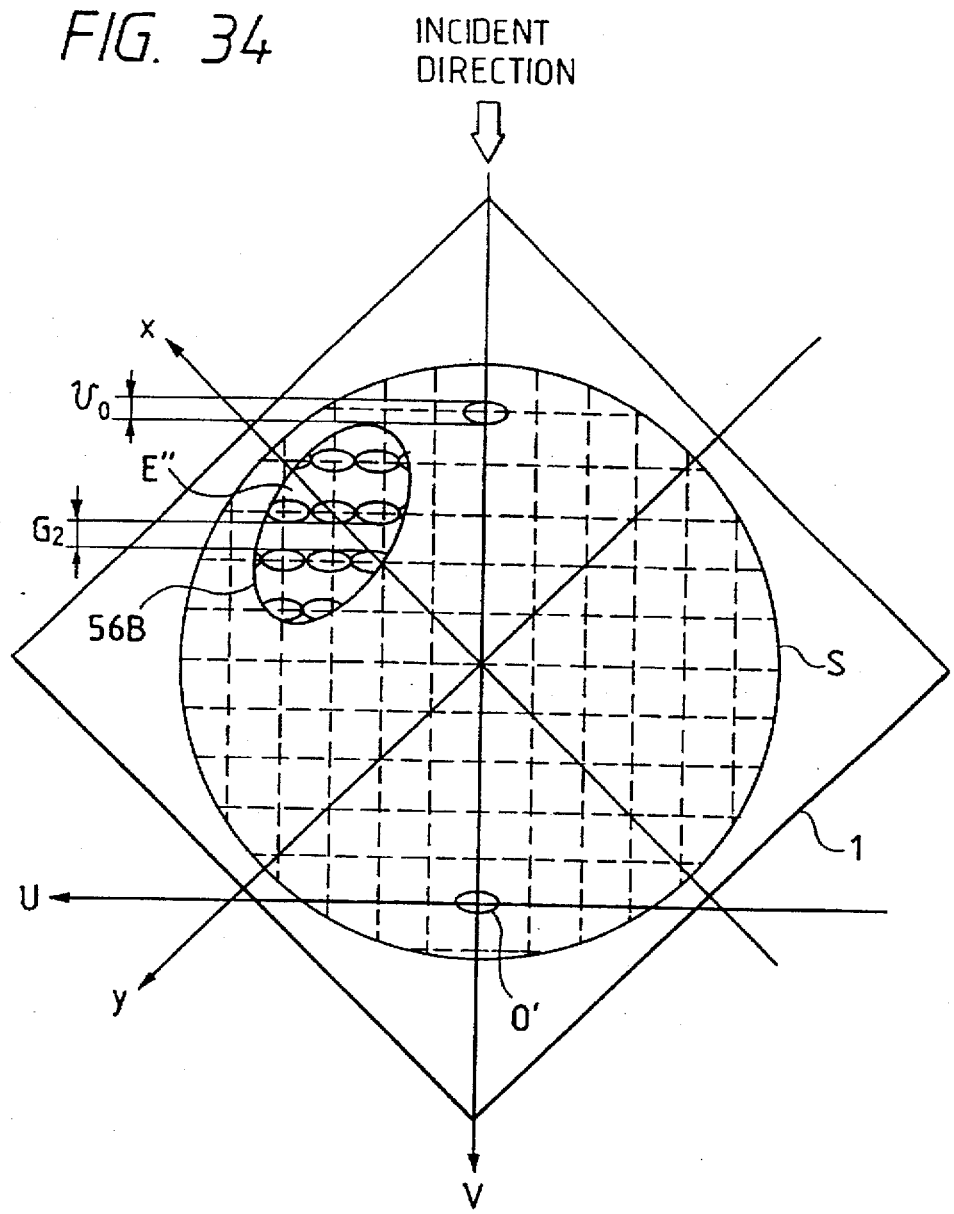

The width of the Fourier spectrum obtained from an area in the absence of diffracted light in the V direction is represented by $G_1$. FIG. 34 shows a Fourier spectrum of a two-dimensional periodic pattern when the substrate 1 is rotated through 45° in the θ direction within the X-Y plane. The coordinates of central points (to be referred to as inverse lattice points hereinafter) of discrete spectra of the two-dimensional periodic pattern on the Fourier plane are rotated through 45° about the spectral point O' of the 0th-order diffracted light component during rotation of the substrate 1. In this case, as the incident beam is inclined, the elliptical Fourier distribution of the spectrum of the incident beam always has a major axis in the U direction. For this reason, the state of the Fourier spectrum observed within E" is different from that described above, and the width of the area in the absence of the diffracted light in the V direction is represented by $G_2$ ($G_2 > G_1$). When the width of the area in the absence of the diffracted light in the V direction increases, better spectral discrimination (discrimination by discreteness) can be performed.

Figure 35:
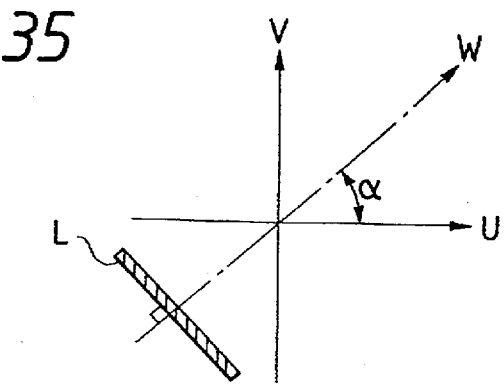
FIG. 35 shows an example of an image processing method.
Figure 36A:
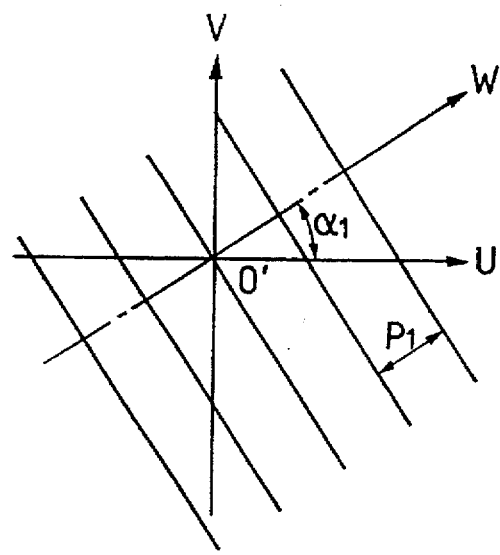
FIGS. 36A to 36D are views for explaining periodic directions detected by image processing.
Figure 36B:
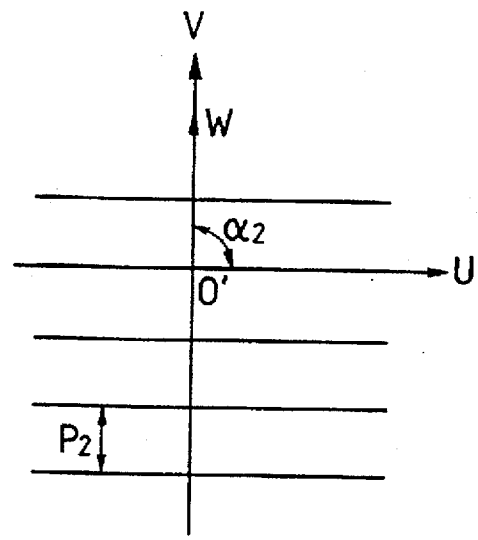
Figure 36C:
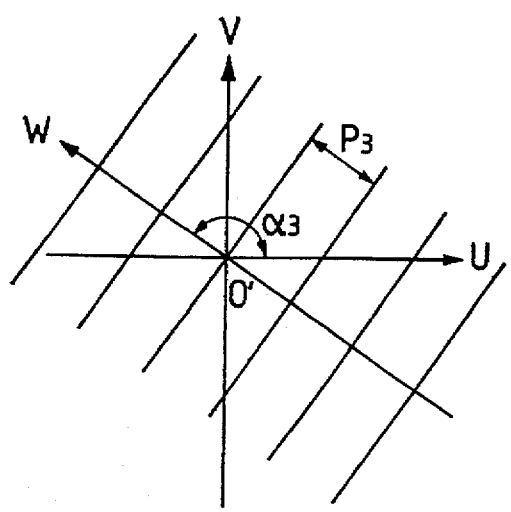
Figure 36D:
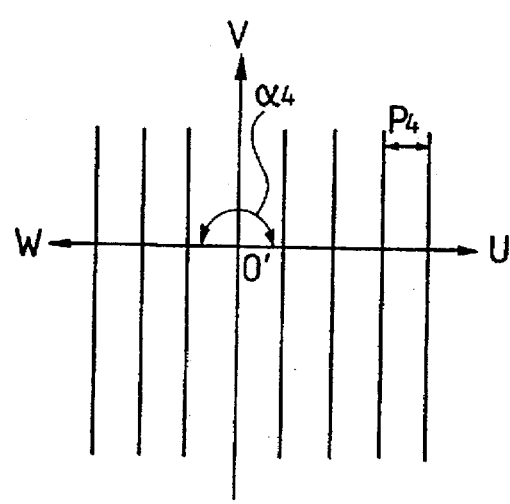

A method of processing an image on the Fourier plane will be described below. As shown in FIG. 35, a linear convolution mask L perpendicular to coordinates W plotted to form an angle α with respect to the U axis is used, and convolution integration of, e.g., the pattern shown in FIG. 8A is performed along the coordinates W using a as a parameter. When a peak value is then extracted, and the Fourier spectrum is the one shown in FIG. 8B, periodic line sequences at $\alpha = \alpha_1$, $\alpha_2$, $\alpha_3$, $\alpha_4$ are obtained, as shown in FIGS. 36A, 36B, 36C, and 36D.

In this case, α corresponding to a maximum one of the pitches $P_1$, $P_2$, $P_3$, and $P_4$ of each periodic line sequence is selected. The direction of the incident plane with respect to the inspecting plane is determined such that the direction of a line N corresponding to this α is a longitudinal direction of the spectrum of the incident beam. That is, the direction of the line W is aligned with the direction of the incident plane.

A method of measuring a Fourier spectrum of a two-dimensional periodic pattern of the substrate 1 and a foreign particle inspecting operation will be described below.

Figure 37A:
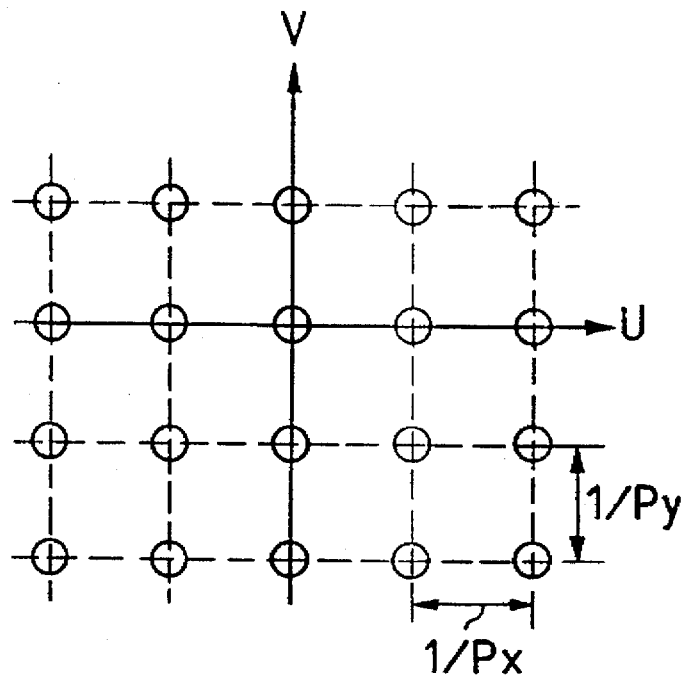
FIGS. 37A and 37B are views for explaining the numerical aperture of a light guide system and the magnitude of a Fourier spectrum.
Figure 37B:
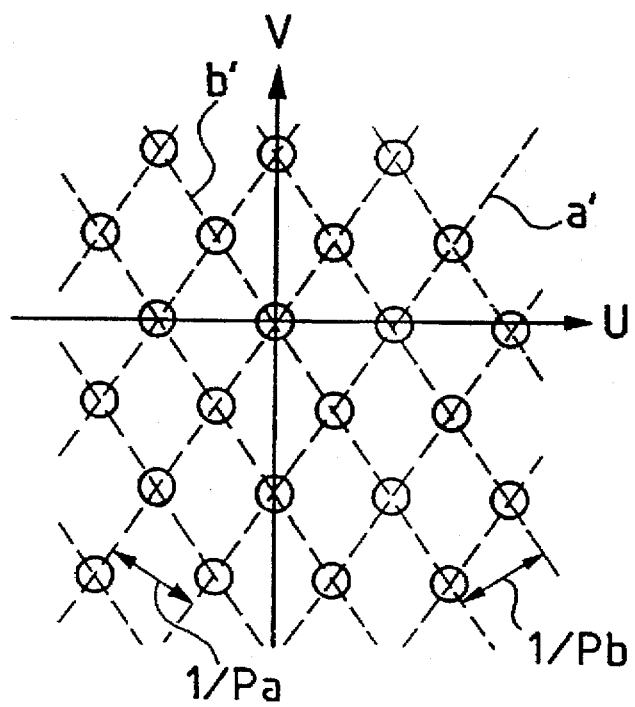

The beam expander 52 is retracted from the optical axis of the light guide system by the driving means 69 in FIG. 30. The NA of the light guide system is reduced, and the beam diameter at the inspecting point O increases in inverse proportion to the numerical aperture of the light guide system. In this case, the numerical aperture for the incident beam can decrease, the irradiated area can increase, and the Fourier spectrum measurement time can be shorted. At the same time, as shown in FIGS. 37A and 37B, the spectra of the Fourier spectrum decrease, and a dot-like Fourier spectral distribution almost free from the influence of the Fourier spectrum of the incident beam can be obtained. Note that FIG. 37A corresponds to FIG. 7B, and FIG. 37B corresponds to FIG. 8B.

If the expander magnification is, for example, set to 10 times, a Fourier spectrum can be measured with a beam having a one-to-one size (the size is 10 times as compared with the case wherein the expander is inserted) upon removal of the expander.

If an area of the substrate 1 on which the two-dimensional periodic pattern is present is known, only this area is scanned with light, and the direction of the incident plane with respect to the substrate is determined in accordance with the above-described "method of processing an image on the Fourier plane". The stage 70 is rotated by the stage driving means 71 to rotate the substrate 1 in a predetermined direction. The substrate 1 is then stopped and fixed. The preparation for measuring the spectrum and performing the inspection is completed. In inspection, the beam expander 52 is returned to the optical axis by the driving means 69, and the beam size is optimized for inspecting the foreign particle, thereby starting inspection of the foreign particle.

Figure 38:
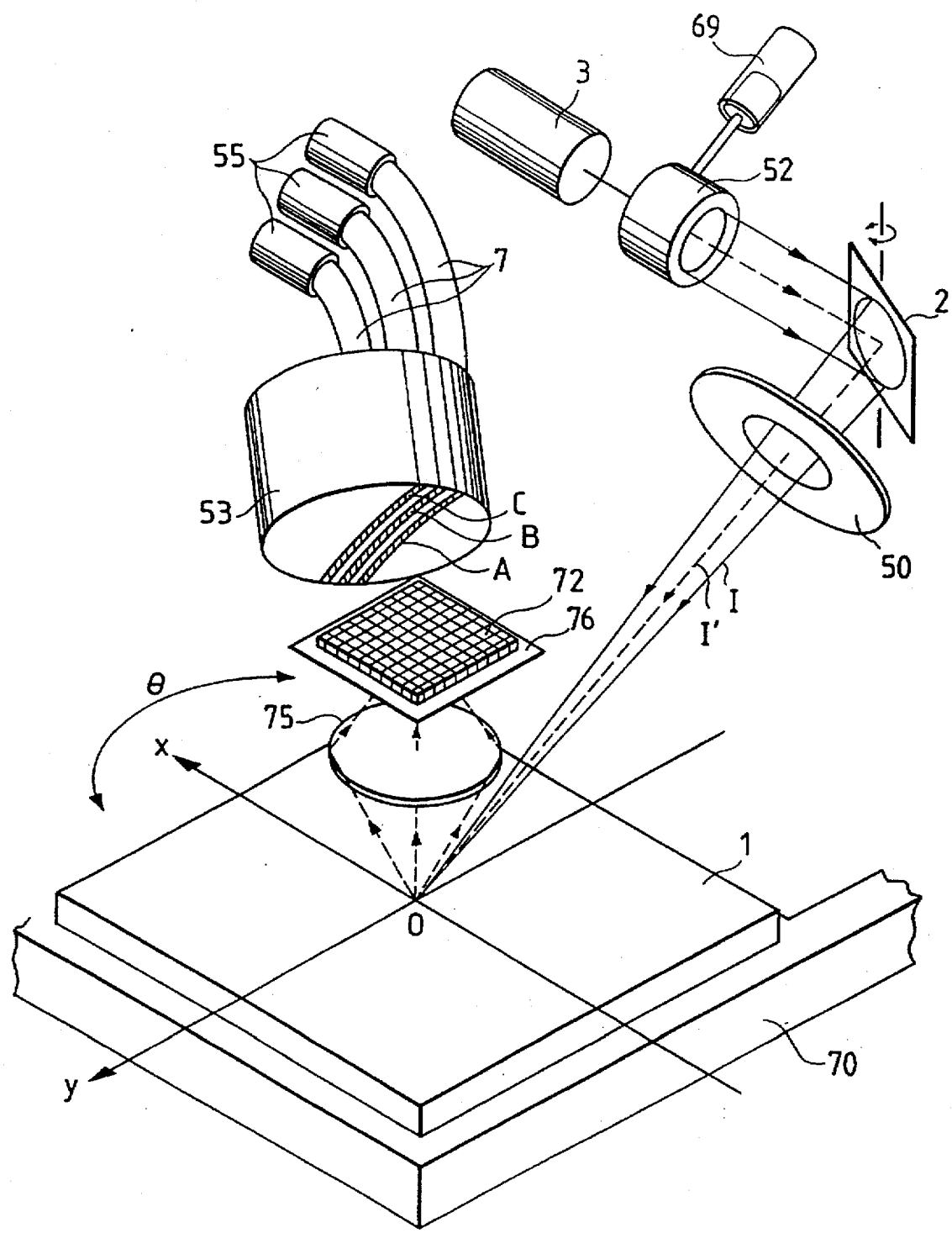
FIG. 38 is a perspective view schematically showing a defect inspecting apparatus according to a modification of the seventh embodiment of the present invention.

FIG. 38 is a perspective view schematically showing an apparatus suitable for a modification of the seventh embodiment, and the same reference numerals as in FIG. 30 denote the same parts in FIG. 38.

The apparatus in FIG. 38 is different from that in FIG. 30 in that an optical system 75 for measuring only a Fourier spectrum of a two-dimensional periodic pattern is arranged. The spectrum measurement optical system causes a Fourier transform lens 75 to form a Fourier plane 76. This plane is aligned with the two-dimensional photoelectric conversion element array 72 to measure a Fourier spectrum at a measuring point O. This modification also comprises the driving means 69 such as an air cylinder. The beam expander 52 is retracted from the optical path by th driving means 69 to variably set the beam spot size on the measuring point O.

In this modification, the Fourier transform lens 75 is used in measurement of the Fourier spectrum. For this reason, when a spectrum is measured while scanning the substrate with the vibrating mirror 2, the field of view of the Fourier transform lens 75 must sufficiently cover the scanning range. Elements of the photoelectric conversion element array 72 may be properly selected to form the light receiving areas A, B, and C, and foreign particles may be inspected on the basis of signals from the light receiving areas A, B, and C. That is, the measurement of the Fourier spectrum and the inspection of the foreign particles can be simultaneously performed by the photoelectric conversion element array 72 located on the Fourier plane.

In the third, fourth, fifth, and sixth embodiments, a Fourier spectrum may be measured, the arrangement direction of the light receiving areas and the distance between the light receiving areas may be optimized, and image processing may be performed in the same manner as in the seventh embodiment (i.e., the embodiment using the Fourier transform optical elements 72 and 75). In this case, both measurement of a Fourier spectrum and inspection of a foreign particle may be performed using the photoelectric conversion element array 72 located on the Fourier plane even in the third, fourth, fifth, and sixth embodiments.

In the seventh embodiment described above, although a Fourier spectrum is optically measured, but can be calculated on the basis of design data of circuit patterns.

Figure 39:
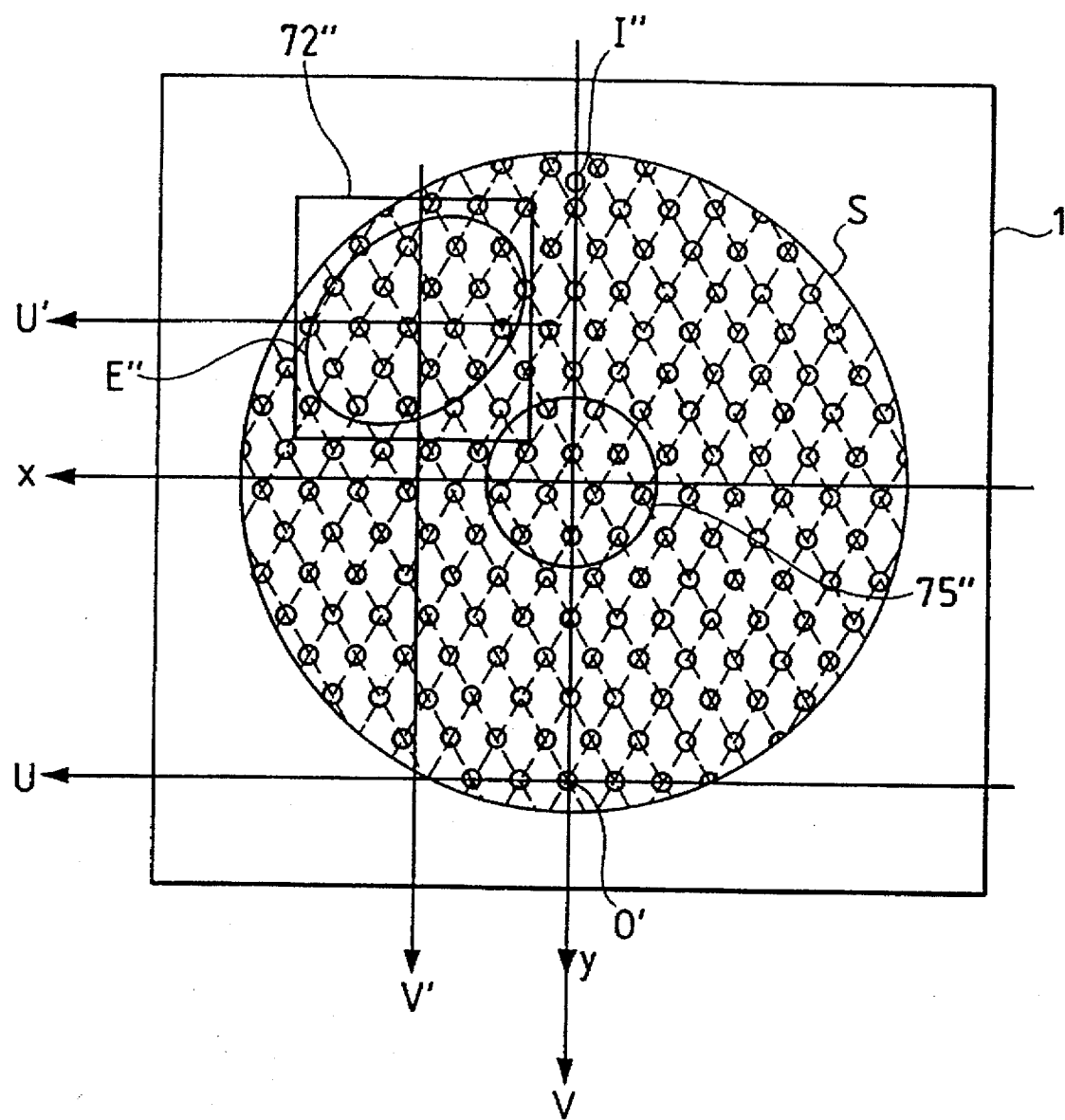
FIG. 39 is a view showing a Fourier spectrum measurement range in the apparatus of FIG. 30 and the Fourier spectrum measurement range in the apparatus of FIG. 38.

FIG. 39 shows a Fourier spectrum measurement range 72" of the seventh embodiment and a Fourier spectrum measurement range 75" of the modification of the seventh embodiment. FIG. 39 also shows a Fourier spectrum of a general two-dimensional periodic pattern together with a spectrum i" of the incident beam.

In the seventh embodiment described above, by rotating the substrate 1, the relationship between the incident beam I and the periodic direction of the circuit pattern is optimized, i.e., a distance between the Fourier spectra of the diffracted light components is set maximum with respect to the widthwise direction of the light receiving area. A light guide system constituted by the light source 3, the mirror 2, the f-θ lens 50, and the like may be moved to optimize the relationship between the incident beam I and the periodic direction of the circuit pattern. In this case, the light guide system may be moved together with the optical receiver 53. Alternatively, only the light guide system is moved, and the optical receiver 53 may be rotated such that the longitudinal direction of the diffracted light changing upon movement of the light guide system is aligned with the longitudinal direction of the light receiving areas.

In the seventh embodiment, light receiving elements of the photoelectric conversion element array 72 may be appropriately selected to perform defect inspection on the basis of signals from the light receiving areas A, B, and C. That is, the photoelectric conversion element array 72 may perform both Fourier spectrum measurement and defect inspection.

In the seventh embodiment, light receiving lenses 172 comprising a first objective lens $L_1$ and a second objective lens $L_2$ may be arranged between the substrate 1 and the optical receiver 53, and the light receiving surface 56 of the optical receiver 53 may be formed on the pupil plane of the light receiving lenses 172 or a plane conjugate to the pupil plane. The light receiving lenses 172 are located to cover a scanning line L-O-R on the substrate 1 and to cause an image plane slit 171 located almost parallel to the scanning line L-O-R to eliminate the stray light of the beam incident on the first objective lens $L_1$ at a position conjugate to the substrate 1. The resultant beam is incident on the second objective lens $L_2$ and then the light receiving surface 56 located on the pupil plane of the light receiving lens 172 or a plane conjugate to the pupil plane.

Figure 41:
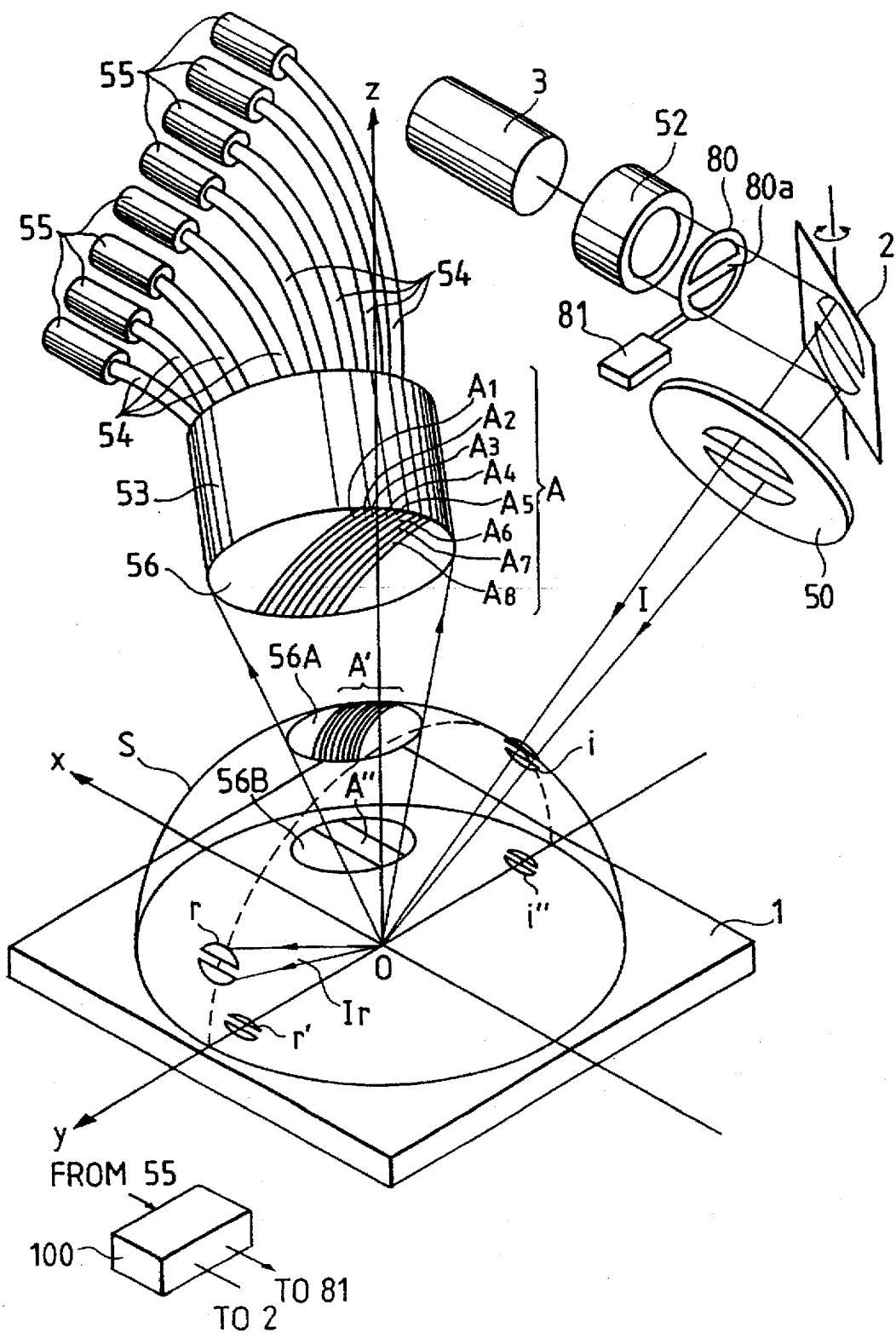
FIG. 41 is a perspective view schematically showing a defect inspecting apparatus according to the eighth embodiment of the present invention.

FIG. 41 is a perspective view showing an arrangement of the eighth embodiment of the present invention. The same reference numerals as in FIGS. 1, 13, and 30 denote the same parts in FIG. 41. The eighth embodiment is characterized in that an aperture 80 is arranged to partially shield an incident beam or partially change the phase of the incident beam. A detailed description of members having the same functions as in FIGS. 1, 13, and 30 will be omitted in FIG. 41. A beam emitted from a laser source 3 in FIG. 41 passes through a beam expander 52 and the aperture 80 and is focused on an inspecting point O on a substrate 1 (e.g., a reticle or wafer) having a circuit pattern through an f-θ lens 50 constituting a moving means for relatively moving the substrate 1 and the beam. The focused incident beam I is scanned by a vibrating mirror 2 on the substrate 1 in the X direction. The substrate 1 is placed on a stage (not shown) movable in the Y direction. Foreign particles can be inspected on the entire surface of the substrate 1 by the vibrating mirror 2 and the stage. The aperture 80 is located at or near a pupil of the irradiation optical system constituted by the beam expander 52 and the f-θ lens 50. An optical receiver 53 has a light receiving surface 56 having light receiving areas $A_1$, $A_2$, $A_3$, $A_4$, $A_5$, $A_6$, $A_7$, and $A_8$ capable of performing independent photoelectric conversion operations. The beams incident on the light receiving areas A ($A_1$ to $A_8$) are guided to photoelectric converters (photoelectric conversion elements) 55 through optical fibers 54, respectively. These beams are then photoelectrically converted into electrical signals. The signals from the photoelectric conversion elements 55 are incident on a controller 100. Since the diffracted light from the circuit patterns from the substrate 1 is discrete, at least one of the signals from the photoelectric conversion elements 55 is not output (zero or a predetermined level or less). The controller 100 logically ANDs the signals from the photoelectric conversion elements 55 to discriminate the circuit pattern from the foreign particle (to be described in detail later). The controller 100 systematically controls the overall apparatus.

Figure 42:
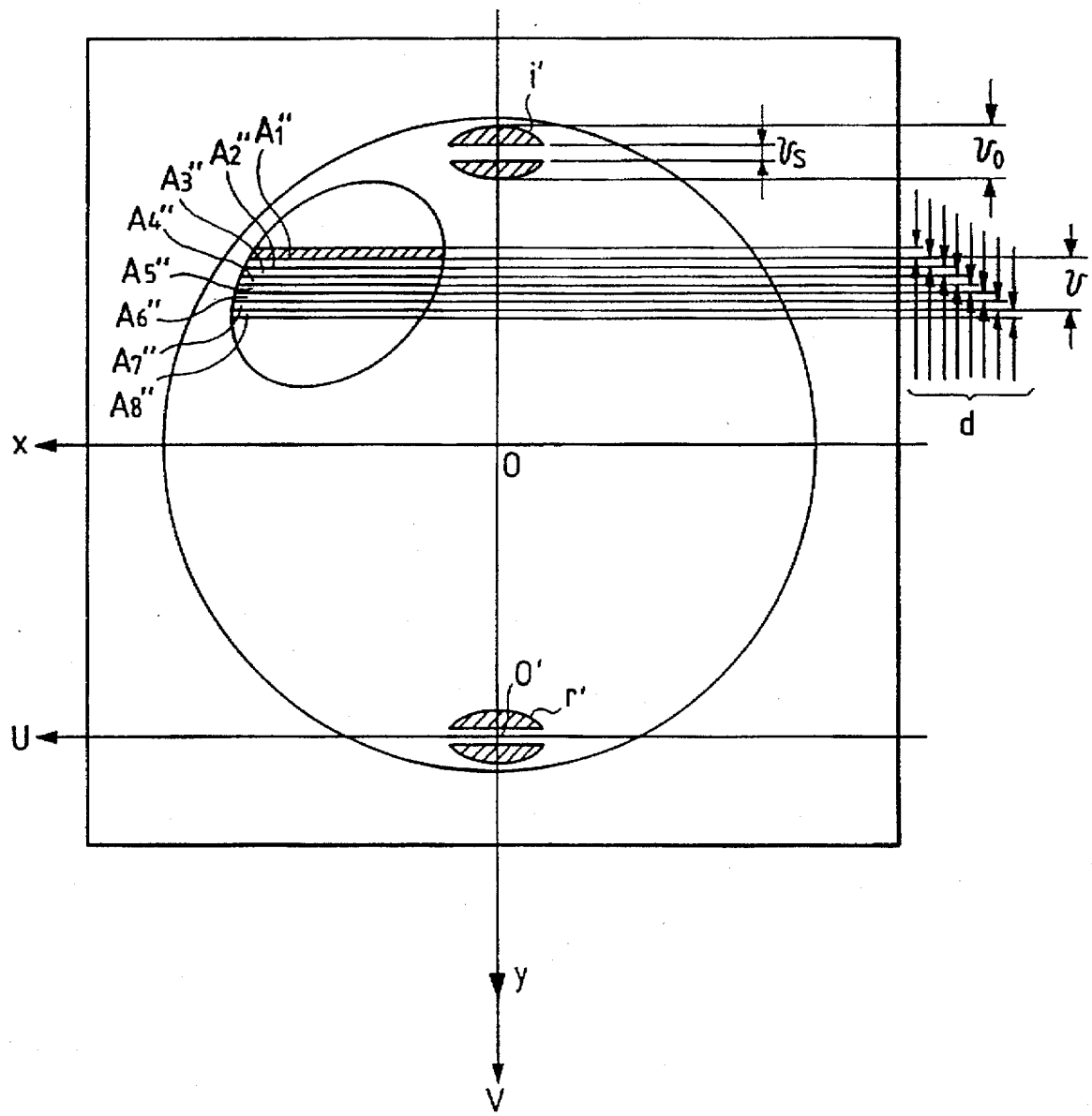
FIG. 42 a view illustrating the surface of a substrate in FIG. 41 when viewed from the Z direction.

FIG. 42 is a view illustrating the apparatus of FIG. 41 when viewed from the Z direction as in FIG. 14. More specifically, FIG. 42 shows a Fourier spectrum corresponding to the beam incident on each light receiving area and a Fourier spectrum of the incident beam. A positive projection r' (Fourier spectrum) of a curved section r as an overlapping area between a positively reflected light Ir (FIG. 42) and a sphere S is obtained. The U-V coordinate system in FIG. 42 is a new orthogonal coordinate system having as an origin the central position of the positive projection r'.

The positive projections i' and r' have a longitudinal direction parallel to the U axis (X axis) in FIG. 42 and are spaced apart from each other by a distance vs. The distance vs represents the width (i.e., the width of the non-spectrum region) of the area (a light-shielding body 80a) shielded by the aperture 80 of FIG. 41 in the V direction, and $v_0$ represents the width of the Fourier spectrum of the incident beam in the V direction. The width of each of positive projections (Fourier spectra) $A_1"$, $A_2"$, $A_3"$, $A_4"$, $A_5"$, $A_6"$, $A_7"$, and $A_8"$ of the respective light receiving areas in the Y direction is d. The width d of the positive projection of each light receiving area is preferably minimum in view of the capability of discriminating the pattern from the foreign particle. A decrease in light receiving area caused by decreasing the width d can be compensated by increasing the length in a direction parallel to the U direction.

The width d of each light receiving area is set to satisfy condition (22). A distance v between the Fourier spectra $A_1"$ and $A_8"$ is set equal to $v_0$.

The principle of discriminating a circuit pattern from a foreign particle by discreteness regardless of the degree of micropatterning of the circuit patterns, as described with reference to the second, third, fourth, fifth, sixth, and seventh embodiments will be described with reference to FIGS. 43A to 45B together with states of diffracted light components.

To perform discrimination of discreteness in this embodiment, the incident beam is divided by the aperture 80, and the divided components are incident on the substrate 1. The reason why the incident light is divided as shown in FIGS. 41 and 42 so as to discriminate discreteness will be described. When the circuit pattern pitch increases, the distribution of the light scattering from the pattern is generally localized in a direction of positively reflected light.

When a pattern pitch increases, the pitch of the light components discretely diffracted from the patterns decreases on the Fourier plane. As described in the conventional case, when only a beam from a coordinate point farther away from the coordinate point of the positive projection view which represents a direction of positive reflection is received, the layout of the optical receiver is restricted. The intensity of scattering light from a pattern may be higher than the intensity of scattering light from a foreign particle, depending on the size of the pattern, thus posing a problem on defect inspection.

Assume that the threshold value $Th_1$ is decreased to a threshold value $Th_2$ to detect a smaller foreign particle in FIG. 31D, as described with reference to the seventh embodiment. In the diffracted light (light diffracted from a pattern) in FIG. 43A, the diffracted light is spatially continuous at a signal level exceeding the threshold value $Th_2$. Discrimination by discreteness cannot be performed.

Figure 43A:
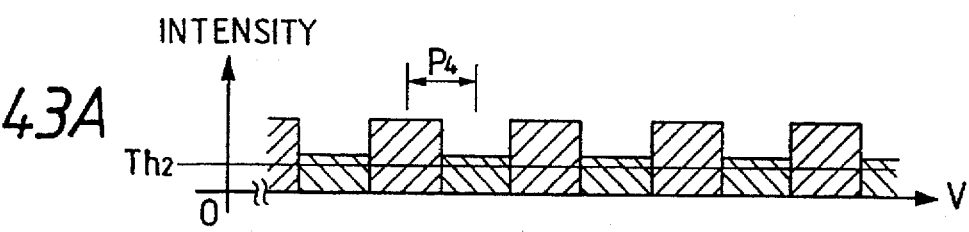
FIG. 43A is a view showing a one-dimensional intensity distribution of diffracted light.
Figure 43B:
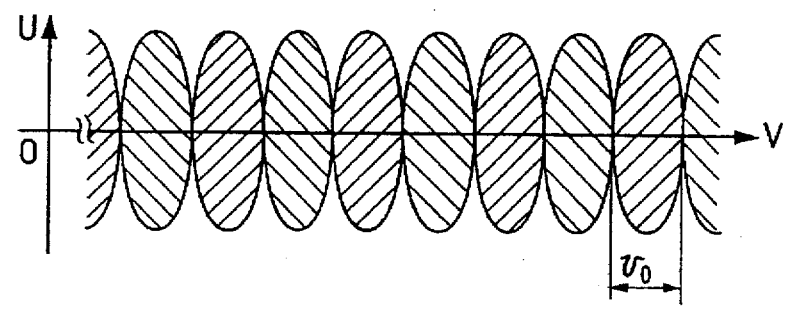
FIG. 43B is a view showing a Fourier plane distribution of diffracted light.

States of diffracted light components with a large pattern pitch are shown in FIGS. 43A and 43B. FIG. 43A shows a one-dimensional intensity distribution of the state of light diffracted from a periodic pattern on the positive projection in the V direction. Referring to FIG. 43A, the pitch of the light components discretely diffracted from the periodic pattern is determined by a pattern periodic direction and a degree of micropatterning of the pattern. FIG. 43B shows the diffracted light distribution of FIG. 43A in the U-V coordinate system. Hatched portions in FIG. 43A correspond to those in FIG. 43B, respectively. Referring to FIGS. 43A and 43B, when the pitch on the Fourier plane becomes $P_4$, the intensity distribution of the diffracted light becomes continuous in the V direction. In this embodiment, even if the intensity distribution of the diffracted light is continuous, discrimination of discreteness can be performed. More specifically, in this embodiment, as shown in FIG. 41, the incident beam I is partially shielded by the aperture 80 having the light-shielding body 80a to discriminate the discreteness. That is, when the incident beam is partially shielded by the light-shielding body 80a, light components diffracted from a coarse pattern can be produced with pseudo discreteness, as shown in FIGS. 43A an 43B. Scattering light from the foreign particle is continuous regardless of the presence of the light-shielding body 80a. When the width of the light-shielding band is optimized, a beam size in one direction (Y direction in FIG. 41) can be reduced smaller than that obtained by an interference effect of two beams. The beam spot size in other directions is kept almost unchanged. Even if this incident light is used, an optimization technique for the optical receiver can satisfy the following condition based on condition (21):

$$vs \geq 2d + [v_0-(n-2)d]/(n-1) = R_a(n) \quad (22)$$

where d, $v_0$, and n are defined as in condition (21).

Figure 44B:
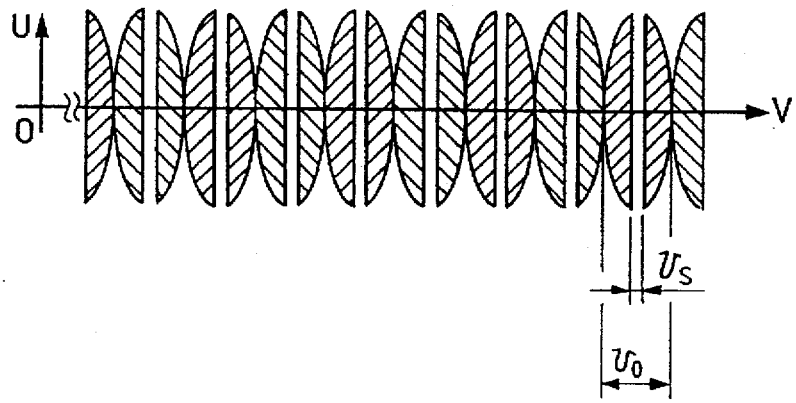
FIG. 44B is a view showing a Fourier plane distribution of diffracted light when the aperture 80 in FIG. 41 is arranged.
Figure 45A:
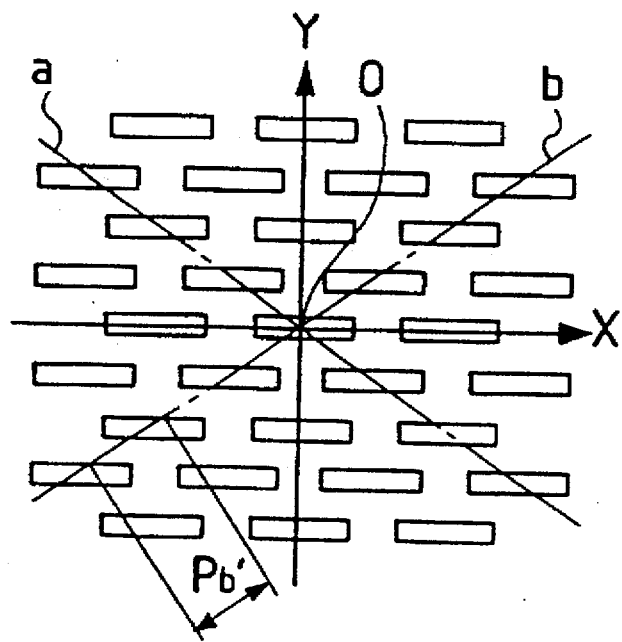
FIG. 45A is a view showing a circuit pattern in FIG. 8A.
Figure 45B:
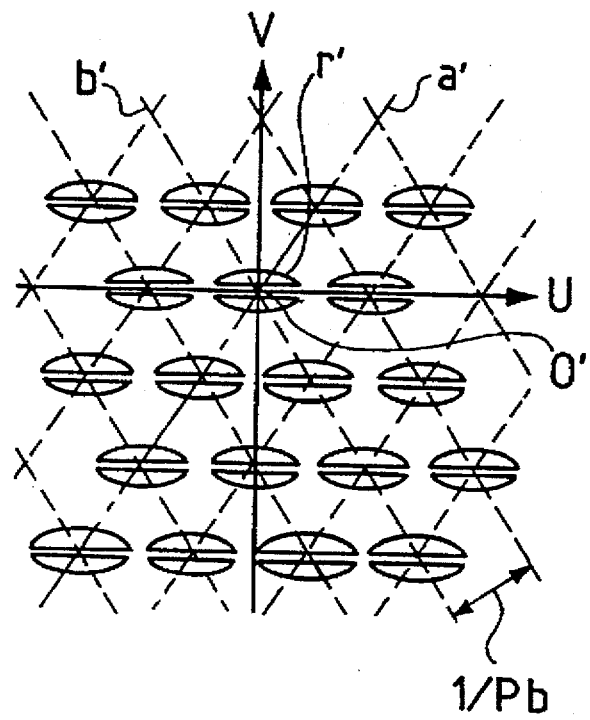
FIG. 45B is a view showing the distribution of diffracted light on the Fourier plane from the pattern in FIG. 45A when the aperture 80 in FIG. 41 is arranged.

The states of diffracted light components obtained using the incident system (arrangement of the aperture 80) of this embodiment are shown in FIGS. 45A and 45B by exemplifying the light components diffracted from the patterns shown in FIG. 8A. The pattern in FIG. 8A is shown as that in FIG. 45A. As shown in FIG. 45B, each light component diffracted from a pattern element has a gap at the central portion, as shown in FIG. 44B. The respective Fourier spectra are discrete, and the positional relationship between the Fourier spectra and the pattern elements is kept unchanged. This also applies to the diffracted light components from the patterns in FIGS. 7A and 9A.

In this apparatus, only a foreign particle which scatters light at a level exceeding a threshold value $Th_3$ is detected.

Figure 44A:
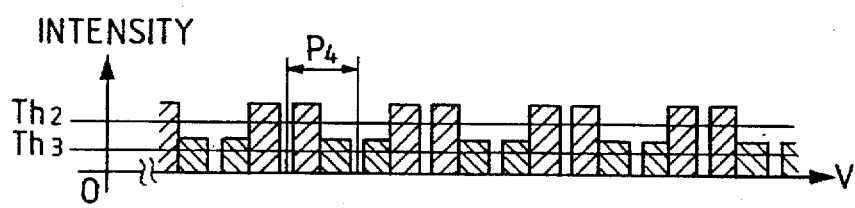
FIG. 44A is a view showing a one-dimensional intensity distribution of diffracted light when an aperture 80 in FIG. 41 is arranged.

The light components diffracted by the patterns and having levels exceeding the threshold value $Th_3$ shown in FIGS. 44A and 44B can satisfy condition (22).

In this embodiment, the Fourier spectrum corresponding to a beam to be incident and the Fourier spectrum corresponding a beam incident when the incident system shown in FIG. 41 is used will be described with reference to FIG. 42.

As shown in FIG. 41, the incident beam is partially shielded with a predetermined light-shielding body, and the size of the incident beam I in a direction of the incident plane is reduced by two-beam interference. For example, optimization is performed by giving the light-shielding distance vs of the positive projection as $v_1=0.2v_0$ and the number n of light receiving areas as n=8 to obtain the following condition:

$$vs=0.2v_0 \geq 2d+[v_0-(8-2)d]/(8-1) \quad (23)$$

$$\therefore d \leq 0.05 \, v_0$$

In this embodiment, $vs=0.2 \, v_0$ is given in FIG. 42. When $vs=0.2v_0$, the beam size can be reduced by about 20% in the direction of the incident plane by two-beam interference. However, a power loss occurs to reduce a total peak luminance to about 50%. A decrease in total peak luminance can be solved by increasing the length of the light receiving area in the longitudinal direction, as described above, or by increasing the quantity of incident light. The quantity of incident light can be easily increased when an $Ar^+$ laser is used as a light source.

The power loss occurs due to the light-shielding operation of the aperture 80, as described above. Assume that the quantity of light is constant regardless of the presence/absence of the aperture 80. Even if the beam spot size is slightly reduced, the maximum luminance within the beam spot decreases. In this case, a desired sensitivity cannot be obtained unless the threshold value decreases. When $vs=0.2v_0$, the threshold value $Th_3$ must be 50% or less the threshold value $Th_2$, as shown in FIGS. 43A and 43B.

The shape of the aperture 80 in FIG. 40 will be described below.

Figure 46:
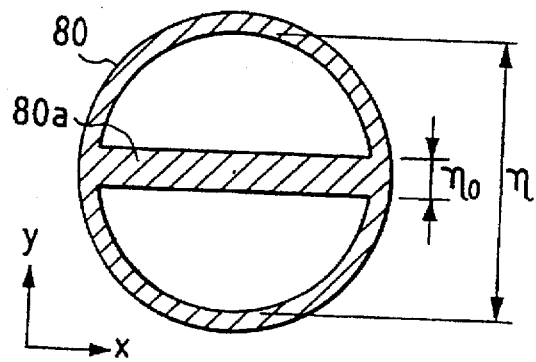
FIG. 46 is a view showing the shape of the aperture 80.

FIG. 46 is a view showing the shape of the aperture 80 of this embodiment. The Y-Z direction (i.e., a direction within the Y-Z plane) and the X direction correspond to the X and Y directions on the substrate 1, respectively. The light-shielding body 80a is a light-shielding body having its longitudinal direction in the X direction. The longitudinal direction of the Fourier spectrum (actually a non-Fourier spectrum) corresponding to the light-shielding body 80a is almost the same as the longitudinal direction of the Fourier spectrum of each light receiving area. The aperture 80 is arranged to adjust the shape of the beam incident on the substrate 1. In other words, the aperture 80 adjusts the shape of the Fourier spectrum of the beam itself incident on the substrate 1.

The number and width of light receiving areas are optimized with respect to the width vs of the Fourier spectrum of the light-shielding body 80a (width $\eta_0$) in accordance with condition (22). At least two of the light receiving areas $A_1$, $A_2$, $A_3$, $A_4$, $A_5$, $A_6$, $A_7$, and $A_8$ are selected by the controller 100 in accordance with condition (22) to cope with all the intervals (pitches) of all diffracted light components. For example, pairs of light receiving areas may be obtained such as ($A_1$ and $A_2$), ($A_3$ and $A_4$), ($A_5$ and $A_6$), and ($A_7$ and $A_8$) to determine the width of the light receiving area, and at the same time the number of light receiving areas may be set to be four. The width $\eta_0$ (the width $v_0$ of the Fourier spectrum of the incident light) of the light-shielding body 80a of the aperture 80 is preferably about 20% the diameter $\eta$ of the aperture, as previously described. However, when the width of the light receiving area is reduced to adversely affect the detection sensitivity of the foreign particle in relation to the width $\eta_0$ and the number of light receiving areas, the width $\eta_0$ may be larger than 20% the diameter $\eta$ of the aperture. The diameter $\eta$ of the aperture is determined in accordance with the diameter of the incident beam and is optimized in each apparatus. Note that the position of the aperture 80 need not be limited to the pupil plane of the incident optical system, but may be located at an arbitrary position in the optical path between the f-θ lens 50 and the substrate 1.

When the pitches between the diffracted light components are known, the diffracted light components may be predicted without depending on condition (22), and a smaller number of light receiving areas may be set at positions where these diffracted light components are not incident.

The aperture 80 is retractable from the optical path by means of a drive unit 81. If a circuit pattern pitch is not small (the interval between the diffracted light components is small), the aperture 80 is located in the optical path, and the light receiving areas are optimized in accordance with condition (22). When a circuit pattern pitch is small (the interval between the diffracted light components is large), the aperture 80 is retracted from the optical path by the drive unit 81. The number and width of light receiving areas may be optimized in accordance with condition (21) as in the seventh embodiment. In this case, a smaller number of light receiving areas is preferable.

If real-time processing (in this case, the areas are sequentially scanned, and parallel signal processing is performed) is not performed, scanning is stopped for every inspecting point. The light receiving surface is shifted for every inspecting point, thereby adjusting the layout of the light receiving areas. To the contrary, the light-shielding portion for the incident beam may be shifted.

Modifications of the aperture will be described below.

Figure 47:
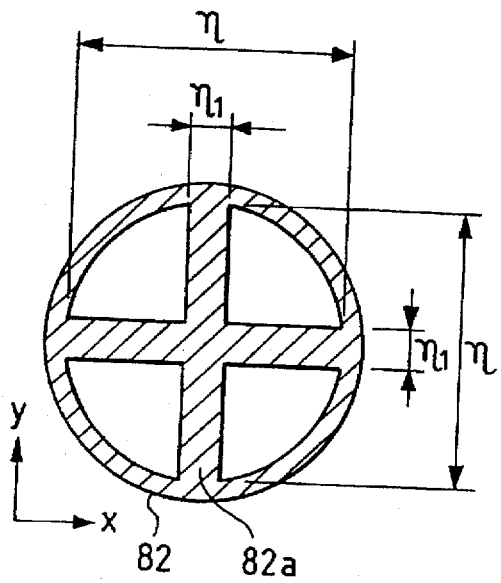
FIG. 47 is a view showing the shape of an aperture 82 according to the first modification of the aperture 80.

FIG. 47 shows the first modification of the shape of the aperture 80 in FIG. 41. FIG. 47 shows an aperture 82 having a light-shielding body (crossed light-shielding body) having widths in both the X and Y directions. This aperture is used when light receiving areas are arranged in a two-dimensional manner (e.g., light receiving areas are arranged in a checkerboard manner; or a light receiving area having a longitudinal direction in the U direction of the Fourier plane and a light receiving area having a longitudinal direction in the V direction of the Fourier plane are arranged). A width $\eta_0$ (width in the Y direction) and a width $\eta_1$ (width in the X direction) of the light-shielding body of this aperture are determined in the same manner as in the width of aperture shown in FIG. 46. Each width of the aperture in FIG. 47 is preferably about 20% the diameter $\eta$ of the aperture. Even if the aperture 82 shown in FIG. 47 is used, a method of optimizing the light receiving areas, an operation of inserting/removing the aperture, and real-time processing are the same as in use of the aperture 80 of FIG. 46. The directions along which the light-shielding body extends almost coincide with the X and Y directions.

The second modification of the shape of the aperture 80 shown in FIG. 46 (FIG. 41) will be described below.

Figure 48:
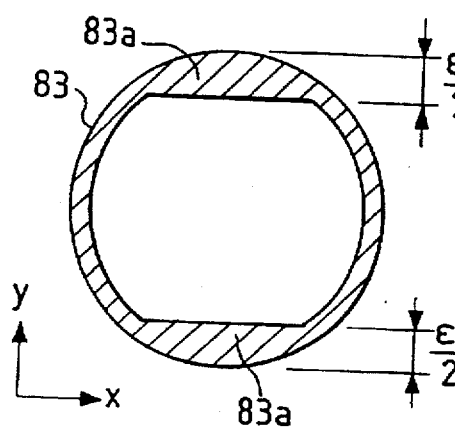
FIG. 48 is a view showing the shape of an aperture 83 according to the second modification of the aperture 80.
Figure 49:
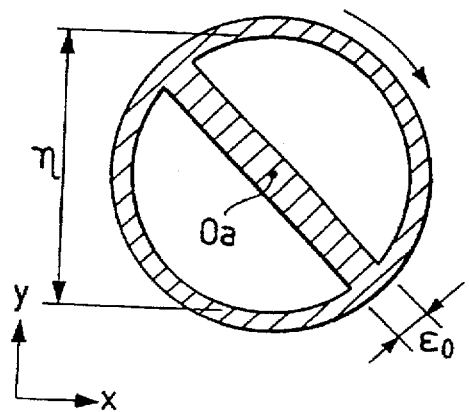
FIG. 49 is a view showing the layout (shape) of an aperture 80 according to the third modification of the aperture 80.

The second modification exemplifies an aperture 83 having light-shielding bodies at both ends of the aperture 80 of FIG. 46 (FIG. 41), as shown in FIG. 48. The longitudinal direction of each light-shielding body almost coincides with the X direction as in the aperture 80 of FIG. 45. The sum of the widths of the light-shielding bodies 83a of the aperture 83 is equal to the width $\eta_0$ of the light-shielding body 80a of the aperture 80. By this aperture 83, a predetermined interval can be formed between the Fourier spectra of a plurality of diffracted light components.

The third modification of the shape of the aperture 80 in FIG. 41 will be described below.

The third modification is obtained by rotating the aperture 80. The aperture having the shape shown in FIG. 45 is rotated by the drive unit 81 in FIG. 41.

In this modification, the aperture can be rotated about the point O. A foreign particle is inspected while the aperture is being rotated. In this modification, in real-time inspection, the aperture is rotated at a higher speed than that of optical scanning on the substrate surface, and a light receiving signal is intensity-modulated by rotation of the aperture. The intensity-modulated light receiving signal includes only a light receiving signal corresponding to the light components diffracted by the patterns, as shown in FIGS. 44A and 44B, so that a modulated component may be subtracted during signal processing. More specifically, although the light receiving signal corresponding to the light component diffracted by the pattern is intensity-modulated by rotation of the aperture, the peak intensity of the beam is kept unchanged even with rotation of the aperture. Therefore, the signal intensity of the scattering light from the foreign particle is rarely modulated. For this reason, as the modulated light receiving signal is influenced by only the light component diffracted from the pattern, and the modulated component is subtracted to obtain a light receiving signal representing only the scattering light. When the light receiving signal obtained upon subtracting the light receiving signal corresponding the diffracted light component from the total light receiving signal is compared with a predetermined slice level to detect the foreign particle. In this modification, if a foreign particle is not detected in real time, scanning is stopped for every inspecting point, and the degree of modulation of the intensity of the light receiving signal is checked by rotation of the aperture for every inspecting point. In the same manner as in real-time inspection, the modulated light-receiving signal is subtracted to obtain a light receiving signal representing only the scattering light. By using this light receiving signal, the foreign particle can be detected.

The fourth modification of the shape of the aperture 80 shown in FIG. 46 will be described below.

Figure 50:
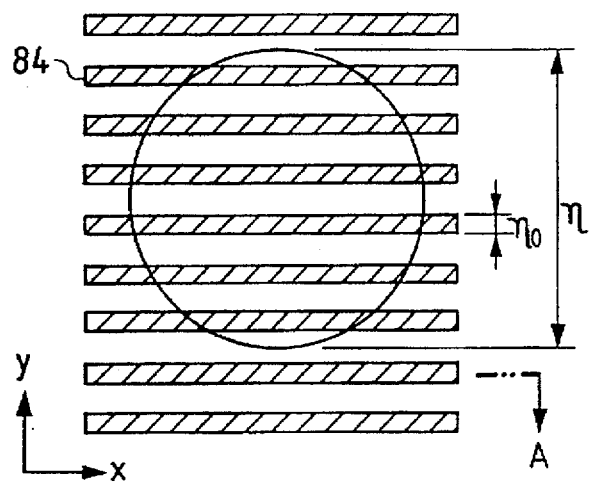
FIG. 50 is a view showing the shape of an aperture 84 according to the fourth modification of the aperture 80.

The fourth modification exemplifies an aperture 84 obtained by forming grating fringes in the aperture 80 in FIG. 46, as shown in FIG. 50. A circle having a radius $\eta$ in FIG. 50 represents an incident beam. In this modification, the aperture is arranged to have a size larger than this circle.

In real-time inspection in this modification, the aperture 84 (grating fringes) is moved in the Y direction of FIG. 50 to intensity-modulate only a light receiving signal representing a light component diffracted from the pattern.

In this modification, when the peak intensity of the incident beam is modulated, it is difficult to discriminate a defect from a pattern. For this reason, th radius $\eta$ of the incident beam is set sufficiently larger than the width $\eta_0$ of each light-shielding portion. In this case, the light receiving system is optimized with reference to the width $\eta_0$ of the light-shielding portion in accordance with condition (22).

When the width $\eta_0$ of the light-shielding portion cannot be much smaller than the radius $\eta$ of the incident light, the peak intensity of the incident beam is modulated. In this case, the degree of modulation of the intensity of the peak of the incident beam is different from the intensity modulation of the light component diffracted from the pattern. If the degree of modulation of the peak intensity of the incident beam is obtained beforehand, it is possible to eliminate the modulated component of the peak intensity of the incident beam by signal processing. Therefore, the modulated component of the peak intensity of the incident beam and the intensity-modulated component of the light receiving signal of the diffracted light component are subtracted to obtain a light receiving signal. This signal is compared with a predetermined slice level to detect a foreign particle. When real-time processing is not performed, the modulated component of the peak intensity of the incident beam and the intensity-modulated component of the light receiving signal of the diffracted light component are subtracted to obtain a light receiving signal. This signal is compared with the predetermined slice level to detect a foreign particle.

The fifth modification of the shape of the aperture 80 shown in FIG. 46 will be described below.

Figure 51:
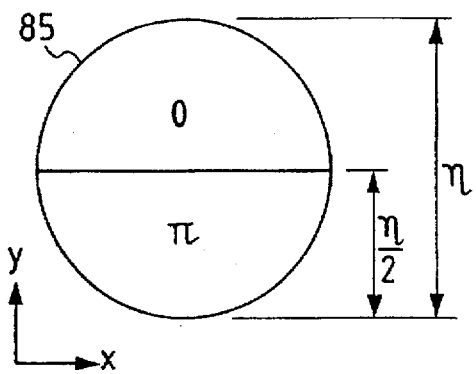
FIG. 51 is a view showing the shape of an aperture 85 according to the fifth modification of the aperture 80.
Figure 52:
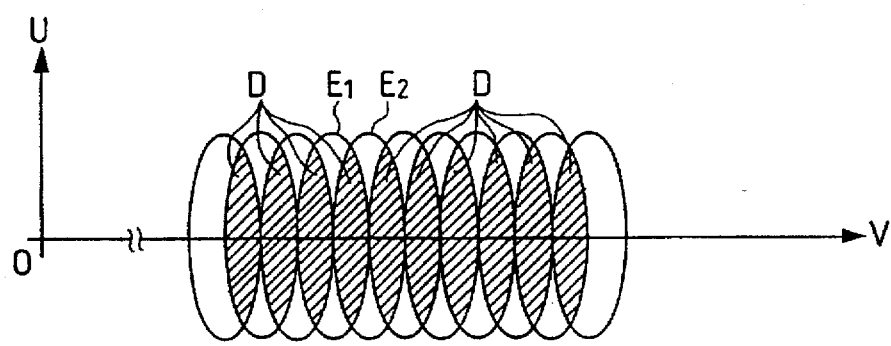
FIG. 52 is a view for explaining the distribution of diffracted light when the aperture 85 is arranged.
Figure 53:
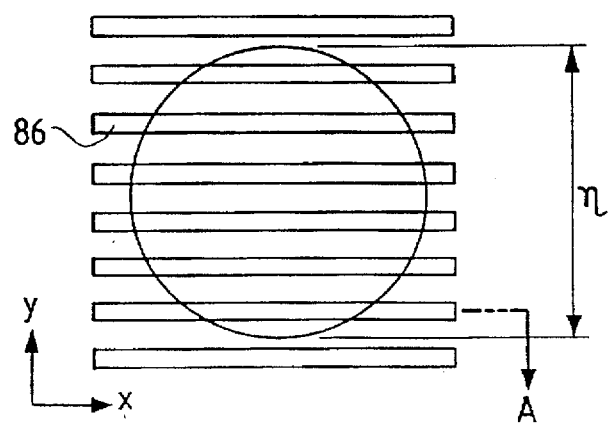
FIG. 53 is a view for explaining an operation when a shifter is arranged in an aperture 84.

This modification is obtained by partially arranging a shifter portion in the aperture 80 of FIG. 46, thereby obtaining an aperture 85 shown in FIG. 51. A light-transmitting material for giving a phase difference of $\pi$ to the wavelength of the incident beam is applied to the half of the aperture 85 in the Y direction (V direction). When the pitches of light components diffracted by patterns are very small, the overlapping components are canceled to each other, as indicated by portions D in FIG. 52. FIG. 52 shows an intensity distribution of the diffracted light on the substrate 1 in the U-V coordinate system. If the intensities of the diffracted light components $E_1$ and $E_2$ are perfectly equal to each other, the intensity becomes zero in the portion D. The light-shielding portions of the grating fringes shown in FIG. 50 may be formed of a light-transmitting material for giving a phase difference of $\pi$ to obtain an aperture 86. This aperture is shown in FIG. 53.

In the eighth embodiment, a Fourier transform plane may be formed using the Fourier transform optical element 75 shown in the seventh embodiment, a light receiving plane may be formed on this Fourier transform plane, and the width, pitches, and number of light receiving areas on this Fourier transform plane may be optimized in accordance with condition (22).

Figure 40:
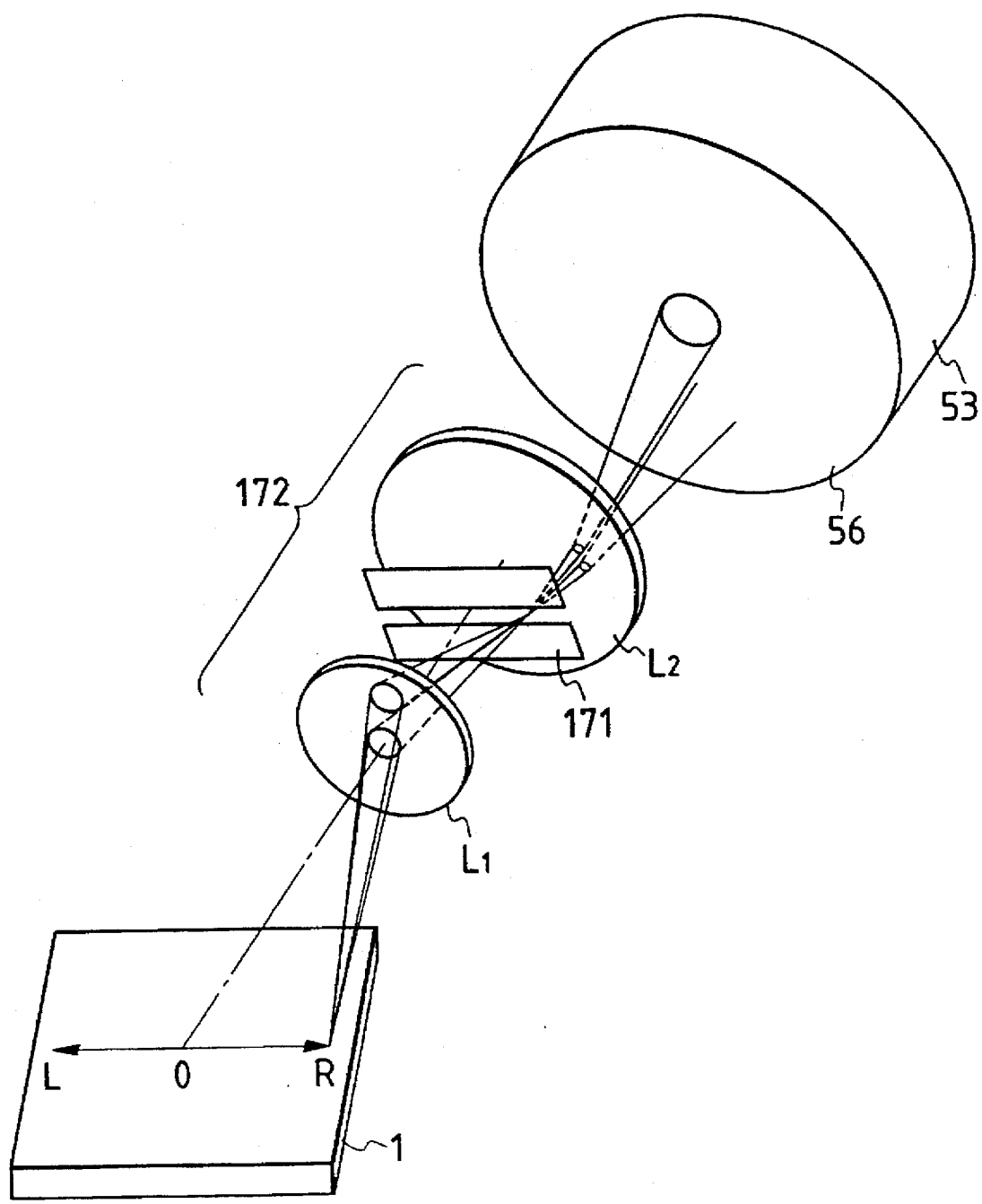
FIG. 40 is a view for explaining an arrangement in which a light receiving surface is formed on the pupil plane of a light receiving optical system.

In the eighth embodiment, as in FIG. 40, light receiving lenses 172 comprising a first objective lens $L_1$ and a second objective lens $L_2$ may be arranged between the substrate 1 and the optical receiver 53, and the light receiving surface 56 of the optical receiver 53 may be formed on the pupil plane of the light receiving lenses 172 or a plane conjugate to the pupil plane. The light receiving lenses 172 are located to cover a scanning line L-O-R on the substrate 1 and to cause an image plane slit 171 located almost parallel to the scanning line L-O-R to eliminate the stray light of the beam incident on the first objective lens $L_1$ at a position conjugate to the substrate 1. The resultant beam is incident on the second objective lens $L_2$ and then the light receiving surface 56 located on the pupil plane of the light receiving lens 172 or a plane conjugate to the pupil plane.

In the first to eighth embodiments, the principle of the present invention and the relationship between positive projection of the light receiving area and the Fourier spectrum have been described in the Fourier coordinate system. One point on the Fourier coordinate system corresponds to one point on the light receiving surface in a one-to-one correspondence, so that the Fourier coordinate system described above can be transformed into the coordinate system of the actual light receiving surface. Therefore, the light receiving area can be set on the actual light receiving surface in the same manner as in the principle of the present invention which has been described with reference to the Fourier transform system, i.e., the relationship between the positive projection of the light receiving area and the Fourier spectrum.

The Fourier transform optical element of the seventh embodiment will be described below.

For example, in the manufacture of semiconductor elements using photolithographic techniques, a photomask drawn with a circuit pattern is used. In a defect inspecting apparatus for such a photomask, light from the pattern on the photomask is Fourier-transformed to obtain a spatial frequency pattern. Using this spatial frequency pattern, the presence/absence of a defect in the pattern is determined, or the defects are classified. In this manner, a Fourier transform optical element is used to optically Fourier-transform light from an object.

In general, when diffracted light obtained upon incidence of a plane wave in a two-dimensional aperture is observed at an observation point infinite from the aperture, a diffraction pattern is obtained by Fraunhofer diffraction. This diffraction pattern is obtained by optically Fourier-transforming the aperture. To mathematically express this, a plane in which the two-dimensional aperture is called an aperture plane, and orthogonal x and y axes are plotted thereon. The amplitude distribution of the incident plane wave on the aperture plane is defined as F(x,y). The observation point infinite from this aperture is represented by a spatial frequency (u,v). If the amplitude distribution of the diffraction pattern at this observation point is defined as f(u,v), the amplitude distribution F(x,y) and the amplitude distribution f(u,v) have a Fourier transform relationship represented by equation (13) below.

$$f(u,v) = Ca \int \int_{-\infty}^{\infty} F(x,y)\exp[-2\pi i(ux+vy)]dxdy \qquad (13)$$

where an integral symbol $\iint$ represents an integration as a function of variables x and y from $-\infty$ to $+\infty$. The coordinates x and y of the position of the aperture plane and the coordinates u and v of the spatial frequency space at the infinite observation point have equations (14) and (15) below:

$$(l-l_0)/\lambda = u \qquad (14)$$

$$(m-m_0)/\lambda = v \qquad (15)$$

where $\lambda$ is the wavelength of the incident plane wave, $l_0$ and $m_0$ are direction cosine values of the x and y axes when the incident plane wave is incident on the aperture plane, and l and m are direction cosine values of the x and y axes of light propagating from the aperture plane to the observation point having the infinity coordinates (u,v).

A lens (Fourier transform lens) is conventionally used as a Fourier transform optical element of this type. The conditions of a one-dimensional Fourier transform lens will be described below.

Figure 60:
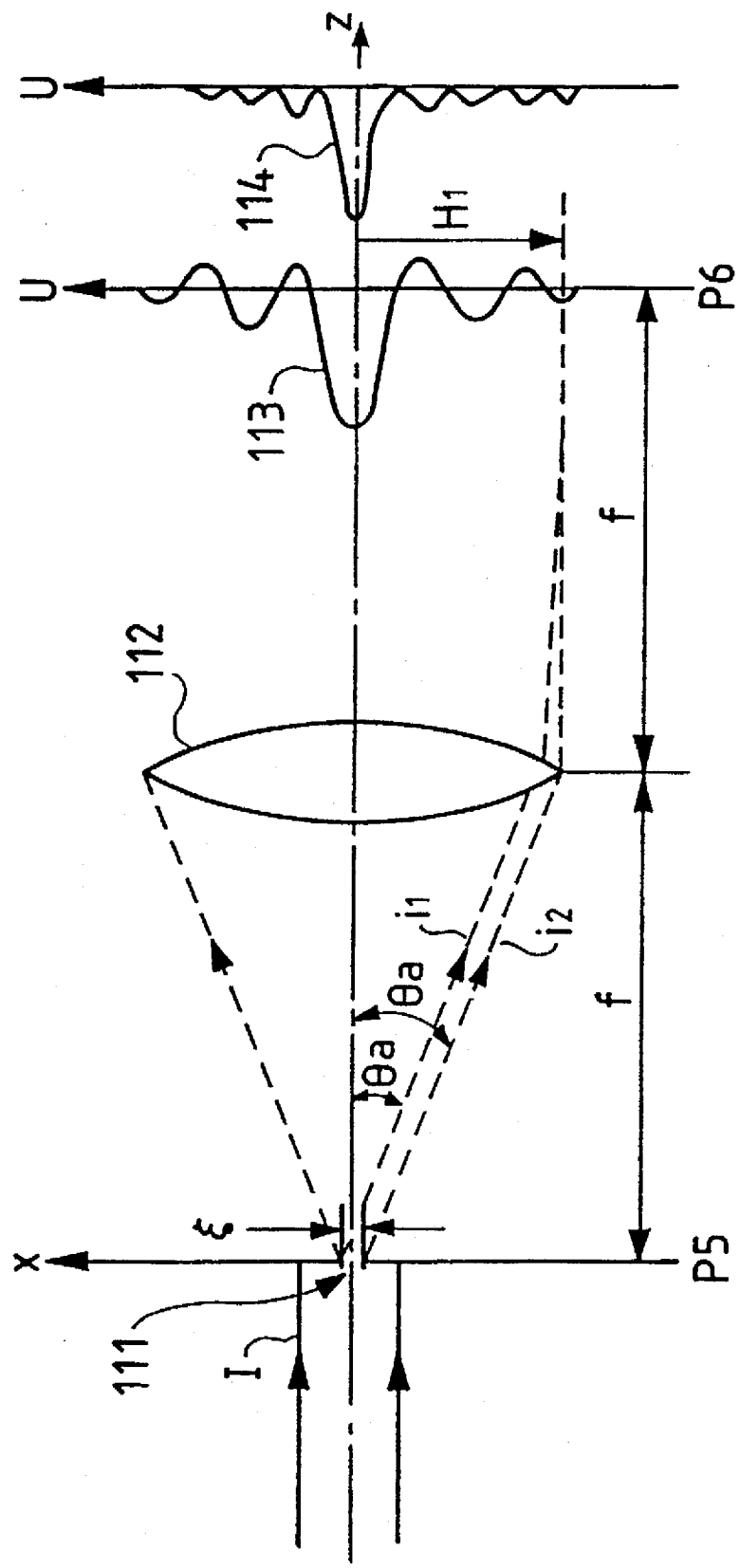
FIG. 60 is a view for explaining the principle of a conventional Fourier transform lens.

FIG. 60 shows an optical system for performing one-dimensional Fourier transform. Referring to FIG. 60, in an orthogonal coordinate system where a normal to an aperture plane P5 is aligned with the z axis, orthogonal x and y axes are plotted on the aperture plane P5, and an aperture 111 having an x axis direction width $\xi$ is formed on the aperture plane 5 so as to include the origin of the coordinate system. The aperture 111 is kept illuminated with a plane wave I incident from the left direction. A Fourier transform lens having a focal length f has an optical axis aligned with the z axis. The aperture plane 5 is located within the object focal plane of a lens 112. An observation plane P6 perpendicular to the optical axis is formed within the image focal plane of the lens 112. U and V axes parallel to the x and y axes are plotted on the observation plane P6. The Fourier transform lens 112 must have the following two conditions.

Condition ①: To obtain an observation result equivalent to that at an infinity point, diffracted light components (e.g., diffracted light components $i_1$ and $i_2$ at a diffraction angle $\theta_a$) of the same direction cosine must be focused on one point. For this purpose, the aperture plane P5 must be aligned with the front focal plane of the Fourier transform lens 112, and the observation plane P6 must be aligned with the rear focal plane thereof. If this condition is not satisfied, the spatial frequency does not correspond to the direction cosine in a one-to-one correspondence.

Condition ②: To observe a Fourier transform pattern on the U–V plane along the coordinate U and V axes of the coordinate system having the origin as the optical axis of the rear focal plane of the Fourier transform lens 112, the Fourier transform lens 112 has characteristics represented by equations (24) and (25):

$$U = f \sin \theta_x = fl \quad (24)$$

$$V = f \sin \theta_y = fm \quad (25)$$

where f is the focal length of the lens, $\theta_1$ is the x component of the angle of field, and $\theta_y$ is the y component thereof. The Fourier transform information is generally represented on the orthogonal coordinate system of the spatial frequency (u,v) as follows by its definition:

$$u = (l - l_0)/\lambda \quad (26)$$

$$v = (m - m_0)/\lambda \quad (27)$$

where l: direction cosine of diffracted light (i.e., a component parallel to the x axis)

$l_0$: direction cosine of 0th-order diffracted light (i.e., a component parallel to the x axis)

m: direction cosine of diffracted light (i.e., a component parallel to the y axis)

$m_0$: direction cosine of 0th-order diffracted light (i.e., a component parallel to the y axis)

The position of the 0th-order diffracted light on the U–V plane is represented by $U_0$ and $V_0$ of equations (28) and (29) below:

$$U_0 = fl_0 \quad (28)$$

$$V_0 = fm_0 \quad (29)$$

From equations (24) to (29), $$u = \frac{1}{\lambda f}(U - U_0) \quad (30)$$

$$v = \frac{1}{\lambda f}(V - V_0) \quad (31)$$

Equations (30) and (31) represent that spectral distributions obtained by performing similar transform of the orthogonal coordinates of the spatial frequency (u,v) having the point ($U_0,V_0$) as the origin on the U–V plane, using the $\lambda f$ coefficient can be observed.

In the following description, the U–V plane as the spectral observation plane is called a Fourier transform plane.

By the above two conditions, the diffraction image of the amplitude distribution 113 is formed on the observation plane P6 of the rear focal plane of the Fourier transform lens 112. The orthogonal coordinates in the spatial frequency space of the observation plane P6 are given as (u,v). When these orthogonal coordinates are caused to correspond to equation (13), the amplitude distribution of the incident plane wave I at the aperture 111 on the aperture plane 15 is represented by F(x,y), and the amplitude distribution of the diffraction image at the observation plane P6 is represented by f(u,v). The intensity of this diffraction image is |f(u,v)|² as indicated by a distribution 114.

In the optical system using the conventional Fourier transform lens 112 shown in FIG. 60, the diameter of the lens is increased to perform Fourier transform in a wide spatial frequency range. When the thickness of the lens in the axial direction is also considered, it is impractical and very difficult to use the Fourier transform lens 112 to perform Fourier transform of diffracted light near the diffraction angle $\theta_a$ of 90°. The diffraction angle $\theta_a$ is increased to this value when the structure of an object illuminated with the incident plane wave is micropatterned.

For example, an f-θ lens is a lens for focusing a beam emerging at the angle $\theta_a$ on a position proportional to the angle $\theta_a$. Even in this case, when the angle $\theta_a$ is increased, the lens diameter must be considerably increased. However, an increase in lens diameter is limited.

In consideration of the above problem, assume to provide an optical element capable of focusing light emerging from a predetermined area at a large exit angle of, e.g., near 90° on a plane in accordance with a predetermined conversion rule.

Figure 55:
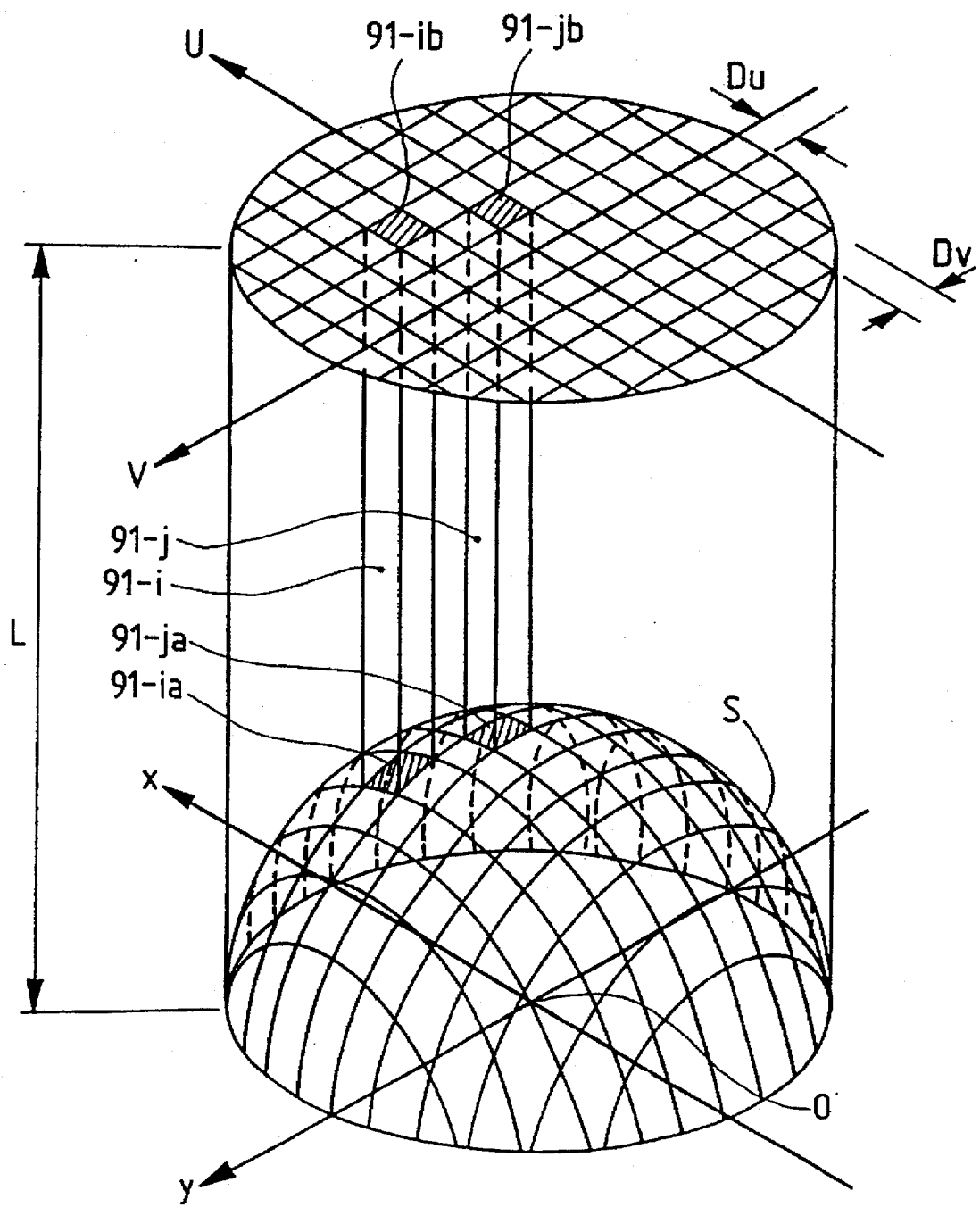
FIG. 55 is a perspective view showing part of the first application example of the optical element according to the present invention.

For example, a first optical element for solving the above problem is shown in FIG. 55. A plurality of optical transmission elements (91-1, 91-j) are bundled such that their light incident ends are located on different positions of a spherical surface S and their light exit ends are two-dimensionally arranged in a matrix form.

A second optical element is arranged such that an arrangement obtained by positively projecting the light exit ends of the plurality of the optical transmission elements (91-i, 91-j) in the first optical element on a plane passing through a center O of the spherical surface S is similar to that obtained by positively projecting the light exit ends thereof.

In this case, the plurality of optical transmission elements (91-i, 91-j) are preferably light guides, respectively.

The light incident ends of the plurality of optical transmission elements are preferably perpendicular to the spherical surface S, as indicated by light incident ends (94-1a, 94-2a).

In the second optical element, the arrangement obtained by positively projecting the light incident ends of the plurality of optical transmission elements (91-1, 91-j) and the arrangement obtained by positively projecting the light exit ends thereof are preferably arrangements on the orthogonal coordinate system.

According to the first optical element, the light incident ends of the plurality of the optical transmission elements are located on the spherical surface S. When a target observation object or the like is located near the center O of the spherical surface S and is illuminated with, e.g., a plane wave, light emerging from the target observation object at a predetermined angle is incident on the incident end of the corresponding optical transmission element on the spherical surface S. When the exit end of this optical transmission element is arranged on the basis of the light incident angle in accordance with a conversion rule as of the Fourier transform lens, the f-θ lens, or a normal lens. The first optical element can perform optical conversion equivalent to that of the Fourier transform lens, the f-θ lens or the normal lens.

The second optical element is an element for performing optical Fourier transform. The second optical element is proposed on the basis of the following two points. First, optical Fourier transform is used in an apparatus for inspecting a fine defect. For example, in this defect inspecting apparatus, an amount of scattered light caused by a defect upon illumination of an object in a sufficiently large light amount must have a level which allows photoelectric conversion. For this reason, in many defect inspecting apparatuses, illumination light is focused by an optical system to illuminate only a very small area of the target inspection object, thereby assuring an illumination light amount for the defect.

Second, when information on the Fourier transform plane is to be processed in real time, information of the intensity distribution of a Fourier transform image is generally used. For this reason, a one- or two-dimensional image sensor is generally arranged on the Fourier transform plane, and the light intensity distribution is converted into an electrical signal by this image sensor.

The first and second points described above will be supplementarily described below.

As for the first point, as shown in the prior art of FIG. 60, when the range (i.e., the aperture 111 having the width $\xi$) of the target object subjected to Fourier transform on the aperture plane P5 serving as the front focal plane of the Fourier transform lens 112 is sufficiently small, a light amount distribution equivalent to that at the infinite observation point, which is the condition of the Fraunhofer diffraction, can be obtained even if the focusing function of the lens is not used.

More specifically, when the object subjected to Fourier transform is limited within the range of ±xe in the x direction and the range of ±ye in the y direction (i.e., a direction perpendicular to the surface of the drawing sheet in FIG. 60), diffracted light beams $i_1$ and $i_2$ in FIG. 60 cannot be split any longer under the condition that equation (26) is satisfied. The characteristics for focusing a beam on the observation plane P6 as the rear focal plane of the Fourier transform lens 112 are not required for the Fourier transform lens 112:

$$f >> [2(xe^2+ye^2)]/\lambda \qquad (32)$$

For example, if λ=633 [nm] and xe=ye=0.1 [mm], then f>>60 [mm]. That is, the x and y direction ranges of the target object and the focal length f can be properly adjusted to eliminate the first condition, i.e., "focusing condition" of the Fourier transform optical element.

As for the second point described above, the amplitude distribution 113 of a Fourier-transformed image including phase information is obtained on the observation plane P6 serving as the Fourier transform plane in the Fourier transform lens 112 in FIG. 60. If only the intensity distribution of the Fourier-transformed image is taken into consideration, phase information need not be obtained. In recent years, although a one- or two-dimensional image sensor is used to observe the intensity distribution of light, a continuous Fourier spectrum cannot be obtained because the pixel of the one- or two-dimensional image sensor has a finite size. In practice, however, any continuous Fourier spectrum is not necessary. Only a discrete spectrum corresponding to the pixels of the image sensor is required.

The Fourier transform optical element described above has a relatively small range of the target object subjected to Fourier transform. When a one- or two-dimensional image sensor (i.e., a photoelectric conversion element array) is arranged on the Fourier transform plane, an optimal Fourier transform optical element is obtained to observe the intensity distribution of an image on the Fourier transform plane.

Figure 61:
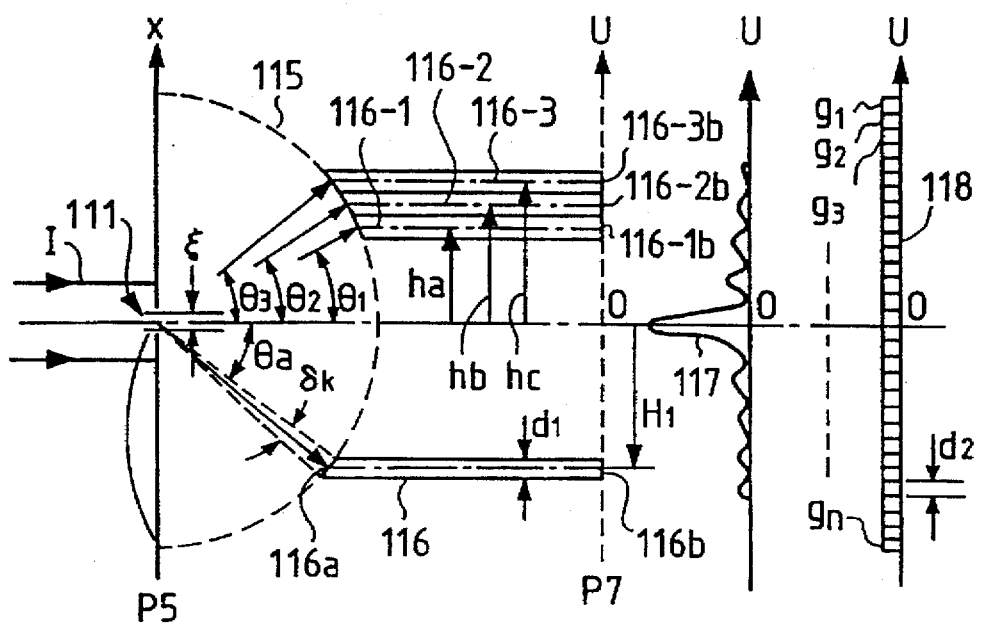
FIG. 61 is a view for explaining the principle of transmissive illumination of the optical element of the present invention.

The basic principle of the second optical element will be described with reference to FIG. 61. The same reference numerals as in FIG. 60 denote the same parts in FIG. 61, and a detailed description thereof will be omitted. Referring to FIG. 61, assume a circumference 115 having a radius f and centered on the aperture 111 having the x direction width $\xi$ on the aperture plane P5. If this radius f is substituted into the focal length f in condition (32) and conditions ye=0 and 2xe>$\xi$ are established, the radius f is determined to satisfy condition (32).

An incident end face 116a of a light transmission element 116 is located on the circumference 115 to satisfy the second condition as "image height condition" of the Fourier transform optical element. An exit end face 116b of the optical transmission element 116 is located on a Fourier transform plane P7 of the coordinate system (U,V). That is, if an angle formed between light propagating from the aperture 111 to the incident end face 116a and a normal to the aperture plane P5 within the plane wave I incident on the aperture 111 from the left direction is defined as $\theta_a$, the optical transmission element 116 transmits light such that its image height $H_1$ of the optical transmission element 116 is set to f·sin $\theta_a$. For this reason, the exit end face 116b of the optical transmission element 116 is located on the Fourier transform plane P7 so that light emerging from the exit end face 116b of the optical transition element 116 has the image height $H_1$ on the Fourier transform plane P7.

In the arrangement shown in FIG. 61, the Fourier transform plane P7 is formed parallel to the aperture plane P5 because the optical transmission element 116 is parallel to a normal of the aperture plane P5 and the exit end face 116b is an end face parallel to the aperture plane P5. The resolution of the Fourier spectrum depends on the size of the incident end face 116a of the optical transmission element 116. That is, light emerging from the aperture 111 and incident on the incident end face 116a has an incident angle $\theta_a$ in FIG. 61. In practice, however, the incident end face 116a is not a point, but has a width as an angular width $\delta_k$ when viewed from the aperture 111. Therefore, the resolution of the Fourier spectrum corresponds to about the angular width $\delta_k$.

In correspondence with necessary portions of the Fourier spectrum, to increase optical transmission elements 116-1, 116-2, and 116-3 having incident end faces 116-1a, 116-2a, and 116-3a in directions of angles $\theta_4$, $\theta_5$, and $\theta_6$ on the circumference 115 and exit end faces 116-1b, 116-2b, and 116-3b on the Fourier transform plane P7, the angles of the incident end faces of the respective optical transmission elements on the circumference 115 are set such that image heights ha, hb, and hc are set to ha=f·sin $\theta_1$, hb=f·sin $\theta_2$, and hc=f·sin $\theta_3$, respectively.

The intensity distribution of Fourier spectra is formed on the Fourier transform plane P7, as described above. When the incident end faces of the respective optical transmission elements are reduced to increase the resolution, an almost continuous Fourier spectrum intensity distribution indicated as a distribution 117 in FIG. 61 is obtained. To photoelectrically convert the intensity distribution of the Fourier transform plane P7, for example, an image sensor 118 having pixels g1, g2, . . . , gn constituted by light receiving elements each having a width d2 and arranged at a predetermined pitch in the u direction is arranged on the Fourier transform plane P7.

Figure 62:
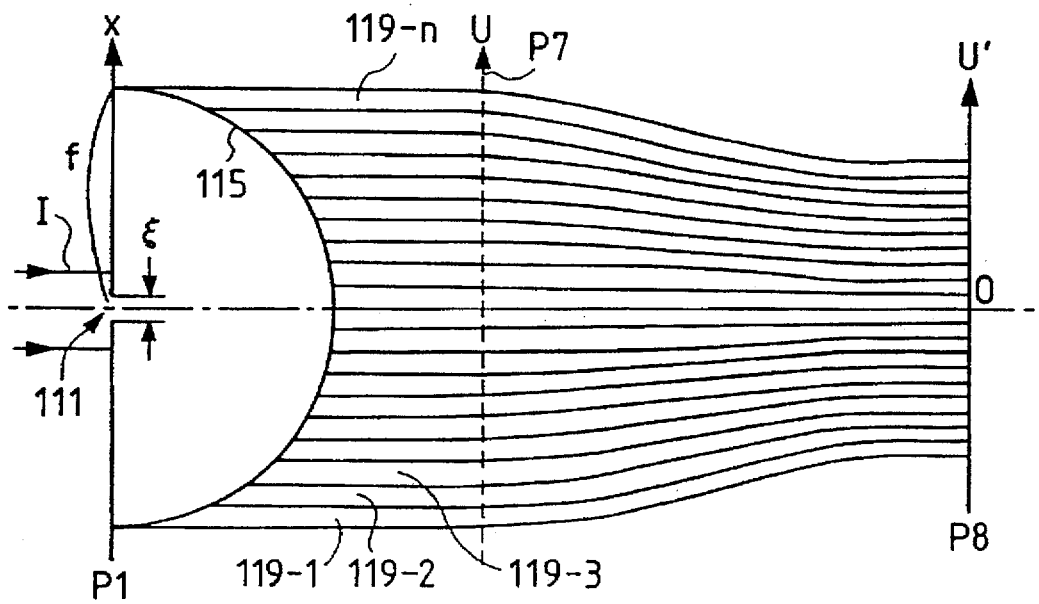
FIG. 62 is a view for explaining the principle when the optical element in FIG. 61 is modified.

When use of a commercially available image sensor is considered, the pixel size and the pixel count cannot be arbitrarily determined. In this case, the size of the Fourier transform plane must be reduced or enlarged in accordance with the specifications of the image sensor, and its simple application is shown in FIG. 62. As shown in FIG. 62, a series of optical transmission elements 119-1 to 119-$n$ having incident end faces respectively located on a circumference 115 centered on an aperture 111 on an aperture plane P1 are bundled. If a coordinate point at which an arbitrary optical transmission element 119-$i$ ($i$=1 to n) passes on a Fourier transform plane P7 parallel to the aperture plane P1 is defined as U, and a coordinate point at which the optical transmission element 119-$i$ passes through a transform plane P8 located to the right of the transform plane P7 is defined as U', relation U'=kU (k is a constant smaller than 1) is established by reducing the diameters of the exit portions of the optical transmission elements 119-1 to 119-$n$.

In the optical transmission elements shown in FIGS. 61 and 62, the arrangement obtained by positively projecting the light incident end faces of the plurality of optical transmission elements (116-1, 119-1, . . . ) on the plane passing through the center O of the circumference 115 is similar to the arrangement of the exit end faces thereof on the Fourier transform plane P7 or P8.

Figure 63:
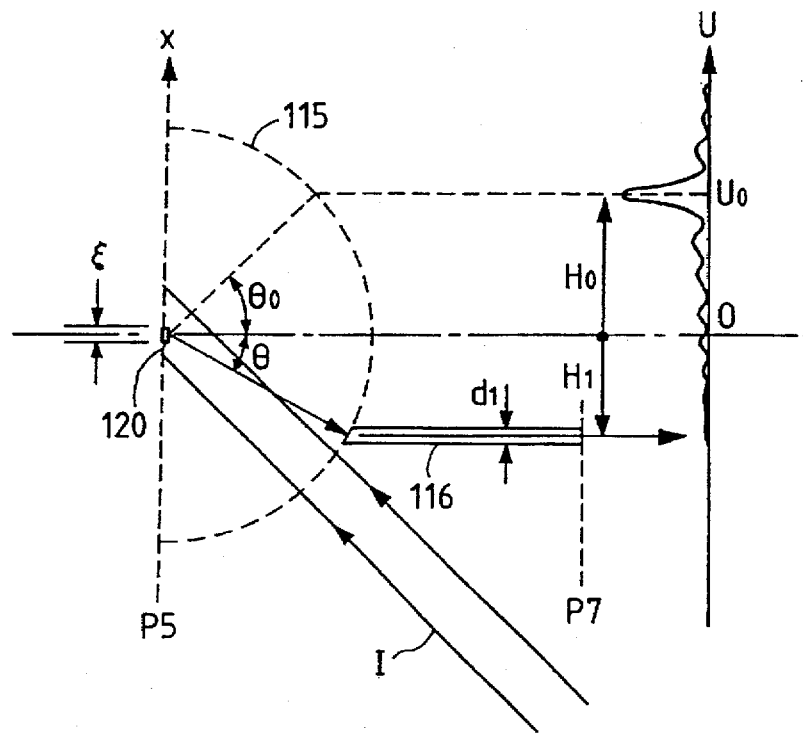
FIG. 63 is a view for explaining the principle of reflective illumination of the optical element of the present invention.

Incidence illumination will be described with reference to FIG. 63. Referring to FIG. 63, a reflective pattern 120 having an x direction width ξ as a target object subjected to Fourier transform is located on an aperture plane P5. An incident plane wave I having a wavelength λ illuminates the aperture plane P5 so that the reflection angle in the regular reflection direction normal to the aperture plane P5 is set to $\theta_0$. In this case, the incident plane wave I has a phase distribution sinusoidally changing on the aperture plane P5 along the x axis due to an influence of oblique incidence on the aperture plane P5, and the Fourier spectrum intensity distribution has a lateral shift.

If the image height obtained when reflected light having the reflection angle $\theta_0$ crosses the circumference 115 is defined as $H_0$, the Fourier spectrum intensity distribution on the Fourier transform plane P7 is shifted by only $u_0$ represented by $V_0$=$fl_0$ of equation (28) along the U axis as compared with the case in FIG. 61.

However, when the optical transmission element 116 is arranged such that its incident end face is in contact with the circumference 115, a laterally shifted Fourier spectrum intensity distribution is obtained on the Fourier transform plane P7 as in FIG. 61.

When the optical transmission elements (116-1, 119-1, . . . ) are constituted by light guides such as optical fibers or columnar mirrors whose inner surfaces are mirror-polished, light can be efficiently guided from the incident surfaces to the corresponding exit surfaces.

Figure 58:
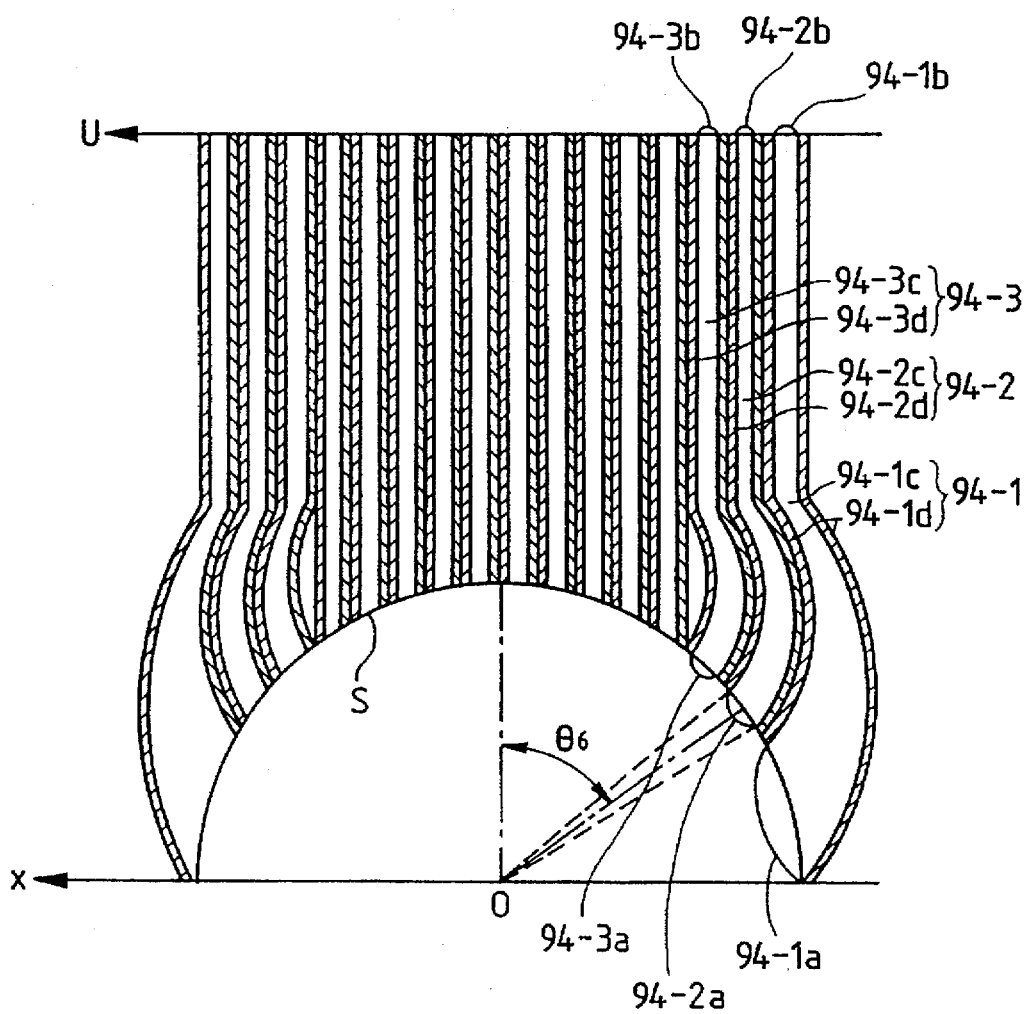
FIG. 58 is a schematic sectional view showing the third application example of the optical element according to the present invention.

In addition, when the light incident ends of a plurality of optical transmission elements are almost perpendicular to a spherical surface, as shown in FIG. 58, light components near the center of the spherical surface S can be efficiently incident on the corresponding optical transmission elements.

In the second optical element, if the arrangement obtained by positively projecting the light incident ends of the plurality of optical transmission elements on the plane passing through the center of the spherical surface S and the arrangement obtained by positively projecting the exit end faces thereof are the arrangements on the orthogonal coordinate system, the light intensity distribution on the Fourier transform plane can be obtained on the orthogonal coordinate system, and subsequent processing can be facilitated.

The first application example of the optical element will be described with reference to FIGS. 55 and 56. This optical element performs optical Fourier transform.

FIG. 55 is a perspective view of the optical element according to the first application example. Referring to FIG. 55, assume a spherical surface S having a predetermined radius and centered on an origin O of an orthogonal coordinate system having x and y axes, and also assume an orthogonal coordinate system having U an V axes and spaced apart from the plane (x–y plane) having the x and y axes by a distance L. The x axis is set parallel to the U axis, and the y axis is set parallel to the V axis. A straight line passing through the origin O of the x–y plane and a plane (U–V plane) having the U and V axes is perpendicular to the x–y and U–V planes.

When the quadrangularly prismatic optical fibers having a bottom surface whose width in the U direction is Du and width in the V direction is Dv are densely bundled. Two of these quadrangularly prismatic optical fibers are represented by quadrangularly prismatic optical fibers 91-$i$ and 91-$j$, and other quadrangularly prismatic optical fibers are not illustrated. In this case, one end face (e.g., end faces 91-$ib$ and 91-$jb$ indicated by hatched portions) of each of the large number of the quadrangularly prismatic optical fibers is located as a square in the matrix on the U–V plane. The other end face (e.g., end faces 91-$ia$ and 91-$ja$ indicated by hatched portions) of each of the large number of quadrangularly prismatic optical fibers constitutes part of the spherical surface S. The quadrangularly prismatic optical fibers each having the other end face not located on the spherical surface S are not illustrated.

FIG. 56 is a schematic sectional view along a plane passing through the center of the spherical surface S in FIG. 55. Referring to FIG. 56, the quadrangularly prismatic optical fibers 91-1, 91-2, 91-3, . . . are densely arranged from an end of the spherical surface S. The respective quadrangularly prismatic optical fibers comprise a core 91-1$c$ and a cladding layer 91-1$d$, a core 91-2$c$ and a cladding layer 91-2$d$, a core 91-3$c$ and a cladding layer 91-3$d$, . . . , respectively. In this case, for example, light having exit angles $\theta_4$ to $\theta_5$ is incident on the core portion of the other end face 91-6$a$ of the quadrangularly prismatic optical fiber 91-6, and this light emerges from one end face 91-6$b$. Similarly, light having an exit angle close to $\theta_6$ is incident on the core portion of the other end face 91-2$a$ of the quadrangularly prismatic optical fiber 91-2, and this light emerges from one end face 91-2$b$ thereof.

If the radius of the spherical surface S is defined as f, for example, the following relation is apparently established between an exit angle $\theta_3$ of light incident on the other (incident side) end face 11-2$a$ of the quadrangularly prismatic optical fiber 11-2 and a coordinate $u_3$ on the U axis of one (exit side) end face 11-2$b$ thereof:

$$u_3 = f \sin \theta_3$$

This relation also applies to other quadrangular prismatic optical fibers 91-$k$ ($k$=1, 3, 4, . . . ). It is thus apparent that the optical element arranged by bundling these quadrangularly prismatic optical fibers serves as a Fourier transform optical element.

In this application example, light emerging from a portion near the center of the spherical surface S at an angular of about 90° with respect to the optical axis can efficiently propagate to the U–V plane by, e.g., the quadrangularly prismatic optical fiber 91-1. Therefore, a Fourier spectrum in a wide frequency range can be observed with a high S/N ratio.

Columnar optical fibers may be used in place of the quadrangularly prismatic optical fibers 91-$i$. Although the columnar optical fiber has a lower focusing efficiency than the quadrangularly prismatic optical fiber, the columnar optical fibers can be easily manufactured.

The second application example of the Fourier transform optical element will be described with reference to FIGS. 57A and 57B.

FIG. 57A is a schematic sectional view of an optical element according to the second application example. Referring to FIG. 57A, the quadrangularly prismatic optical fibers 91-$i$ (i=1, 2, . . . ) in FIG. 56 are replaced with quadrangularly prismatic hollow pipes 92-1. Any other arrangement is the same as in the first application example. FIG. 57B shows a quadrangular prismatic pipe 92 as a representative of the quadrangularly prismatic pipes 92-$i$. The quadrangularly prismatic pipe 92 is surrounded by partition walls 93 to constitute four inner mirror surfaces 92$d$. Light passes through a hollow portion 92$c$.

Referring to FIG. 57A, light emerging from the inside of the spherical surface S is reflected by the mirror surfaces 92-1$c$, 92-2$c$, 92-3$c$, . . . , passes through the hollow portions 92-1$d$, 92-2$d$, 92-3$d$, . . . , and reaches a U–V plane serving as a Fourier transform plane. In this embodiment, one end face (91-1$b$, 92-2$b$, 92-3$b$, . . . ) of each pipe is located on the U–V plane, and the other end face (91-1$a$, 92-2$a$, 92-3$a$, . . . ) thereof is arranged in contact with the spherical surface S.

The third application example of the Fourier transform optical element will be described with reference to FIG. 58. In this third application example, each optical transmission element is constituted by an optical fiber as in the first application example of FIG. 56. The positional relationship between the center of the incident end face of each optical fiber and the center of the exit end face thereof is the same as in the optical element of the first application example. However, in the third application example, the light propagation efficiency is higher than that in the first application example. More specifically, the light propagation efficiency in the quadrangularly prismatic optical fiber 91-2 which receives light at an average exit angle $\theta_3$ is generally lower than that in the quadrangularly prismatic optical fiber 91-6 which receives light at exit angles $\theta_1$ to $\theta_2$ in the example of FIG. 56. This can be solved when the beam incident angle at the incident end face of the optical fiber comes close to 90°.

FIG. 58 is a schematic sectional view of the optical element according to the third application example. Referring to FIG. 58, optical fibers 94-1, 94-2, 94-3, . . . are arranged from an end of a spherical surface S centered on an origin O. The respective optical fibers comprise a core 94-1$c$ and a cladding layer 94-1$d$, a core 94-2$c$ and a cladding layer 94-2$d$, a core 94-3$c$ and a cladding layer 94-3$d$, . . . , respectively. Of all the optical fibers, an optical fiber closest to the end of the spherical surface S has the incident end face brought into contact with the spherical surface S at an almost right angle by deforming the shape of the incident end portion. For example, the optical axes of the optical fibers close to the incident end faces 94-1$a$, 94-2$a$, 94-3$a$, . . . thereof are perpendicular to the spherical surface S. The exit end faces 94-1$b$, 94-2$b$, 94-3$b$, . . . of the optical fibers are located on the U–V plane.

Light incident on the end face 94-3$a$ of the optical fiber at, e.g., an exit angle $\theta_6$ efficiently propagates through the core 94-3$c$ and reaches the end face 94-3$b$. In this manner, according to the third application example, light emerging from the inside of the spherical surface S is efficiently supplied to the U–V plane serving as the Fourier transform plane.

The first to third application examples described above are based on equations (25) and (26) in the description of principles. As shown in FIG. 62 in the description of principle, the Fourier transform plane may be reduced or enlarged.

The fourth application example of the Fourier transform optical element will be described with reference to FIG. 59. This example shows a reflective optical system.

Figure 59:
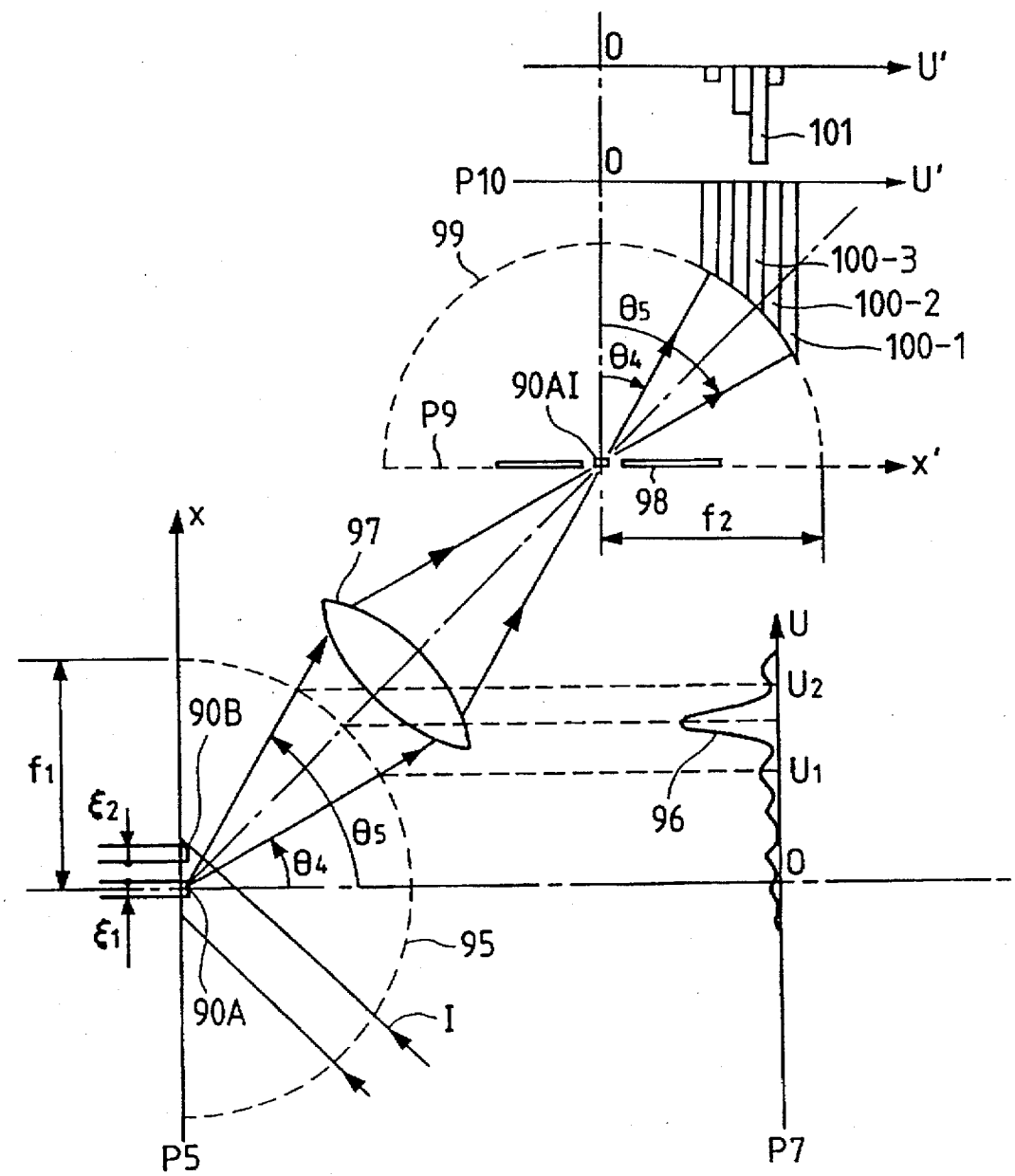
FIG. 59 is a view showing an optical path so as to include part of the arrangement of the fourth application example of the optical element of the present invention.

FIG. 59 is a schematic sectional view of the fourth application example. Referring to FIG. 59, assume a semispherical surface 95 having a radius $f_1$ and centered on the origin of an aperture plane P5. A reflective pattern 90A having an x direction width $\xi_1$ and a reflective pattern 90B having an x direction width $\xi_2$, both of which serve as target objects subjected to Fourier spectral measurement, are located on the aperture plane P5. Assuming that an incident plane wave I passes part of the semispherical surface 95 and is obliquely incident on the aperture plane P5, a Fourier spectrum corresponding to an observation direction from an angle $\theta_1$ to an angle $\theta_2$ in FIG. 59 is to be measured.

When only the reflective pattern 90A is present in the illumination area of the plane wave I obliquely incident, a Fourier spectrum having the same distribution as that on the plane P7 (FIG. 63) referred to in the description of principles must be obtained. This Fourier spectrum is represented by a distribution 96 on a plane P7 of FIG. 59. In FIG. 59, since the reflective pattern 90B is also present in the plane wave I, a composite Fourier spectrum of the Fourier spectra of the reflective patterns 90A and 90B is observed. According to the fourth application example, a lens 97 and a slit plate 98 are further added to obtain a Fourier spectrum of an arbitrary region from the incident plane wave I.

Light reflected by the reflective pattern 90A in the aperture plane P5 is focused within the central slit of the slit plate 98 on a plane P9. Light reflected by an object around the reflective pattern 90A is shielded by the slit plate 98. For example, when an optical system shown in FIG. 59 is actually incorporated and used in a defect inspecting apparatus, unnecessary stray light and the like generated from objects except for the target object can be advantageously shielded by the slit plate 98.

Referring to FIG. 59, an image on the aperture plane P5 is formed on the plane P9 by the lens 97, and an image 90AI of the reflective pattern 90A is formed within the slit of the slit plate 98. That is, light around the image 90AI is shielded by the slit plate 98, and only the spectra of light rays constituting the image 90AI are extracted. A semispherical plane 99 having a radius $f_2$ and centered on the slit plate 98 is assumed. Optical transmission elements 100-1, 100-2, 100-3, . . . , are arranged so that the incident end faces thereof are in contact with a semispherical surface 99. The exit end faces of these optical transmission elements are located on a Fourier transform plane P10 parallel to the plane P9. The coordinate system of this plane P9 is represented by x' and y' axes, and the coordinate system on the Fourier transform plane P10 is represented by U' and V' axes.

In this case, the radius $f_2$ is determined to satisfy condition (32), and light from the reflective pattern image 90AI on the plane P9 is guided to the Fourier transform plane P10 through the optical transmission elements 100-1, 100-2, 100-3, . . . . The Fourier spectrum intensity distribution corresponding to the resolution of the optical transmission elements is obtained on the Fourier transform plane P10, as indicated by a distribution 101.

In the fourth application example, the reflective pattern 90A is fine or micropatterned. However, even if an object subjected to Fourier transform on the aperture plane P5 is reflective or transmissive, it is difficult to always satisfy condition (32) so as to obtain Fourier spectra of target objects having different sizes. There are two methods of obtaining a Fourier spectrum of a target object having an arbitrary size.

According to the first method, the size of the slit of the slit plate 98 in the fourth application example in FIG. 59 is set small to satisfy condition (32).

According to the second method, in the fourth application example of FIG. 59 or in the arrangements (FIGS. 61 and 62) in the description of principles, the illumination area of the incident plane wave I on the aperture plane P5 is reduced to satisfy condition (32). As described above, the second method can be easily realized by a general illumination optical system in an inspecting apparatus for inspecting a fine defect. That is, this is because a laser beam having a very small spot is illuminated on a target object in this defect inspecting apparatus.

The Fourier spectrum obtained using the first method is measured such that the Fourier spectrum of the slit of the slit plate 98 is convoluted. The Fourier spectrum obtained using the second method is measured such that the Fourier spectrum of the illumination area is convoluted. When the Fourier transform of the real space function f(x,y) is represented by F[f(x,y)], and the convolution of the two functions $f_1(u,v)$ and $f_2(u,v)$ of the spatial frequency space is represented by $f_1(u,v)*f_2(u,v)$, the Fourier spectra obtained by the first and second methods are represented by equations (33) and (34), respectively:

$$F[A(x,y) \cdot B_1(x,y)] = a(u,v) * b_1(u,v) \tag{33}$$

$$F[A(x,y) \cdot B_2(x,y)] = a(u,v) * b_2(u,v) \tag{34}$$

where

A(x,Y): amplitude reflectance (transmittance) distribution at aperture plane of target object a(u,v): Fourier spectrum of A(x,y)

$B_1(x,y)$: amplitude transmittance distribution of slit $B_2(x,y)$: amplitude distribution in illumination region of incident beam $b_1(u,v)$: Fourier spectrum of $B_1(x,y)$ $b_2(u,v)$: Fourier spectrum of $B_2(x,y)$ In this case, to extract only the Fourier spectrum of the target object, convolution of the function $(b_1(u,v))^{-1}$ or $(b_2(u,v))^{-1}$ is performed on the left-hand side of equation (33) or (34).

Fourier transform optical elements are not limited to the application examples described above. For example, an f-θ lens or a normal lens may be used to constitute a Fourier transform optical element.

According to this Fourier transform optical element, since light emerging at a large inclination angle can be guided to the exit end of an optical transmission element, the light can be focused on a plane even at a large exit angle as close to 90° in accordance with a predetermined conversion rule.

Since Fourier transform can be accurately performed for light having a large exit angle, the Fourier spectrum of a fine object can be observed in a wider frequency range than that in the conventional arrangement. For example, the present invention is suitably applicable to an apparatus such as a substrate defect inspecting apparatus using intensity distribution information of a Fourier transform plane or an apparatus based on the principle of analyzing the intensity distribution of a Fourier transform plane in real time.

When an optical transmission element is constituted by a light Guide, or the incident end of an optical transmission element is almost perpendicular to a spherical surface, the light propagation efficiency is further increased.

If an arrangement obtained by positively projecting the light incident ends of a plurality of optical transmission elements on a plane passing through the center of a spherical surface and an arrangement obtained by positively projecting the light exit ends thereof are arrangements on the orthogonal coordinate systems, image processing and the like can be facilitated.

The ninth embodiment of the present invention will be described below. First of all, a Fourier transform optical system will be described in association with a defect inspecting apparatus with reference to FIGS. 81A to 83B.

Referring to FIG. 81B, a one-dimensional periodic pattern $A_p$ (FIG. 81C) along the X direction is arranged on an object plane $B_p$ of a Fourier transform lens 141. The periodic pattern $A_p$ has hatched portions (FIG. 81C) as light reflective portions and a remaining portion as a transparent portion. The pattern $A_p$ is illuminated within an area l on the circuit pattern with parallel light I'. A rear focal plane F of the lens 141 serves as a Fourier transform plane, and light beams 151 to 154 emerging from the area l form diffracted images on the Fourier transform plane F (u–v plane), as shown in FIG. 81A, so that dot-like Fourier spectra $d_1$ to $d_4$ are observed. This Fourier transform lens 141 requires two conditions, i.e., "focusing condition" and "image height condition" described above.

These conditions will be described again.

Condition ①: To obtain an observation result equivalent to that at an infinity point, diffracted light components (e.g., diffracted light components at almost the same diffraction angle) from different points on the object plane $B_p$ must be focused on one point. For this purpose, the circuit pattern $A_p$ must be aligned with the front focal plane of the Fourier transform lens 141, and the Fourier transform F must be aligned with the rear focal plane thereof. If this condition is not satisfied, the spatial frequency does not correspond to direction cosine in a one-to-one correspondence.

Condition ②: To set the image height and the spatial frequency from the 0th-order spectrum in a proportional relationship, if the image height from the 0th-order spectrum in the X direction is defined as U, equation (35) must be satisfied from equations (26) and (27):

$$U \propto u = (l - l_0)/\lambda \tag{35}$$

In the following description, condition 1 is called the "focusing condition" and condition 2 is called the "image height condition". The following equation is established due to the definition of the direction cosine:

$$l - l_0 = \sin \theta_s - \sin \theta_0 \tag{36}$$

wherein the angle $\theta_s$ in the X direction is an X-direction angle formed between a normal to the object plane $B_p$ and the light beam, and the angle $\theta_0$ is an angle formed between a normal to the object plane $B_p$ and the incident direction of a plane wave I.

The following equation is also established from equations (35) and (36):

$$U \propto u = (\sin \theta_s - \sin \theta_0)/\lambda \quad (37)$$

A normal lens has a relation H=f·tan η between an image height H and an angle η formed between the optical axis and the observation direction. However, in the Fourier transform lens 141, a relation H=f·sin η is established. Therefore, when the following condition is established, the image height condition is satisfied.

$$U = f(\sin \theta_s - \sin \theta_0) = f \cdot u \cdot \lambda \quad (38)$$

In the process of deriving equation (38), $H_1 = f \cdot \sin \theta_s$, $H_0 = f \cdot \sin \theta_0$, and $U = H_1 - H_0$ are applied.

As similar relations are also established in the Y direction, the following two equations are established:

$$U = f(l - l_0) = u\lambda f \quad (39)$$

$$V = f(m - m_0) = v\lambda f \quad (40)$$

In FIG. 81B, when f=1/λ, U=u and V=v from equations (39) and (40).

By the above conditions, a diffraction image is formed on the Fourier transform plane F of the rear focal plane of the Fourier transform lens 141. Orthogonal coordinates of the spatial frequency of the Fourier transform plane F are given as (u,v). When these coordinates are caused to correspond to equation (13), the amplitude distribution of an incident plane wave I on the object plane $B_p$ with respect to the circuit pattern $A_p$ is represented by F(x,y), and the amplitude distribution of the diffraction image on the Fourier transform plane is represented by f(u,v). Although the intensity of the diffraction image is given as |f(u,v)|², this intensity distribution is observed as shown in FIG. 81A. In the following description, the diffraction image intensity distribution is simply referred to as a Fourier spectrum. FIG. 81A represents a Fourier spectrum on the Fourier transform plane, FIG. 81B represents diffracted light from the Fourier transform lens and the circuit pattern $A_p$, and FIG. 81C shows the circuit pattern $A_p$.

In a defect inspecting apparatus for a reticle or the like in the manufacture of semiconductor elements, a defect is illuminated in a sufficient light amount, and an amount of light scattered by a defect must be converted to a level capable of performing photoelectric conversion. For this reason, in a defect inspecting apparatus of this type, illumination light is focused by an optical system to illuminate only a small portion of an inspecting object, thereby assuring an amount of light radiated on the defective portion.

As shown in FIG. 82B, when the range of objects to be Fourier-transformed on the front focal plane (i.e., the object plane $B_p$) of the Fourier transform lens 141 is sufficiently narrow, a light amount distribution equivalent to that at the infinity observation point, which is the condition in Fraunhofer diffraction without using the focusing function of the lens, as described above, can be obtained.

FIG. 82A shows the Fourier spectrum on the Fourier transform plane (i.e., the infinity observation point), and FIG. 82B shows the Fourier transform lens 141, light receiving Optical systems $L_1$ and $L_2$ of the defect inspecting apparatus, and diffracted light components.

More specifically, assume that an object to be Fourier-transformed, i.e., a target illumination area on the circuit pattern $A_p$ is limited to the range of $\pm x_e$ in the x direction and $\pm y_e$ in the y direction (i.e., a direction perpendicular to the surface of the drawing in FIGS. 82A and 82B). If equation (32) is satisfied, diffracted light components 155 to 158 are regarded to be generated from one point. The Fourier transform lens 141 need not have characteristics for focusing a light beam on the Fourier transform plane as the rear focal plane of the Fourier transform lens 141.

More specifically, the "focusing condition" as the first condition of the Fourier transform optical element need not be used due to a combination of the ranges $x_e$ and $y_e$ of the conversion object and the focal length f.

FIG. 82B shows the arrangement of an optical system in which the "focusing condition" is not required. This arrangement satisfies condition (39). Fourier spectra observed by the optical system (141, $L_1$, and $L_2$) in FIG. 82B are repetitive patterns of elliptical bright points, as indicated by bright points $d_5$ to $d_8$ in FIG. 82A. This is an influence from the Fourier spectrum of an incident light beam I' (i.e., an angle formed between the optical axis of the illumination optical system and the object plane $B_p$ is 10°). A central coordinate point O' of the bright points $d_5$ to $d_8$ corresponds to a central coordinate point O' of the bright points $d_1$ to $d_4$ in FIG. 81A.

In an optical system using the above Fourier transform lens 141, the lens diameter is increased to perform Fourier transform at a wide spatial frequency range. When the thickness of the lens in the optical direction is also taken into consideration, it is very difficult to cause the Fourier transform lens to perform Fourier transform of diffracted light at a diffraction angle of about 90° in practice. Such a large diffraction angle is obtained when the structure of an object illuminated with an incident plane wave is micropatterned.

The circuit patterns of semiconductor elements have been micropatterned year by year. In a defect inspecting apparatus of this type, a light receiving means (a pupil plane is represented by Ep) for receiving a light beam from an inspecting point and discriminating a circuit pattern from defects is located at a position where an angle formed between the optical axis and the object plane is, e.g., about 30°. To measure the Fourier spectrum of a light beam incident on the light receiving means in FIG. 82B, the diameter of the lens 141 must be greatly increased.

In this case, if it is difficult to use a Fourier transform lens having a large diameter, in place of directly measuring a Fourier spectrum, a two-dimensional sensor may be used to measure a scattered light distribution state near a plane Ps which is conjugate to the incident pupil determined by an aperture or aperture stop 159 of the first objective lens $L_1$ of the light receiving means in FIG. 82 and which is perpendicular to the optical axis of the objective lens. In this embodiment, since the object is a point O, a plane Eps conjugate to the pupil is also a plane on which an image 159a of the aperture stop 159 is formed by the second objective lens $L_2$ (focal length: $f_2$) in which an image point O' is located at the front focal position.

Foreign particle inspection is performed using a high-sensitivity photomultiplier having a light receiving surface located on the plane Ep or Eps. The ninth embodiment is associated with optimization of an arrangement (array) of photoelectric conversion elements located near the pupil plane Ep of the light receiving optical system or its conjugate plane Eps and is characterized by arranging a scattering distribution measuring means using a two-dimensional photoelectric conversion element such as a CCD having a large number of segments at a relatively low sensitivity.

Figure 79:
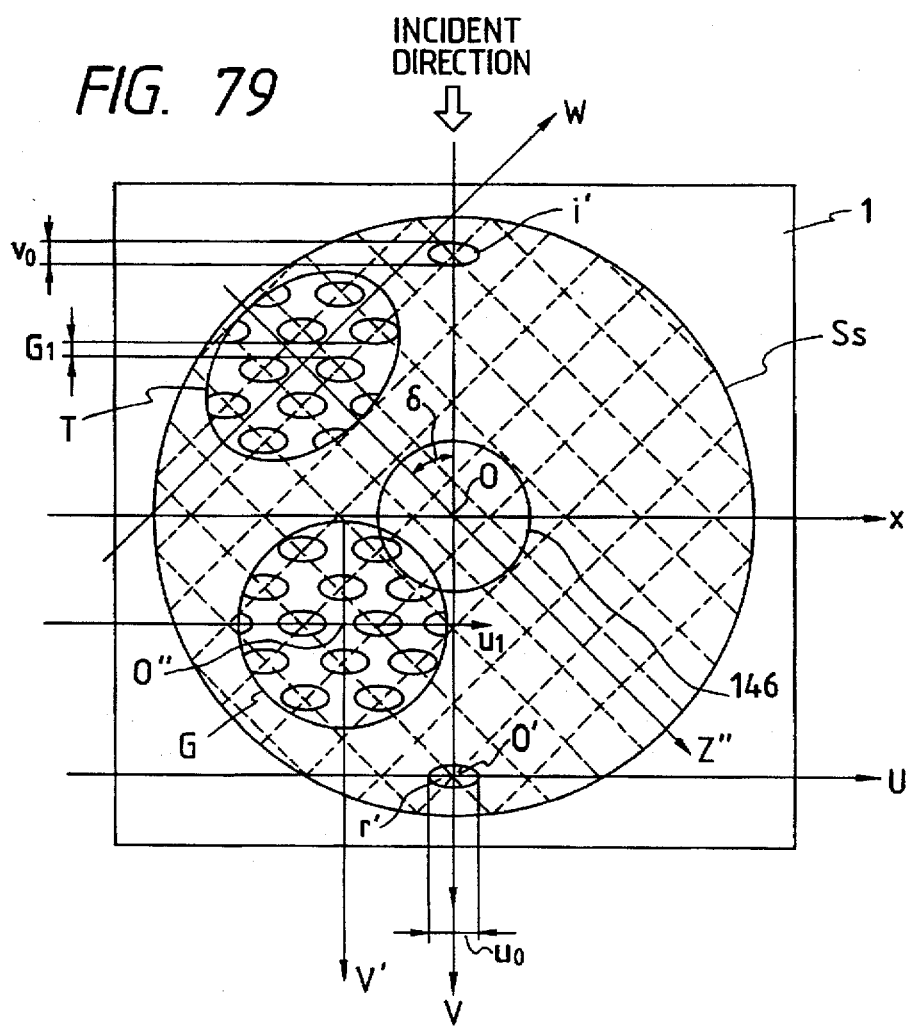
FIG. 79 is a view for explaining the principle of a distribution of diffracted light components on the Fourier plane.

The ninth embodiment is compatible with an arrangement in which the optical axis of a light receiving optical system is different from the optical axis of a scattered light distribution measuring means. The distribution (i.e., the distribution of light scattered from a periodic pattern which is important to discriminate foreign particles from a pattern using scattered light) of scattered light incident on an inspection high-sensitivity light receiving means having an optical axis different from that of the scattering distribution measuring means can be estimated from the measurement result of the scattering distribution measuring means. The scattered light distributions near the optical axes can be correlated on the Fourier transform plane (FIG. 79). As shown in FIG. 82B, in particular, the high-sensitivity light receiving means arranged near the incident direction of incident light and having light receiving lenses $L_1$ and $L_2$ whose optical axis is aligned with a direction perpendicular to the substrate does not strictly have any Fourier transform. In this case, it is preferable to convert a pupil conjugate plane into a Fourier transform plane by appropriate coordinate transform.

FIG. 83B is a view showing an arrangement in which Fourier transform can also be performed using an optical element using a fiber bundle shown in FIGS. 55 and 56. This optical element has a function of positively projecting, on a Fourier transform plane F parallel to an object plane $B_p$, an optical pattern (overlapping areas between light beams 155 to 158 and a sphere S) formed on the spherical surface of the sphere S having a radius f illustrated centered on the focal point of the incident light source. By the optical element using this optical fiber bundle, resultant Fourier spectra $d_5$ to $d_8$ (FIG. 83A) coincide with the fourier spectra $d_5$ to $d_8$ in FIG. 82A.

The optical system shown in FIG. 83B can obtain a Fourier spectrum corresponding to a light beam (emerging from a point O) having an arbitrary angle of up to 90° defined between the propagation direction of the light beam emerging from the point O and the normal to the object plane $B_p$. Therefore, a Fourier spectrum $j_0$ corresponding to the light beam incident on the pupil conjugate plane of the light receiving optical system of the light receiving means and a Fourier spectrum $i_0$ of the incident light beam I can be measured.

The Fourier spectrum will be described in more detail. The repetitive patterns of the elliptical bright points $d_5$ to $d_8$ are regarded as patterns obtained by convolution between the Fourier spectrum of the incident beam I and the Fourier spectrum of the circuit pattern $A_p$.

If the following definitions are given, $A_p(x,y)$: the amplitude reflectance distribution of the circuit pattern on the object plane $a(u,v)$: the Fourier spectrum of $A_p(x,y)$ $J(x,y)$: the amplitude distribution of illumination light on the object plane $j(u,v)$: the Fourier spectrum of $J(x,y)$ the diffraction image is represented by equation (41):

$$F(A(x,y) \times J(x,y)) = F[(A(x,y)] * F[(J(x,y))] = a(u,v) * j(u,v) \qquad (41)$$

where $F[f(x,t)]$ is the Fourier transform of function $f(x,y)$ of the real space, * is the convolution integral, and $(A(x,y) \times J(x,y))$ is the amplitude distribution of illumination light within the illumination area of the object plane.

For this reason, the ellipse $i_0$ and the ellipses $d_5$ to $d_8$ are congruent ellipses in FIG. 83A. In FIG. 83A, since the incident angle is 80° (=90°−10°), 10° ellipses are formed. That is, the Fourier spectra observed in FIG. 83A are congruent regardless of the coordinate points on the u–v plane to facilitate image processing.

A method of optimizing the arrangement of light receiving areas formed on the Fourier transform plane or the pupil plane of a light receiving optical system ($L_1$ and $L_2$) in FIG. 82B on the basis of the measurement result of the Fourier spectrum will be described with reference to FIGS. 79 and 80A to 80F. In the following description, assume an imaginary sphere S having a radius f (=1/λ where λ is the wavelength of incident light) and the center as the focal point of incident light I. If a point on the sphere S is positively projected on an inspecting substrate, the coordinate point (u,v) on the Fourier transform plane F is converted into a U–V coordinate point proportional to the u–v coordinate point, and the origin is defined as the 0th-order light position (O'). In the following description, for the descriptive convenience, the U–V plane is called a Fourier plane, and the scattering distribution state on the Fourier plane is called a Fourier spectrum. In the following description, equation (41) is assumed to be satisfied.

FIG. 79 shows the Fourier spectrum of a two-dimensional periodic pattern. The Fourier spectrum of the two-dimensional periodic pattern is scattered uniformly within an area $S_s$. The periodic direction and pitch of the Fourier spectrum remain the same in all the partial areas within the area $S_s$. For this reason, when a measurement area is set at an arbitrary coordinate point within the area $S_s$, the pitch of the Fourier spectrum can be measured. Assume that a measurement area G and an area 146 are set. Also assume the center O" of the area G and coordinates U' and V'. The coordinate U' is parallel to the coordinate U, and the coordinate V' is parallel to the coordinate V. For this reason, the coordinate system in the area 146 is also defined as a U'–V' coordinate system. The scattering distribution measuring system of the ninth embodiment performs measurement within the area 146.

FIG. 79 shows elliptical Fourier spectra discretely generated in an area T and the area G within the area $S_s$ and only central points (as intersections of the dotted lines) of Fourier spectra discretely generated in other areas. The Fourier spectrum of the incident light I is represented by i', and the Fourier spectrum of regularly reflected light r is represented by r'. As described above, an orthogonal coordinate system having, as the origin, the center O' of the Fourier spectrum r' is given as the U–V coordinate system. The area T represents an area corresponding to the light receiving surface. A center $P_o$ and coordinates W' and Z' of the area T are set. Within the Fourier plane, an axis passing through the central point $P_o$ of the light receiving surface and the central point O of the coordinates X and Y is defined as Z" axis, and an axis passing through the central point $P_o$ and perpendicular to the Z" axis is defined as a W" axis.

A method of performing image processing of a Fourier spectrum within a measurement area will be described below. As shown in FIG. 80B, a convolution mask (slit plate) 170 located on a straight line perpendicular to an axis H which forms an angle α with the U' axis is used. A convolution integral between the Fourier transform within the measurement area and the convolution mask 170 within the measurement area is performed along the axis H using α as a parameter.

Figure 80A:
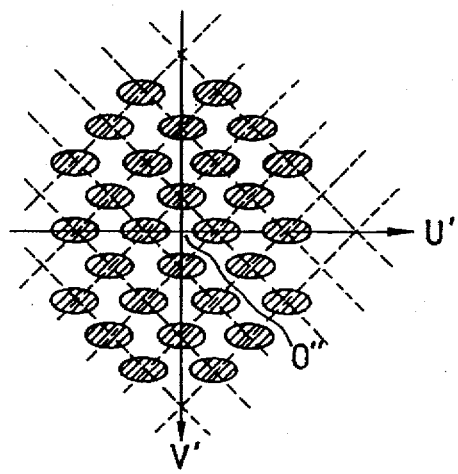
FIGS. 80A to 80F are views for explaining the principle of image processing of a Fourier spectrum.
Figure 80B:
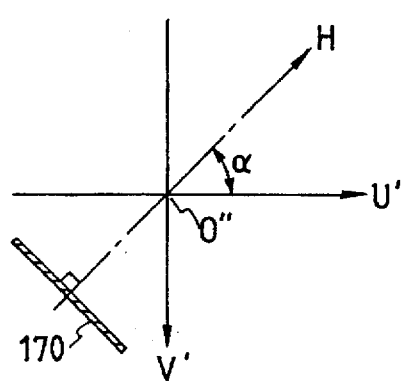
Figure 80C:
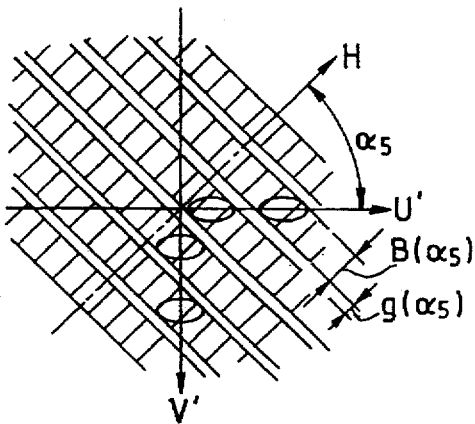
Figure 80D:
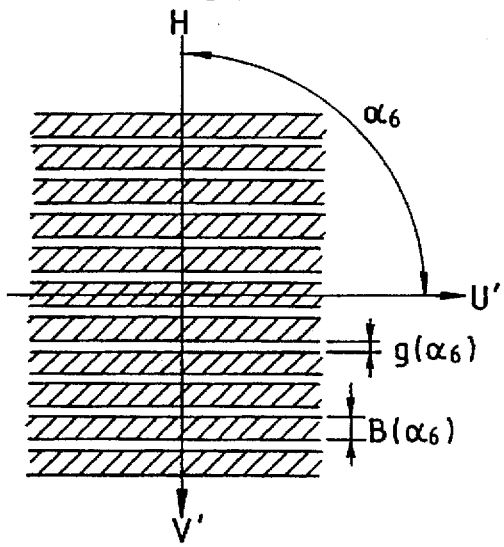
Figure 80E:
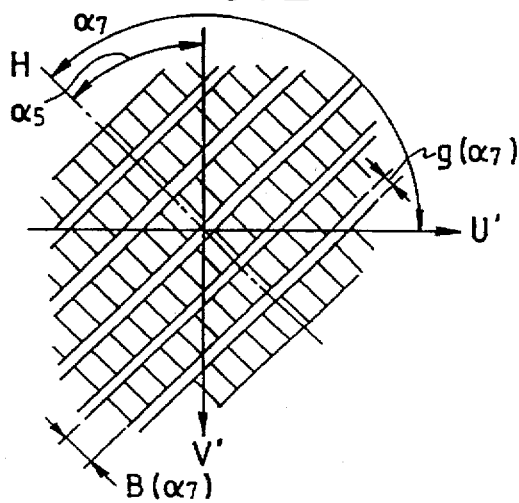
Figure 80F:
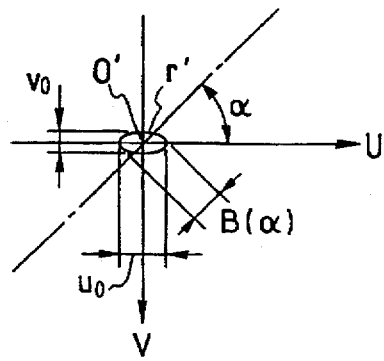

When Fourier spectra shown in FIG. 80A are given (these spectra are arranged at a predetermined pitch in the a and b axes which are inclined at a predetermined angle with respect to the V' axis and are in line symmetry with the U' and V' axes; these spectra correspond to those in FIGS. 8A to 8E), the convolution integral result exhibits periodic bands in all three directions, i.e., $α_5$, $α_6$, and $α_7$, which are shown in FIGS. 80C to 80E. FIG. 80C shows the case in which the angle formed between the U' and H axes is $\alpha_5$, FIG. 80D shows the case in which the angle formed between the U' and H axes is $\alpha_6$, and FIG. 80E shows the case in which the angle formed between the U' and H axes is $\alpha_7$. As shown in FIG. 80F, a width $B(\alpha)$ of each band is the width of the Fourier spectrum of the incident light in the $\alpha$ direction.

To optimize the arrangement of the light receiving areas, in all the periodic bands in FIGS. 80C to 80E, an angle $\alpha$ for maximizing a band interval $g(\alpha)$ of the bands is obtained. The interval $g(\alpha)$ represents an area in which light diffracted by a pattern is not present. An increase in $g(\alpha)$ facilitates discrete discrimination of a pattern from foreign particles. Condition (21) represents a condition for discrete discrimination in the V axis. When the direction of the axis is changed to the H axis, condition (42) is obtained:

$$g(\alpha) \geq 2 \times d(\alpha) + \{B(\alpha) - (n-2) \times d(\alpha)\}/(n-1) = R' \quad (42)$$

where $d(\alpha)$: the width of the Fourier spectrum of the light receiving area in the H axis $g(\alpha)$: the H-direction width of the Fourier spectral area in which diffracted light is not present $B(\alpha)$: the H-direction width of the Fourier spectrum of the incident light $n$: the number of light receiving areas That is, the light receiving areas are arranged such that condition (42) is satisfied in the H direction for maximizing, at the angle $\alpha$, the band interval $g(\alpha)$ obtained in the above-mentioned convolution integral. The interval between two end light receiving areas of all the light receiving areas is set almost equal to $B(\alpha)$.

The first application example of the ninth embodiment of the present invention will be described below.

Figure 64:
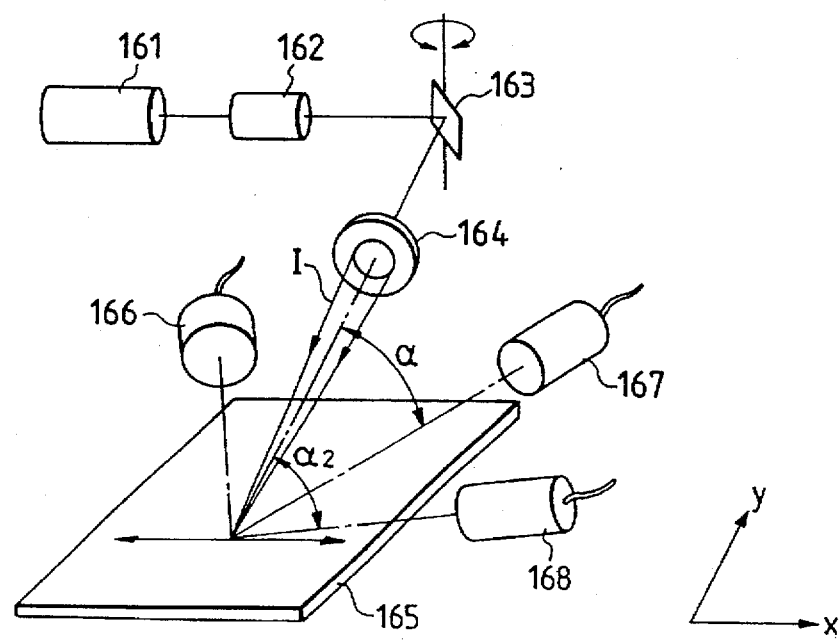
FIG. 64 is a view illustrating the structure of a defect inspecting apparatus according to the prior art.
Figure 64A:
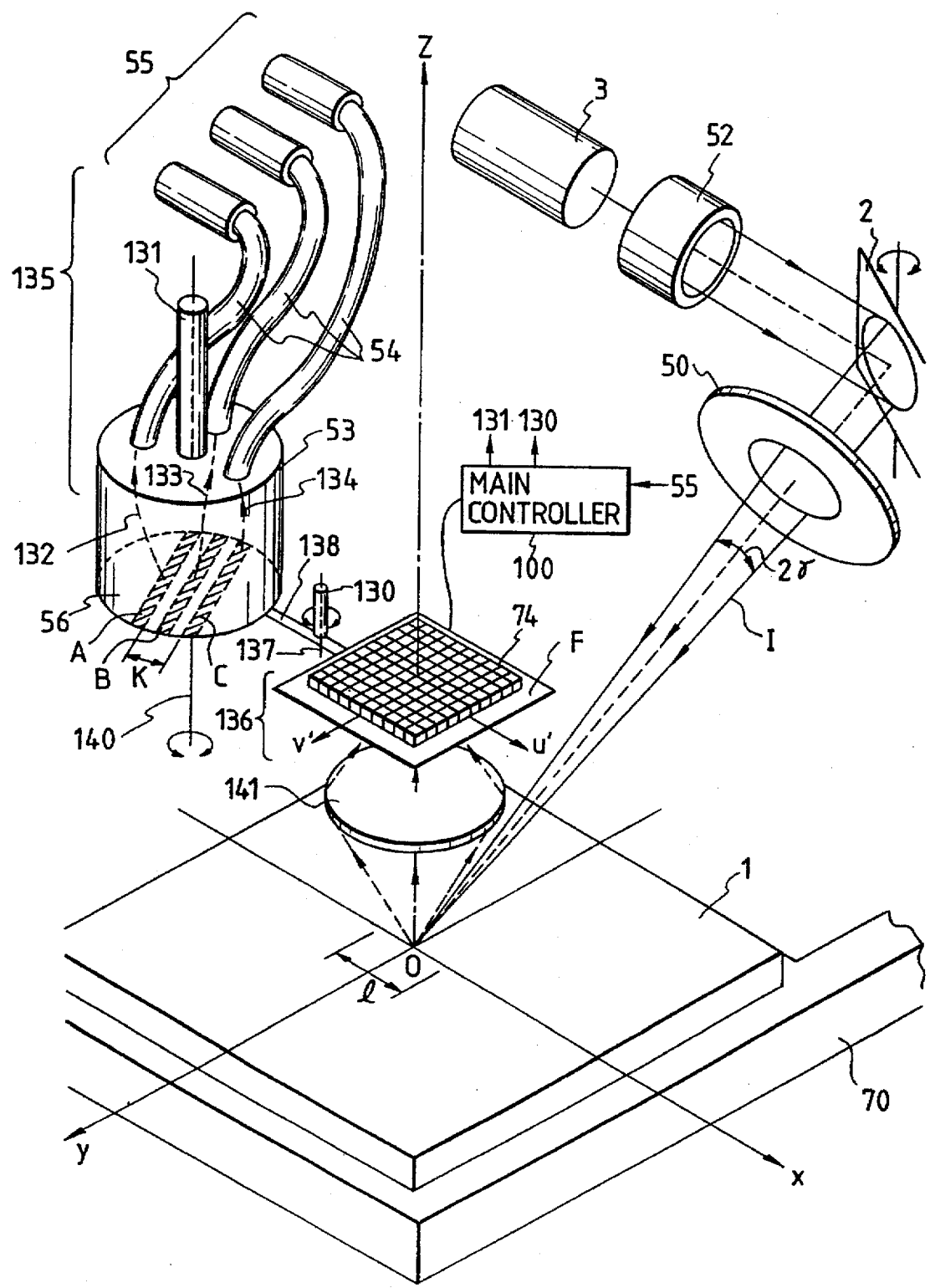
FIG. 64A is a perspective view showing the arrangement of the main part of a defect inspecting apparatus according to the first application example of the ninth embodiment of the present invention.
Figure 66:
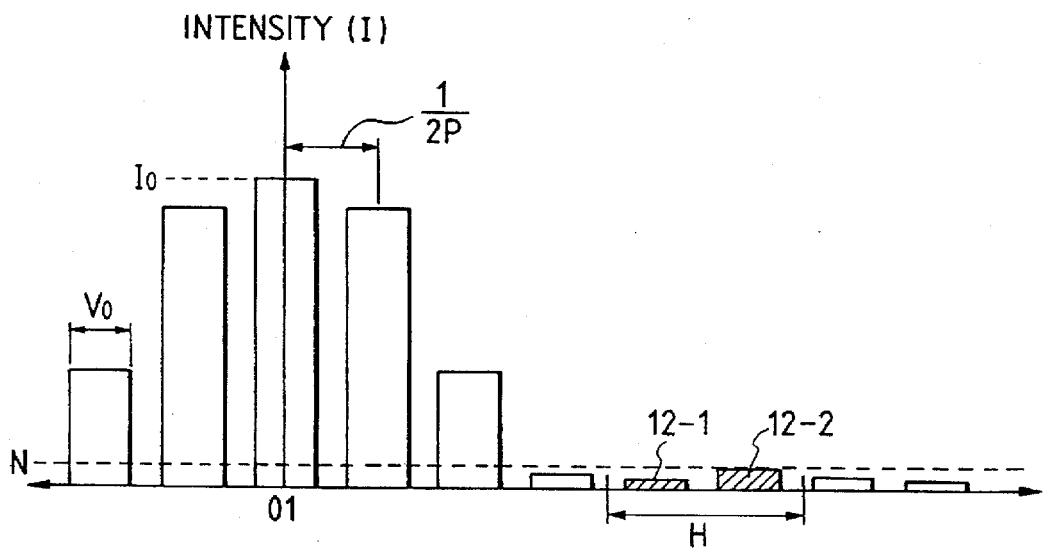
FIG. 66 is a view showing the intensity distribution of diffractive light from the circuit pattern which has a high minuteness.

FIG. 64A is a perspective view showing the arrangement of a defect inspecting apparatus suitable for the ninth embodiment of the present invention. The same reference numerals as in FIG. 30 denote the same parts in FIG. 64A, and a detailed description thereof will be omitted.

A light beam emitted from a laser source 3 in FIG. 64A passes through a beam expander 52 and an f-θ lens (scanning lens) 50 constituting part of a moving means for relatively moving a substrate 1 (e.g., a reticle or wafer) and a light beam and is then focused on an inspecting point O of the substrate on which a circuit pattern is formed. The focused incident light beam I is optically scanned by a vibration mirror 2 by a distance l within the field of view of an objective lens 141 along the X axis. The scanning lens 50 is a lens system having a large focal length. The incident surface of the incident light beam I is almost parallel to each point within a scanning range l. The substrate 1 is placed on a stage 70 movable in the X and Y directions. Foreign particles can be inspected on the entire surface of the substrate 1 by a cooperation between the stage 70 and a scanning optical system (i.e., the vibration mirror 2 and the scanning lens 50).

A scattering distribution measuring means 136 is arranged on an axis (Z axis) passing through the optical scanning range l and perpendicular to the substrate 1. The scattering distribution measuring means 136 comprises the Fourier transform lens (objective lens) 141 located such that the front focal plane is aligned with the upper surface of the substrate 1, and a two-dimensional photoelectric conversion element array 74. The element array 74 is located almost on the rear focal plane F (Fourier transform plane F) of the lens 141, and the optical axis of the lens 141 is almost aligned with the Z axis.

A light receiver 53 is arranged along an optical axis 140 almost parallel to the Z axis. Light receiving areas A, B, and C are formed on a light receiving surface 56 of the light receiver 53. Long side portions of the light receiving areas A, B, and C along the longitudinal direction are linear and are parallel to each other. An interval K between the end light receiving areas A and C is defined to almost equal to the short-side width (e.g., $v_0$ in FIG. 79) of discrete Fourier spectra observed on, e.g., the Fourier plane F. The width $v_0$ is represented by equation (43) if the image height of the lens 141 is defined as $H=f\cdot\sin\eta$ wherein $f=1/\lambda$:

$$v_0 = 2H_0/(f\lambda) = 2f\sin\gamma/(f\lambda) = 2\sin\gamma/\lambda \quad (43)$$

where f is the focal length of the lens 141 and $H_0$ is $f\cdot\sin\gamma$, and $\gamma$ is the angular aperture of the incident light beam I.

$K=v_0$ is established because the corresponding discrete Fourier spectra represent ellipses and the major axis of each ellipse is parallel to the u direction, as shown in FIG. 79. That is, the minor axis of the ellipse is parallel to the Y direction, and the interval K between the areas A and C is set to equal to $v_0$ in favor of the resolution.

The measurable range of the lens 141 for Fourier spectra is represented by the area 146 in FIG. 79.

To obtain a higher discrimination capability, short-side widths $D_0$ of the light receiving areas A, B, and C in FIG. 64A are equal to each other. Light components incident on these light receiving areas are independently transmitted to photoelectric conversion elements 55 through fiber bundles 54, respectively. The photosensitive conversion elements 55 comprise photoelectric conversion elements $a_1$, $a_2$, and $a_3$. The fiber bundles 54 extend to the light receiving areas, as indicated by dotted lines 132, 133, and 134, respectively. Incident light components on the light receiving areas are photoelectrically converted to outputs $A_{OUT1}$, $A_{OUT2}$, and $A_{OUT3}$ by the photoelectric conversion elements $a_1$, $a_2$, and $a_3$, respectively.

The light receiver 53, the optical fiber bundles 54, and a rotation driving portion 131 constitute a light receiving means 135, and the rotation driving portion 131 can rotate the light receiver 53 about a shaft 140. The light receiver 53 is coupled to the two-dimensional photoelectric conversion element array 74 through an arm 138. The arm 138 is rotatable about a rotating shaft 137 through 180° by means of a switching portion 130. Therefore, this makes it possible to locate the light receiving surface 56 and the two-dimensional photoelectric conversion element array 74 on the Fourier transform plane F.

The light receiving surface 56 is rotatable about an optical axis (rotating axis) 140 by means of the rotation driving portion 131 to make it possible to set the direction of the light receiving areas A, B, and C to an arbitrary direction on the basis of the distribution of light scattered from the substrate 1.

Measurement of the scattered light distribution will be described below.

The switching portion 130 is driven to locate the two-dimensional photoelectric conversion element 74 on the Fourier transform plane F. The stage 70 is moved while the vibration mirror 2 is vibrated to form the optical scanning range l. The entire surface of the substrate is optically scanned with an almost uniform optical energy. Meanwhile, an optical energy incident on the two-dimensional photoelectric conversion element 74 is accumulated as an electric charge. Upon completion of the optical scanning, a main controller 100 reads the charge accumulated in the two-dimensional photoelectric conversion element array 74 as image data. The main controller 100 performs image processing of the read image data to measure the scattered light distribution as described above. The optimal direction of the light receiving areas A, B, and C on the light receiving surface 56 is determined on the Fourier transform plane F, i.e., an optimal angle α with respect to the u' axis is determined. As previously described, the angle α is determined so as to maximize an interval (i.e., the H-direction width of the Fourier spectral area in which diffracted light is not present) between the Fourier spectra in the direction (H direction) determined by the angle α.

A method of inspecting foreign particles will be described below.

The main controller 100 drives the switching portion 130 to rotate the arm 138 through 180°, thereby aligning the Z axis with the optical axis 140. The main controller 100 causes the rotation driving portion 131 to rotate the light receiving surface 56 about the optical axis 140, thereby setting the direction of the light receiving areas A, B, and C to an optimal direction obtained in measurement of the scattered light distribution. The stage 70 is moved while the vibration mirror 2 is vibrated to form the scanning range 1, so that the entire surface of the substrate 1 is optically scanned with an almost uniform optical energy. Meanwhile, the light beams incident on the light receiving areas A, B, and C are photoelectrically converted into electrical signals by the photoelectric conversion elements $a_1$, $a_2$, and $a_3$ to inspect foreign particles in real time.

Figure 76:
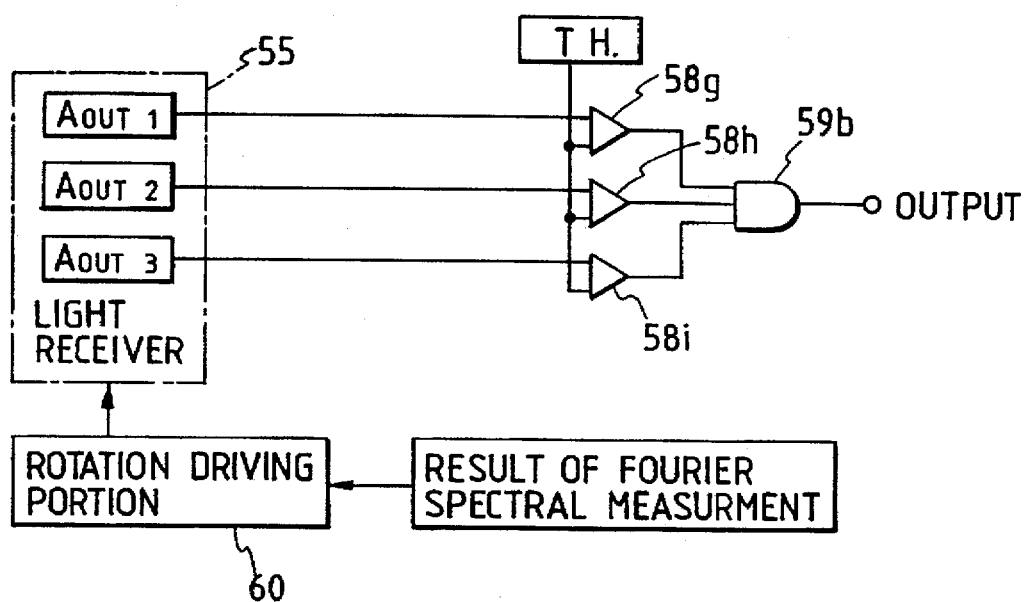
FIG. 76 is a block diagram showing the arrangement of a signal processing system in the defect inspecting apparatus shown in FIG. 64.

FIG. 76 is a view showing the schematic arrangement of a signal processing system of this application example. Referring to FIG. 76, the result of a Fourier spectral measurement output from the photoelectric conversion element array 74 is input to a rotation driving portion 60. The rotation driving portion 60 determines, from the result of the Fourier spectral measurement, a direction for maximizing the interval of diffracted light on the light receiving surface 56. The rotation driving portion 60 rotates the light receiver 53 about the optical axis 140 so that this optimal direction is aligned with the short-side direction of the light receiving areas. In this state, the substrate 1 is optically scanned to receive light from the inspecting point O. The output signal $A_{OUT1}$, $A_{OUT2}$, and $A_{OUT3}$ from the light receiving areas are output to comparators 58g, 58h, and 58i, respectively. The comparators 58g, 58h, and 58i compare the corresponding output signals with a threshold value TH. When the output signals $A_{OUT1}$, $A_{OUT2}$, and $A_{OUT3}$ exceed the threshold value TH, the comparators 58g, 58h, and 58i output signals to an AND circuit 59b. The AND circuit 59 logically ANDs the signals from the comparators 58g, 58h, and 58i to discriminate the circuit pattern from the foreign particles.

Figure 65:
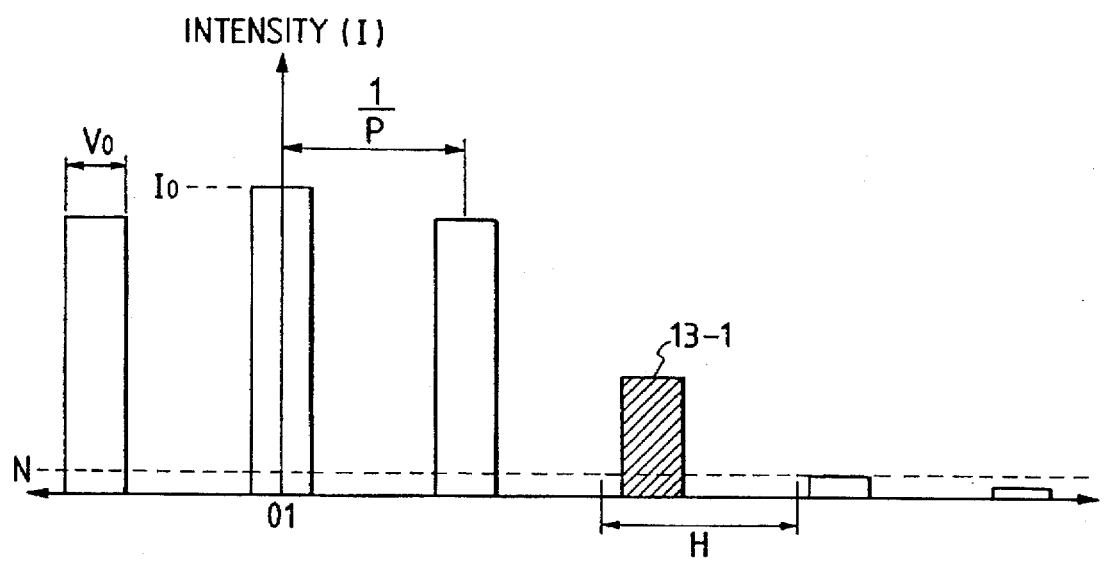
FIG. 65 is a view showing the intensity distribution of diffractive light from the circuit pattern which has a low minuteness.
Figure 65A:
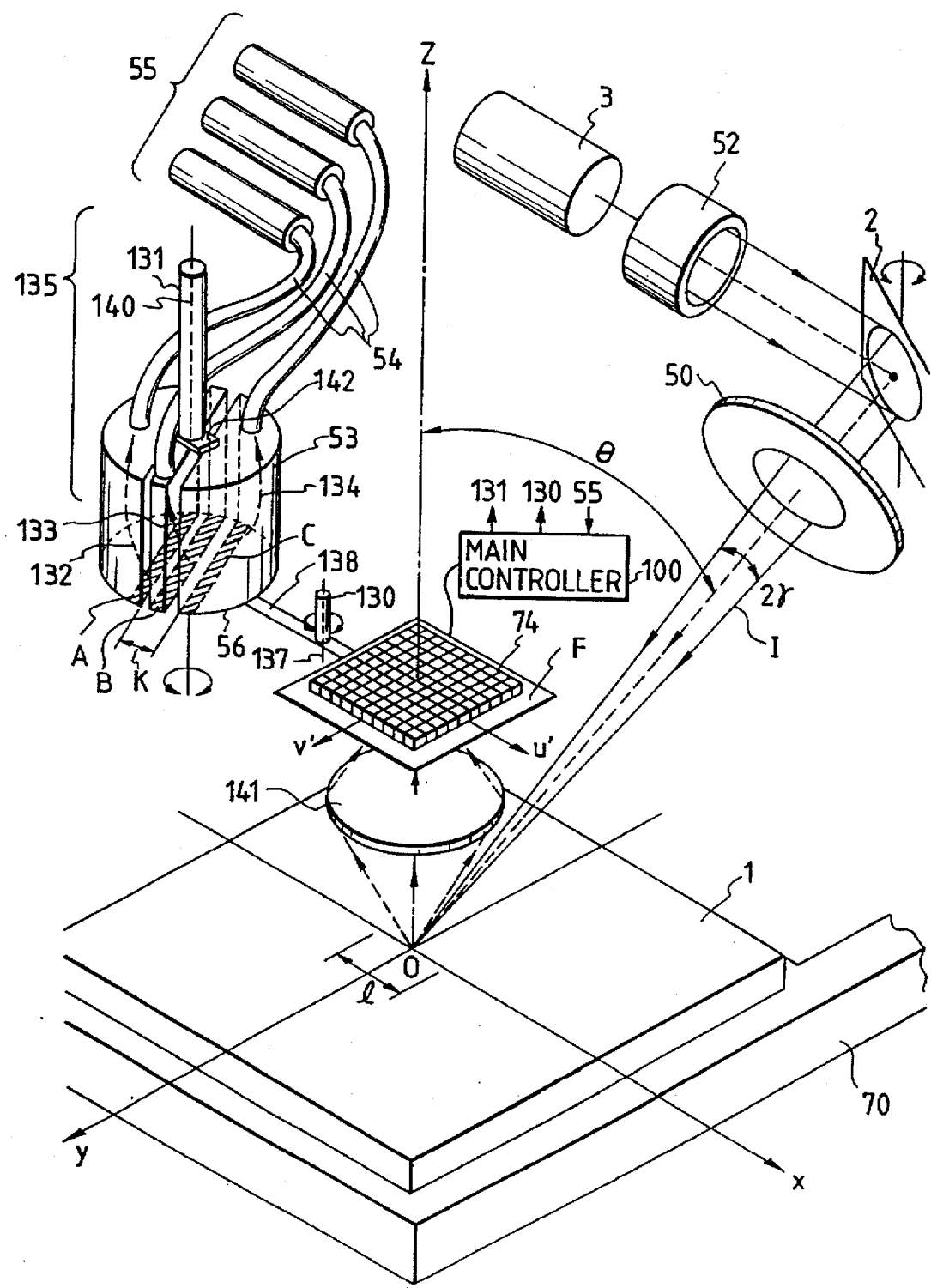
FIG. 65A is a perspective view showing the arrangement of the main part of a defect inspecting apparatus according to the second application example of the ninth embodiment of the present invention.

FIG. 65A is a perspective view showing the second application example of the ninth embodiment. The same reference numerals as in the first application example of the ninth embodiment denote the same parts in the second application example thereof. In this application example, the direction of light receiving areas A, B, and C and the interval between the light receiving areas are arbitrarily set by a linear driving portion 142. An interval K between the end light receiving areas A and C can also be arbitrarily set. As in the first application example of the ninth embodiment, the light receiving areas A, B, and C are rotatable about an optical axis 140. The longitudinal direction of each light receiving area can be set on a Fourier transform plane F at an arbitrary angle with respect to the u' axis. In this application example, the incident angle of an incident light beam I is θ.

The shape of each of the discretely generated Fourier spectra is of an ellipse (FIG. 79). A major axis $u_0$ and a minor axis $v_0$ of each ellipse can be calculated as follows.

As described with reference to equations (2) and (3), $$u_0 = 2\sin\gamma/\lambda \tag{44}$$

$$\begin{aligned}v_0 &= 2\sin\gamma \cdot \cos\theta/\lambda \tag{45}\\ &= [\sin(\theta+\gamma) - \sin(\theta-\gamma)]/\lambda\end{aligned}$$

Let the interval K between the light receiving areas be B(α) in FIG. 80F, i.e., K=B(α).

The equation of an ellipse r' is derived from FIG. 80F as follows:

$$(4U^2/u_0^2)+(4V^2/v_0^2)=1 \tag{46}$$

In addition, $$\begin{aligned}B(\alpha) &= 2\sin\alpha\sqrt{(u_0/2)^2(1/\tan\alpha)^2 + (v_0/2)^2} \tag{47}\\ &= \sin\alpha\sqrt{(u_0/\tan\alpha)^2 + v_0^2}\end{aligned}$$

where α is the angle with respect to u' axis.

As described above, the interval K between the light receiving areas is changed in accordance with the angle α. Although the angle α is determined with respect to the u axis in FIG. 80F, the angle α can be determined with respect to the u' axis parallel to the u axis in FIG. 65A.

In this application example, the scattered light distribution is measured by a two-dimensional photoelectric conversion element array 74. The measurement result is input to a main controller 100. The main controller 100 controls a rotation driving portion 131 and the linear driving portion 142 on the basis of this measurement result to change the direction of the light receiving areas A, B, and C, and their interval in accordance with equation (62).

In the first and second application examples of the ninth embodiment, the two-dimensional photoelectric conversion element array 74 and the light receiver 53 are switched therebetween. However, the element array 74 may also be used in defect detection, and light receiving areas may be selected electrically or using a light-shielding band.

Figure 66A:
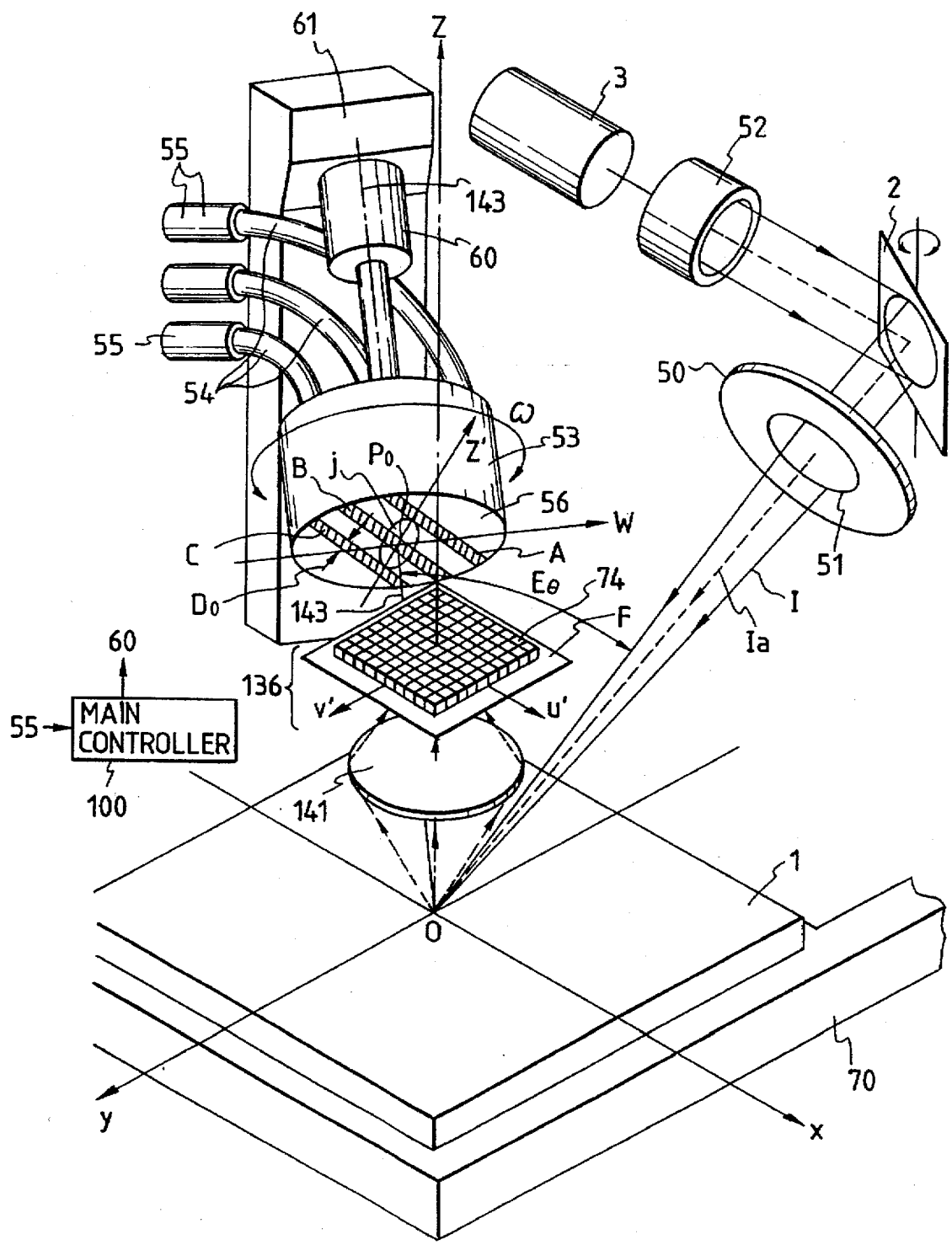
FIG. 66A is a perspective view showing the arrangement of the main part of a defect inspecting apparatus according to the third application example of the ninth embodiment of the present invention.

FIG. 66A is a perspective view showing the third application example of the ninth embodiment. The same reference numerals as in the first application example of the ninth embodiment denote the same parts in the third application example thereof. A light receiver 53 has light receiving areas A, B, and C on the pupil plane or a plane conjugate to the pupil plane of an optical system (e.g., a lens $L_1$ or $L_2$ in FIG. 82B) of a light receiving means in the same manner as in the arrangement shown in FIG. 82B. The light beams incident on these light receiving areas are guided to photoelectric converters 55 through optical fiber bundles 54. The light beams are photoelectrically converted into outputs $A_{OUT1}$, $A_{OUT2}$, and $A_{OUT3}$ by the photoelectric converters 55. An axis passing through a central point $P_o$ of a light receiving surface 56 and parallel to the x–y plane is defined as a W axis, and an axis passing through a central point $P_o$ and perpendicular to the W axis is defined as a Z' axis.

The light receiver 53 is located on a support means 61 through a rotation driving portion 60 and is rotatable about an optical axis 143a of the light receiver 53. The rotation driving portion 60 can arbitrarily set an angle φ formed between the W axis and the long sides of the light receiving areas A, B, and C.

In this application example, an angle $E_\theta$ formed between a light receiving optical axis 143 and an optical axis Ia of the incident optical system is set to be relatively small so that a diameter e of diffracted light j discretely incident on the light receiving surface 56 of the light receiver 53 is kept almost constant regardless of a rotational angle ω. When the angle $E_\theta$ is reduced, the shape of the diffracted light j comes close to a circle, and the interval between the end light receiving areas A and C can always be set almost equal to the width of the diffracted light. An exit pupil 51 of a scanning lens (f-θ lens) 50 is circular in this application example, but the shape of the exit pupil 51 may be changed such that the diffracted light j incident on the light receiver 53 is set to be circular.

Foreign particles are discriminated from a circuit pattern using a signal processing system shown in FIG. 76 according to the third application example of the ninth embodiment. Prior to the discrimination from the foreign particles from the circuit pattern, the result of a Fourier spectral measurement obtained in the same procedures as in the first application example of the ninth embodiment is input to the rotation driving portion 60 through a main controller 100. The main controller 100 determines a direction (H direction) in which an interval of diffracted light components on the light receiving surface 56 becomes maximum. The light receiver 53 is rotated about the optical axis 143 by the rotation driving portion 60 so that the determined direction coincides with the short-side direction of each light receiving area.

Assume one diffracted light j of all the diffracted light components discretely incident on the light receiving surface 56 of the light receiver 53. Assume that the light receiving surface 56 is perpendicular to the light receiving optical axis 143 and that an incident light beam I has a regular conical shape. The shape of the diffracted light j is changed in accordance with an angle formed between the optical axis 143 of the light receiver and the optical axis Ia of the focusing means. If the angle $E_\theta=0$, then the shape of the diffracted light j becomes almost circular. If the angle $E_\theta \neq 0$, then ellipses having various ellipticities, i.e., ellipses obtained by mapping ellipses of the Fourier transform plane on the light receiving surface 56, are obtained. FIGS. 67A to 69B are views when the light receiving surface 56 of the light receiver 53 is viewed from the direction of the light receiving optical axis 143.

An angle $\phi$ is defined as an angle formed between the longitudinal direction of each light receiving area and the W axis. As will be described later, the angle $\phi$ is obtained from the angle α.

Figure 67A:
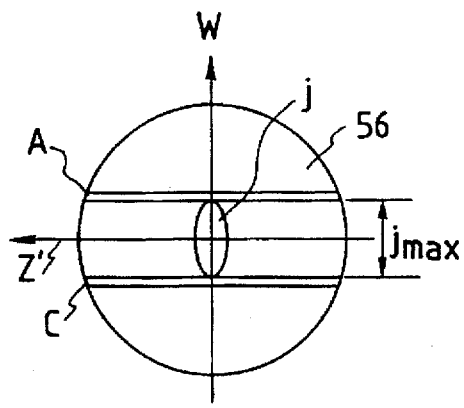
FIGS. 67A and 67B, 68A and 68B, and 69A and 69B are views for explaining the principle of positional relationships between light receiving areas and diffracted light on the pupil plane of a light receiver.
Figure 67B:
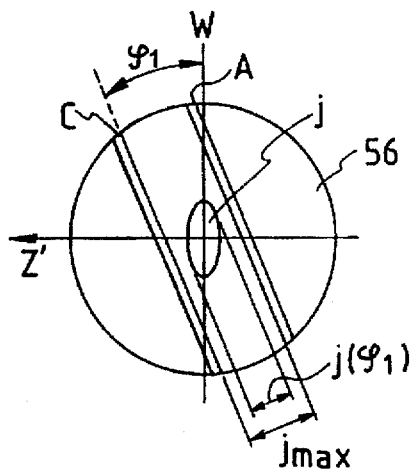
Figure 69A:
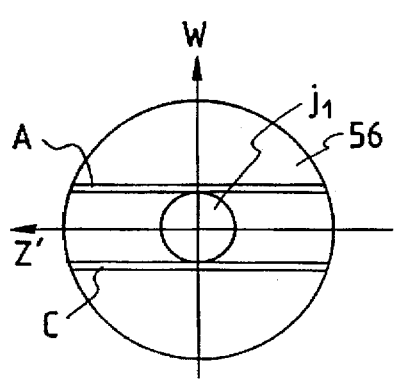
Figure 69B:
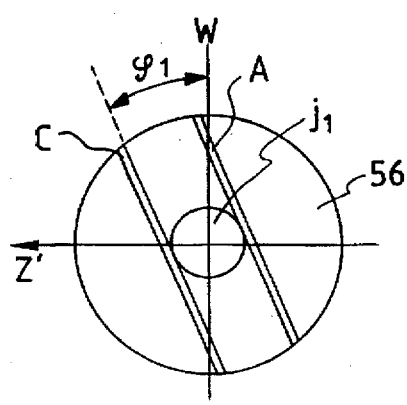

FIG. 69A shows the case for $E_\theta=0$. A diffraction image ($j_1$) of the diffracted light discretely incident on the light receiving surface 56 is almost circular. FIGS. 69A and 69B show a state in which the light receiving areas A and C are parallel to the Z' axis. FIG. 69B shows the state in which the light receiving areas A and C are located such that a direction in which an angle with respect to the W axis is $\phi_1$ coincides with the longitudinal direction of each light receiving area. As described above, in the third application example of the ninth embodiment, on the basis of the result of the Fourier spectral measurement, the angle $\phi_1$ is set in a direction where the interval between the diffracted light components becomes maximum. As shown in FIGS. 67A and 67B, if the shape of the diffracted light on the light receiving surface 56 is circular, the widths of the diffracted light are equal to each other in all directions. In this case, the interval between the light receiving areas can be set equal to the width of the diffracted light regardless of the arrangement directions of the light receiving areas.

To the contrary, FIGS. 67A and 67B show a case for $E_\theta \neq 0$. Each diffracted light discretely incident on the light receiving surface 56 has an elliptical shape. For this reason, the width of diffracted light varies depending on a direction (e.g., a longitudinal or widthwise direction). The light receiver 52 is rotated such that the longitudinal direction of each light receiving area is aligned with the direction in which the angle formed with respect to the W axis is $\phi_1$ from a state in which the end light receiving areas A and C are located parallel to the W axis to set the interval to $j_{max}$. In this case, the width (i.e., the width in the arrangement direction of the light receiving areas) of diffracted light in FIG. 67B becomes $j(\phi_1)$ smaller than $j_{max}$. To discriminate a circuit pattern from foreign particles by discreteness, equations (12), (21), and (42) are preferably satisfied, as described above. That is, it is preferable that the width of diffracted light coincides with the interval between the light receiving areas even upon rotation of the light receiver 53. In the fourth application example of the ninth embodiment to be described later, the interval between the light receiving areas A and C is changed in accordance with the angle α for $E_\theta \neq 0$ using equation (62) to be described below.

Figure 70:
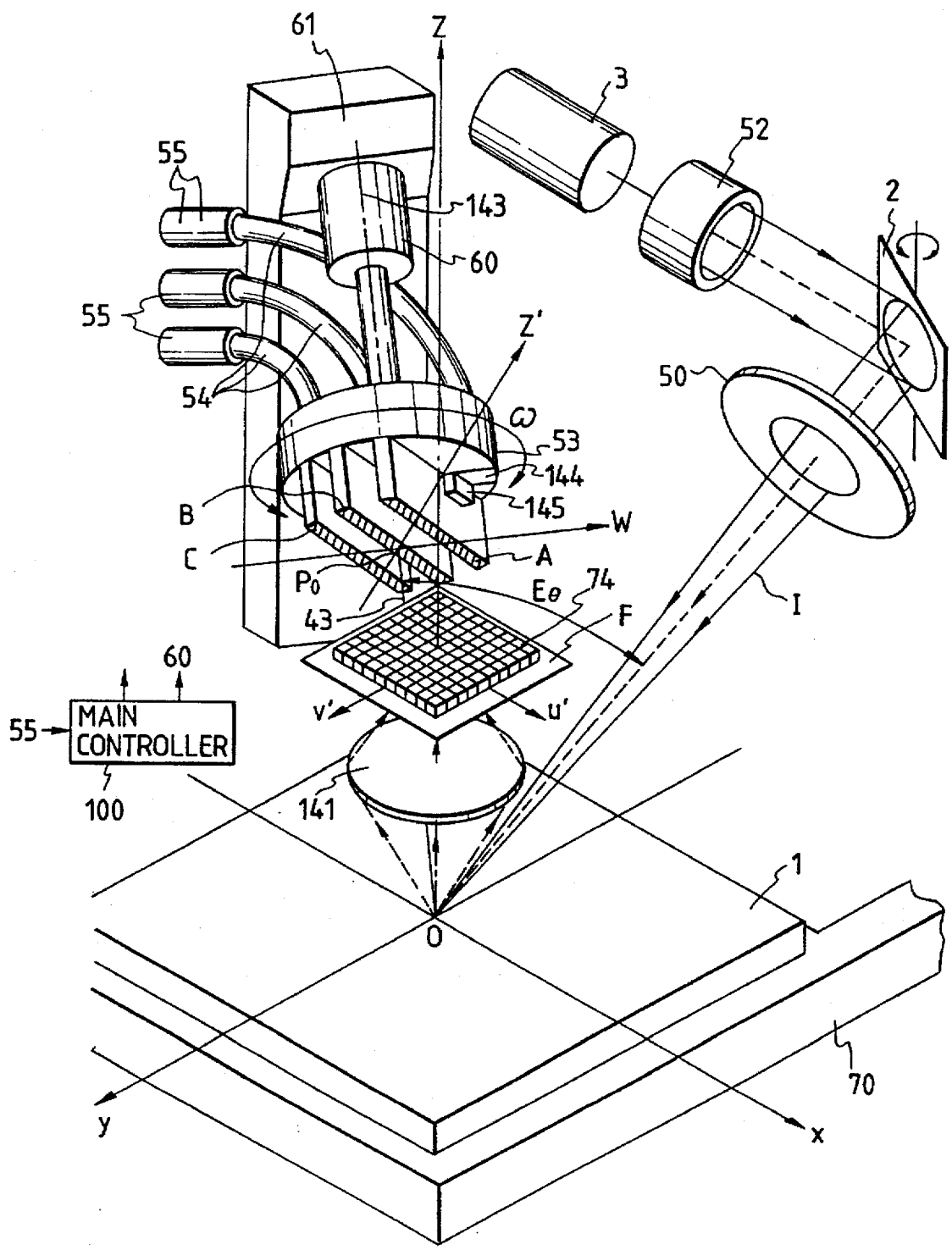
FIG. 70 is a perspective view showing the arrangement of the main part of a defect inspecting apparatus according to the fourth application example of the ninth embodiment of the present invention.

An apparatus of the fourth application example of the ninth embodiment in FIG. 70 is substantially the same as that of the third application example of the ninth embodiment, except that a mechanism for adjusting an interval between light receiving areas A, B, and C is provided. More specifically, a groove 144 is formed in a direction perpendicular to the longitudinal direction of the light receiving areas A, B, and C. An adjustment member 145 can be moved parallel to the groove 144. A main controller 100 slides the adjustment member 145 to change an interval between the light receiving areas A, B, and C in accordance with an angle $\phi$ (angle α).

Figure 68A:
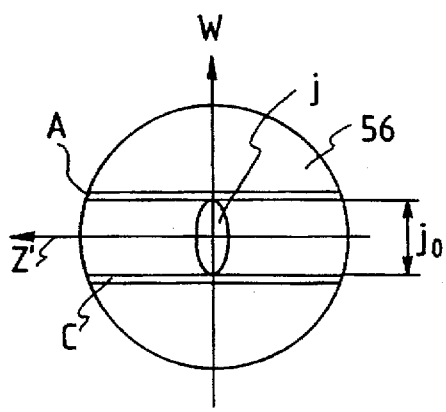
Figure 68B:
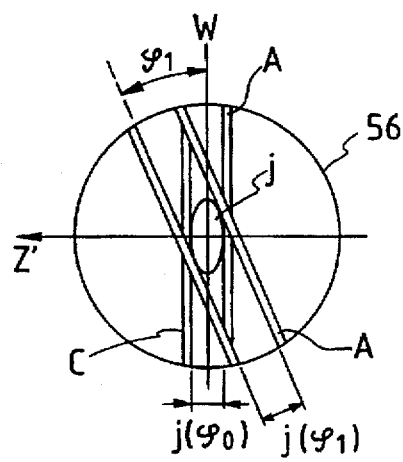

The adjustment of the interval between the light receiving areas will be described with reference to FIGS. 68A and 68B. FIG. 68A shows an interval $j_0$ between the light receiving areas A and C. FIG. 68B shows a state in which a light receiver 53 is rotated from the state in FIG. 68A and an angle formed between the longitudinal direction of the light receiving areas and the W axis is represented by $\phi$. If $\phi=\phi_1$, then the interval of the diffracted light components is $j(\phi_1)$. If $\phi=0$ (or 180°), then the interval between the diffracted light components becomes $j(\phi_0)$ which is smaller than $j_0$. In this application example, the adjustment member 145 is slid to change the interval between the light receiving areas A and C in accordance with the angle $\phi$. That is, the interval between the light receiving areas A and C is set to $j(\phi_1)$ for $\phi=\phi_1$; and the interval is set to $j(\phi_0)$ for $\phi=0$ (or 180°), thereby always satisfying the equations (12) and (21).

An operation for changing the arrangement of the light receiving areas in accordance with the angle a in the third and fourth application examples of the ninth embodiment will be described in detail. In the third and fourth application examples of the ninth embodiment, the light receiving optical axis is not aligned with the optical axis of a two-dimensional photoelectric conversion element array 74 (scattering distribution measuring means). For this reason, light receiving areas A, B, and C cannot be optimized using the angle α formed between a u' axis and the light receiving areas and obtained as a result of image processing of a Fourier spectrum obtained by the scattering distribution measuring means. Since a light receiving surface 56 of a light receiver 53 is a plane obtained by mapping the Fourier plane, some calculations are required.

Referring to FIG. 66A, assume an optical axis 143 which passes through the light receiving surface 56, a central point $P_o$ of the light receiving surface 56, and an inspecting point O and is perpendicular to the light receiving surface 56.

Assume that the coordinates of the central point $P_o$ are given as (a,b,c). A plane including the light receiving surface is represented by equation (48) below:

$$a(x-a)+b(y-b)+c(z-c)=0 \tag{48}$$

A direction cosine (l,m) of a point on the light receiving surface is represented by equations (49) and (50) below:

$$l = x/\sqrt{(x^2 + y^2 + z^2)} \tag{49}$$
$$m = x/\sqrt{(x^2 + y^2 + z^2)} \tag{50}$$

From the definitions of the spatial frequency:

$$U' = U + l_o/\lambda = l/\lambda = x/[\lambda \cdot \sqrt{(x^2 + y^2 + z^2)}] \tag{51}$$
$$V' = V + m_o/\lambda = m/\lambda = x/[\lambda \cdot \sqrt{(x^2 + y^2 + z^2)}] \tag{52}$$

If (x,y,z) is close to the point $P_o$, then $$\sqrt{(x^2 + y^2 + z^2)} \approx \sqrt{(a^2 + b^2 + c^2)}$$

If $\lambda\sqrt{(a^2+b^2+c^2)}=1$, then $$U'=x \tag{53}$$
$$V'=y \tag{54}$$

More specifically, when each point on the light receiving surface 56 is positively projected on the X–Y plane, an image projected near the point $P_o$ exhibits a Fourier spectrum.

An axis passing through a central point $P_o$ of the light receiving surface 56 and parallel to the X–Y plane is defined as a W axis. An axis on the light receiving surface 56 perpendicular to the W axis is defined as a Z' axis. If positive projection of the Z' axis on the X–Y plane is defined as a Z" axis, as shown in FIG. 79, then $$Z'' = Z' \cdot \sqrt{(a^2 + b^2)}/\sqrt{(a^2 + b^2 + c^2)} \tag{55}$$

Assume a relationship between the X–Y plane, i.e., the U'–V' plane and the W–Z' plane. FIG. 79 shows an angle δ formed between the Z" axis and the V' axis. The U'–V' plane satisfies equations (51) and (52), and the point O" coincides with the point O. The relationship between the U'–V' plane and the W–Z' plane is represented by equation (56).

$$\begin{bmatrix} W \\ Z'' \end{bmatrix} = \begin{bmatrix} \cos\delta & -\sin\delta \\ \sin\delta & \cos\delta \end{bmatrix} \begin{bmatrix} U' \\ V' \end{bmatrix}$$

$$= \frac{1}{\sqrt{a^2+b^2}} \begin{bmatrix} a & -b \\ b & a \end{bmatrix} \begin{bmatrix} U' \\ V' \end{bmatrix}$$

From equation (55), $$\begin{bmatrix} W \\ Z' \end{bmatrix} = \begin{bmatrix} \dfrac{a}{\sqrt{a^2+b^2}} & \dfrac{-b}{\sqrt{a^2+b^2}} \\ \dfrac{b}{\sqrt{a^2+b^2+c^2}} & \dfrac{a}{\sqrt{a^2+b^2+c^2}} \end{bmatrix} \begin{bmatrix} U' \\ V' \end{bmatrix} \tag{56}$$

Relations (FIGS. 67A, 67B, 68A, 68B, 69A, and 69B) of the angle α (FIGS. 80A to 80F) with respect to the U' axis on the U'–V' plane and the angle φ with respect to the W axis on the W–Z' plane are given as follows:

$$\tan \alpha = V'/U' \tag{57}$$

$$\tan \phi = Z'/W \tag{58}$$

Equation (59) is then derived from equations (56), (57), and (58) as follows:

$$\tan\phi = \frac{Z'}{W} = \frac{(b + a \cdot \tan\alpha)\sqrt{a^2+b^2}}{(a - b \cdot \tan\alpha)\sqrt{a^2+b^2+c^2}} \tag{59}$$

The relationship between j(φ) and B(α) associated with the optimal width of the light receiving area can be obtained by multiplying equation (47) with the magnitude of a vector obtained by mapping a unit vector, in the direction perpendicular to the line of an angle α on the U'–V' plane, on the W–Z' plane.

The unit vector of the angle α on the U'–V' plane is defined as (cos α, sin α), and a unit vector perpendicular thereto is defined as (–sin α, cos α).

Equation (60) is derived from equation (56).

$$\begin{bmatrix} W(\alpha) \\ Z'(\alpha) \end{bmatrix} = \begin{bmatrix} \dfrac{a}{\sqrt{a^2+b^2}} & \dfrac{-b}{\sqrt{a^2+b^2}} \\ \dfrac{b}{\sqrt{a^2+b^2+c^2}} & \dfrac{a}{\sqrt{a^2+b^2+c^2}} \end{bmatrix} \begin{bmatrix} -\sin\alpha \\ \cos\alpha \end{bmatrix} \tag{60}$$

$$= \begin{bmatrix} \dfrac{-(a \cdot \sin\alpha + b \cdot \cos\alpha)}{\sqrt{a^2+b^2}} \\ \dfrac{a \cdot \cos\alpha - b \cdot \sin\alpha}{\sqrt{a^2+b^2+c^2}} \end{bmatrix}$$

The magnitude of a vector (W(α),Z'(α)) is defined by equation (61). Equation (62) is therefore obtained as follows:

$$\sqrt{W(\alpha)^2 + Z'(\alpha)^2} = \sqrt{\frac{(a \cdot \sin\alpha + b \cdot \cos\alpha)^2}{a^2+b^2} + \frac{(a \cdot \cos\alpha - b \cdot \sin\alpha)^2}{a^2+b^2+c^2}} \tag{61}$$

$$j(\phi) = \beta(\alpha) \times \sqrt{W(\alpha)^2 + Z'(\alpha)^2} \tag{62}$$

$$= \sin\alpha \sqrt{\left(\frac{u_0}{\tan\alpha}\right)^2 + v_0^2} \times$$

$$\sqrt{\frac{(a \cdot \sin\alpha + b \cdot \cos\alpha)^2}{a^2+b^2} + \frac{(a \cdot \cos\alpha - b \cdot \sin\alpha)^2}{a^2+b^2+c^2}}$$

FIGS. 67A and 67B, FIGS. 68A and 68B, and FIGS. 69A and 69B show diffracted light components j discretely incident on the light receiving surface 56 on the Z'–W plane. FIGS. 67A and 67B and FIGS. 68A and 68B show cases for $E_\theta \neq 0$, and FIGS. 69A and 69B show a case for $E_\theta = 0$.

In the third application example of the ninth embodiment, the interval between the light receiving areas A and C is caused to coincide with the maximum value $j_{max}$ obtained by equation (62). The interval then remains the same, and only the angle φ is changed in a direction obtained by equation (59). The results are shown in FIGS. 67A and 67B and FIGS. 69A and 69B.

In the fourth application example of the ninth embodiment, j(φ) is changed on the basis of equation (62). A result is shown in FIGS. 68A and 68B.

Figure 71A:
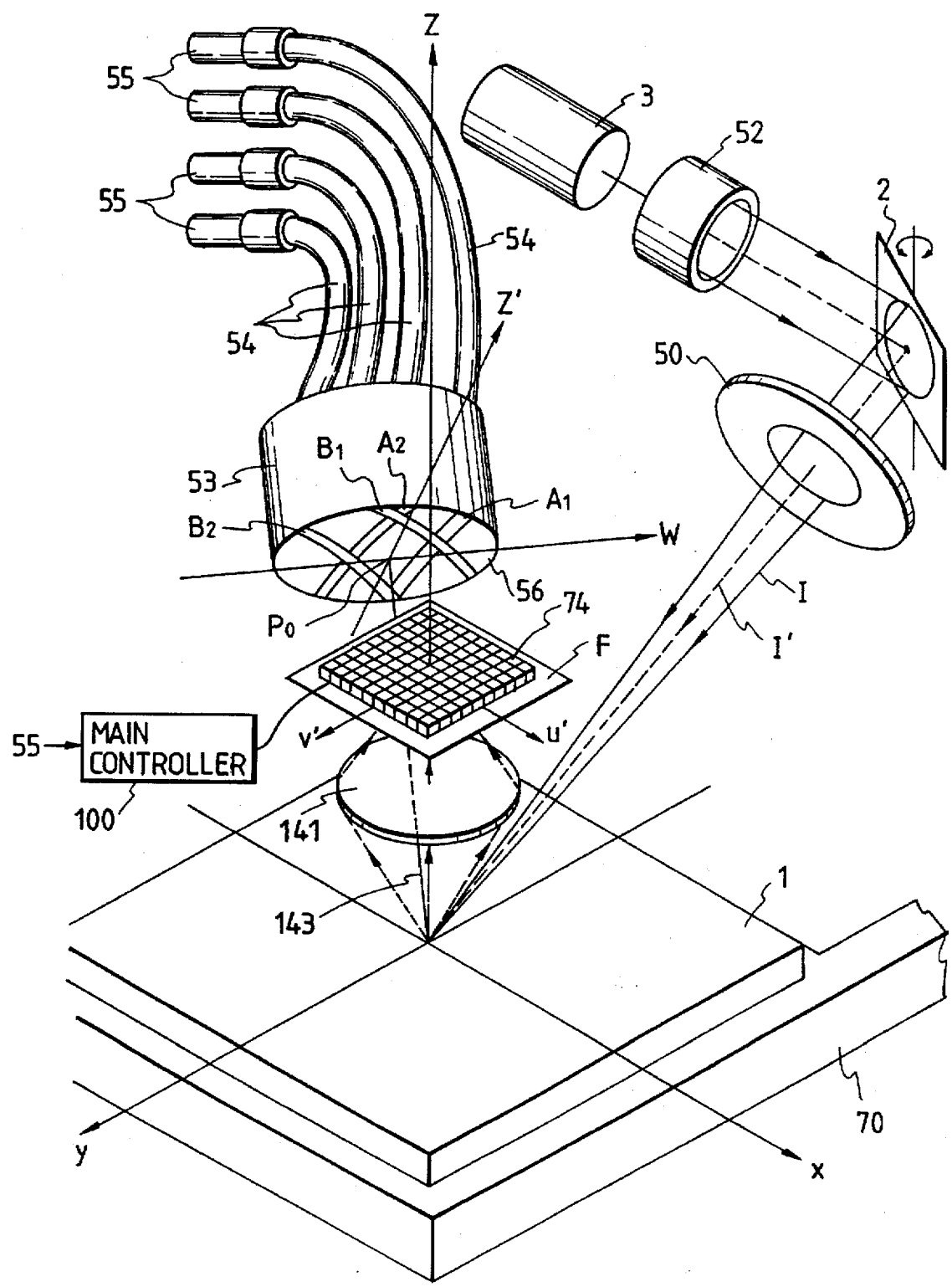
FIG. 71A is a perspective view showing the arrangement of the main part of a defect inspecting apparatus according to the fifth application example of the ninth embodiment of the present invention.

The fifth application example of the ninth embodiment will be described with reference to FIGS. 71A, 71B, and 72. An apparatus according to the fifth application example of the ninth embodiment shown in FIG. 71A is substantially the same as that of the third application example of the ninth embodiment, except for an arrangement of a means for selecting the arrangement of a light receiver and light receiving areas. A Fourier spectral measuring means 74 comprises a Fourier transform lens and a photoelectric conversion element array as in the first application example of the ninth embodiment, and the descriptive repetition will be omitted.

Figure 71B:
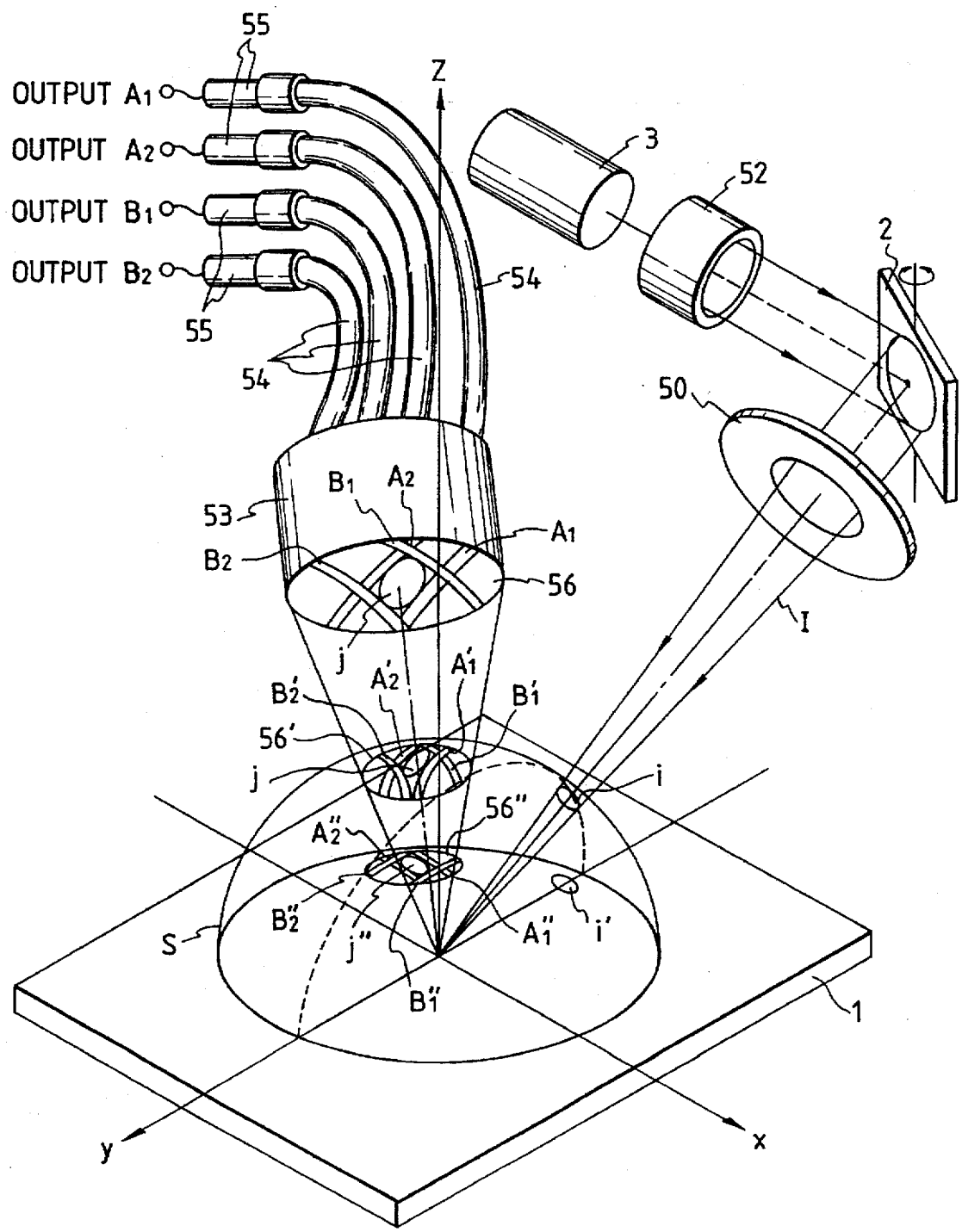
FIG. 71B is a view showing a principle corresponding to FIG. 71A.

Referring to FIGS. 71A and 71B, a light receiver 53 has a light receiving surface 56 having light receiving areas $A_1$, $A_2$, $B_1$, and $B_2$ which can independently perform photoelectric conversion. Each light receiving area has a longitudinal direction and a widthwise direction. The arrangement of the light receiving areas $A_1$, $A_2$, $B_1$, and $B_2$ will be described later. Light beams incident on the light receiving areas $A_1$, $A_2$, $B_1$, and $B_2$ are photoelectrically converted by photoelectric conversion elements 55. The respective photoelectric conversion elements 55 output output signals $A_{OUT1}$, $A_{OUT2}$, $B_{OUT1}$, and $B_{OUT2}$ independently from the respective light receiving areas $A_1$, $A_2$, $B_1$, and $B_2$.

Assume a sphere S illustrated centered on an inspecting point O (focusing point of an incident light beam I) with reference to FIGS. 71A and 71B illustrating part of the apparatus in FIG. 71A. A curved section as an overlapping area between the incident light beam I and the spherical surface of the sphere is defined as i, positive projection of the curved section i on the surface (X–Y plane) of a substrate 1, i.e., a Fourier spectrum of the incident light beam I is defined as i'. The light receiving surface 56 corresponds to a curved section 56' of the spherical surface of the sphere S, and positive projection of the curved section 56' on the surface of the substrate 1, i.e., a Fourier spectrum of a light beam incident on the entire light receiving surface, is represented by 56''.

A figure j on the light receiving surface 56 represents an irradiation area (diffraction image) when diffracted light discretely generated is incident on the center of the light receiving surface 56. Referring to FIG. 71B, a curved section as an overlapping area between this diffracted light and the spherical surface of the sphere S is represented by j', and positive projection of the curved section j' on the surface of the substrate 1, i.e., a Fourier spectrum of the diffracted light, is represented by j''. The shape of the Fourier spectrum j'' is congruent to that of the Fourier spectrum i' of the incident light beam I. Positive projection components of curved sections $A_1'$, $A_2'$, $B_1'$, and $B_2'$ as overlapping areas between the sphere S and light beams propagating from an inspecting point O to the light receiving areas $A_1$, $A_2$, $B_1$, and $B_2$, i.e., Fourier spectra, are represented as $A_1''$, $A_2''$, $B_1''$, and $B_2''$, respectively. The longitudinal direction of the Fourier spectra $A_1''$ and $A_2''$ is parallel to the Y axis, and an interval therebetween in the widthwise direction is equal to the width of the Fourier spectrum j'' of the diffracted light in the X direction. Similarly, the longitudinal direction of the Fourier spectra $B_1''$ and $B_2''$ is parallel to the X axis, and an interval thereof in the widthwise direction is equal to the width of the Fourier spectrum j'' of the diffracted light in the Y direction. That is, the light receiving areas $A_1$, $A_2$, $B_1$, and $B_2$ of this application example are formed to surround the Fourier spectra of diffracted light components on the Fourier plane. A method of mapping the W–Z' plane of the light receiving surface on the Fourier plane (u–v plane) is the same as in the third and fourth application examples of the ninth embodiment.

Figure 72:
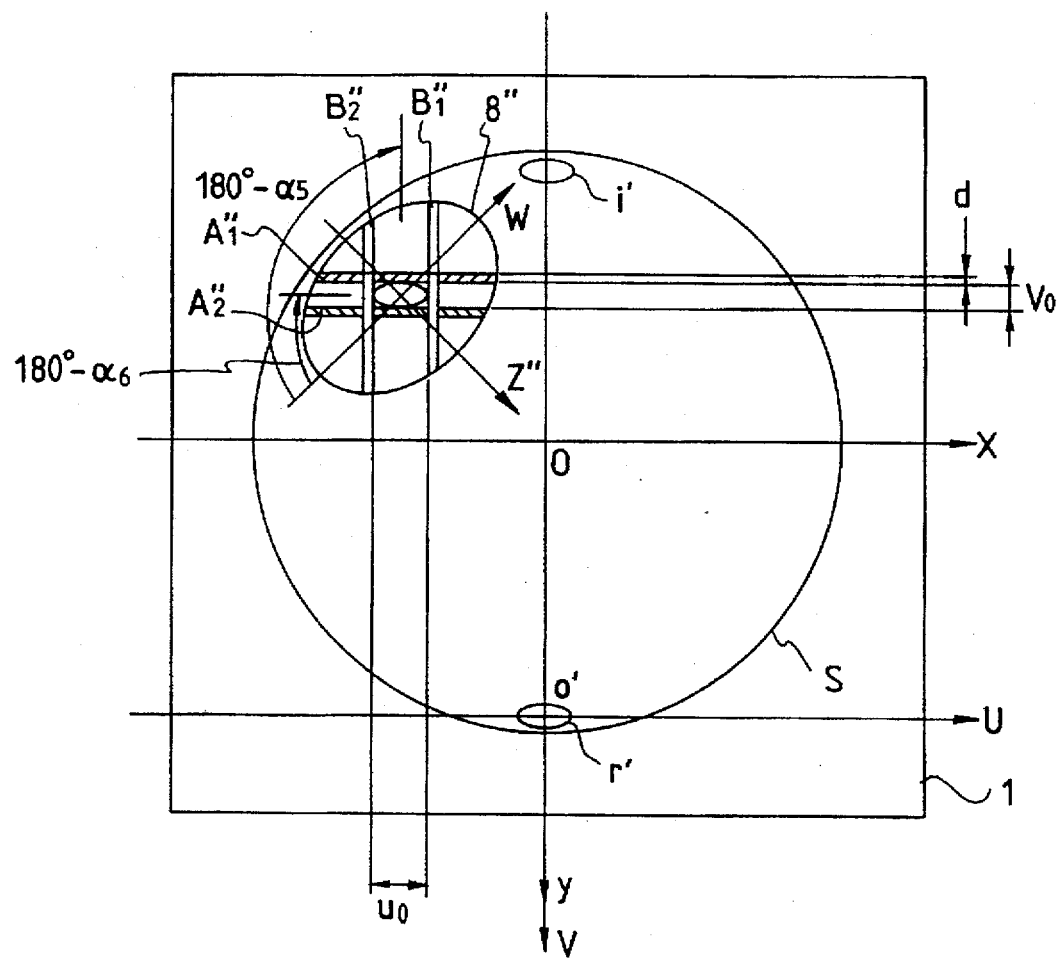
FIG. 72 is a view for explaining the principle of a positional relationship between light receiving areas and diffracted light on the Fourier plane in FIG. 71A.

FIG. 72 is a view illustrating a Fourier plane. The Fourier spectra $A_1''$, $A_2''$, $B_1''$, and $B_2''$ of the respective light receiving areas are illustrated. In FIG. 72, a regularly reflected light beam $I_r$ has a Fourier spectrum r', an incident light beam has a Fourier spectrum i', and diffracted light has a Fourier spectrum j''. Figures i', j'', and r' are similar figures. The U–V coordinate system in FIG. 72 is an orthogonal coordinate system having an origin O' as the central position of the Fourier spectrum r'.

The arrangement and shape of the light receiving areas are determined such that the Fourier spectra $A_1''$ and $A_2''$ in FIG. 72 are parallel to the U axis (X axis) with an interval $V_0$, and that the light receiving areas $A_1$ and $A_2$ are parallel to the V axis with an interval $u_0$. The widths of the Fourier spectra $A_1''$ and $A_2''$ in the widthwise direction are equal to each other as a width $D_0$ so as to obtain equal light receiving sensitivities. In this case, even if the Fourier spectra $A_1''$ and $A_2''$ have the same width $D_0$, the light receiving areas of the light receiving areas $A_1$ and $A_2$ of the light receiver 53 in FIG. 71 will not be equal to each other but may be properly adjusted as needed. The width $D_0$ is preferably smallest in consideration of the capability of discriminating a circuit pattern from foreign particles. A decrease in reducing area of each light receiving area can be compensated by the its length in the longitudinal direction, thereby preventing a decrease in electrical S/N ratio.

An f-θ lens 50 and the light receiver 53 are preferably located at far positions as compared with the optical scanning distance due to the following reason. If optical scanning is performed using a vibration mirror 2 to move the inspecting point O, the relationship between the Fourier spectra can remain the same as much as possible.

Figure 77:
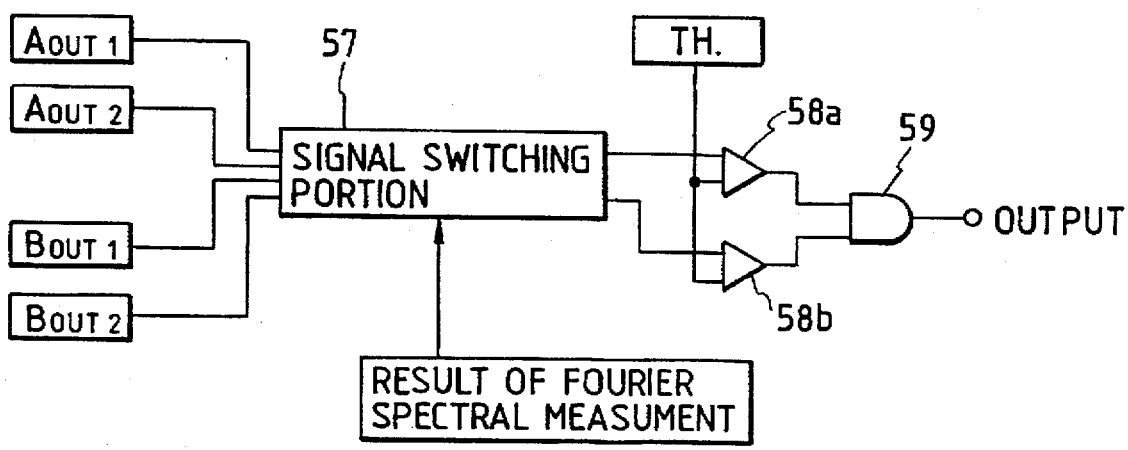
FIG. 77 is a block diagram showing the arrangement of a signal processing system in the defect inspecting apparatus shown in FIG. 71A.

A signal processing method according to the fifth application example of the ninth embodiment will be described with reference to FIG. 77. Referring to FIG. 77, the output signals $A_{OUT1}$, $A_{OUT2}$, $B_{OUT1}$, and $B_{OUT2}$ from the respective light receiving areas are input to a signal switching portion 57 constituting a selecting means in the present invention. The result of a Fourier spectral measurement is also input to this signal switching portion 57. On the basis of these input signals, a signal used for signal processing is selected from the output signals $A_{OUT1}$, $A_{OUT2}$, $B_{OUT1}$, and $B_{OUT2}$. Information obtained from the result of the Fourier spectral measurement corresponds to the angle a described with reference to FIG. 80F. The signal switching portion 57 selects a light receiving area located such that an interval between diffracted light components becomes maximum in accordance with the angle α.

More specifically, the longitudinal direction and interval of the light receiving areas $A_1$ and $A_2$ in FIG. 71A are determined to be optimal for $180°-\alpha_5$. The longitudinal direction and interval of the light receiving areas $B_1$ and $B_2$ are determined to be optimal for $180°-\alpha_6$. In this application example, the two sets of light receiving areas correspond to the two cases as $180°-\alpha_5$ and $180°-\alpha_6$. The light receiving areas closer to $180°-\alpha_5$ or $180°-\alpha_6$ are selected in accordance with the angle α obtained from the result of the Fourier spectral measurement.

Referring to FIG. 77, outputs ($A_{OUT1}$ and $A_{OUT2}$) or ($B_{OUT1}$ and $B_{OUT2}$) from the selected light receiving areas are output to a comparator 58a or 58b. The comparator 58a or 58b compare a threshold value TH with the output signals ($A_{OUT1}$ and $A_{OUT2}$) or the output signals ($B_{OUT1}$ and $B_{OUT2}$). When the output signals from the signal switching portion 57 exceed the threshold value, the comparator 58a or 58b outputs a signal to an AND circuit 59. The AND circuit 59 logically ANDs the signals from the comparator 58a and 58b to discriminate a circuit pattern from foreign particles. That is, in this application example, of all the sets of light receiving areas ($A_1$ and A) and ($B_1$ and $B_2$), one set (i.e., diffracted light from a pattern is not incident on at least one of the light receiving areas) which satisfies equation (12) is selected. For this reason, if no foreign particles are present on the surface of the substrate 1, the arithmetic result of the AND circuit 59 represents 0 (L). To the contrary, if foreign particles are present, light scattered from the foreign particles is spatially continuously generated. For this reason, both the output signals $A_{OUT1}$ and $A_{OUT2}$ (or $B_{OUT1}$ and $B_{OUT2}$) exceed the threshold value. The arithmetic result of the AND circuit 59 becomes "1" (H). That is, the foreign particles are detected. An output supplied to the signal switching portion only corresponds to a light intensity and may be an optical output or a photoelectrically converted output. If an arrangement in which the optical output is switched by the signal switching portion, and only the selected optical output is photoelectrically converted, the number of photoelectric conversion elements can be reduced from four to two. In this case, however, the arrangement of the signal switching portion is complicated.

Figure 73:
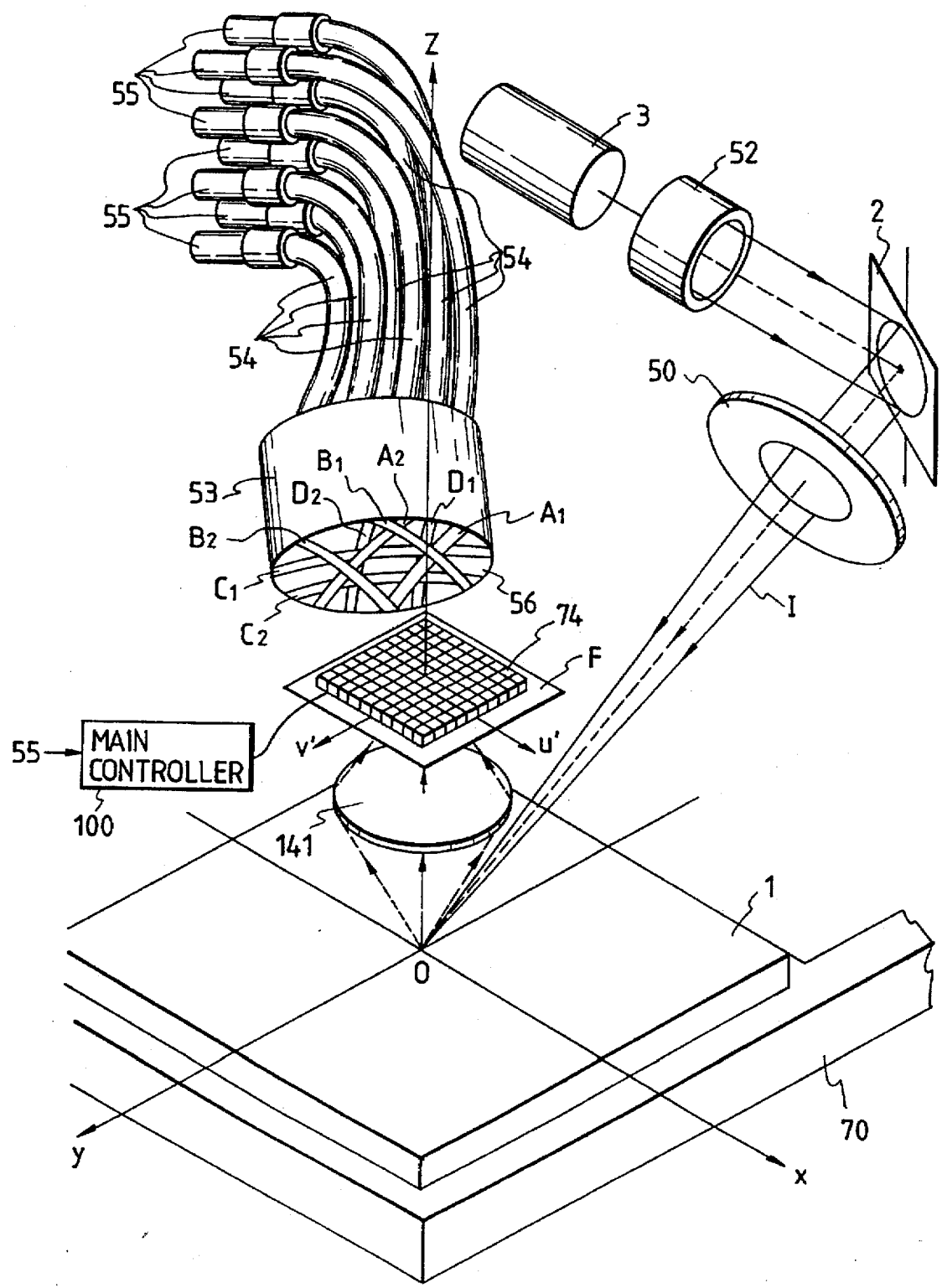
FIG. 73 is a perspective view showing the arrangement of the main part of a defect inspecting apparatus according to the sixth application example of the ninth embodiment of the present invention.
Figure 74:
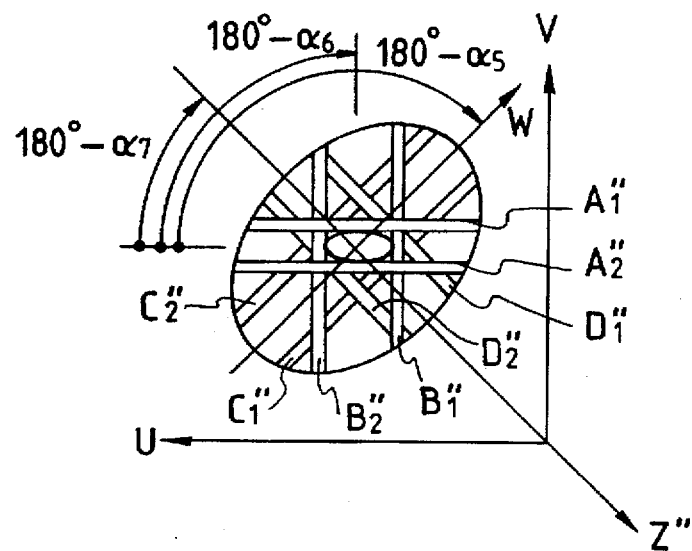
FIGS. 74 and 75 are views showing the principle of a relationship between light receiving areas and diffracted light on the Fourier plane in FIG. 73.

The seventh application example of the ninth embodiment of the present invention is shown in FIG. 73. An apparatus of this application example is basically the same as that of the fifth application example of the ninth embodiment, except that light receiving areas CC and DD are additionally formed. FIG. 74 shows light receiving areas on the Fourier transform plane and Fourier spectra of diffracted light components. Pairs of light receiving areas ($A_1$ and $A_2$), ($B_1$ and $B_2$), ($C_1$ and $C_2$), and ($D_1$ and $D_2$) are arranged such that angles formed with a U axis are smaller than $180°-\alpha_5$, $180°-\alpha_6$, and $180°-\alpha_7$. The interval between the light receiving areas is set to satisfy equations (12) and (42).

As described above, since the light receiving areas are additionally formed, the arrangement of light receiving areas can be optimized for periodical circuit patterns in various directions (e.g., examples in FIGS. 7A to 9E) in addition to the circuit patterns (e.g., an example in FIGS. 8A to 8E) having line symmetry in the X and Y axes. In general, in a two-dimensional periodic pattern shown in FIGS. 8A to 8E, an angle between the a and b axes is often limited to some extent. The value of $180°-\alpha_7$ is optimized to realize the arrangement having a high discrimination capability. In this case, if pitches in two directions (a and b directions in FIG. 8A) are equal to each other, light receiving areas in one of the orthogonal directions may be selected. Alternatively, light receiving areas may be arranged in both the directions.

Figure 78:
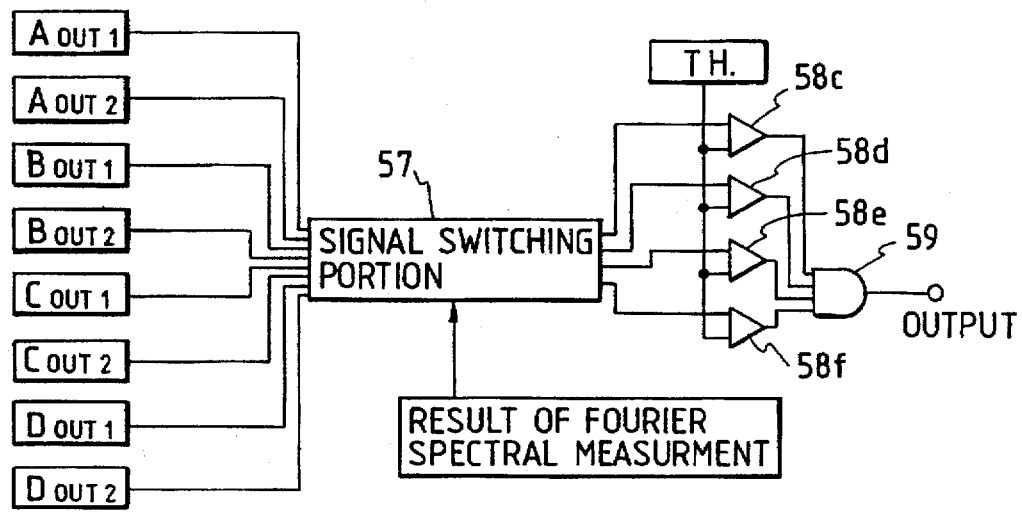
FIG. 78 is a block diagram showing the arrangement of a signal processing system in the defect inspecting apparatus shown in FIG. 73.

The arrangement of a signal processing system according to this application example is shown in FIG. 78. The arrangement of this signal processing system is basically the same as that in FIG. 77. Referring to FIG. 78, output signals $A_{OUT1}$, $A_{OUT2}$, $B_{OUT1}$, $B_{OUT2}$, $C_{OUT1}$, $C_{OUT2}$, $D_{OUT1}$, and $D_{OUT2}$ from the respective light receiving areas are input to a signal switching portion 57. The signal switching portion 57 also receives a result of a Fourier spectral measurement. Signals used for signal processing are selected from the output signals corresponding to the light receiving areas on the basis of the result of the Fourier spectral measurement. The signal switching portion 57 outputs selected output signals (e.g., the signals $A_{OUT1}$ and $A_{OUT2}$ and the signals $B_{OUT1}$ and $B_{OUT2}$) to comparators 58c, 58d, 58e, and 58f. The comparators 58c, 58d, 58e, and 58f compare a threshold value with the selected output signals. If the output signal from the signal switching portion 57 exceeds the threshold value TH, each comparator outputs a signal to an AND circuit 59a. The AND circuit 59a logically ANDs the signals from the comparators 58c, 58d, 58e, and 58f to discriminate foreign particles from a circuit pattern.

In the above application example, the output signals from the light receiving areas are switched by the signal switching portion to select specific light receiving areas. However, as previously described, light receiving areas may be arranged in all possible directions corresponding to all possible periodic directions of circuit patterns, signals from all the light receiving areas may be photoelectrically converted, and the resultant signals may be logically ANDed to discriminate foreign particles from a circuit pattern signal. Unused light receiving areas may be masked with a light-shielding member. Masking may be electrically performed using a liquid crystal or an electroluminescent element in addition to a slit or the like.

Figure 75:
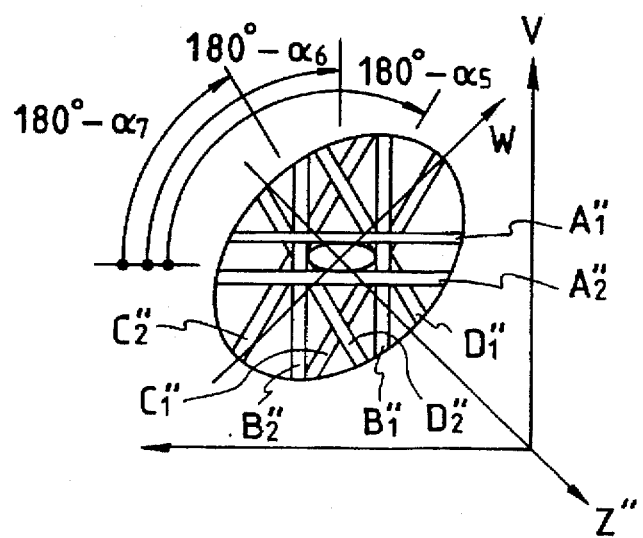

FIG. 75 shows another arrangement of light receiving areas on a Fourier transform plane according to the sixth application example of the ninth embodiment. This application example is different from that in FIG. 74 in an angle of $180°-\alpha_5$. That is, pairs of light receiving areas ($A_1$ and $A_2$), ($B_1$ and $B_2$), ($C_1$ and $C_2$), and ($D_1$ and $D_2$) are arranged such that angles formed with a U axis are set to be $180°-\alpha_5$, $180°-\alpha_6$, and $180°-\alpha_7$.

The seventh application example of the ninth embodiment of the present invention will be described with reference to FIGS. 55 and 56. In the first and second application examples of the ninth embodiment, a lens is used as a Fourier transform element. However, the seventh application example is different from the first and second application examples in that a new optical element different from a Fourier transform lens is used to perform Fourier transform. The principle of defect detection itself is the same as that of the first and second application example of the ninth embodiment, and a Fourier spectral measuring means will be mainly described below.

Referring to FIG. 55, assume a sphere S having a predetermined radius centered on an origin O on an orthogonal coordinate system having x and y axes. An orthogonal coordinate system having U and V axes is assumed at a position spaced apart from a plane (x–y plane) having the x and y axes by a distance L. The x axis is set to be parallel to the U axis, and the y axis is set to be parallel to the V axis. A straight line extending through the origin O of the plane (U–V plane) having the origin O of the x–y plane and the U and V axes is perpendicular to the x–y and U–V planes.

When the quadrangularly prismatic optical fibers having a bottom surface whose width in the U direction is Du and width in the V direction is Dv are densely bundled. Two of these quadrangularly prismatic optical fibers are represented by quadrangularly prismatic optical fibers 91-i and 91-j, and other quadrangularly prismatic optical fibers are not illustrated. In this case, one end face (e.g., end faces 91-ib and 91-jb indicated by hatched portions) of each of the large number of the quadrangularly prismatic optical fibers is located as a square in the matrix on the U–V plane. The other end face (e.g., end faces 91-ia and 91-3a indicated by hatched portions) of each of the large number of quadrangularly prismatic optical fibers constitutes part of the spherical surface S. The quadrangularly prismatic optical fibers each having the other end face not located on the spherical surface S are not illustrated.

FIG. 56 is a schematic sectional view along a plane passing through the center of the spherical surface S in FIG. 55. Referring to FIG. 56, the quadrangularly prismatic optical fibers 91-1, 91-2, 91-3, ... are densely arranged from an end of the spherical surface S. The respective quadrangularly prismatic optical fibers comprise a core 91-1c and a cladding layer 91-1d, a core 91-2c and a cladding layer 91-2d, a core 91-3c and a cladding layer 91-3d, ..., respectively. In this case, for example, light having exit angles $\theta_4$ to $\theta_5$ is incident on the core portion of the other end face 91-6a of the quadrangularly prismatic optical fiber 91-6, and this light emerges from one end face 91-6b. Similarly, light having an exit angle close to $\theta_6$ is incident on the core portion of the other end face 91-2a of the quadrangularly prismatic optical fiber 91-2, and this light emerges from one end face 91-2b thereof.

If the radius of the spherical surface S is defined as f, for example, the following relation is apparently established between an exit angle $\theta_3$ of light incident on the other (incident side) end face 11-2a of the quadrangularly prismatic optical fiber 11-2 and a coordinate $U_3$ on the U axis of one (exit side) end face 11-2b thereof:

$$U_3 = f/\sin \theta_3 \tag{63}$$

This relation also applies to other quadrangular prismatic optical fibers 91-k (k=1, 3, 4, . . . ). It is thus apparent that the optical element arranged by bundling these quadrangularly prismatic optical fibers serves as a Fourier transform optical element.

In this application example, light emerging from a portion near the center of the sphere S at an angle of about 90° with respect to the optical axis can efficiently propagate to the U-V plane by the quadrangularly prismatic optical fiber. Therefore, when a photoelectric conversion element array as in the first application example of the ninth embodiment is arranged, a Fourier spectrum in a wide frequency range can be observed with a high S/N ratio. Columnar optical fibers may be used in place of the quadrangularly prismatic optical fibers 91-i. Although the columnar optical fiber has a lower focusing efficiency than the quadrangularly prismatic optical fiber, the columnar optical fibers can be easily manufactured.

In this application example, the above-mentioned optical element is used to measure a Fourier spectrum, and the arrangement of light receiving areas of a light receiver is selected on the basis of the result of the spectral measurement. As a means for selecting the arrangement of light receiving areas, a means for mechanically rotating a light receiver as in the third and fourth application examples of the ninth embodiment may be used, or any other means may be used (e.g., light receiving areas may be selected as in the fifth and sixth application examples of the ninth embodiment). In the seventh application example, Fourier transform can be performed for a light beam having a diffraction angle close to 90° without using a Fourier transform lens. In addition, in the first and second application examples of the ninth embodiment, light receiving areas may be selected on the basis of the result of the Fourier spectral measurement as in the fifth and sixth application examples of the ninth embodiment.

Even if a Fourier transform optical element shown in FIGS. 55, 56 or FIGS. 83A and 83B is used, light receiving areas may be located on a pupil plane Eps of a light receiving optical system (a lens $L_1$ or $L_2$) in FIGS. 82A and 82B. A Fourier spectrum on the pupil plane Eps is calculated on the basis of the result of measurement using a Fourier spectrum using a Fourier transform optical element. On the basis of this result, the arrangement of the light receiving areas may be optimized using equation (12).

The above description has exemplified detection of foreign particles. However, a defect inspecting apparatus according to the present invention can be used to inspection except for foreign particle inspection. For example, a defect such as an unnecessary projection on a pattern itself can be detected, as a matter of course.

An apparatus according to the present invention is also applicable to defect detection of a phase shift reticle in addition to a reticle in which a light-shielding pattern made of chromium or the like is formed. That is, a focused light beam is illuminated to obtain light components diffracted from a pattern formed of a phase member (dielectric film). Therefore, detection of separation between a phase shift pattern and foreign particles and detection of a defect of a phase shift pattern itself can be performed.

As has been described above, the embodiment described above is based on the finding that diffracted light components are discretely generated if a plurality of circuit patterns are present within an irradiation area of an incident light beam upon micropatterning of circuit patterns. In this case, the light receiving surface of the light receiving means includes a portion on which light diffracted from a pattern is incident and a portion on which light diffracted from the pattern is not incident. If a substrate to be inspected is a reticle for manufacturing a semiconductor element, a unique pattern is often formed on each substrate. In this embodiment, a plurality of light receiving areas which can independently perform photoelectric conversion are formed on the light receiving surface of the light receiving means, and the arrangement of light receiving areas is selected in accordance with a circuit pattern.

To select the proper arrangement of light receiving areas, the state of the distribution of light scattered from an inspecting point is measured, and the light receiving areas are arranged based on this measurement result such that light diffracted from a pattern is not incident on at least one of the plurality of light receiving areas. When this arrangement is selected and outputs from the light receiving areas are logically ANDed to discriminate discretely generated diffracted light components from a spatially continuous light scattered from foreign particles.

As a method of measuring the state of the distribution of the scattered light, light from the inspecting point is focused using a Fourier transform lens or an optical element shown in FIGS. 55 to 59 to cause a two-dimensional photoelectric conversion element array or the like arranged on the Fourier transform plane to detect a Fourier spectrum. Alternatively, the distribution of amplitudes of light from the inspecting point may be measured on the light receiving surface of the light receiving means. In this case, a Fourier spectrum can be calculated as needed.

As described above, according to this embodiment, the Fourier spectrum of a light beam from an inspecting point is measured, and the arrangement of light receiving areas is selected on the basis of the result of this measurement. For this reason, a fine two-dimensional pattern can be discriminated from foreign particles with high efficiency and high precision. In addition, defects such as a pitch error of the fine periodic pattern itself or an unnecessary projection and an omission can be detected with high precision.

What is claimed is:

1. A defect inspecting apparatus for inspecting defectives on an inspecting surface, including the following:

irradiating means to irradiate a given beam onto said inspecting surface;

a plurality of light receiving means to receive scattering rays of light from said inspecting surface and output photoelectric conversion signals individually in accordance with the intensity of said light received;

a first comparison means to compare the size of each of said plural photoelectric conversion signals with a predetermined first fiducial level and output a first detection signal when all of said plural photoelectric signals exceed said first fiducial level;

a second comparison means to compare the size of each of said plural photoelectric conversion signals with a second fiducial level which is set higher than said first fiducial level and output a second detection signal when at least one of said plural photoelectric signals exceeds said second fiducial level; and detecting means to output a signal indicating the detection of said defectives on the basis of at least one signal of said first detection signal and said second detection signal.

2. A defect inspecting apparatus according to claim 1, wherein
said detection means includes the following:
a first selection means to compare the sizes of each of said plural photoelectric conversion signals and select a signal of the largest size;
a second selection means to compare the sizes of each of said plural photoelectric conversion signals and select a signal of the smallest size; and
a third selection means to select at least one of the signal selected by said first selection means and the signal selected by said second selection means.

3. A defect inspecting apparatus according to claim 1, wherein
said apparatus further includes the following:
selecting means to select said photoelectric conversion signals for comparison with said fiducial levels in accordance with the directivity of said scattering rays of light; and
said irradiating means having converging means to converge beams to said inspecting surface, and
a plurality of said light receiving means includes:
a first light receiving means having an angle of 0° to 90° formed by each of optical axes and the optical axis of said converging means; and
a second light receiving means having an angle of 90° to 180°.

4. A defect inspecting apparatus according to claim 1, wherein
said apparatus further includes the following:
position detecting means to detect the positions of said defectives;
visual means capable of allowing visual observation of said defectives; and
shifting means to shift said visual means, which shifts said visual means in accordance with at least one signal of said first detection signal and said second detection signal.

5. A defect inspecting apparatus for inspecting defectives on an inspecting surface, said apparatus including the following:
irradiating means to irradiate a given beam onto said inspecting surface;
a plurality of light receiving means to receive scattering rays of light from said inspecting surface and output photoelectric conversion signals individually in accordance with the intensity of said light received;
a first comparison means to compare the size of each of said plural photoelectric conversion signals with a predetermined first fiducial level and output a first detection signal when all of said plural photoelectric signals exceed said first fiducial level;
a second comparison means to compare the size of each of said plural photoelectric conversion signals with a second fiducial level which is set higher than said first fiducial level and output a second detection signal when at least one of said plural photoelectric signals exceeds said second fiducial level; and
detecting means to output a signal indicating the detection of said defectives on the basis of at least one signal of said first detection signal and said second detection signal, and
the difference between the size of said photoelectric conversion signals and said first fiducial level differs from the difference between the size of said photoelectric conversion signals and said second fiducial level.

6. A defect inspecting apparatus for inspecting defectives on an inspecting surface, said apparatus including the following:

irradiating means to irradiate a given beam onto said inspecting surface;
a plurality of light receiving means to receive scattering rays of light from said inspecting surface and output photoelectric conversion signals individually in accordance with the intensity of said light received;
a first comparison means to compare the size of each of said plural photoelectric conversion signals with a predetermined first fiducial level and output a first detection signal when all of said plural photoelectric signals exceed said first fiducial level;
a second comparison means to compare the size of each of said plural photoelectric conversion signals with a second fiducial level, substantially the same as said first fiducial level, and output a second detection signal when at least one of said plural photoelectric signals exceeds said second fiducial level;
detecting means to output a signal indicating the detection of said defectives on the basis of at least one signal of said first detection signal and said second detection signal; and
means for causing the difference between the size of said photoelectric conversion signals and said first fiducial level to differ from the difference between the size of said photoelectric conversion signals and said second fiducial level by making the size of said photoelectric conversion signals variable.

7. A foreign particle detecting apparatus which comprises:
a) a light source for radiating light onto a surface on which a miniaturized pattern is formed;
b) a focusing device for focusing the light radiated by said light source onto said surface with a predetermined angular aperture;
c) moving means for moving the focused light relative to said surface;
d) detection means including an array of light-receiving elements for receiving light from said surface and independently outputting photoelectric signals according to the quantity of light received, focused light incident on said miniaturized pattern producing discrete diffracted light components having a periodic distribution in a first direction, n light-receiving elements of said array being arranged in order along a direction of arrangement determined by said first direction, the minimum spatial angle defined between light-receiving elements located at respective ends of said order being substantially equal to or slightly larger than said angular aperture of the focused light, and the maximum spatial angle defined between adjacent light-receiving elements in said order being equal to or smaller than the pitch between adjacent diffracted light components along said direction of arrangement;
e) a first comparison means to compare the size of each of said photoelectric signals with a predetermined first fiducial level and output a first detection signal when all of said photoelectric signals exceed said first fiducial level;
f) a second comparison means to compare the size of each of said photoelectric signals with a second fiducial level which is set higher than said first fiducial level and output a second detection signal when at least one of said photoelectric signals exceeds said second fiducial level; and
g) discrimination means for discriminating foreign particles on the basis of at least one signal of said first detection signal and said second detection signal.

* * * * *